US007943318B2

(12) United States Patent
Croce et al.

(10) Patent No.: US 7,943,318 B2
(45) Date of Patent: May 17, 2011

(54) MICRORNA-BASED METHODS AND COMPOSITIONS FOR THE DIAGNOSIS, PROGNOSIS AND TREATMENT OF LUNG CANCER

(75) Inventors: Carlo M. Croce, Columbus, OH (US); Nozomu Yanaihara, Kanagawa (JP); Curtis C. Harris, Garrett Park, MD (US)

(73) Assignees: The Ohio State University Research Foundation, Columbus, OH (US); The United States of America as represented by the Secretary of the Department of Health and Human Services, Washington, DC (US)

( * ) Notice: Subject to any disclaimer, the term of this patent is extended or adjusted under 35 U.S.C. 154(b) by 93 days.

(21) Appl. No.: 12/160,034

(22) PCT Filed: Jan. 3, 2007

(86) PCT No.: PCT/US2007/000103
§ 371 (c)(1),
(2), (4) Date: Jul. 3, 2008

(87) PCT Pub. No.: WO2007/081720
PCT Pub. Date: Jul. 19, 2007

(65) Prior Publication Data
US 2008/0306017 A1 Dec. 11, 2008

Related U.S. Application Data

(60) Provisional application No. 60/756,400, filed on Jan. 5, 2006.

(51) Int. Cl.
*C12Q 1/68* (2006.01)
*C07H 21/02* (2006.01)
(52) U.S. Cl. .......................................... 435/6; 536/23.1
(58) Field of Classification Search .................. None
See application file for complete search history.

(56) References Cited

U.S. PATENT DOCUMENTS

| | | | |
|---|---|---|---|
| 4,172,124 A | 10/1979 | Koprowski et al. |
| 4,196,265 A | 4/1980 | Koprowski et al. |
| 4,608,337 A | 8/1986 | Croce |
| 4,693,975 A | 9/1987 | Kozbor et al. |
| 4,701,409 A | 10/1987 | Croce |
| 5,015,568 A | 5/1991 | Tsujimoto et al. |
| 5,149,628 A | 9/1992 | Croce |
| 5,198,338 A | 3/1993 | Croce |
| 5,202,429 A | 4/1993 | Tsujimoto et al. |
| 5,459,251 A | 10/1995 | Tsujimoto et al. |
| 5,506,106 A | 4/1996 | Croce et al. |
| 5,506,344 A | 4/1996 | Tsujimoto et al. |
| 5,523,393 A | 6/1996 | Tsujimoto et al. |
| 5,567,586 A | 10/1996 | Croce |
| 5,595,869 A | 1/1997 | Tsujimoto et al. |
| 5,633,135 A | 5/1997 | Croce et al. |
| 5,633,136 A | 5/1997 | Croce et al. |
| 5,674,682 A | 10/1997 | Croce et al. |
| 5,688,649 A | 11/1997 | Croce et al. |
| 5,695,944 A | 12/1997 | Croce et al. |
| 5,928,884 A | 7/1999 | Croce et al. |
| 5,939,258 A | 8/1999 | Croce et al. |
| 5,985,598 A | 11/1999 | Russo et al. |
| 6,040,140 A | 3/2000 | Croce et al. |
| 6,130,201 A | 10/2000 | Croce et al. |
| 6,242,212 B1 | 6/2001 | Croce et al. |
| 6,255,293 B1 | 7/2001 | Kimchi |
| 6,258,541 B1 | 7/2001 | Chapkin et al. |
| 6,774,217 B1 | 8/2004 | Croce et al. |
| 6,924,414 B2 | 8/2005 | Croce et al. |
| 7,060,811 B2 | 6/2006 | Aldaz et al. |
| 7,141,417 B1 | 11/2006 | Croce et al. |
| 7,175,995 B1 | 2/2007 | Russo et al. |
| 7,217,568 B2 | 5/2007 | Jamieson et al. |
| 7,220,834 B2 | 5/2007 | Croce et al. |
| 7,232,806 B2 | 6/2007 | Tuschl et al. |
| 7,390,792 B2 | 6/2008 | Srivastava et al. |
| 7,585,969 B2 | 9/2009 | Stoffel et al. |
| 7,592,441 B2 | 9/2009 | Bentwich et al. |
| 7,618,814 B2 | 11/2009 | Bentwich et al. |
| 7,642,348 B2 | 1/2010 | Bentwich et al. |
| 7,667,090 B2 | 2/2010 | Croce |
| 7,670,840 B2 | 3/2010 | Croce et al. |
| 7,709,616 B2 | 5/2010 | Bentwich et al. |
| 7,723,030 B2 | 5/2010 | Croce et al. |
| 7,723,035 B2 | 5/2010 | Croce et al. |

(Continued)

FOREIGN PATENT DOCUMENTS

WO 90/15156 12/1990

(Continued)

OTHER PUBLICATIONS

Croce et al., "miRNAs, cancer, and stem cell division", Cell, Jul. 15, 2005, vol. 122, No. 1. pp. 6-7 [online]. [Retrieved on Sep. 12, 2007]. [Retrieved from the internet: http://www.sciencedirect.com/sience?_ob=ArtlcieURL&_udi=B2WSN-4GMHOPG-4&_user=10&_coverDate=07%2F15%2R2005&_rdoc=1&_urlVersion=O&_userId=10&md5=3cd56a72bebd431 be2feOOdb402dbfBb).

Thomson et al., "A Custom microaray platoform for analysis of microRNA gene expression, Nature Methods", Oct. 2004. vol. 1, No. 1, pp. 47-53 [online]. [Retrieved on Sep. 12, 2007]. [Retrieved from the Internet: http://www.nature.com/nmeth/journal/v1/n1/pdf/nemth704.pdf].

PCT International Search Report, Application No. PCT/US 07/00103, Jan. 3, 2007.

(Continued)

*Primary Examiner* — Amy Bowman
(74) *Attorney, Agent, or Firm* — MacMillan, Sobanski & Todd, LLC

(57) ABSTRACT

The present invention provides novel methods and compositions for the diagnosis, prognosis and treatment of lung cancer. The invention also provide methods of identifying anti-lung cancer agents.

22 Claims, 12 Drawing Sheets

U.S. PATENT DOCUMENTS

| | | | |
|---|---|---|---|
| 7,728,189 B2 | 6/2010 | Croce | |
| 7,749,715 B2 | 7/2010 | Russo et al. | |
| 7,777,005 B2 | 8/2010 | Croce et al. | |
| 2001/0026796 A1 | 10/2001 | Croce et al. | |
| 2002/0086331 A1 | 7/2002 | Croce et al. | |
| 2002/0116726 A1 | 8/2002 | Croce et al. | |
| 2004/0033502 A1 | 2/2004 | Williams et al. | |
| 2004/0078834 A1 | 4/2004 | Croce | |
| 2004/0152112 A1 | 8/2004 | Croce et al. | |
| 2004/0265316 A1 | 12/2004 | Croce et al. | |
| 2004/0265930 A1 | 12/2004 | Sun et al. | |
| 2005/0019890 A1 | 1/2005 | Croce | |
| 2005/0059005 A1 | 3/2005 | Tuschl et al. | |
| 2005/0069918 A1 | 3/2005 | Claret | |
| 2005/0074797 A1 | 4/2005 | Croce et al. | |
| 2005/0112630 A1 | 5/2005 | Shaughnessy et al. | |
| 2005/0176025 A1 | 8/2005 | McSwiggen et al. | |
| 2005/0181385 A1 | 8/2005 | Linsley et al. | |
| 2005/0186589 A1 | 8/2005 | Kowalik et al. | |
| 2005/0256072 A1 | 11/2005 | Aronin et al. | |
| 2005/0260639 A1 | 11/2005 | Nakamura et al. | |
| 2005/0266443 A1 | 12/2005 | Croce et al. | |
| 2005/0287530 A1 | 12/2005 | Croce et al. | |
| 2006/0019286 A1 | 1/2006 | Horvitz et al. | |
| 2006/0024780 A1 | 2/2006 | Aldaz et al. | |
| 2006/0037088 A1 | 2/2006 | Li | |
| 2006/0075511 A1 | 4/2006 | Croce et al. | |
| 2006/0084059 A1 | 4/2006 | Yip et al. | |
| 2006/0099619 A1 | 5/2006 | Remacle et al. | |
| 2006/0105340 A1 | 5/2006 | Croce et al. | |
| 2006/0105360 A1 | 5/2006 | Croce et al. | |
| 2006/0127895 A1 | 6/2006 | Sabapathy | |
| 2006/0165659 A1 | 7/2006 | Croce et al. | |
| 2006/0166918 A1 | 7/2006 | Heidenreich et al. | |
| 2006/0185027 A1 | 8/2006 | Bartel et al. | |
| 2006/0188924 A1 | 8/2006 | Russo et al. | |
| 2006/0188959 A1 | 8/2006 | Croce et al. | |
| 2006/0189557 A1 | 8/2006 | Slack et al. | |
| 2006/0247448 A1 | 11/2006 | Boivin et al. | |
| 2006/0292616 A1 | 12/2006 | Neely et al. | |
| 2007/0050146 A1 | 3/2007 | Bentwich et al. | |
| 2007/0054849 A1 | 3/2007 | Nakamura et al. | |
| 2007/0065840 A1 | 3/2007 | Naguibneva et al. | |
| 2007/0065844 A1 | 3/2007 | Golub et al. | |
| 2007/0072230 A1 | 3/2007 | Croce et al. | |
| 2007/0099196 A1 | 5/2007 | Kauppinen et al. | |
| 2007/0123482 A1 | 5/2007 | Stoffel et al. | |
| 2007/0161004 A1 | 7/2007 | Brown et al. | |
| 2007/0178105 A1 | 8/2007 | Croce et al. | |
| 2007/0178502 A1 | 8/2007 | Reed | |
| 2007/0212727 A1 | 9/2007 | Szalay et al. | |
| 2007/0213292 A1 | 9/2007 | Stoffel et al. | |
| 2007/0292878 A1 | 12/2007 | Raymond | |
| 2008/0026951 A1 | 1/2008 | Brown et al. | |
| 2008/0050744 A1 | 2/2008 | Brown et al. | |
| 2008/0171667 A1 | 7/2008 | Brown et al. | |
| 2008/0176766 A1 | 7/2008 | Brown et al. | |
| 2008/0182245 A1 | 7/2008 | Brown et al. | |
| 2008/0193943 A1 | 8/2008 | Murray | |
| 2008/0254473 A1 | 10/2008 | Chen et al. | |
| 2008/0256650 A1 | 10/2008 | Croce | |
| 2008/0261908 A1 | 10/2008 | Croce et al. | |
| 2008/0306006 A1 | 12/2008 | Croce et al. | |
| 2008/0306017 A1 | 12/2008 | Croce et al. | |
| 2008/0306018 A1 | 12/2008 | Croce et al. | |
| 2009/0005336 A1 | 1/2009 | Wang | |
| 2009/0023594 A1 | 1/2009 | Mouritzen et al. | |
| 2009/0029932 A1 | 1/2009 | Voinnet et al. | |
| 2009/0061424 A1 | 3/2009 | Chen | |
| 2009/0092974 A1 | 4/2009 | Davison et al. | |
| 2009/0099034 A1 | 4/2009 | Ahlquist et al. | |
| 2009/0123533 A1 | 5/2009 | Croce et al. | |
| 2009/0123912 A1 | 5/2009 | Raymond | |
| 2009/0123933 A1 | 5/2009 | Mishra | |
| 2009/0131348 A1 | 5/2009 | Labourier et al. | |
| 2009/0131354 A1 | 5/2009 | Bader et al. | |
| 2009/0131356 A1 | 5/2009 | Bader et al. | |
| 2009/0163430 A1 | 6/2009 | Johnson et al. | |
| 2009/0163434 A1 | 6/2009 | Bader et al. | |
| 2009/0163435 A1 | 6/2009 | Bader et al. | |
| 2009/0175827 A1 | 7/2009 | Byrom et al. | |
| 2009/0176723 A1 | 7/2009 | Brown et al. | |
| 2009/0192102 A1 | 7/2009 | Bader et al. | |
| 2009/0192111 A1 | 7/2009 | Bader et al. | |
| 2009/0192114 A1 | 7/2009 | Ovcharenko et al. | |
| 2009/0209450 A1 | 8/2009 | Croce et al. | |
| 2009/0222934 A1 | 9/2009 | Croce | |
| 2009/0227533 A1 | 9/2009 | Bader et al. | |
| 2009/0232893 A1 | 9/2009 | Bader et al. | |
| 2009/0253780 A1 | 10/2009 | Takeshita et al. | |
| 2009/0263803 A1 | 10/2009 | Beaudenon et al. | |
| 2009/0270484 A1 | 10/2009 | Croce et al. | |
| 2009/0281167 A1 | 11/2009 | Shen et al. | |
| 2009/0306194 A1 | 12/2009 | Ford et al. | |
| 2010/0004322 A1 | 1/2010 | Croce | |
| 2010/0048681 A1 | 2/2010 | Croce | |
| 2010/0120898 A1 | 5/2010 | Croce et al. | |
| 2010/0137410 A1 | 6/2010 | Croce | |
| 2010/0144850 A1 | 6/2010 | Croce | |
| 2010/0173319 A1 | 7/2010 | Croce et al. | |
| 2010/0184032 A1 | 7/2010 | Georgantas et al. | |
| 2010/0184830 A1 | 7/2010 | Croce et al. | |
| 2010/0184842 A1 | 7/2010 | Croce | |
| 2010/0192235 A1 | 7/2010 | Croce | |
| 2010/0197770 A1 | 8/2010 | Wang et al. | |
| 2010/0197774 A1 | 8/2010 | Croce et al. | |
| 2010/0203544 A1 | 8/2010 | Croce et al. | |
| 2010/0234241 A1 | 9/2010 | Croce et al. | |
| 2010/0249213 A1 | 9/2010 | Croce | |
| 2010/0257618 A1 | 10/2010 | Croce et al. | |

FOREIGN PATENT DOCUMENTS

| | | |
|---|---|---|
| WO | 91/00364 | 1/1991 |
| WO | 91/07424 | 5/1991 |
| WO | 93/12136 | 6/1993 |
| WO | 94/10343 | 5/1994 |
| WO | 94/24308 | 10/1994 |
| WO | 94/26930 | 11/1994 |
| WO | 96/13514 | 5/1996 |
| WO | 96/35124 | 11/1996 |
| WO | 97/29119 | 8/1997 |
| WO | 98/09510 | 3/1998 |
| WO | 00/03685 | 1/2000 |
| WO | 00/50565 | 8/2000 |
| WO | 00/55169 | 9/2000 |
| WO | 01/44466 | 6/2001 |
| WO | 01/68666 | 9/2001 |
| WO | 01/77343 | 10/2001 |
| WO | 01/87958 | 11/2001 |
| WO | 02/064171 | 8/2002 |
| WO | 02/064172 | 8/2002 |
| WO | 03/029459 | 4/2003 |
| WO | 03/078662 | 9/2003 |
| WO | 03/092370 | 11/2003 |
| WO | 2004/033659 | 4/2004 |
| WO | 2004/043387 | 5/2004 |
| WO | 2004/079013 | 9/2004 |
| WO | 2004/094377 | 11/2004 |
| WO | 2005/017711 | 2/2005 |
| WO | 2005/020795 | 3/2005 |
| WO | 2005/078139 | 8/2005 |
| WO | 2005078139 A2 | 8/2005 |
| WO | 2005/080601 | 9/2005 |
| WO | 2005/118806 | 12/2005 |
| WO | 2005118806 A2 | 12/2005 |
| WO | 2006/105486 | 10/2006 |
| WO | 2006/108718 | 10/2006 |
| WO | 2006/119266 | 11/2006 |
| WO | 2006/133022 | 12/2006 |
| WO | 2006/137941 | 12/2006 |
| WO | 2007/016548 | 2/2007 |
| WO | 2007/033023 | 3/2007 |
| WO | 2007/044413 | 4/2007 |
| WO | 2007/081680 | 7/2007 |
| WO | 2007/081720 | 7/2007 |
| WO | 2007/081740 | 7/2007 |
| WO | 2007/084485 | 7/2007 |

| | | |
|---|---|---|
| WO | 2007/109236 | 9/2007 |
| WO | 2007/127190 | 11/2007 |
| WO | 2008/008430 | 1/2008 |
| WO | 2008/036776 | 3/2008 |
| WO | 2008/054828 | 5/2008 |
| WO | 2008/070082 | 6/2008 |
| WO | 2008/073920 | 6/2008 |
| WO | 2008/094545 | 8/2008 |
| WO | 2008/097277 | 8/2008 |
| WO | 2008/136971 | 11/2008 |
| WO | 2008/153987 | 12/2008 |
| WO | 2008/157319 | 12/2008 |
| WO | 2009/018303 | 2/2009 |
| WO | 2009/020905 | 2/2009 |
| WO | 2009/026487 | 2/2009 |
| WO | 2009/033140 | 3/2009 |
| WO | 2009/049129 | 4/2009 |
| WO | 2009/055773 | 4/2009 |
| WO | 2009/064590 | 5/2009 |
| WO | 2009/070653 | 6/2009 |
| WO | 2009/100029 | 8/2009 |
| WO | 2009/108853 | 9/2009 |
| WO | 2009/108856 | 9/2009 |
| WO | 2009/108860 | 9/2009 |
| WO | 2009/108866 | 9/2009 |
| WO | 2009/152300 | 12/2009 |
| WO | 2010/019694 | 2/2010 |
| WO | 2010/059779 | 5/2010 |
| WO | 2010/065156 | 6/2010 |
| WO | 2010/099161 | 9/2010 |

OTHER PUBLICATIONS

Hayashita et al., A Polycistronic MicroRNA Cluster, miR-17-92, Is Overexpressed in Human Lung Cancers and Enhances Cell Proliferation, Cancer Research, 2005, pp. 9628-9632, vol. 21.

Johnson et al., RAS Is Regulated by the let-7 MicroRNA Family, Cell, Mar. 11, 2005, pp. 635-647, vol. 120. Johnson et al., RAS Is Regulated by the let-7 MicroRNA Family, Supplemental Data.

Lu et al., MicroRNA expression profiles classify human cancers, Nature, 2005, pp. 834-838, vol. 435/9.

Takamizawa, et al., Reduced Expression of the let-7 MicroRNA's in Human Lung Cancers in Association with Shortened Postoperative Survival, Cancer Research, Jun. 1, 2004, pp. 3753-3756, vol. 64.

Yanaihara, et al., Unique microRNA molecular profiles in lung cancer diagnosis and prognosis, Cancer Cell, 2006, pp. 189-198, vol. 9.

Calin, et al., Human microRNA genes are frequently located at fragile sites and genomic regions involved in cancers, PNAS, 2004, vol. 101, No. 9, pp. 2999-3004.

European Patent Office Communication, dated Nov. 9, 2009, PCT/US2007000103.

Akahoshi, M. et al., "Myeloproliferative Disorders Terminating in Acute Megakaryoblastic Leukemia with Chromosome 3q26 Abnormality," Cancer, 1987, pp. 2654-2661, vol. 60.

Akao, Y. et al., "let-7 MicroRNA Functions as a Potential Growth Suppressor in Human Colon Cancer Cells," Biol. Pharm. Bull., May 2006, pp. 903-906, vol. 29, No. 5.

Ambs, S. et al., "Genomic Profiling of MicroRNA and Messenger RNA Reveals Deregulated MicroRNA Expression in Prostate Cancer," Cancer Research, Aug. 2008, pp. 6162-6170, vol. 68, No. 15.

Aqeilan, R. I. et al., "Targeted Deletion of WWOX Reveals a Tumor Suppressor Function," PNAS, Mar. 2007, pp. 3949-3954, vol. 104, No. 10.

Bandres, E. et al., "Identification by Real-Time PCR of 13 Mature MicroRNAs Differentially Expressed in Colorectal Cancer and Non-Tumoral Tissues," Molecular Cancer, Jul. 2006, 10 pages, vol. 5, No. 29.

Bartel, D. P., "MicroRNAs: Target Recognition and Regulatory Functions," Cell, Jan. 2009, pp. 215-233, vol. 136.

Bednarek, A. K. et al., "WWOX, the FRA16D Gene, Behaves as a Suppressor of Tumor Growth," Cancer Research, Nov. 2001, pp. 8068-8073, vol. 61.

Bejenaro, et al., "Ultraconserved Elements in the Human Genome," Electronic Suppl. Data, Science, 2004.

Bejerano, G. et al., "Ultraconserved Elements in the Human Genome," Science, May 2004, pp. 1321-1325, vol. 304.

Bell, D. A., "Origins and Molecular Pathology of Ovarian Cancer," Modern Pathology, 2005, pp. S19-S32, vol. 18.

Bichi, R. et al., "Human Chronic Lymphocytic Leukemia Modeled in Mouse by Targeted TCL1 Expression," PNAS, May 2002, pp. 6955-6960, vol. 99, No. 10.

Brueckner, B. et al., "The Human let-7a-3 Locus Contains an Epigenetically Regulated MicroRNA Gene with Oncogenic Function," Cancer Research, Feb. 2007, pp. 1419-1423, vol. 67, No. 4.

Budhu, A. et al., "A Unique Metastasis-Related MicroRNA Expression Signature is a Prognostic Indicator of Survival and Recurrence in Hepatocellular Carcinoma," Hepatology, 2007, p. 791A, vol. 46, No. 4, Suppl. 1, Abstract #1249.

Budhu, A. et al., "Identification of Metastasis-Related MicroRNAs in Hepatocellular Carcinoma," Hepatology, Mar. 2008, pp. 897-907, vol. 47, No. 3.

Calin, G. A. et al., "A MicroRNA Signature Associated with Prognosis and Progression in Chronic Lymphocytic Leukemia," The New England Journal of Medicine, Oct. 2005, pp. 1793-1801, vol. 353, No. 17.

Calin, G. A. et al., "Chromosomal Rearrangements and MicroRNAs: A New Cancer Link with Clinical Implications," The Journal of Clinical Investigation, Aug. 2007, pp. 2059-2066, vol. 117, No. 8.

Calin, G. A. et al., "Frequent Deletions and Down-Regulation of MicroRNA Genes miR15 and miR16 at 13q14 in Chronic Lymphocytic Leukemia," PNAS, Nov. 2002, pp. 15524-15529, vol. 99, No. 24.

Calin, G. A. et al., "Human MicroRNA Genes are Frequently Located at Fragile Sites and Genomic Regions Involved in Cancers," PNAS, Mar. 2004, pp. 2999-3004, vol. 101, No. 9.

Calin, G. A. et al., "MicroRNA Profiling Reveals Distinct Signatures in B Cell Chronic Lymphocytic Leukemias," PNAS, Aug. 2004, pp. 11755-11760, vol. 101, No. 32.

Calin, G. A. et al., "MicroRNA Signatures in Human Cancers," Nature Reviews Cancer, Nov. 2006, pp. 857-866, vol. 6.

Calin, G. A. et al., "MiR-15a and MiR-16-1 Cluster Functions in Human Leukemia," PNAS, Apr. 2008, pp. 5166-5171, vol. 105, No. 13.

Calin, G. A. et al., "Ultraconserved Regions Encoding ncRNAs are Altered in Human Leukemias and Carcinomas," Cancer Cell, Sep. 2007, pp. 215-229, vol. 12.

Chan, J. A. et al., "MicroRNA-21 is an Antiapoptotic Factor in Human Glioblastoma Cells," Cancer Research, Jul. 2005, pp. 6029-6033, vol. 65, No. 14.

Chang, N.-S. et al., "Molecular Mechanisms Underlying WOX1 Activation During Apoptotic and Stress Responses," Biochemical Pharmacology, 2003, pp. 1347-1354, vol. 66.

Chang, T.-C. et al., "Widespread MicroRNA Repression by Myc Contributes to Tumorigenesis," Nat Genet., Jan. 2008, pp. 43-50, vol. 40, No. 1.

Chen, C.-Z. et al., "MicroRNAs as Regulators of Mammalian Hematopoiesis," Seminars in Immunology, 2005, pp. 155-165, vol. 17.

Cheng, A. M. et al., "Antisense Inhibition of Human miRNAs and Indications for an Involvement of miRNA in Cell Growth and Apoptosis," Nucleic Acids Research, 2005, pp. 1290-1297, vol. 33, No. 4.

Ciafre, S. A. et al., "Extensive Modulation of a Set of MicroRNAs in Primary Glioblastoma," Biochemical and Biophysical Research Communications, 2005, pp. 1351-1358, vol. 334.

Cimmino, A. et al., "miR-15 and miR-16 Induce Apoptosis by Targeting BCL2," PNAS, Sep. 2005, pp. 13944-13949, vol. 102, No. 39.

Cimmino, A. et al., Corrections to "miR-15 and miR-16 Induce Apoptosis by Targeting BCL2," PNAS, Feb. 2006, pp. 2464-2465, vol. 103, No. 7.

Costinean, S. et al., "Pre-B Cell Proliferation and Lymphoblastic Leukemia/ High-Grade Lymphoma in Eμ-miR155 Transgenic Mice," PNAS, May 2006, pp. 7024-7029, vol. 103, No. 18.

Croce, C. M. et al., "miRNAs, Cancer, and Stem Cell Division," Cell, 2005, pp. 6-7, vol. 36.

Croce, C. M. et al., "Role of FHIT in Human Cancer," Journal of Clinical Oncology, May 1999, pp. 1618-1624, vol. 17, No. 5.

Croce, C. M., "Causes and Consequences of MicroRNA Dysregulation in Cancer," Nature Reviews Genetics, Oct. 2009, pp. 704-714, vol. 10.

Croce, C. M., "Oncogenes and Cancer," The New England Journal of Medicine, Jan. 2008, pp. 502-511, vol. 358, No. 5.

Dalmay, T. et al., "MicroRNAs and the Hallmarks of Cancer," Oncogene, 2006, pp. 6170-6175, vol. 25.

Davies, F. E. et al., "Insights into the Multistep Transformation of MGUS to Myeloma Using Microarray Expression Analysis," Blood, Dec. 2003, pp. 4504-4511, vol. 102, No. 13.

Dohner, H. et al., "Genomic Aberrations and Survival in Chronic Lymphocytic Leukemia," The New England Journal of Medicine, Dec. 2000, pp. 1910-1916, vol. 343, No. 26.

Druck, et al., "FHIT," Atlas of Genetics and Cytogenetics in Oncology and Haematology, 2007, pp. 171-178, vol. 2.

Eis, P. S. et al., "Accumulation of miR-155 and BIC RNA in Human B Cell Lymphomas," PNAS, Mar. 2005, pp. 3627-3632, vol. 102, No. 10.

European Patent Application, EP 1795203 A2, Croce et al., Application No. 06010581.4, filed Feb. 7, 1997, published Jun. 13, 2007.

European Search Report, Application No. 06800599.0 dated Oct. 19, 2009.

European Search Report, Application No. 06814375.9 dated Oct. 8, 2009.

European Search Report, Application No. 06825457.2 dated Sep. 16, 2009.

European Search Report, Application No. 07716208.9 dated Nov. 10, 2009.

European Search Report, Application No. 07717734.3 dated Nov. 9, 2009.

European Search Report, Application No. 07717903.4 dated Oct. 23, 2009.

European Search Report, Application No. 07753450.1 dated Jan. 12, 2009.

European Search Report, Application No. 07810382.7 dated Sep. 14, 2009.

European Search Report, Application No. 07867402.5 dated Mar. 16, 2010.

European Search Report, Application No. 07872618.9 dated Jul. 5, 2010.

European Search Report, Application No. 08767439.6 dated May 12, 2010.

European Search Report, Application No. 08768266.2 dated Jul. 1, 2010.

European Search Report, Application No. 08796821.0 dated Aug. 4, 2010.

European Search Report, Application No. 08841700.1 dated Jun. 2, 2010.

Fabbri, M. et al., "MicroRNA-29 Family Reverts Aberrant Methylation in Lung Cancer by Targeting DNA Methyltransferases 3A and 3B," PNAS, Oct. 2007, pp. 15805-15810, vol. 104, No. 40.

Fabbri, M. et al., "MicroRNAs," The Cancer Journal, Jan./Feb. 2008, pp. 1-6, vol. 14, No. 1.

Fabbri, M. et al., "WWOX Gene Restoration Prevents Lung Cancer Growth In Vitro and In Vivo," PNAS, Oct. 2005, pp. 15611-15616, vol. 102, No. 43.

Fong, Y. et al., "Muir-Torre-Like Syndrome in FHIT-Deficient Mice," PNAS, Apr. 2000, pp. 4742-4747, vol. 97, No. 9.

Fox, T. et al., "A Single Amino Acid Substitution Makes ERK2 Susceptible to Pyridinyl Imidazole Inhibitors of p38 MAP Kinase," Protein Science, 1998, pp. 2249-2255, vol. 7.

Garzon, et al., "MicroRNA 29b Functions in Acute Myeloid Leukemia," Prepublished Online, www.bloodjournal.org, Oct. 2009, doi:10.1182/blood-2009-03-211938, pp. 5331-5341, vol. 114.

Garzon, R. et al., "MicroRNA Fingerprints During Human Megakaryocytopoiesis," PNAS, Mar. 2006, pp. 5078-5083, vol. 103, No. 13.

Garzon, R. et al., "MicroRNA Signatures Associated with Cytogenetics and Prognosis in Acute Myeloid Leukemia," Blood, Published Online Jan. 2008, DOI: 10.1182/blood-2007-07-098749.

Godlewski, J. et al., "Targeting of the Bmi-1 Oncogene/Stem Cell Renewal Factor by MicroRNA-128 Inhibits Glioma Proliferation and Self-Renewal," Cancer Research, Nov. 2008, pp. 9125-9130, vol. 68, No. 22.

Gourley, C. et al., "WWOX Gene Expression Abolishes Ovarian Cancer Tumorigenicity In Vivo and Decreases Attachment to Fibronectin via Integrin α3," Cancer Research, Jun. 2009, pp. 4835-4842, vol. 69, No. 11.

Griffiths-Jones, S. et al., "miRBase: MicroRNA Sequences, Targets and Gene Nomenclature," Nucleic Acids Research, 2006, pp. D140-D144, vol. 34.

Guimaraes-Sternberg, C. et al., "MicroRNA Modulation of Megakaryoblast Fate Involves Cholinergic Signaling," Leukemia Research, 2006, pp. 583-595, vol. 30.

Guweidhi, A. et al. "Enhanced Expression of 14-3-3sigma in Pancreatic Cancer and its Role in Cell Cycle Regulation and Apoptosis," Carcinogenesis, 2004, pp. 1575-1585, vol. 25, No. 9.

Havelange, V. et al., "MicroRNAs: New Players in Acute Myeloid Leukemia," British Journal of Cancer, 2009, pp. 743-748, vol. 101.

Hayashita, Y. et al., "A Polycistronic MicroRNA Cluster, miR-17-92, is Overexpressed in Human Lung Cancers and Enhances Cell Proliferation," Cancer Research, Nov. 2005, pp. 9628-9632, vol. 65, No. 21.

Herling, et al., "TCL1 Shows a Regulated Expression Pattern in Chronic Lymphocytic Leukemia that Correlates with Molecular Subtypes and Proliferative State," Leukemia, Feb. 2006, pp. 280-285, vol. 20, No. 2.

Hiromura, M. et al., "Identification of Nerve Growth Factor-Responsive Element of the TCL1 Promoter as a Novel Negative Regulatory Element," The Journal of Biological Chemistry, Sep. 2006, pp. 27753-27764, vol. 281, No. 38.

Huang, Y.-S. et al., "Microarray Analysis of MicroRNA Expression in Hepatocellular Carcinoma and Non-Tumorous Tissues Without Viral Hepatitis," Journal of Gastroenterology and Hepatology, 2008, pp. 87-94, vol. 23.

Iliopoulos, D. et al., "Fragile Genes as Biomarkers: Epigenetic Control of WWOX and FHIT in Lung, Breast and Bladder Cancer," Oncogene, 2005, pp. 1625-1633, vol. 24.

Iliopoulos, D. et al., "Inhibition of Breast Cancer Growth In Vitro and In Vivo: Effect of Restoration of WWOX Expression," Clin. Cancer Research, Jan. 2007, pp. 268-274, vol. 13, No. 1.

Iorio, M. V. et al., "MicroRNA Gene Expression Deregulation in Human Breast Cancer," Cancer Research, Aug. 2005, pp. 7065-7070, vol. 65, No. 16.

Iorio, M. V. et al., "MicroRNA Signatures in Human Ovarian Cancer," Cancer Research, Sep. 2007, pp. 8699-8707, vol. 67, No. 18.

Ivanovska, I. et al., "MicroRNAs in the miR-106b Family Regulate p21/CDKN1A and Promote Cell Cycle Progression," Molecular and Cellular Biology, Apr. 2008, pp. 2167-2174, vol. 28, No. 7.

Jansen, A. P. et al., "Epidermal Expression of the Translation Inhibitor Programmed Cell Death 4 Suppresses Tumorigenesis," Cancer Research, Jul. 2005, pp. 6034-6041, vol. 65, No. 14.

Ji, J. et al., "MicroRNA Expression, Survival, and Response to Interferon in Liver Cancer," The New England Journal of Medicine, Oct. 2009, pp. 1437-1447, vol. 361, No. 15.

Ji, J. et al., "New Kids on the Block: Diagnostic and Prognostic MicroRNAs in Hepatocellular Carcinoma," Cancer Biology & Therapy, Aug. 2009, pp. 1-8, vol. 8, No. 16.

Ji, L. et al., "Induction of Apoptosis and Inhibition of Tumorigenicity and Tumor Growth by Adenovirus Vector-Mediated Fragile Histidine Triad (FHIT) Gene Overexpression," Cancer Research, Jul. 1999, pp. 3333-3339, vol. 59.

Jiang, J. et al., "Association of MicroRNA Expression in Hepatocellular Carcinomas with Hepatitis Infection, Cirrhosis, and Patient Survival," Clin Cancer Research, Jan. 2008, pp. 419-427, vol. 14, No. 2.

Jiang, J. et al., "Real-Time Expression Profiling of MicroRNA Precursors in Human Cancer Cell Lines," Nucleic Acids Research, 2005, pp. 5394-5403, vol. 33, No. 17.

John, B. et al., "Human MicroRNA Targets," PLOS Biology, Nov. 2004, pp. 1862-1879, vol. 2, Issue 11.

Johnson, S. M. et al., "RAS is Regulated by the let-7 MicroRNA Family," Cell, Mar. 2005, pp. 635-647, vol. 120.

Johnson, S. M. et al., "RAS is Regulated by the let-7 MicroRNA Family," Supplemental Data, Cell, Mar. 2005, pp. 635-647, vol. 120.

Kawasaki, H. et al., "MicroRNA-196 Inhibits HOXB8 Expression in Myeloid Differentiation of HL60 Cells," Nucleic Acids Symposium Series, 2004, pp. 211-212, No. 48.

Kim, H. et al., "Elevated mRNA Levels of DNA Methyltransferase-1 as an Independent Prognostic Factor in Primary Nonsmall Cell Lung Cancer," Cancer, Sep. 2006, pp. 1042-1049, vol. 107, No. 5.

Kotoula, V. et al., "In Situ Detection of MicroRNAs 146b, 221 and 222 in Human Carcinoma Tissues Reveals Tumor-Type Specific Expression Patterns," In: Proceedings of the 98th Annual Meeting of the American Association for Cancer Research, Apr. 14-18, 2007 Los Angeles, CA: AACR, 2007, 2 pages, Abstract No. 1780.

Koturbash, I. et al., "Role of Epigenetic Effectors in Maintenance of the Long-Term Persistent Bystander Effect in Spleen In Vivo," Carcinogenesis, 2007, pp. 1831-1838, vol. 28, No. 8.

Krek, A. et al., "Combinatorial MicroRNA Target Predictions," Nature Genetics, May 2005, pp. 495-500, vol. 37, No. 5.

Kulshreshtha, R. et al., "A MicroRNA Signature of Hypoxia," Molecular and Cellular Biology, Mar. 2007, pp. 1859-1867, vol. 27, No. 5.

Kuroki, et al., "Genetic Alterations of the Tumor Suppressor Gene WWOX in Esophageal Squamous Cell Carcinoma," Cancer Research, Apr. 2002, pp. 2258-2260, vol. 62.

Kutay, H. et al., "Down regulation of miR-122 in the Rodent and Human Hepatocellular Carcinomas," Journal of Cellular Biochemistry, 2006, pp. 671-678, vol. 99.

Lagos-Quintana, M. et al., "New MicroRNAs From Mouse to Human," RNA, 2003, pp. 175-179, vol. 9, No. 2.

Landi, M. T. et al., "Gene Expression Signature of Cigarette Smoking and Its Role in Lung Adenocarcinoma Development and Survival," PLOS One, Feb. 2008, pp. 1-8, vol. 3, Issue 2.

Lee, E. J. et al., "Expression Profiling Identifies MicroRNA Signature in Pancreatic Cancer," Int. J. Cancer, 2006, pp. 1046-1054, vol. 120.

Lewis, B. P. et al., "Prediction of Mammalian MicroRNA Targets," Cell, Dec. 2003, pp. 787-798, vol. 115.

Lin, R.-K. et al., "Alteration of DNA Methyltransferases Contributes to 5'CpG Methylation and Poor Prognosis in Lung Cancer," Lung Cancer, 2007, pp. 205-213, vol. 55.

Lipp, E., "MicroRNAs Inform Cancer Research: Alterations in the Expression of miRNA Genes Contribute to Pathogenesis on Broad Basis," Genetic Engineering & Biotechnology News, Dec. 2009, pp. 38-39, genengnews.com.

Liu, C.-G. et al., "An Oligonucleotide Microchip for Genome-Wide MicroRNA Profiling in Human and Mouse Tissues," PNAS, Jun. 2004, pp. 9740-9744, vol. 101, No. 26.

Lu, J. et al., "MicroRNA Expression Profiles Classify Human Cancers," Nature, Jun. 2005, pp. 834-838, vol. 435, Supplementary Information.

Lu, J. et al., "MicroRNA Expression Profiles Classify Human Cancers," Nature, Jun. 2005, pp. 834-838, vol. 435.

Ma, G. et al., "Expression of Programmed Cell Death 4 and Its Clinicopathological Significance in Human Pancreatic Cancer," Department of General Surgery, the First Affiliated Hospital, China Medical University, Oct. 2005, pp. 597-600.

Mack, G. S., "MicroRNA Gets Down to Business," Nature Biotechnology, Jun. 2007, pp. 631-638, vol. 25, No. 6.

Marchetti, A. et al., "EGFR Mutations in Non-Small-Cell Lung Cancer: Analysis of a Large Series of Cases and Development of a Rapid and Sensitive Method for Diagnostic Screening with Potential Implications on Pharmacologic Treatment," Journal of Clinical Oncology, Feb. 2005, pp. 857-865, vol. 23, No. 4.

Marcucci, et al., "MicroRNA Expression in Cytogenetically Normal Acute Myeloid Leukemia," NEJM, May 2008, pp. 1919-1928, vol. 358, No. 18.

Mattie, M. D. et al., "Optimized High-Throughput MicroRNA Expression Profiling Provides Novel Biomarker Assessment of Clinical Prostate and Breast Cancer Biopsies," Molecular Cancer, Jun. 2006, 14 pages, vol. 5, No. 24.

McManus, M. T., "MicroRNAs and Cancer," Seminars in Cancer Biology, 2003, pp. 253-258, vol. 13.

Megraw, M. et al., "miRGen: A Database for the Study of Animal MicroRNA Genomic Organization and Function," Nucleic Acids Research, 2007, pp. D149-D155, vol. 35.

Meng, F. et al., "Involvement of Human MicroRNA in Growth and Response to Chemotherapy in Human Cholangiocarcinoma Cell Lines," Gastroenterology, 2006, pp. 2113-2129, vol. 130.

Mi, S. et al., "MicroRNA Expression Signatures Accurately Discriminate Acute Lymphoblastic Leukemia from Acute Myeloid Leukemia," PNAS, Dec. 2007, pp. 19971-19976, vol. 104, No. 50.

Michael, M. Z. et al., "Reduced Accumulation of Specific MicroRNAs in Colorectal Neoplasia," Molecular Cancer Research, Oct. 2003, pp. 882-891, vol. 1.

Miller, M. K. et al., "Concurrent Chronic Lymphocytic Leukemia Cutis and Acute Myelogenous Leukemia Cutis in a Patient with Untreated CLL," The American Journal of Dermatopathology, 2001, pp. 334-340, vol. 23, No. 4.

Mitchell, P. S. et al., "Circulating MicroRNAs as Stable Blood-Based Markers for Cancer Detection," PNAS, Jul. 2008, pp. 10513-10518, vol. 105, No. 30.

Mitrovic, T. et al., "Cancer Gene Therapy," Arch. Oncology, 2005, pp. 23-26, vol. 13, No. 1.

Mountzios, G. et al., "Mechanisms of Disease: Signal Transduction in Lung Carcinogenesis—A Comparison of Smokers and Never-Smokers," Nature Clinical Practice Oncology, Oct. 2008, pp. 610-618, vol. 5, No. 10.

Murakami, Y. et al., "Comprehensive Analysis of MicroRNA Expression Patterns in Hepatocellular Carcinoma and Non-Tumorous Tissues," Oncogene, 2006 pp. 2537-2545, vol. 25., published online Dec. 5, 2005.

Nakanishi, H. et al., "ALL1 Fusion Proteins Induce Deregulation of EphA7 and ERK Phosphorylation in Human Acute Leukemias," PNAS, Sep. 2007, pp. 14442-14447, vol. 104, No. 36.

Negrini, M. et al., "MicroRNAs in Human Cancer: From Research to Therapy," Journal of Cell Science, Apr. 2007, pp. 1833-1840, vol. 120.

Notice of Allowance and Fees Due in U.S. Appl. No. 12/160,064, filed Jul. 3, 2008, mailing date Nov. 20, 2009.

Notice of Allowance and Fees Due in U.S. Appl. No. 12/298,221, filed Nov. 10, 2008, mailing date Nov. 30, 2009.

Office Action issued in U.S. Appl. No. 12/083,067, filed Jun. 20, 2008, mailing date Jul. 8, 2010.

Office Action issued in U.S. Appl. No. 12/160,034, filed Jul. 3, 2008, mailing date Jun. 7, 2010.

Office Action issued in U.S. Appl. No. 12/160,061, filed Jul. 3, 2008, mailing date Mar. 12, 2010.

Office Action issued in U.S. Appl. No. 12/160,061, filed Jul. 3, 2008, mailing date Apr. 24, 2009.

Office Action issued in U.S. Appl. No. 12/160,061, filed Jul. 3, 2008, mailing date Oct. 30, 2009.

Office Action issued in U.S. Appl. No. 12/160,064, filed Jul. 3, 2008, mailing date Aug. 10, 2009.

Office Action issued in U.S. Appl. No. 12/293,471, filed Oct. 9, 2008, mailing date Jun. 8, 2010.

Office Action issued in U.S. Appl. No. 12/373,358, filed Feb. 11, 2009, mailing date Aug. 20, 2010.

Office Action issued in U.S. Appl. No. 12/442,018, filed Mar. 27, 2009, mailing date Apr. 15, 2010.

Palamarchuk, A. et al., "Akt Phosphorylates Tcl1 Oncoprotein and Inhibits Its Repressor Activity," Cancer Research, Jun. 2005, pp. 4515-4519, vol. 65, No. 11.

Pawelczyk, T. et al., "Expression in *Escherichia Coli* and Simple Purification of Human Fhit Protein," Protein Expr. Purlf., Apr. 2000, pp. 320-326, vol. 18, No. 3.

PCT International Preliminary Report on Patentability, PCT/US/2007/023660 filed Nov. 1, 2007, dated May 5, 2009.

PCT International Preliminary Report on Patentability, PCT/US/2008/072081 filed Aug. 4, 2008, dated Feb. 9, 2010.

PCT International Preliminary Report on Patentability, PCT/US2006/029889 filed Jul. 31, 2006, dated Feb. 5, 2008.

PCT International Preliminary Report on Patentability, PCT/US2006/035100 filed Sep. 11, 2006, dated Mar. 18, 2008.

PCT International Preliminary Report on Patentability, PCT/US2006/038824 filed Oct. 4, 2006, dated Apr. 9, 2008.

PCT International Preliminary Report on Patentability, PCT/US2007/000024 filed Jan. 3, 2007, dated Jul. 8, 2008.
PCT International Preliminary Report on Patentability, PCT/US2007/000103 filed Jan. 3, 2007, dated Jul. 8, 2008.
PCT International Preliminary Report on Patentability, PCT/US2007/000159 filed Jan. 3, 2007, dated Jul. 8, 2008.
PCT International Preliminary Report on Patentability, PCT/US2007/006824 filed Mar. 19, 2007, dated Sep. 23, 2008.
PCT International Preliminary Report on Patentability, PCT/US2007/009910 filed Apr. 24, 2007, dated Oct. 28, 2008.
PCT International Preliminary Report on Patentability, PCT/US2007/015892 filed Jul. 12, 2007, dated Jan. 13, 2009.
PCT International Preliminary Report on Patentability, PCT/US2007/020215 filed Sep. 17, 2007, dated Mar. 24, 2009.
PCT International Preliminary Report on Patentability, PCT/US2008/001157 filed Jan. 29, 2008, dated Aug. 4, 2009.
PCT International Preliminary Report on Patentability, PCT/US2008/005503 filed Apr. 29, 2008, dated Nov. 3, 2009.
PCT International Preliminary Report on Patentability, PCT/US2008/007196 filed Jun. 9, 2008, dated Dec. 11, 2009.
PCT International Preliminary Report on Patentability, PCT/US2008/066870 filed Jun. 13. 2008, dated Dec. 17, 2009.
PCT International Preliminary Report on Patentability, PCT/US2008/071532 filed Jul. 30, 2008, dated Feb. 2, 2010.
PCT International Preliminary Report on Patentability, PCT/US2008/073964 filed Aug. 22, 2008, dated Feb. 24, 2010.
PCT International Preliminary Report on Patentability, PCT/US2008/075565 filed Sep. 8, 2008, dated Mar. 9, 2010.
PCT International Preliminary Report on Patentability, PCT/US2008/079482 filed Oct. 10, 2008, dated Apr. 13, 2010.
PCT International Preliminary Report on Patentability, PCT/US2008/081294 filed Oct. 27, 2008, dated Apr. 27, 2010.
PCT International Preliminary Report on Patentability, PCT/US2009/035458 filed Feb. 27, 2009, dated Aug. 31, 2010.
PCT International Preliminary Report on Patentability, PCT/US2009/035463 filed Feb. 27, 2009, dated Aug. 31, 2010.
PCT International Preliminary Report on Patentability, PCT/US2009/035470 filed Feb. 27, 2009, dated Aug. 31, 2010.
PCT International Preliminary Report on Patentability, PCT/US2009/035482 filed Feb. 27, 2009, dated Aug. 31, 2010.
PCT International Search Report and the Written Opinion, PCT/US2007/006824 filed Mar. 19, 2007, dated Mar. 3, 2008.
PCT International Search Report and the Written Opinion, PCT/US2006/29889 filed Jul. 31, 2006, dated Jul. 10, 2007.
PCT International Search Report and the Written Opinion, PCT/US2006/35100 filed Sep. 11, 2006, dated Sep. 5, 2007.
PCT International Search Report and the Written Opinion, PCT/US2006/38824 filed Oct. 4, 2006, dated Aug. 9, 2007.
PCT International Search Report and the Written Opinion, PCT/US2007/00024 filed Jan. 3, 2007, dated Nov. 5, 2007.
PCT International Search Report and the Written Opinion, PCT/US2007/00103 filed Jan. 3, 2007, dated Dec. 3, 2007.
PCT International Search Report and the Written Opinion, PCT/US2007/00159 filed Jan. 3, 2007, dated Apr. 11, 2008.
PCT International Search Report and the Written Opinion, PCT/US2007/006824 filed Mar. 19, 2007, dated May 14, 2008.
PCT International Search Report and the Written Opinion, PCT/US2007/09910 filed Apr. 24, 2007, dated Feb. 13, 2008.
PCT International Search Report and the Written Opinion, PCT/US2007/15892 filed Jul. 12, 2007, dated Sep. 30, 2008.
PCT International Search Report and the Written Opinion, PCT/US2007/20215 filed Sep. 17, 2007, dated Jul. 25, 2008.
PCT International Search Report and the Written Opinion, PCT/US2007/23660 filed Nov. 1, 2007, dated Sep. 16, 2008.
PCT International Search Report and the Written Opinion, PCT/US2008/01157 filed Jan. 29, 2008, dated Aug. 7, 2008.
PCT International Search Report and the Written Opinion, PCT/US2008/05503 filed Apr. 29, 2008, dated Sep. 25, 2008.
PCT International Search Report and the Written Opinion, PCT/US2008/07196 filed Jun. 9, 2008, dated Nov. 19, 2008.
PCT International Search Report and the Written Opinion, PCT/US2008/66870 filed Jun. 13, 2008, dated Nov. 10, 2008.
PCT International Search Report and the Written Opinion, PCT/US2008/71532 filed Jul. 30, 2008, dated Apr. 17, 2009.
PCT International Search Report and the Written Opinion, PCT/US2008/72081 filed Aug. 4, 2008, dated Jan. 14, 2009.
PCT International Search Report and the Written Opinion, PCT/US2008/73964 filed Aug. 22, 2008, dated Dec. 24, 2008.
PCT International Search Report and the Written Opinion, PCT/US2008/75565 filed Sep. 8, 2008, dated Dec. 9, 2008.
PCT International Search Report and the Written Opinion, PCT/US2008/79482 filed Oct. 10, 2008, dated Dec. 22, 2008.
PCT International Search Report and the Written Opinion, PCT/US2008/81294 filed Oct. 27, 2008, dated Mar. 26, 2009.
PCT International Search Report and the Written Opinion, PCT/US2008/84821 filed Nov. 26, 2008, dated Feb. 17, 2009.
PCT International Search Report and the Written Opinion, PCT/US2009/35458 filed Feb. 27, 2009, dated Jul. 28, 2009.
PCT International Search Report and the Written Opinion, PCT/US2009/35463 filed Feb. 27, 2009, dated Aug. 13, 2009.
PCT International Search Report and the Written Opinion, PCT/US2009/35470 filed Feb. 27, 2009, dated Jun. 16, 2009.
PCT International Search Report and the Written Opinion, PCT/US2009/35482 filed Feb. 27, 2009, dated Jul. 17, 2009.
PCT International Search Report and the Written Opinion, PCT/US2009/38214 filed Mar. 25, 2009, dated Aug. 14, 2009.
PCT International Search Report and the Written Opinion, PCT/US2009/46999 filed Jun. 11, 2009, dated Nov. 23, 2009.
PCT International Search Report and the Written Opinion, PCT/US2009/53586 filed Aug. 12, 2009, dated Oct. 28, 2009.
PCT International Search Report and the Written Opinion, PCT/US2009/65072 filed Nov. 19, 2009, dated Mar. 3, 2010.
PCT International Search Report and the Written Opinion, PCT/US2010/025173 filed Feb. 24, 2010, dated Jul. 6, 2010.
Pedersen, I. M. et al., "Interferon Modulation of Cellular MicroRNAs as an Antiviral Mechanism," Nature, Oct. 2007, pp. 919-922, vol. 449.
Pekarsky, Y. et al., "Animal Models for Chronic Lymphocytic Leumekia," Journal of Cellular Biochemistry, 2007, pp. 1109-1118, vol. 100.
Pekarsky, Y. et al., "Tcl1 Enhances Akt Kinase Activity and Mediates Its Nuclear Translocation," PNAS, Mar. 2000, pp. 3028-3033, vol. 97, No. 7.
Pekarsky, Y. et al., "Toll Expression in Chronic Lymphocytic Leukemia is Regulated by miR-29 and miR-181," Cancer Research, Dec. 2006, pp. 11590-11593, vol. 66, No. 24.
Pekarsky, Y. et al., "Tcl1 Functions as a Transcriptional Regulator and is Directly Involved in the Pathogenesis of CLL," PNAS, Dec. 2008, pp. 19643-19648, vol. 105, No. 50.
Petrocca, F. et al., "E2F1-Regulated MicroRNAs Impair TGF6-Dependent Cell-Cycle Arrest and Apoptosis in Gastric Cancer," Cancer Cell, Mar. 2008, pp. 272-286, vol. 13.
Prueitt, R. L. et al., "Expression of MicroRNAs and Protein-Coding Genes Associated with Perineural Invasion in Prostate Cancer," The Prostate, 2008, pp. 1152-1164, vol. 68.
Qin, H. R. et al., "A Role for the WWOX Gene in Prostate Cancer," Cancer Research, Jul. 2006, pp. 6477-6481, vol. 66, No. 13.
Ramkissoon, S. H, et al., "Hematopoietic-Specific MicroRNA Expression in Human Cells," Leukemia Research, 2006, pp. 643-647, vol. 30.
Roldo, C. et al., "MicroRNA Expression Abnormalities in Pancreatic Endocrine and Acinar Tumors Are Associated With Distinctive Pathologic Feature and Clinical Behavior," Journal of Clinical Oncology, Oct. 2006, pp. 4677-4684, vol. 24, No. 29.
Rozovskaia, T. et al., "Expression Profiles of Acute Lymphoblastic and Myeloblastic Leukemias with ALL-1 Rearrangements," PNAS, Jun. 2003, pp. 7853-7858, vol. 100, No. 13.
Schetter, A. J. et al., "MicroRNA Expression Profiles Associated With Prognosis and Therapeutic Outcome in Colon Adenocarcinoma," JAMA, Jan. 2008, pp. 425-436, vol. 299, No. 4.
Schmittgen, T. D. et al., "A High-Throughput Method to Monitor the Expression of MicroRNA Precursors," Nucleic Acids Research, Feb. 2004, vol. 32, No. 4.

Seike, M. et al., "MiR-21 is an EGFR-Regulated Anti-Apoptotic Factor in Lung Cancer in Never-Smokers," PNAS, Jul. 2009, pp. 12085-12090. vol. 106, No. 29.

Seike, M. et al., "MiR-21 is an EGFR-Regulated Anti-Apoptotic Factor in Lung Cancer in Never-Smokers," Supporting Information, Pnas, Jul. 2009, pp. 12085-12090. vol. 106, No. 29.

Seike, M., "MicroRNA Expression Profiles in Lung Cancer Cooperated with Drug Sensitivity to EGFR Tyrosine Kinase Inhibitor," J. Nippon Med. School, 2009, pp. 275-276, vol. 76, No. 5.

Seth, P., "Vector-Mediated Cancer Gene Therapy," Cancer Biology & Therapy, May 2005, pp. 512-517, vol. 4, Issue 5.

Sevinsky, J. R. et al., "Extracellular Signal-Regulated Kinase Induces the Megakaryocyte GPIIb/CD41 Gene Through MafB/Kreisler," Molecular and Cellular Biology, May 2004, pp. 4534-4545, vol. 24, No. 10.

Sharma, S. et al., "Development of Inhalational Agents for Oncologic Use," Journal of Clinical Oncology, Mar. 2001, Abstract, vol. 19, Issue 6.

Shen, H, et al., "A Novel Polymorphism in Human Cytosine DNA-Methyltransferase-3B Promoter is Associated with an Increased Risk of Lung Cancer," Cancer Research, Sep. 2002, pp. 4992-4995, vol. 62.

Takamizawa, J. et al., "Reduced Expression of the let-7 MicroRNAs in Human Lung Cancers in Association with Shortened Postoperative Survival," Cancer Research, Jun. 2004, pp. 3753-3756, vol. 64.

Tang, X. et al., "A Simple Array Platform for MicroRNA Analysis and Its Application in Mouse Tissues," RNA, Aug. 2007, pp. 1-20, vol. 13.

Thomson, J. M. et al., "A Custom Microarray Platform for Analysis of MicroRNA Gene Expression," Nature Methods, Oct. 2004, pp. 1-7, vol. 1, No. 1.

Thorgeirsson, S. S. et al., "Functional Genomics of Hepatocellular Carcinoma," Hepatology, Feb. 2006, pp. S145-S150, vol. 43, No. 2, Suppl. 1.

Tockman, M. S. et al., "Considerations in Bringing a Cancer Biomarker to Clinical Application," Cancer Research, May 1992, pp. 2711s-2718s, vol. 52.

Trapasso, F. et al., "FHIT Interaction with Ferredoxin Reductase Triggers Generation of Reactive Oxygen Species and Apoptosis of Cancer Cells," Journal of Biological Chemistry, May 2008, pp. 13736-13744, vol. 283, No. 20.

Tricoli, J. V. et al., "MicroRNA: Potential for Cancer Detection, Diagnosis, and Prognosis," Cancer Research, May 2007, pp. 4553-4555, vol. 67, No. 10.

Ueda, T. et al., "Relation Between MicroRNA Expression and Progression and Prognosis of Gastric Cancer: A MicroRNA Expression Analysis," Published Online; www.thelancet.com/oncology, Dec. 2009, DOI:10.1016/S1470-2045(09)70343-2.

Valeri, N. et al., "Epigenetics, miRNAs, and Human Cancer: A New Chapter in Human Gene Regulation," Mamm Genome, Aug. 2009, pp. 573-580, vol. 20.

Varnholt, H. et al., "MicroRNA Gene Expression Profile of Hepatitis C Virus-Associated Hepatocellular Carcinoma," Hepatology, Apr. 2008, pp. 1223-1232, Vo. 47, No. 4.

Virgilio, L. et al., "Identification of the TCL1 Gene Involved in T-Call Malignancies," Proc. Natl. Acad. Sci., Dec. 1994, pp. 12530-12534, vol. 91.

Visone, R. et al., "MiRNAs and Cancer," The American Journal of Pathology, Apr. 2009, pp. 1131-1138, vol. 174, No. 4.

Volinia, et al., "Reprogramming of MirRNA Networks in Cancer and Leukemia," Genome Research, 2010, pp. 589-599, vol. 20.

Volinia, S. et al., "A MicroRNA Expression Signature of Human Solid Tumors Defines Cancer Gene Targets," PNAS, Feb. 2006, pp. 2257-2261, vol. 103, No. 7.

Wang, E. et al., "Ontogeny and Oncogenesis Balance the Transcriptional Profile of Renal Cell Cancer," Cancer Research, Oct. 2004, pp. 7279-7287, vol. 64.

Wang, X. et al., "Association Between CpG Island Methylation of the WWOX Gene and Its Expression in Breast Cancers," Tumor Biology, Feb. 2009, pp. 8-14, vol. 30.

Weidhaas, J., "Using MicroRNAs to Understand Cancer Biology," Published Online Dec. 21, 2009, DOI: 10.1016/S1470-2045(09)70386-9.

Yamashita, T. et al., "Activation of Hepatic Stem Cell Marker EpCAM by Wnt-β-Catenin Signaling in Hepatocellular Carcinoma," Cancer Research, Nov. 2007, pp. 10831-10839, vol. 67, No. 22.

Yamashita, T. et al., "EpCAM and α-Fetoprotein Expression Defines Novel Prognostic Subtypes of Hepatocellular Carcinoma," Cancer Research, Mar. 2008, pp. 1451-1461, vol. 68, No. 5.

Yanaihara, N. et al., "Unique MicroRNA Molecular Profiles in Lung Cancer Diagnosis and Prognosis," Cancer Cell, Mar. 2006, pp. 189-198, vol. 9.

Yang, J. et al., "Analysis of Sequence Variations in 59 MicroRNAs in Hepatocellular Carcinomas," Mutation Research, Aug. 2008, pp. 205-209, vol. 638.

Yendamuri, S. et al., "WW Domain Containing Oxidoreductase Gene Expression is Altered in Non-Small Cell Lung Cancer," Cancer Research, Feb. 2003, pp. 878-881, vol. 63.

Yoon, S. et al., "Prediction of Regulatory Modules Comprising MicroRNAs and Target Genes," Bioinformatics Genes and Genomes, 2005. pp. ii93-ii100, vol. 21, Suppl. 2.

Yu, L.-G. et al., "Protein Phosphatase 2A, a Negative Regulator of the ERK Signaling Pathway, Is Activated by Tyrosine Phosphorylation of Putative HLA Class II-Associated Protein I (PHAPI)/pp32 in Response to the Antiproliferative Lectin, Jacalin," The Journal of Biological Chemisty, Jul. 2004, pp. 41377-41383, vol. 279, No. 40.

Zeng, Y. et al., "Recognition and Cleavage of Primary MicroRNA Precursors by the Nuclear Processing Enzyme Drosha," The EMBO Journal, 2005, pp. 138-148, vol. 24.

Zhang, L. et al., "Genomic and Epigenetic Alterations Deregulate MicroRNA Expression in Human Epithelial Ovarian Cancer," PNAS, May 2008, pp. 7004-7009, vol. 105, No. 19.

Zhang, L. et al., "MicroRNAs Exhibit High Frequency Genomic Alterations in Human Cancer," PNAS, Jun. 2006, pp. 9136-9141, vol. 103, No. 24.

Zhang, L. et al., Supporting Information, PNAS 2008, pp. 1-11.

Zhang, Z. et al., "Three Biomarkers Identified from Serum Proteomic Analysis for the Detection of Early Stage Ovarian Cancer," Cancer Research, Aug. 2004, pp. 5882-5890, vol. 64.

Zhu, S. et al., "MicroRNA-21 Targets the Tumor Suppressor Gene Tropomyosin 1 (TPM 1)," Journal of Biological Chemistry, May 2007, pp. 14328-14336, vol. 282, No. 19.

SEQUENCE LISTING

<160> NUMBER OF SEQ ID NOS: 498

<210> SEQ ID NO 1
<211> LENGTH: 90
<212> TYPE: RNA
<213> ORGANISM: Homo sapiens

<400> SEQUENCE: 1
cacuguggga ugagguagua gguuguauag uuuuagggguc acacccacca cugggagaua    60
acuauacaau cuacugucuu uccuaacgug                                      90

<210> SEQ ID NO 2
<211> LENGTH: 72
<212> TYPE: RNA
<213> ORGANISM: Homo sapiens

<400> SEQUENCE: 2
agguugaggu aguagguugu auaguuuaga auuacaucaa gggagauaac uguacagccu    60
ccuagcuuuc cu                                                         72

<210> SEQ ID NO 3
<211> LENGTH: 74
<212> TYPE: RNA
<213> ORGANISM: Homo sapiens

<400> SEQUENCE: 3
gggugaggua guagguugua uaguuugggg cucugcccug cuaugggaua acuauacaau    60
cuacugucuu uccu                                                       74

<210> SEQ ID NO 4
<211> LENGTH: 107
<212> TYPE: RNA
<213> ORGANISM: Homo sapiens

<400> SEQUENCE: 4
gugacugcau gcucccaggu ugagguagua gguuguauag uuuagaauua cacaagggag    60
auaacuguac agccuccuag cuuuccuugg ucuugcacu aaacaac                   107

<210> SEQ ID NO 5
<211> LENGTH: 85
<212> TYPE: RNA
<213> ORGANISM: Homo sapiens

<400> SEQUENCE: 5 ggcggggguga gguaguaggu uguguggguuu cagggcagug auguugcccc ucggaagaua    60
acuauacaac cuacugccuu cccug                                           85

<210> SEQ ID NO 6
<211> LENGTH: 84
<212> TYPE: RNA
<213> ORGANISM: Homo sapiens

<400> SEQUENCE: 6
gcauccgggu ugagguagua gguuguaugg uuuagaguua cacccgggga guuaacugua    60
caaccuucua gcuuuccuug gagc                                            84

<210> SEQ ID NO 7
<211> LENGTH: 87
<212> TYPE: RNA

<213> ORGANISM: Homo sapiens

<400> SEQUENCE: 7

| ccuaggaaga gguaguaggu ugcauaguuu uagggcaggg auuuugccca caaggaggua | 60 |
| acuauacgac cugcugccuu ucuuagg | 87 |

<210> SEQ ID NO 8
<211> LENGTH: 85
<212> TYPE: RNA
<213> ORGANISM: Homo sapiens

<400> SEQUENCE: 8

| cuaggaagag guaguaguuu gcauaguuuu agggcaaaga uuuugcccac aaguaguuag | 60 |
| cuauacgacc ugcagccuuu uguag | 85 |

<210> SEQ ID NO 9
<211> LENGTH: 85
<212> TYPE: RNA
<213> ORGANISM: Homo sapiens

<400> SEQUENCE: 9

| cuggcugagg uaguaguuug ugcuguuggu cgguuguga cauugcccgc uguggagaua | 60 |
| acugcgcaag cuacugccuu gcuag | 85 |

<210> SEQ ID NO 10
<211> LENGTH: 79
<212> TYPE: RNA
<213> ORGANISM: Homo sapiens

<400> SEQUENCE: 10

| cccgggcuga gguaggaggu uguauaguug aggaggacac ccaaggagau cacuauacgg | 60 |
| ccuccuagcu uuccccagg | 79 |

<210> SEQ ID NO 11
<211> LENGTH: 87
<212> TYPE: RNA
<213> ORGANISM: Homo sapiens

<400> SEQUENCE: 11

| ucagagugag guaguagauu guauaguugu gggguaguga uuuuacccug uucaggagau | 60 |
| aacuauacaa ucuauugccu cccuga | 87 |

<210> SEQ ID NO 12
<211> LENGTH: 89
<212> TYPE: RNA
<213> ORGANISM: Homo sapiens

<400> SEQUENCE: 12

| cuguggaug agguaguaga uuguauaguu guggguagu gauuuuaccc uguucaggag | 60 |
| auaacuauac aaucuauugc cucccuga | 89 |

<210> SEQ ID NO 13
<211> LENGTH: 85
<212> TYPE: RNA
<213> ORGANISM: Homo sapiens

<400> SEQUENCE: 13

| cuguggaug agguaguaga uuguauaguu uuagggucau accccaucuu ggagauaacu | 60 |
| auacagucua cugcuuucc cacgg | 85 |

```
<210> SEQ ID NO 14
<211> LENGTH: 108
<212> TYPE: RNA
<213> ORGANISM: Homo sapiens

<400> SEQUENCE: 14
uugccugauu ccaggcugag guaguaguuu guacaguuug agggucuaug auaccacccg    60
guacaggaga uaacuguaca ggccacugcc uugccaggaa cagcgcgc                108

<210> SEQ ID NO 15
<211> LENGTH: 85
<212> TYPE: RNA
<213> ORGANISM: Homo sapiens

<400> SEQUENCE: 15
cuggcugagg uaguaguuug ugcuguuggu cggguuguga cauugcccgc uguggagaua    60
acugcgcaag cuacugccuu gcuag                                         85

<210> SEQ ID NO 16
<211> LENGTH: 85
<212> TYPE: RNA
<213> ORGANISM: Homo sapiens

<400> SEQUENCE: 16
accuacucag aguacauacu ucuuuaugua cccauaugaa cauacaaugc uauggaaugu    60
aaagaaguau guauuuuugg uaggc                                         85

<210> SEQ ID NO 17
<211> LENGTH: 108
<212> TYPE: RNA
<213> ORGANISM: Homo sapiens

<400> SEQUENCE: 17
cagcuaacaa cuuaguaaua ccuacucaga guacauacuu cuuuauguac ccauaugaac    60
auacaaugcu auggaaugua aagaaguaug uauuuuuggu aggcaaua                108

<210> SEQ ID NO 18
<211> LENGTH: 85
<212> TYPE: RNA
<213> ORGANISM: Homo sapiens

<400> SEQUENCE: 18
gccugcuugg gaaacauacu ucuuuauaug cccauaugga ccugcuaagc uauggaaugu    60
aaagaaguau guaucucagg ccggg                                         85

<210> SEQ ID NO 19
<211> LENGTH: 71
<212> TYPE: RNA
<213> ORGANISM: Homo sapiens

<400> SEQUENCE: 19
ugggaaacau acuucuuuau augcccauau ggaccugcua agcuauggaa uguaaagaag    60
uauguaucuc a                                                        71

<210> SEQ ID NO 20
<211> LENGTH: 85
<212> TYPE: RNA
<213> ORGANISM: Homo sapiens

<400> SEQUENCE: 20
```

| | |
|---|---|
| accuacucag aguacauacu ucuuuaugua cccauaugaa cauacaaugc uauggaaugu | 60 |
| aaagaaguau guauuuuugg uaggc | 85 |

<210> SEQ ID NO 21
<211> LENGTH: 108
<212> TYPE: RNA
<213> ORGANISM: Homo sapiens

<400> SEQUENCE: 21

| | |
|---|---|
| uggauguugg ccuaguucug ugggaagac uagugauuuu guuguuuuua gauaacuaaa | 60 |
| ucgacaacaa aucacagucu gccauauggc acaggccaug ccucuaca | 108 |

<210> SEQ ID NO 22
<211> LENGTH: 110
<212> TYPE: RNA
<213> ORGANISM: Homo sapiens

<400> SEQUENCE: 22

| | |
|---|---|
| uuggauguug gccuaguucu gugugaaga cuagugauuu uguuguuuuu agauaacuaa | 60 |
| aucgacaaca aaucacaguc ugccauaugg cacaggccau gccucuacag | 110 |

<210> SEQ ID NO 23
<211> LENGTH: 110
<212> TYPE: RNA
<213> ORGANISM: Homo sapiens

<400> SEQUENCE: 23

| | |
|---|---|
| cuggauacag aguggaccgg cuggccccau cuggaagacu agugauuuug uuguugucuu | 60 |
| acugcgcuca caacaaauc ccagucuacc uaauggugcc agccaucgca | 110 |

<210> SEQ ID NO 24
<211> LENGTH: 110
<212> TYPE: RNA
<213> ORGANISM: Homo sapiens

<400> SEQUENCE: 24

| | |
|---|---|
| agauuagagu ggcugugguc uagugcugug uggaagacua gugauuuugu uguucugaug | 60 |
| uacuacgaca caagucaca gccggccuca uagcgcagac ucccuucgac | 110 |

<210> SEQ ID NO 25
<211> LENGTH: 89
<212> TYPE: RNA
<213> ORGANISM: Homo sapiens

<400> SEQUENCE: 25

| | |
|---|---|
| cggggguuggu uguuaucuuu gguuaucuag cuguaugagu ggugugagu cuucauaaag | 60 |
| cuagauaacc gaaaguaaaa auaacccca | 89 |

<210> SEQ ID NO 26
<211> LENGTH: 87
<212> TYPE: RNA
<213> ORGANISM: Homo sapiens

<400> SEQUENCE: 26

| | |
|---|---|
| ggaagcgagu uguuaucuuu gguuaucuag cuguaugagu guauuggucu ucauaaagcu | 60 |
| agauaaccga aaguaaaaac uccuuca | 87 |

<210> SEQ ID NO 27
<211> LENGTH: 90
<212> TYPE: RNA

-continued

<213> ORGANISM: Homo sapiens

<400> SEQUENCE: 27

```
ggaggcccgu uucucucuuu gguuaucuag cuguaugagu gccacagagc cgucauaaag    60
cuagauaacc gaaaguagaa augauucuca                                     90
```

<210> SEQ ID NO 28
<211> LENGTH: 110
<212> TYPE: RNA
<213> ORGANISM: Homo sapiens

<400> SEQUENCE: 28

```
gaucugucug ucuucuguau auacccugua gauccgaauu uguguaagga auuuguggu     60
cacaaauucg uaucuagggg aauauguagu ugacauaaac acuccgcucu              110
```

<210> SEQ ID NO 29
<211> LENGTH: 110
<212> TYPE: RNA
<213> ORGANISM: Homo sapiens

<400> SEQUENCE: 29

```
ccagagguug uaacguuguc uauauauacc cguagaaacc gaauugugu gguauccgua     60
uagucacaga uucgauucua ggggaauaua uggucgaugc aaaaacuuca              110
```

<210> SEQ ID NO 30
<211> LENGTH: 108
<212> TYPE: RNA
<213> ORGANISM: Homo sapiens

<400> SEQUENCE: 30

```
gcgcgaaugu guguuuaaaa aaauaaaac cuuggaguaa aguagcagca cauaaugguu     60
uguggauuuu gaaaaggugc aggccauauu gugcugccuc aaaaauac                108
```

<210> SEQ ID NO 31
<211> LENGTH: 83
<212> TYPE: RNA
<213> ORGANISM: Homo sapiens

<400> SEQUENCE: 31

```
ccuuggagua aaguagcagc acauaagggu uguggauuu ugaaaaggug caggccauau      60
ugugcugccu caaaaauaca agg                                            83
```

<210> SEQ ID NO 32
<211> LENGTH: 64
<212> TYPE: RNA
<213> ORGANISM: Homo sapiens

<400> SEQUENCE: 32

```
cuguagcagc acaucauggu uuacaugcua cagucaagau gcgaaucauu auuugcugcu    60
cuag                                                                 64
```

<210> SEQ ID NO 33
<211> LENGTH: 98
<212> TYPE: RNA
<213> ORGANISM: Homo sapiens

<400> SEQUENCE: 33

```
uugaggccuu aaaguacugu agcagcacau cauggguuuac augcuacagu caagaugcga    60
aucauuauuu gcugcucuag aaauuuaagg aaauucau                             98
```

<210> SEQ ID NO 34
<211> LENGTH: 89
<212> TYPE: RNA
<213> ORGANISM: Homo sapiens

<400> SEQUENCE: 34
gucagcagug ccuuagcagc acguaaauau uggcguuaag auucuaaaau uaucuccagu    60
auuaacugug cugcugaagu aagguugac                                     89

<210> SEQ ID NO 35
<211> LENGTH: 81
<212> TYPE: RNA
<213> ORGANISM: Homo sapiens

<400> SEQUENCE: 35
guuccacucu agcagcacgu aaauauuggc guagugaaau auauuaaa caccaauauu      60 acugugcugc uuuaguguga c                                             81

<210> SEQ ID NO 36
<211> LENGTH: 81
<212> TYPE: RNA
<213> ORGANISM: Homo sapiens

<400> SEQUENCE: 36
gcagugccuu agcagcacgu aaauauuggc guuaagauuc uaaaauuauc uccaguauua    60
acugugcugc ugaaguaagg u                                             81

<210> SEQ ID NO 37
<211> LENGTH: 84
<212> TYPE: RNA
<213> ORGANISM: Homo sapiens

<400> SEQUENCE: 37
gucagaauaa ugucaaagug cuuacagugc agguagugau augugcaucu acugcaguga   60
aggcacuugu agcauuaugg ugac                                          84

<210> SEQ ID NO 38
<211> LENGTH: 71
<212> TYPE: RNA
<213> ORGANISM: Homo sapiens

<400> SEQUENCE: 38
uguucuaagg ugcaucuagu gcagauagug aaguagauua gcaucuacug cccuaagugc   60
uccuucuggc a                                                        71

<210> SEQ ID NO 39
<211> LENGTH: 81
<212> TYPE: RNA
<213> ORGANISM: Homo sapiens

<400> SEQUENCE: 39
uuuuuguucu aaggugcauc uagugcagau agugaaguag auuagcaucu acugcccuaa   60
gugcuccuuc uggcauaaga a                                             81

<210> SEQ ID NO 40
<211> LENGTH: 82
<212> TYPE: RNA
<213> ORGANISM: Homo sapiens

<400> SEQUENCE: 40

```
gcaguccucu guuaguuug cauaguugca cuacaagaag aauguaguug ugcaaaucua      60
ugcaaaacug augguggccu gc                                             82
```

<210> SEQ ID NO 41
<211> LENGTH: 80
<212> TYPE: RNA
<213> ORGANISM: Homo sapiens

<400> SEQUENCE: 41

```
caguccucug uuaguuuugc auaguugcac uacaagaaga auguaguugu gcaaaucuau      60
gcaaaacuga ugguggccug                                                 80
```

<210> SEQ ID NO 42
<211> LENGTH: 87
<212> TYPE: RNA
<213> ORGANISM: Homo sapiens

<400> SEQUENCE: 42

```
cacguucua ugguuaguuu ugcagguuug cauccagcug ugugauauuc ugcugugcaa       60
auccaugcaa aacugacugu gguagug                                         87
```

<210> SEQ ID NO 43
<211> LENGTH: 96
<212> TYPE: RNA
<213> ORGANISM: Homo sapiens

<400> SEQUENCE: 43

```
acauugcuac uuacaauuag uuuugcaggu uugcauuuca gcguauauau guauaugugg      60
cugugcaaau ccaugcaaaa cugauuguga uaaugu                               96
```

<210> SEQ ID NO 44
<211> LENGTH: 80
<212> TYPE: RNA
<213> ORGANISM: Homo sapiens

<400> SEQUENCE: 44

```
uucuauggu aguuuugcag guuugcaucc agcuguguga uauucugcug ugcaaaucca       60
ugcaaaacug acuggguag                                                  80
```

<210> SEQ ID NO 45
<211> LENGTH: 81
<212> TYPE: RNA
<213> ORGANISM: Homo sapiens

<400> SEQUENCE: 45

```
uuacaauuag uuuugcaggu uugcauuuca gcguauauau guauaugugg cugugcaaau      60
ccaugcaaaa cugauuguga u                                               81
```

<210> SEQ ID NO 46
<211> LENGTH: 71
<212> TYPE: RNA
<213> ORGANISM: Homo sapiens

<400> SEQUENCE: 46

```
guagcacuaa agugcuuaua gugcagguag uguuuaguua ucuacugcau uaugagcacu      60
uaaaguacug c                                                          71
```

<210> SEQ ID NO 47
<211> LENGTH: 72
<212> TYPE: RNA

```
<213> ORGANISM: Homo sapiens

<400> SEQUENCE: 47
ugucggguag cuuaucagac ugauguugac uguugaaucu cauggcaaca ccagucgaug    60
ggcugucuga ca                                                       72

<210> SEQ ID NO 48
<211> LENGTH: 81
<212> TYPE: RNA
<213> ORGANISM: Homo sapiens

<400> SEQUENCE: 48
accuugucgg guagcuuauc agacugaugu ugacuguuga aucucauggc aacaccaguc    60
gaugggcugu cugacauuuu g                                             81

<210> SEQ ID NO 49
<211> LENGTH: 85
<212> TYPE: RNA
<213> ORGANISM: Homo sapiens

<400> SEQUENCE: 49
ggcugagccg caguaguucu ucaguggcaa gcuuuauguc cugacccagc uaaagcugcc    60
aguugaagaa cuguugcccu cugcc                                         85

<210> SEQ ID NO 50
<211> LENGTH: 73
<212> TYPE: RNA
<213> ORGANISM: Homo sapiens

<400> SEQUENCE: 50
ggccggcugg gguuccuggg gaugggauuu gcuuccuguc acaaaucaca uugccaggga    60
uuuccaaccg acc                                                      73

<210> SEQ ID NO 51
<211> LENGTH: 97
<212> TYPE: RNA
<213> ORGANISM: Homo sapiens

<400> SEQUENCE: 51
cucaggugcu cuggcugcuu ggguuccugg caugcugauu ugugacuuaa gauuaaaauc    60
acauugccag ggauuaccac gcaaccacga ccuuggc                            97

<210> SEQ ID NO 52
<211> LENGTH: 81
<212> TYPE: RNA
<213> ORGANISM: Homo sapiens

<400> SEQUENCE: 52
ccacggccgg cuggguuccu ggggauggga auuugcuucc ugucacaaau cacauugcca    60
gggauuucca accgacccug a                                             81

<210> SEQ ID NO 53
<211> LENGTH: 68
<212> TYPE: RNA
<213> ORGANISM: Homo sapiens

<400> SEQUENCE: 53
cuccggugcc uacugagcug auaucaguuc ucauuuuaca cacuggcuca guucagcagg    60
aacaggag                                                            68
```

```
<210> SEQ ID NO 54
<211> LENGTH: 73
<212> TYPE: RNA
<213> ORGANISM: Homo sapiens

<400> SEQUENCE: 54
cucugccucc cgugccuacu gagcugaaac acaguugguu uguguacacu ggcucaguuc      60
agcaggaaca ggg                                                       73

<210> SEQ ID NO 55
<211> LENGTH: 81
<212> TYPE: RNA
<213> ORGANISM: Homo sapiens

<400> SEQUENCE: 55
cccugggcuc ugccucccgu gccuacugag cugaaacaca guugguuugu guacacuggc      60
ucaguucagc aggaacaggg g                                              81

<210> SEQ ID NO 56
<211> LENGTH: 71
<212> TYPE: RNA
<213> ORGANISM: Homo sapiens

<400> SEQUENCE: 56
cccuccggug ccuacugagc ugauaucagu ucucauuuua cacacuggcu caguucagca      60
ggaacagcau c                                                         71

<210> SEQ ID NO 57
<211> LENGTH: 84
<212> TYPE: RNA
<213> ORGANISM: Homo sapiens

<400> SEQUENCE: 57
ggccaguguu gagaggcgga gacuugggca auugcuggac gcugcccugg gcauugcacu      60
ugucucgguc ugacagugcc ggcc                                           84

<210> SEQ ID NO 58
<211> LENGTH: 86
<212> TYPE: RNA
<213> ORGANISM: Homo sapiens

<400> SEQUENCE: 58
aggccguggc cucguucaag uauccagga uaggcugugc agguccccaau ggccuaucuu     60 gguuacuugc acgggacgc gggccu                                          86

<210> SEQ ID NO 59
<211> LENGTH: 77
<212> TYPE: RNA
<213> ORGANISM: Homo sapiens

<400> SEQUENCE: 59
guggccucgu ucaaguaauc caggauaggc ugugcagguc ccaaugggcc uauucuuggu     60
uacuugcacg gggacgc                                                   77

<210> SEQ ID NO 60
<211> LENGTH: 84
<212> TYPE: RNA
<213> ORGANISM: Homo sapiens

<400> SEQUENCE: 60
```

```
ggcuguggcu ggauucaagu aauccaggau aggcuguuuc caucugugag gccuauucuu    60
gauuacuugu uucuggaggc agcu                                          84

<210> SEQ ID NO 61
<211> LENGTH: 77
<212> TYPE: RNA
<213> ORGANISM: Homo sapiens

<400> SEQUENCE: 61
ccgggaccca guucaaguaa uucaggauag guugugugcu guccagccug uucuccauua    60
cuuggcucgg ggaccgg                                                  77

<210> SEQ ID NO 62
<211> LENGTH: 78
<212> TYPE: RNA
<213> ORGANISM: Homo sapiens

<400> SEQUENCE: 62
cugaggagca gggcuuagcu gcuugugagc aggguccaca ccaagucgug uucacagugg    60
cuaaguuccg cccccccag                                                78

<210> SEQ ID NO 63
<211> LENGTH: 73
<212> TYPE: RNA
<213> ORGANISM: Homo sapiens

<400> SEQUENCE: 63
aggugcagag cuuagcugau uggugaacag ugauugguuu ccgcuuuguu cacaguggcu    60
aaguucugca ccu                                                      73

<210> SEQ ID NO 64
<211> LENGTH: 97
<212> TYPE: RNA
<213> ORGANISM: Homo sapiens

<400> SEQUENCE: 64
accucucuaa caaggugcag agcuuagcug auuggugaac agugauuggu uccgcuuug     60 uucacagugg cuaaguucug caccugaaga gaaggug                            97

<210> SEQ ID NO 65
<211> LENGTH: 80
<212> TYPE: RNA
<213> ORGANISM: Homo sapiens

<400> SEQUENCE: 65
ccugaggagc agggcuuagc ugcuugugag cagggccac accaagucgu guucacagug     60
gcuaaguucc gccccccagg                                               80

<210> SEQ ID NO 66
<211> LENGTH: 86
<212> TYPE: RNA
<213> ORGANISM: Homo sapiens

<400> SEQUENCE: 66
gguccuugcc cucaaggagc ucacagucua uugaguuacc uuucugacuu ucccacuaga    60
uugugagcuc cuggagggca ggcacu                                        86

<210> SEQ ID NO 67
<211> LENGTH: 108
<212> TYPE: RNA
```

```
<213> ORGANISM: Homo sapiens

<400> SEQUENCE: 67
ccuucuguga ccccuuagag gaugacugau uucuuuuggu guucagaguc aauauaauuu    60
ucuagcacca ucugaaaucg guuauaauga uuggggaaga gcaccaug                108

<210> SEQ ID NO 68
<211> LENGTH: 64
<212> TYPE: RNA
<213> ORGANISM: Homo sapiens

<400> SEQUENCE: 68
augacugauu ucuuuuggug uucagaguca auauaauuuu cuagcaccau cugaaaucgg    60
uuau                                                                 64

<210> SEQ ID NO 69
<211> LENGTH: 81
<212> TYPE: RNA
<213> ORGANISM: Homo sapiens

<400> SEQUENCE: 69
cuucaggaag cugguuucau augguggguuu agauuuaaau agugauuguc uagcaccauu    60
ugaaaucagu guucuugggg g                                              81

<210> SEQ ID NO 70
<211> LENGTH: 81
<212> TYPE: RNA
<213> ORGANISM: Homo sapiens

<400> SEQUENCE: 70
cuucuggaag cugguuucac augguggcuu agauuuuucc aucuuuguau cuagcaccau    60
uugaaaucag uguuuuagga g                                              81

<210> SEQ ID NO 71
<211> LENGTH: 110
<212> TYPE: RNA
<213> ORGANISM: Homo sapiens

<400> SEQUENCE: 71
accacuggcc caucucuuac acaggcugac cgauuucucc uggguguucag agucuguuuu    60 ugucuagcac cauuugaaau cgguuaugau guaggggggaa aagcagcagc               110

<210> SEQ ID NO 72
<211> LENGTH: 71
<212> TYPE: RNA
<213> ORGANISM: Homo sapiens

<400> SEQUENCE: 72
gcgacuguaa acauccucga cuggaagcug ugaagccaca gaugggcuuu cagucggaug    60
uuugcagcug c                                                         71

<210> SEQ ID NO 73
<211> LENGTH: 60
<212> TYPE: RNA
<213> ORGANISM: Homo sapiens

<400> SEQUENCE: 73
auguaaacau ccuacacuca gcuguaauac auggauuggc ugggagguggu auguuuacgu    60

<210> SEQ ID NO 74
```

-continued

```
<211> LENGTH: 88
<212> TYPE: RNA
<213> ORGANISM: Homo sapiens

<400> SEQUENCE: 74
accaaguuuc aguucaugua aacauccuac acucagcugu aauacaugga uuggcuggga      60
gguggauguu uacuucagcu gacuugga                                        88

<210> SEQ ID NO 75
<211> LENGTH: 72
<212> TYPE: RNA
<213> ORGANISM: Homo sapiens

<400> SEQUENCE: 75
agauacugua aacauccuac acucucagcu guggaaagua agaaagcugg gagaaggcug      60
uuuacucuuu cu                                                         72

<210> SEQ ID NO 76
<211> LENGTH: 70
<212> TYPE: RNA
<213> ORGANISM: Homo sapiens

<400> SEQUENCE: 76
guuguuguaa acaucccga cuggaagcug uaagacacag cuaagcuuuc agucagaugu       60
uugcugcuac                                                            70

<210> SEQ ID NO 77
<211> LENGTH: 64
<212> TYPE: RNA
<213> ORGANISM: Homo sapiens

<400> SEQUENCE: 77
cuguaaacau ccuugacugg aagcuguaag guguucagag gagcuuucag ucggauguuu      60
acag                                                                  64

<210> SEQ ID NO 78
<211> LENGTH: 71
<212> TYPE: RNA
<213> ORGANISM: Homo sapiens

<400> SEQUENCE: 78
ggagaggagg caagaugcug gcauagcugu ugaacuggga accugcuaug ccaacauauu      60
gccaucuuuc c                                                          71

<210> SEQ ID NO 79
<211> LENGTH: 70
<212> TYPE: RNA
<213> ORGANISM: Homo sapiens

<400> SEQUENCE: 79
ggagauauug cacauuacua agugcaugu ugucacggcc ucaaugcaau uuagugugug       60
ugauauuuuc                                                            70

<210> SEQ ID NO 80
<211> LENGTH: 110
<212> TYPE: RNA
<213> ORGANISM: Homo sapiens

<400> SEQUENCE: 80
gggggccgag agaggcgggc ggccccgcgg ugcauugcug uugcauugca cgugugugag      60
```

```
gcgggugcag ugccucggca gugcagcccg gagccggccc cuggcaccac            110
```

<210> SEQ ID NO 81
<211> LENGTH: 88
<212> TYPE: RNA
<213> ORGANISM: Homo sapiens

<400> SEQUENCE: 81

```
accaaguuuc aguucaugua aacauccuac acucagcugu aauacaugga uuggcuggga   60 ggugauguu uacuucagcu gacuugga                                       88
```

<210> SEQ ID NO 82
<211> LENGTH: 69
<212> TYPE: RNA
<213> ORGANISM: Homo sapiens

<400> SEQUENCE: 82

```
cuguggugca uuguaguugc auugcauguu cuggugguac ccaugcaaug uuuccacagu   60
gcaucacag                                                           69
```

<210> SEQ ID NO 83
<211> LENGTH: 110
<212> TYPE: RNA
<213> ORGANISM: Homo sapiens

<400> SEQUENCE: 83

```
ggccagcugu gaguguuucu uuggcagugu cuuagcuggu uguugugagc aauaguaagg   60
aagcaaucag caaguauacu gcccuagaag ugcugcacgu uguggggccc              110
```

<210> SEQ ID NO 84
<211> LENGTH: 84
<212> TYPE: RNA
<213> ORGANISM: Homo sapiens

<400> SEQUENCE: 84

```
gugcucgguu uguaggcagu gucauuagcu gauuguacug uggugguuac aaucacuaac   60
uccacugcca ucaaaacaag gcac                                          84
```

<210> SEQ ID NO 85
<211> LENGTH: 77
<212> TYPE: RNA
<213> ORGANISM: Homo sapiens

<400> SEQUENCE: 85

```
agucaguua cuaggcagug uaguuagcug auugcuaaua guaccaauca cuaaccacac    60
ggccagguaa aaagauu                                                  77
```

<210> SEQ ID NO 86
<211> LENGTH: 82
<212> TYPE: RNA
<213> ORGANISM: Homo sapiens

<400> SEQUENCE: 86

```
ucagaauaau gucaaagugc uuacagugca gguagugaua ugcaucua cugcagugaa     60 ggcacuugua gcauuauggu ga                                            82
```

<210> SEQ ID NO 87
<211> LENGTH: 78
<212> TYPE: RNA
<213> ORGANISM: Homo sapiens

```
<400> SEQUENCE: 87
cuuucuacac agguugggau cgguugcaau gcuguguuuc uguaugguau ugcacuuguc    60
ccggccuguu gaguuugg                                                 78

<210> SEQ ID NO 88
<211> LENGTH: 75
<212> TYPE: RNA
<213> ORGANISM: Homo sapiens

<400> SEQUENCE: 88
ucaucccugg guggggauuu guugcauuac uuguguucua auaaaguau ugcacuuguc    60 ccggccugug gaaga                                                    75

<210> SEQ ID NO 89
<211> LENGTH: 80
<212> TYPE: RNA
<213> ORGANISM: Homo sapiens

<400> SEQUENCE: 89 cuggggcuc caaagugcug uucgugcagg uagugugauu acccaaccua cugcugagcu    60
agcacuuccc gagccccgg                                                80

<210> SEQ ID NO 90
<211> LENGTH: 81
<212> TYPE: RNA
<213> ORGANISM: Homo sapiens

<400> SEQUENCE: 90
aacacagugg gcacucaaua aaugucuguu gaauugaaau gcguuacauu caacggguau    60
uuauugagca cccacucugu g                                             81

<210> SEQ ID NO 91
<211> LENGTH: 78
<212> TYPE: RNA
<213> ORGANISM: Homo sapiens

<400> SEQUENCE: 91
uggccgauuu uggcacuagc acauuuuugc uugugucucu ccgcucugag caaucaugug    60
cagugccaau augggaaa                                                 78

<210> SEQ ID NO 92
<211> LENGTH: 80
<212> TYPE: RNA
<213> ORGANISM: Homo sapiens

<400> SEQUENCE: 92
gugagcgacu guaaacaucc ucgacuggaa gcugugaagc cacagauggg cuuucagucg    60
gauguuugca gcugccuacu                                               80

<210> SEQ ID NO 93
<211> LENGTH: 80
<212> TYPE: RNA
<213> ORGANISM: Homo sapiens

<400> SEQUENCE: 93
gugagguagu aaguuguauu guguggggu agggauauua ggccccaauu agaagauaac    60
uauacaacuu acuacuuucc                                               80

<210> SEQ ID NO 94
```

```
<211> LENGTH: 70
<212> TYPE: RNA
<213> ORGANISM: Homo sapiens

<400> SEQUENCE: 94
ggcacccacc cguagaaccg accuugcggg gccuucgccg cacacaagcu cgugucugug    60
gguccguguc                                                          70

<210> SEQ ID NO 95
<211> LENGTH: 81
<212> TYPE: RNA
<213> ORGANISM: Homo sapiens

<400> SEQUENCE: 95
cccauuggca uaaacccgua gauccgaucu uguggugaag uggaccgcac aagcucgcuu    60
cuaugggucu gugucagugu g                                             81

<210> SEQ ID NO 96
<211> LENGTH: 108
<212> TYPE: RNA
<213> ORGANISM: Homo sapiens

<400> SEQUENCE: 96
aagagagaag auauugaggc cuguugccac aaacccguag auccgaacuu gugguauuag    60
uccgcacaag cuuguaucua uagguaugug ucuguuaggc aaucucac                108

<210> SEQ ID NO 97
<211> LENGTH: 80
<212> TYPE: RNA
<213> ORGANISM: Homo sapiens

<400> SEQUENCE: 97
ccuguugcca caaacccgua gauccgaacu ugguguauua guccgcacaa gcuuguaucu    60
auagguaugu gucuguuagg                                               80

<210> SEQ ID NO 98
<211> LENGTH: 110
<212> TYPE: RNA
<213> ORGANISM: Homo sapiens

<400> SEQUENCE: 98
aggcugcccu ggcucaguua ucacagugcu gaugcugucu auucuaaagg uacaguacug    60
ugauaacuga aggauggcag ccaucuuacc uuccaucaga ggagccucac               110

<210> SEQ ID NO 99
<211> LENGTH: 57
<212> TYPE: RNA
<213> ORGANISM: Homo sapiens

<400> SEQUENCE: 99
ucaguuauca cagugcugau gcuguccauu cuaaagguac aguacuguga uaacuga       57

<210> SEQ ID NO 100
<211> LENGTH: 75
<212> TYPE: RNA
<213> ORGANISM: Homo sapiens

<400> SEQUENCE: 100
ugcccuggcu caguuaucac agugcugaug cugucuauuc uaaagguaca guacugau      60 aacugaagga uggca                                                    75
```

```
<210> SEQ ID NO 101
<211> LENGTH: 79
<212> TYPE: RNA
<213> ORGANISM: Homo sapiens

<400> SEQUENCE: 101
acuguccuuu uucgguuauc augguaccga ugcuguauau cugaaaggua caguacugug    60
auaacugaag aauggugggu                                                79

<210> SEQ ID NO 102
<211> LENGTH: 75
<212> TYPE: RNA
<213> ORGANISM: Homo sapiens

<400> SEQUENCE: 102
uguccuuuuu cgguuaucau gguaccgaug cuguauaucu gaaagguaca guacugugau    60
aacugaagaa uggug                                                     75

<210> SEQ ID NO 103
<211> LENGTH: 81
<212> TYPE: RNA
<213> ORGANISM: Homo sapiens

<400> SEQUENCE: 103
cuucuggaag cugguuucac augguggcuu agauuuuucc aucuuuguau cuagcaccau    60
uugaaaucag uguuuuagga g                                              81

<210> SEQ ID NO 104
<211> LENGTH: 81
<212> TYPE: RNA
<213> ORGANISM: Homo sapiens

<400> SEQUENCE: 104
cuucaggaag cugguuucau auggugguuu agauuuaaau agugauuguc uagcaccauu    60
ugaaaucagu guucuugggg g                                              81

<210> SEQ ID NO 105
<211> LENGTH: 78
<212> TYPE: RNA
<213> ORGANISM: Homo sapiens

<400> SEQUENCE: 105
uugugcuuuc agcuucuuua cagugcugcc uuguagcauu caggucaagc aacauuguac    60
agggcuauga aagaacca                                                  78

<210> SEQ ID NO 106
<211> LENGTH: 78
<212> TYPE: RNA
<213> ORGANISM: Homo sapiens

<400> SEQUENCE: 106
uacugcccuc ggcuucuuua cagugcugcc uuguugcaua uggaucaagc agcauuguac    60
agggcuauga aggcauug                                                  78

<210> SEQ ID NO 107
<211> LENGTH: 78
<212> TYPE: RNA
<213> ORGANISM: Homo sapiens

<400> SEQUENCE: 107
```
aaaugucaga cagcccaucg acuggucuug ccaugagauu caacagucaa caucagucug    60
auaagcuacc cgacaagg                                                 78

<210> SEQ ID NO 108
<211> LENGTH: 81
<212> TYPE: RNA
<213> ORGANISM: Homo sapiens

<400> SEQUENCE: 108
ugugcaucgu ggucaaaugc ucagacuccu gugguggcug cucaugcacc acggauguuu    60
gagcaugugc uacggugucu a                                             81

<210> SEQ ID NO 109
<211> LENGTH: 81
<212> TYPE: RNA
<213> ORGANISM: Homo sapiens

<400> SEQUENCE: 109
ugugcaucgu ggucaaaugc ucagacuccu gugguggcug cuuaugcacc acggauguuu    60
gagcaugugc uauggugucu a                                             81

<210> SEQ ID NO 110
<211> LENGTH: 81
<212> TYPE: RNA
<213> ORGANISM: Homo sapiens

<400> SEQUENCE: 110
ccuuggccau guaaaagugc uuacagugca gguagcuuuu ugagaucuac ugcaauguaa    60
gcacuucuua cauuaccaug g                                             81

<210> SEQ ID NO 111
<211> LENGTH: 82
<212> TYPE: RNA
<213> ORGANISM: Homo sapiens

<400> SEQUENCE: 111
ccugccgggg cuaaagugcu gacagugcag auaguggucc ucccgugcu accgcacugu     60 ggguacuugc ugcuccagca gg                                            82

<210> SEQ ID NO 112
<211> LENGTH: 81
<212> TYPE: RNA
<213> ORGANISM: Homo sapiens

<400> SEQUENCE: 112
cucucugcuu ucagcuucuu uacaguguug ccuuguggca uggaguucaa gcagcauugu    60
acagggcuau caaagcacag a                                             81

<210> SEQ ID NO 113
<211> LENGTH: 90
<212> TYPE: RNA
<213> ORGANISM: Homo sapiens

<400> SEQUENCE: 113
acacugcaag aacaauaagg auuuuuaggg gcauuaugac ugagucagaa aacacagcug    60
ccccugaaag ucccucauuu uucuugcugu                                    90

<210> SEQ ID NO 114
<211> LENGTH: 80
<212> TYPE: RNA

<213> ORGANISM: Homo sapiens

<400> SEQUENCE: 114
acugcaagag caauaaggau uuuuaggggc auuaugauag uggaauggaa acacaucugc    60
ccccaaaagu cccucauuuu                                                80

<210> SEQ ID NO 115
<211> LENGTH: 85
<212> TYPE: RNA
<213> ORGANISM: Homo sapiens

<400> SEQUENCE: 115
ccuuagcaga gcuguggagu gugacaaugg uguuugaguc uaaacuauca aacgccauua    60
ucacacuaaa uagcuacugc uaggc                                          85

<210> SEQ ID NO 116
<211> LENGTH: 66
<212> TYPE: RNA
<213> ORGANISM: Homo sapiens

<400> SEQUENCE: 116
agcuguggag ugugacaaug guguuugugu ccaaacuauc aaacgccauu aucacacuaa    60
auagcu                                                               66

<210> SEQ ID NO 117
<211> LENGTH: 61
<212> TYPE: RNA
<213> ORGANISM: Homo sapiens

<400> SEQUENCE: 117
acauuauuac uuuuggguacg cgcugugaca cuucaaacuc guaccgugag uaauaaugcg    60
c                                                                     61

<210> SEQ ID NO 118
<211> LENGTH: 85
<212> TYPE: RNA
<213> ORGANISM: Homo sapiens

<400> SEQUENCE: 118
aggccucucu cuccguguuc acagcggacc uugauuuaaa uguccauaca auuaaggcac    60
gcggugaaug ccaagaaugg ggcug                                          85

<210> SEQ ID NO 119
<211> LENGTH: 110
<212> TYPE: RNA
<213> ORGANISM: Homo sapiens

<400> SEQUENCE: 119
aucaagauua gaggcucugc ucccguguu cacagcggac cuugauuuaa ugcauacaa       60 uuaaggcacg cggugaaugc caagagcgga gccuacggcu gcacuugaag              110

<210> SEQ ID NO 120
<211> LENGTH: 87
<212> TYPE: RNA
<213> ORGANISM: Homo sapiens

<400> SEQUENCE: 120
ugagggcccc ucugcguguu cacagcggac cuugauuuaa ugucuauaca auuaaggcac    60
gcggugaaug ccaagagagg cgccucc                                        87

```
<210> SEQ ID NO 121
<211> LENGTH: 68
<212> TYPE: RNA
<213> ORGANISM: Homo sapiens

<400> SEQUENCE: 121
cucugcgugu ucacagcgga ccuugauuua augucuauac aauuaaggca cgcggugaau     60
gccaagag                                                              68

<210> SEQ ID NO 122
<211> LENGTH: 67
<212> TYPE: RNA
<213> ORGANISM: Homo sapiens

<400> SEQUENCE: 122
cucuccgugu ucacagcgga ccuugauuua augucauaca auuaaggcac gcggugaaug     60
ccaagag                                                               67

<210> SEQ ID NO 123
<211> LENGTH: 86
<212> TYPE: RNA
<213> ORGANISM: Homo sapiens

<400> SEQUENCE: 123
ugccagucuc uaggucccug agacccuuua accugugagg acauccaggg ucacagguga     60
gguucuuggg agccuggcgu cuggcc                                          86

<210> SEQ ID NO 124
<211> LENGTH: 65
<212> TYPE: RNA
<213> ORGANISM: Homo sapiens

<400> SEQUENCE: 124
ggucccugag acccuuuaac cugugaggac auccagggguc acaggugagg uucuugggag    60
ccugg                                                                 65

<210> SEQ ID NO 125
<211> LENGTH: 88
<212> TYPE: RNA
<213> ORGANISM: Homo sapiens

<400> SEQUENCE: 125
ugcgcuccuc ucagucccug agacccuaac uugugauguu uaccguuuaa auccacgggu     60
uaggcucuug ggagcugcga gucgugcu                                        88

<210> SEQ ID NO 126
<211> LENGTH: 89
<212> TYPE: RNA
<213> ORGANISM: Homo sapiens

<400> SEQUENCE: 126
accagacuuu uccuaguccc ugagacccua acuugugagg uauuuuagua acaucacaag     60
ucaggcucuu gggaccuagg cggaggggga                                      89

<210> SEQ ID NO 127
<211> LENGTH: 85
<212> TYPE: RNA
<213> ORGANISM: Homo sapiens

<400> SEQUENCE: 127
```

```
cgcuggcgac gggacauuau uacuuuuggu acgcgcugug acacuucaaa cucguaccgu    60
gaguaauaau gcgccgucca cggca                                          85

<210> SEQ ID NO 128
<211> LENGTH: 61
<212> TYPE: RNA
<213> ORGANISM: Homo sapiens

<400> SEQUENCE: 128
acauuauuac uuuugguacg cgcugugaca cuucaaacuc guaccgugag uaauaaugcg    60
c                                                                    61

<210> SEQ ID NO 129
<211> LENGTH: 97
<212> TYPE: RNA
<213> ORGANISM: Homo sapiens

<400> SEQUENCE: 129
ugugaucacu gucuccagcc ugcugaagcu cagagggcuc ugauucagaa agaucaucgg    60
auccgucuga gcuuggcugg ucggaagucu caucauc                             97

<210> SEQ ID NO 130
<211> LENGTH: 70
<212> TYPE: RNA
<213> ORGANISM: Homo sapiens

<400> SEQUENCE: 130
ccagccugcu gaagcucaga gggcucugau ucagaaagau caucggauccc gucugagcuu    60 ggcuggucgg                                                           70

<210> SEQ ID NO 131
<211> LENGTH: 82
<212> TYPE: RNA
<213> ORGANISM: Homo sapiens

<400> SEQUENCE: 131
ugagcuguug gauucggggc cguagcacug ucugagaggu uuacauuucu cacagugaac    60
cggucucuuu uucagcugcu uc                                             82

<210> SEQ ID NO 132
<211> LENGTH: 110
<212> TYPE: RNA
<213> ORGANISM: Homo sapiens

<400> SEQUENCE: 132
gcccggcagc cacugugcag ugggaagggg ggccgauaca cuguacgaga gugaguagca    60
ggucucacag ugaaccgguc ucuuucccua cugugucaca cuccuaaugg              110

<210> SEQ ID NO 133
<211> LENGTH: 70
<212> TYPE: RNA
<213> ORGANISM: Homo sapiens

<400> SEQUENCE: 133
guuggauucg gggccguagc acugucugag agguuuacau uucucacagu gaaccggucu    60
cuuuuucagc                                                           70

<210> SEQ ID NO 134
<211> LENGTH: 74
<212> TYPE: RNA
```

<213> ORGANISM: Homo sapiens

<400> SEQUENCE: 134
uggaucuuuu ugcggucugg gcuugcuguu ccucucaaca guagucagga agcccuuacc    60
ccaaaaagua ucua    74

<210> SEQ ID NO 135
<211> LENGTH: 90
<212> TYPE: RNA
<213> ORGANISM: Homo sapiens

<400> SEQUENCE: 135
ugcccuucgc gaaucuuuuu gcggucuggg cuugcuguac auaacucaau agccggaagc    60
ccuuacccca aaaagcauuu gcggagggcg    90

<210> SEQ ID NO 136
<211> LENGTH: 89
<212> TYPE: RNA
<213> ORGANISM: Homo sapiens

<400> SEQUENCE: 136
ugcugcuggc cagagcucuu uucacauugu gcuacugucu gcaccuguca cuagcagugc    60
aauguuaaaa gggcauuggc cguguagug    89

<210> SEQ ID NO 137
<211> LENGTH: 110
<212> TYPE: RNA
<213> ORGANISM: Homo sapiens

<400> SEQUENCE: 137
gccaggaggc gggguugguu guuaucuuug guuaucuagc uguaugagug guguggaguc    60
uucauaaagc uagauaaccg aaaguaaaaa uaaccccaua cacugcgcag    110

<210> SEQ ID NO 138
<211> LENGTH: 110
<212> TYPE: RNA
<213> ORGANISM: Homo sapiens

<400> SEQUENCE: 138
cacggcgcgg cagcggcacu ggcuaaggga ggcccguuuc ucucuuuggu uaucuagcug    60
uaugagugcc acagagccgu cauaaagcua gauaaccgaa aguagaaaug    110

<210> SEQ ID NO 139
<211> LENGTH: 72
<212> TYPE: RNA
<213> ORGANISM: Homo sapiens

<400> SEQUENCE: 139
guuguuaucu uugguuaucu agcuguauga guguauuggu cuucauaaag cuagauaacc    60
gaaaguaaaa ac    72

<210> SEQ ID NO 140
<211> LENGTH: 101
<212> TYPE: RNA
<213> ORGANISM: Homo sapiens

<400> SEQUENCE: 140
ccgcccccgc gucuccaggg caaccguggc uuucgauugu uacguggga acuggaggua    60 acagucuaca gccauggucg ccccgcagca cgcccacgcg c    101

```
<210> SEQ ID NO 141
<211> LENGTH: 66
<212> TYPE: RNA
<213> ORGANISM: Homo sapiens

<400> SEQUENCE: 141
gggcaaccgu ggcuuucgau uguuacugug ggaacuggag guaacagucu acagccaugg      60
ucgccc                                                                66

<210> SEQ ID NO 142
<211> LENGTH: 88
<212> TYPE: RNA
<213> ORGANISM: Homo sapiens

<400> SEQUENCE: 142
acaaugcuuu gcuagagcug guaaaaugga accaaaucgc cucuucaaug gauuuggucc      60
ccuucaacca gcuguagcua ugcauuga                                        88

<210> SEQ ID NO 143
<211> LENGTH: 102
<212> TYPE: RNA
<213> ORGANISM: Homo sapiens

<400> SEQUENCE: 143
gggagccaaa ugcuuugcua gagcugguaa aauggaacca aaucgacugu ccaauggauu      60 uggucccuu caaccagcug uagcugugca uugauggcgc cg                         102

<210> SEQ ID NO 144
<211> LENGTH: 68
<212> TYPE: RNA
<213> ORGANISM: Homo sapiens

<400> SEQUENCE: 144
gcuagagcug guaaaaugga accaaaucgc cucuucaaug gauuuggucc ccuucaacca      60
gcuguagc                                                              68

<210> SEQ ID NO 145
<211> LENGTH: 119
<212> TYPE: RNA
<213> ORGANISM: Homo sapiens

<400> SEQUENCE: 145
ccucagaaga aagaugcccc cugcucuggc uggucaaacg gaaccaaguc cgucuuccug      60
agagguuugg uccccuucaa ccagcuacag cagggcuggc aaugcccagu ccuuggaga      119

<210> SEQ ID NO 146
<211> LENGTH: 80
<212> TYPE: RNA
<213> ORGANISM: Homo sapiens

<400> SEQUENCE: 146
gcccccugcu cuggcugguc aaacggaacc aaguccgucu ccugagagg uuuggucccc      60 uucaaccagc uacagcaggg                                                 80

<210> SEQ ID NO 147
<211> LENGTH: 73
<212> TYPE: RNA
<213> ORGANISM: Homo sapiens

<400> SEQUENCE: 147
```

```
cagggugugu gacugguuga ccagaggggc augcacugug uucacccugu gggccaccua    60
gucaccaacc cuc                                                      73

<210> SEQ ID NO 148
<211> LENGTH: 71
<212> TYPE: RNA
<213> ORGANISM: Homo sapiens

<400> SEQUENCE: 148
agggugugug acugguugac cagaggggca ugcacugugu cacccugug gccaccuag      60 ucaccaaccc u                                                        71

<210> SEQ ID NO 149
<211> LENGTH: 90
<212> TYPE: RNA
<213> ORGANISM: Homo sapiens

<400> SEQUENCE: 149
aggccucgcu guucucuaug gcuuuuauu ccuaugugau ucuacugcuc acucauauag     60
ggauuggagc cguggcgcac ggcggggaca                                    90

<210> SEQ ID NO 150
<211> LENGTH: 100
<212> TYPE: RNA
<213> ORGANISM: Homo sapiens

<400> SEQUENCE: 150
agauaaauuc acucuagugc uuuauggcuu uuuauuccua ugugauagua auaaagucuc    60
auguagggau ggaagccaug aaauacauug ugaaaaauca                        100

<210> SEQ ID NO 151
<211> LENGTH: 60
<212> TYPE: RNA
<213> ORGANISM: Homo sapiens

<400> SEQUENCE: 151
cuauggcuuu uuauuccuau gugauucuac ugcucacuca uaugggauu ggagccgugg     60

<210> SEQ ID NO 152
<211> LENGTH: 97
<212> TYPE: RNA
<213> ORGANISM: Homo sapiens

<400> SEQUENCE: 152
cacucugcug uggccuaugg cuuuucauuc cuaugugauu gcugucccaa acucauguag    60
ggcuaaaagc caugggcuac agugaggggc gagcucc                            97

<210> SEQ ID NO 153
<211> LENGTH: 82
<212> TYPE: RNA
<213> ORGANISM: Homo sapiens

<400> SEQUENCE: 153
ugagcccucg gaggacucca uuuguuuuga ugauggauuc uuaugcucca ucaucgucuc    60
aaaugagucu ucagaggguu cu                                            82

<210> SEQ ID NO 154
<211> LENGTH: 62
<212> TYPE: RNA
<213> ORGANISM: Homo sapiens
```

```
<400> SEQUENCE: 154
gaggacucca uuuguuuga ugauggauuc uuaugcucca ucaucgucuc aaaugagucu    60
uc                                                                 62

<210> SEQ ID NO 155
<211> LENGTH: 73
<212> TYPE: RNA
<213> ORGANISM: Homo sapiens

<400> SEQUENCE: 155
cuucggugac ggguauucuu gguggauaa uacggauuac guuguuauug cuuaagaaua    60
cgcguagucg agg                                                     73

<210> SEQ ID NO 156
<211> LENGTH: 99
<212> TYPE: RNA
<213> ORGANISM: Homo sapiens

<400> SEQUENCE: 156
cccuggcaug guguggugg gcagcuggug uugugaauca ggccguugcc aaucagagaa    60
cggcuacuuc acaacaccag ggccacacca cacuacagg                         99

<210> SEQ ID NO 157
<211> LENGTH: 84
<212> TYPE: RNA
<213> ORGANISM: Homo sapiens

<400> SEQUENCE: 157
cguugcugca gcggguguug ugaaucaggc cgacgagcag cgcauccucu uacccggcua   60
uuucacgaca ccagggguugc auca                                        84

<210> SEQ ID NO 158
<211> LENGTH: 71
<212> TYPE: RNA
<213> ORGANISM: Homo sapiens

<400> SEQUENCE: 158
cagcuggugu ugugaaucag gccgacgagc agcgcauccu cuuacccggc uauuucacga   60
caccaggguu g                                                       71

<210> SEQ ID NO 159
<211> LENGTH: 68
<212> TYPE: RNA
<213> ORGANISM: Homo sapiens

<400> SEQUENCE: 159
guguauucua cagugcacgu gucuccagug uggcucggag gcuggagacg cggcccuguu   60
ggaguaac                                                           68

<210> SEQ ID NO 160
<211> LENGTH: 100
<212> TYPE: RNA
<213> ORGANISM: Homo sapiens

<400> SEQUENCE: 160 ugugcucuc ucugugaccu gccaguggu uuacccuaug guagguuacg ucaugcuguu    60
cuaccacagg guagaaccac ggacaggaua ccggggcacc                       100

<210> SEQ ID NO 161
```

```
<211> LENGTH: 72
<212> TYPE: RNA
<213> ORGANISM: Homo sapiens

<400> SEQUENCE: 161
uccugccagu gguuuuaccc uaugguaggu uacgucaugc uguucuacca caggguagaa    60
ccacggacag ga                                                       72

<210> SEQ ID NO 162
<211> LENGTH: 70
<212> TYPE: RNA
<213> ORGANISM: Homo sapiens

<400> SEQUENCE: 162
ccugccagug guuuuacccu auggguagguu acgucaugcu guucuaccac agggguagaac   60 cacggacagg                                                          70

<210> SEQ ID NO 163
<211> LENGTH: 95
<212> TYPE: RNA
<213> ORGANISM: Homo sapiens

<400> SEQUENCE: 163
cggccggccc uggguccauc uuccaguaca guguuggaug gucuaauugu gaagcuccua    60
acacugucug guaaagaugg cucccggguug gguuc                             95

<210> SEQ ID NO 164
<211> LENGTH: 72
<212> TYPE: RNA
<213> ORGANISM: Homo sapiens

<400> SEQUENCE: 164
ggguccaucu uccaguacag guuggaugg ucuaauugug aagcuccuaa cacugucugg     60
uaaagauggc cc                                                       72

<210> SEQ ID NO 165
<211> LENGTH: 64
<212> TYPE: RNA
<213> ORGANISM: Homo sapiens

<400> SEQUENCE: 165
acccauaaag uagaaagcac acuaacagc acuggagggu guaguguuuc cuacuuuaug     60
gaug                                                                64

<210> SEQ ID NO 166
<211> LENGTH: 106
<212> TYPE: RNA
<213> ORGANISM: Homo sapiens

<400> SEQUENCE: 166
gcgcagcgcc cugucuccca gccugaggug cagugcugca ucucuggucca guugggaguc   60 ugagaugaag cacuguagcu caggaagaga gaaguugu ugcagc                    106

<210> SEQ ID NO 167
<211> LENGTH: 63
<212> TYPE: RNA
<213> ORGANISM: Homo sapiens

<400> SEQUENCE: 167
ccugaggugc agugcugcau cucuggucag uugggagucu gagaugaagc acuguagcuc    60
```

```
agg                                                            63

<210> SEQ ID NO 168
<211> LENGTH: 86
<212> TYPE: RNA
<213> ORGANISM: Homo sapiens

<400> SEQUENCE: 168
uggggcccug gcugggauau caucauauac uguaaguuug cgaugagaca cuacaguaua    60
gaugauguac uaguccgggc accccc                                        86

<210> SEQ ID NO 169
<211> LENGTH: 66
<212> TYPE: RNA
<213> ORGANISM: Homo sapiens

<400> SEQUENCE: 169
ggcugggaua ucaucauaua cuguaaguuu gcgaugagac acuacaguau agaugaugua    60
cuaguc                                                              66

<210> SEQ ID NO 170
<211> LENGTH: 88
<212> TYPE: RNA
<213> ORGANISM: Homo sapiens

<400> SEQUENCE: 170
caccuugucc ucacggucca guuucccag gaaucccuua gaugcuaaga uggggauucc     60
uggaaauacu guucuugagg ucaugguu                                      88

<210> SEQ ID NO 171
<211> LENGTH: 70
<212> TYPE: RNA
<213> ORGANISM: Homo sapiens

<400> SEQUENCE: 171
cucacggucc aguuucccca ggaaucccuu agaugcuaag augggauuc cuggaaauac     60 uguucuugag                                                          70

<210> SEQ ID NO 172
<211> LENGTH: 99
<212> TYPE: RNA
<213> ORGANISM: Homo sapiens

<400> SEQUENCE: 172
ccgaugugua uccucagcuu ugagaacuga auuccauggg uugugucagu gucagaccuc    60
ugaaauucag uucuucagcu gggauaucuc ugucaucgu                          99

<210> SEQ ID NO 173
<211> LENGTH: 65
<212> TYPE: RNA
<213> ORGANISM: Homo sapiens

<400> SEQUENCE: 173
agcuuugaga acugaauucc augggguugug ucagucag accugugaaa uucaguucuu    60
cagcu                                                               65

<210> SEQ ID NO 174
<211> LENGTH: 72
<212> TYPE: RNA
<213> ORGANISM: Homo sapiens
```

```
<400> SEQUENCE: 174
aaucuaaaga caacauuucu gcacacacac cagacuaugg aagccagugu guggaaaugc    60
uucugcuaga uu                                                      72

<210> SEQ ID NO 175
<211> LENGTH: 68
<212> TYPE: RNA
<213> ORGANISM: Homo sapiens

<400> SEQUENCE: 175
gaggcaaagu ucugagacac uccgacucug aguaugauag aagucagugc acuacagaac    60
uuugucuc                                                           68

<210> SEQ ID NO 176
<211> LENGTH: 99
<212> TYPE: RNA
<213> ORGANISM: Homo sapiens

<400> SEQUENCE: 176
caagcacgau uagcauuuga ggugaaguuc uguuauacac ucaggcugug gcucucugaa    60
agucagugca ucacagaacu uugcucgaa agcuuucua                          99

<210> SEQ ID NO 177
<211> LENGTH: 70
<212> TYPE: RNA
<213> ORGANISM: Homo sapiens

<400> SEQUENCE: 177
aagcacgauu agcauuugag gugaaguucu guuauacacu caggcugugg cucucugaaa    60
gucagugcau                                                         70

<210> SEQ ID NO 178
<211> LENGTH: 89
<212> TYPE: RNA
<213> ORGANISM: Homo sapiens

<400> SEQUENCE: 178
gccggcgccc gagcucuggc uccgugucuu cacucccgug cuugucagag gagggaggga   60
gggacggggg cugugcuggg gcagcugga                                    89

<210> SEQ ID NO 179
<211> LENGTH: 53
<212> TYPE: RNA
<213> ORGANISM: Homo sapiens

<400> SEQUENCE: 179
gcucuggcuc cgugucuuca cucccgugcu guccgagga gggagggagg gac           53

<210> SEQ ID NO 180
<211> LENGTH: 84
<212> TYPE: RNA
<213> ORGANISM: Homo sapiens

<400> SEQUENCE: 180
cuccccaugg cccugucucc caaccccuugu accagugcug ggcucagacc cugguacagg   60 ccuggggac agggaccugg ggac                                          84

<210> SEQ ID NO 181
<211> LENGTH: 64
<212> TYPE: RNA
```

-continued

<213> ORGANISM: Homo sapiens

<400> SEQUENCE: 181
cccugucucc caacccuugu accagugcug ggcucagacc cugguacagg ccuggggac    60 aggg                                                                64

<210> SEQ ID NO 182
<211> LENGTH: 72
<212> TYPE: RNA
<213> ORGANISM: Homo sapiens

<400> SEQUENCE: 182
uuuccugccc ucgaggagcu cacagucuag uaugucucau ccccuacuag acugaagcuc    60
cuugaggaca gg                                                       72

<210> SEQ ID NO 183
<211> LENGTH: 69
<212> TYPE: RNA
<213> ORGANISM: Homo sapiens

<400> SEQUENCE: 183
ccuguccuca aggagcuuca gucuaguagg ggaugagaca uacuagacug ugagcuccuc    60
gagggcagg                                                           69

<210> SEQ ID NO 184
<211> LENGTH: 87
<212> TYPE: RNA
<213> ORGANISM: Homo sapiens

<400> SEQUENCE: 184 ugucccccc ggcccagguu cugugauaca cuccgacucg ggcucuggag cagucagugc     60
augacagaac uugggcccgg aaggacc                                       87

<210> SEQ ID NO 185
<211> LENGTH: 71
<212> TYPE: RNA
<213> ORGANISM: Homo sapiens

<400> SEQUENCE: 185
ggcccagguu cugugauaca cuccgacucg ggcucuggag cagucagugc augacagaac    60
uugggccccg g                                                        71

<210> SEQ ID NO 186
<211> LENGTH: 90
<212> TYPE: RNA
<213> ORGANISM: Homo sapiens

<400> SEQUENCE: 186
cucacagcug ccagugucau uuuugugauc ugcagcuagu auucucacuc caguugcaua    60
gucacaaaag ugaucauugg cagguguggc                                    90

<210> SEQ ID NO 187
<211> LENGTH: 71
<212> TYPE: RNA
<213> ORGANISM: Homo sapiens

<400> SEQUENCE: 187
ucucucucuc ccucacagcu gccagugca uugucacaaa agugaucauu ggcaggugug     60
gcugcugcau g                                                        71

```
<210> SEQ ID NO 188
<211> LENGTH: 87
<212> TYPE: RNA
<213> ORGANISM: Homo sapiens

<400> SEQUENCE: 188
agcgguggcc agugucauuu uugugauguu gcagcuagua auaugagccc aguugcauag    60
ucacaaaagu gaucauugga aacugug                                        87

<210> SEQ ID NO 189
<211> LENGTH: 69
<212> TYPE: RNA
<213> ORGANISM: Homo sapiens

<400> SEQUENCE: 189
cagugucauu uuugugaugu ugcagcuagu aauaugagcc caguugcaua gucacaaaag    60
ugaucauug                                                            69

<210> SEQ ID NO 190
<211> LENGTH: 84
<212> TYPE: RNA
<213> ORGANISM: Homo sapiens

<400> SEQUENCE: 190
gugguacuug aagauagguu auccguguug ccuucgcuuu auuugugacg aaucauacac    60
gguugaccua uuuucagua ccaa                                            84

<210> SEQ ID NO 191
<211> LENGTH: 66
<212> TYPE: RNA
<213> ORGANISM: Homo sapiens

<400> SEQUENCE: 191
gaagauaggu uauccguguu gccuucgcuu uauuugugac gaaucauaca cgguugaccu    60
auuuuu                                                               66

<210> SEQ ID NO 192
<211> LENGTH: 65
<212> TYPE: RNA
<213> ORGANISM: Homo sapiens

<400> SEQUENCE: 192
cuguuaaugc uaaucgugau aggguuuuu gccuccaacu gacuccuaca uauuagcauu     60
aacag                                                                65

<210> SEQ ID NO 193
<211> LENGTH: 82
<212> TYPE: RNA
<213> ORGANISM: Homo sapiens

<400> SEQUENCE: 193
ccuaacacug ucugguaaag auggcucccg gguggguucu cucggcagua accuucaggg    60
agcccugaag accauggagg ac                                             82

<210> SEQ ID NO 194
<211> LENGTH: 110
<212> TYPE: RNA
<213> ORGANISM: Homo sapiens

<400> SEQUENCE: 194
```

```
gccgagaccg agugcacagg gcucugaccu augaauugac agccagugcu cucgucuccc      60
cucuggcugc caauuccaua ggucacaggu auguucgccu caaugccagc                 110

<210> SEQ ID NO 195
<211> LENGTH: 80
<212> TYPE: RNA
<213> ORGANISM: Homo sapiens

<400> SEQUENCE: 195
ucccgccccc uguaacagca acuccaugug gaagugccca cugguccag uggggcugcu       60 guuaucuggg gcgagggcca                                                   80

<210> SEQ ID NO 196
<211> LENGTH: 70
<212> TYPE: RNA
<213> ORGANISM: Homo sapiens

<400> SEQUENCE: 196
aaagcugggu ugagagggcg aaaaaggaug aggugacugg ucugggcuac gcuaugcugc      60
ggcgcucggg                                                              70

<210> SEQ ID NO 197
<211> LENGTH: 64
<212> TYPE: RNA
<213> ORGANISM: Homo sapiens

<400> SEQUENCE: 197
cauuggccuc cuaagccagg gauugugggu ucgagucccca cccgggguaa agaaaggccg    60
aauu                                                                    64

<210> SEQ ID NO 198
<211> LENGTH: 70
<212> TYPE: RNA
<213> ORGANISM: Homo sapiens

<400> SEQUENCE: 198
ccuaagccag ggauuguggg uucgaguccc accggggua gaggugaaag uuccuuuuac       60
ggaauuuuuu                                                              70

<210> SEQ ID NO 199
<211> LENGTH: 108
<212> TYPE: RNA
<213> ORGANISM: Homo sapiens

<400> SEQUENCE: 199
caaugucagc agugccuuag cagcacguaa auauuggcgu uaagauucua aaauuaucuc      60
caguauuaac ugugcugcug aaguaagguu gaccauacuc uacaguug                  108

<210> SEQ ID NO 200
<211> LENGTH: 81
<212> TYPE: RNA
<213> ORGANISM: Homo sapiens

<400> SEQUENCE: 200
gggcuuucaa gucacuagug guuccguuua guagaugauu ugcauuguu ucaaaauggu       60 gcccuaguga cuacaaagcc c                                                81

<210> SEQ ID NO 201
<211> LENGTH: 70
<212> TYPE: RNA
```

<213> ORGANISM: Homo sapiens

<400> SEQUENCE: 201
acgcaagugu ccuaagguga gcucagggag cacagaaacc uccaguggaa cagaagggca    60
aaagcucauu                                                          70

<210> SEQ ID NO 202
<211> LENGTH: 70
<212> TYPE: RNA
<213> ORGANISM: Homo sapiens

<400> SEQUENCE: 202
caugugucac uuucaggugg aguuucaaga gucccuuccu gguuccacgu cuccuuugcu    60
cuuccacaac                                                          70

<210> SEQ ID NO 203
<211> LENGTH: 110
<212> TYPE: RNA
<213> ORGANISM: Homo sapiens

<400> SEQUENCE: 203
agaagggcua ucaggccagc cuucagagga cuccaaggaa cauucaacgc ugucggugag    60
uuugggauuu gaaaaaacca cugaccguug acuguaccuu gggguccuua              110

<210> SEQ ID NO 204
<211> LENGTH: 110
<212> TYPE: RNA
<213> ORGANISM: Homo sapiens

<400> SEQUENCE: 204
ccugugcaga gauuauuuuu uaaaagguca caaucaacau ucauugcugu cgguggguug    60
aacugugugg acaagcucac ugaacaauga augcaacugu ggccccgcuu              110

<210> SEQ ID NO 205
<211> LENGTH: 89
<212> TYPE: RNA
<213> ORGANISM: Homo sapiens

<400> SEQUENCE: 205
cugauggcug cacucaacau ucauugcugu cggugggut uu gagucugaau caacucacug    60
aucaaugaau gcaaacugcg gaccaaaca                                     89

<210> SEQ ID NO 206
<211> LENGTH: 110
<212> TYPE: RNA
<213> ORGANISM: Homo sapiens

<400> SEQUENCE: 206
cggaaaauuu gccaaggguu uggggaaca uucaaccugu cggugaguuu ggcagcuca      60 ggcaaaccau cgaccguuga guggacccug aggccuggaa uugccauccu               110

<210> SEQ ID NO 207
<211> LENGTH: 110
<212> TYPE: RNA
<213> ORGANISM: Homo sapiens

<400> SEQUENCE: 207
gagcugcuug ccucccccg uuuuuggcaa ugguagaacu cacacuggug agguaacagg     60
auccgguggu ucuagacuug ccaacuaugg ggcgaggacu cagccggcac              110

```
<210> SEQ ID NO 208
<211> LENGTH: 70
<212> TYPE: RNA
<213> ORGANISM: Homo sapiens

<400> SEQUENCE: 208
uuuuuggcaa ugguagaacu cacacuggug agguaacagg auccgguggu ucuagacuug      60
ccaacuaugg                                                             70

<210> SEQ ID NO 209
<211> LENGTH: 110
<212> TYPE: RNA
<213> ORGANISM: Homo sapiens

<400> SEQUENCE: 209
ccgcagagug ugacuccugu ucuguguaug gcacugguag aauucacugu gaacagucuc      60
agucagugaa uuaccgaagg gccauaaaca gagcagagac agauccacga                110

<210> SEQ ID NO 210
<211> LENGTH: 84
<212> TYPE: RNA
<213> ORGANISM: Homo sapiens

<400> SEQUENCE: 210
ccagucacgu ccccuuauca cuuuccagc ccagcuuugu gacuguaagu guuggacgga       60
gaacugauaa ggguaggugu uuga                                             84

<210> SEQ ID NO 211
<211> LENGTH: 65
<212> TYPE: RNA
<213> ORGANISM: Homo sapiens

<400> SEQUENCE: 211
ccuuaucacu uuccagccc agcuuuguga cuguaagugu uggacggaga acugauaagg       60
guagg                                                                  65

<210> SEQ ID NO 212
<211> LENGTH: 82
<212> TYPE: RNA
<213> ORGANISM: Homo sapiens

<400> SEQUENCE: 212
agggggcgag ggauuggaga gaaaggcagu uccugauggu ccccuccca ggggcuggcu       60 uuccucuggu ccuucccucc ca                                               82

<210> SEQ ID NO 213
<211> LENGTH: 66
<212> TYPE: RNA
<213> ORGANISM: Homo sapiens

<400> SEQUENCE: 213
agggauugga gagaaaggca guuccugaug gucccucccc caggggcugg cuuuccucug      60
guccuu                                                                 66

<210> SEQ ID NO 214
<211> LENGTH: 86
<212> TYPE: RNA
<213> ORGANISM: Homo sapiens

<400> SEQUENCE: 214
```

```
ugcuuguaac uuuccaaaga auucuccuuu ugggcuuucu gguuuuauuu uaagcccaaa    60
ggugaauuuu uugggaaguu ugagcu                                        86

<210> SEQ ID NO 215
<211> LENGTH: 71
<212> TYPE: RNA
<213> ORGANISM: Homo sapiens

<400> SEQUENCE: 215 acuuccaaa gaauucuccu uugggcuuu cugguuuuau uuaagccca aaggugaauu      60 uuuugggaag u                                                        71

<210> SEQ ID NO 216
<211> LENGTH: 109
<212> TYPE: RNA
<213> ORGANISM: Homo sapiens

<400> SEQUENCE: 216
ggucgggcuc accaugacac agugugagac ucgggcuaca acacaggacc cggggcgcug   60
cucugacccc ucgugucuug uguugcagcc ggagggacgc agguccgca              109

<210> SEQ ID NO 217
<211> LENGTH: 86
<212> TYPE: RNA
<213> ORGANISM: Homo sapiens

<400> SEQUENCE: 217
ugcucccucu cucacauccc uugcauggug gagggugagc uuucugaaaa ccccucccac   60
augcaggguu ugcaggaugg cgagcc                                        86

<210> SEQ ID NO 218
<211> LENGTH: 68
<212> TYPE: RNA
<213> ORGANISM: Homo sapiens

<400> SEQUENCE: 218
ucucacaucc cuugcauggu ggagggugag cuuucugaaa accccuccca caugcagggu   60
uugcagga                                                            68

<210> SEQ ID NO 219
<211> LENGTH: 102
<212> TYPE: RNA
<213> ORGANISM: Homo sapiens

<400> SEQUENCE: 219
cugucgauug dacccgcccu ccggugccua cugagcugau aucaguucuc auuuuacaca   60
cuggcucagu ucagcaggaa caggagucga gcccuugagc aa                     102

<210> SEQ ID NO 220
<211> LENGTH: 68
<212> TYPE: RNA
<213> ORGANISM: Homo sapiens

<400> SEQUENCE: 220
cuccggugcc uacugagcug auaucaguuc ucauuuuaca cacuggcuca guucagcagg   60
aacaggag                                                            68

<210> SEQ ID NO 221
<211> LENGTH: 85
<212> TYPE: RNA
```

```
<213> ORGANISM: Homo sapiens

<400> SEQUENCE: 221
ugcaggccuc ugugugauau guuugauaua uuagguuguu auuuaaucca acuauauauc    60
aaacauauuc cuacaguguc uugcc                                         85

<210> SEQ ID NO 222
<211> LENGTH: 67
<212> TYPE: RNA
<213> ORGANISM: Homo sapiens

<400> SEQUENCE: 222
cugugugaua uguuugauau auuaggyugu uauuuaaucc aacuauauau caaacauauu    60
ccuacag                                                             67

<210> SEQ ID NO 223
<211> LENGTH: 92
<212> TYPE: RNA
<213> ORGANISM: Homo sapiens

<400> SEQUENCE: 223
cggcuggaca gcgggcaacg gaaucccaaa agcagcuguu gucuccagag cauuccagcu    60
gcgcuuggau uucguccccu gcucuccugc cu                                 92

<210> SEQ ID NO 224
<211> LENGTH: 74
<212> TYPE: RNA
<213> ORGANISM: Homo sapiens

<400> SEQUENCE: 224
agcgggcaac ggaaucccaa aagcagcugu ugucuccaga gcauuccagc ugcgcuugga    60
uuucgucccc ugcu                                                     74

<210> SEQ ID NO 225
<211> LENGTH: 108
<212> TYPE: RNA
<213> ORGANISM: Homo sapiens

<400> SEQUENCE: 225
ccgagaccga gugcacaggg cucugaccua ugaauugaca gccagugcuc ucgucucccc    60
ucuggcugcc aauuccauag gucacaggua uguucgccuc aaugccag                108

<210> SEQ ID NO 226
<211> LENGTH: 110
<212> TYPE: RNA
<213> ORGANISM: Homo sapiens

<400> SEQUENCE: 226
gccgagaccg agugcacagg gcucugaccu augaauugac agccagugcu cucgucuccc    60
cucuggcugc caauuccaua ggucacaggu auguucgccu caaugccagc              110

<210> SEQ ID NO 227
<211> LENGTH: 88
<212> TYPE: RNA
<213> ORGANISM: Homo sapiens

<400> SEQUENCE: 227
cgaggauggg agcugagggc ugggucuuug cgggcgagau gagggugucg gaucaacugg    60
ccuacaaagu cccaguucuc ggcccccg                                      88
```

```
<210> SEQ ID NO 228
<211> LENGTH: 58
<212> TYPE: RNA
<213> ORGANISM: Homo sapiens

<400> SEQUENCE: 228
gcugggucuu ugcgggcgag augagggugu cggaucaacu ggccuacaaa gucccagu        58

<210> SEQ ID NO 229
<211> LENGTH: 85
<212> TYPE: RNA
<213> ORGANISM: Homo sapiens

<400> SEQUENCE: 229
augguguuau caaguguaac agcaacucca ugggacugu guaccaauuu ccaguggaga        60
ugcuguuacu uuugaugguu accaa                                            85

<210> SEQ ID NO 230
<211> LENGTH: 63
<212> TYPE: RNA
<213> ORGANISM: Homo sapiens

<400> SEQUENCE: 230
guguaacagc aacuccaugu ggacugugua ccaauuucca guggagaugc uguuacuuuu       60
gau                                                                    63

<210> SEQ ID NO 231
<211> LENGTH: 87
<212> TYPE: RNA
<213> ORGANISM: Homo sapiens

<400> SEQUENCE: 231
agcuucccug gcucuagcag cacagaaaua uuggcacagg aagcgaguc ugccaauauu        60 ggcugugcug cuccaggcag gguggug                                          87

<210> SEQ ID NO 232
<211> LENGTH: 58
<212> TYPE: RNA
<213> ORGANISM: Homo sapiens

<400> SEQUENCE: 232
uagcagcaca gaaauauugg cacagggaag cgagucugcc aauauuggcu gugcugcu        58

<210> SEQ ID NO 233
<211> LENGTH: 110
<212> TYPE: RNA
<213> ORGANISM: Homo sapiens

<400> SEQUENCE: 233
cuagagcuug aauuggaacu gcugagugaa uuagguaguu ucauguuguu gggccugggu      60
uucugaacac aacaacauua aaccacccga uucacggcag uuacugcucc                 110

<210> SEQ ID NO 234
<211> LENGTH: 70
<212> TYPE: RNA
<213> ORGANISM: Homo sapiens

<400> SEQUENCE: 234
gugaauuagg uaguucaug uuguugggcc uggguuucug aacacaacaa cauuaaacca       60
cccgauucac                                                             70
```

```
<210> SEQ ID NO 235
<211> LENGTH: 110
<212> TYPE: RNA
<213> ORGANISM: Homo sapiens

<400> SEQUENCE: 235
ugcucgcuca gcugaucugu ggcuuaggua guuucauguu guugggauug aguuuugaac      60
ucggcaacaa gaaacugccu gaguuacauc agucgguuuu cgucgagggc                110

<210> SEQ ID NO 236
<211> LENGTH: 70
<212> TYPE: RNA
<213> ORGANISM: Homo sapiens

<400> SEQUENCE: 236
gugaauuagg uaguuucaug uuguugggcc uggguuucug aacacaacaa cauuaaacca      60
cccgauucac                                                             70

<210> SEQ ID NO 237
<211> LENGTH: 84
<212> TYPE: RNA
<213> ORGANISM: Homo sapiens

<400> SEQUENCE: 237
acuggucggu gauuuaggua guuccuguu guugggaucc accuuucucu cgacagcacg       60
acacugccuu cauuacuuca guug                                             84

<210> SEQ ID NO 238
<211> LENGTH: 75
<212> TYPE: RNA
<213> ORGANISM: Homo sapiens

<400> SEQUENCE: 238
ggcugugccg gguagagagg gcagugggag guaagagcuc uucacccuuc accaccuucu      60
ccacccagca uggcc                                                       75

<210> SEQ ID NO 239
<211> LENGTH: 60
<212> TYPE: RNA
<213> ORGANISM: Homo sapiens

<400> SEQUENCE: 239
gugcaugugu auguaugugu gcaugugcau guguaugugu augagugcau gcgugugugc      60

<210> SEQ ID NO 240
<211> LENGTH: 62
<212> TYPE: RNA
<213> ORGANISM: Homo sapiens

<400> SEQUENCE: 240
ucauuggucc agagggggaga uagguuccug ugauuuuucc uucuucucua uagaauaaau     60
ga                                                                     62

<210> SEQ ID NO 241
<211> LENGTH: 71
<212> TYPE: RNA
<213> ORGANISM: Homo sapiens

<400> SEQUENCE: 241
gccaacccag uguucagacu accuguucag gaggcucuca augugacag uagucugcac      60
```

```
auugguuagg c                                                 71

<210> SEQ ID NO 242
<211> LENGTH: 110
<212> TYPE: RNA
<213> ORGANISM: Homo sapiens

<400> SEQUENCE: 242
aggaagcuuc uggagauccu gcuccgucgc cccaguguuc agacuaccug uucaggacaa    60
ugccguugua caguagucug cacauugguu agacugggca agggagagca              110

<210> SEQ ID NO 243
<211> LENGTH: 110
<212> TYPE: RNA
<213> ORGANISM: Homo sapiens

<400> SEQUENCE: 243
ccagaggaca ccuccacucc gucuacccag uguuuagacu aucguucag gacucccaaa    60 uuguacagua gucugcacau ugguuaggcu gggcuggguu agacccucgg              110

<210> SEQ ID NO 244
<211> LENGTH: 71
<212> TYPE: RNA
<213> ORGANISM: Homo sapiens

<400> SEQUENCE: 244
gccaacccag uguucagacu accuguucag gaggcucuca auguguacag uagucugcac    60
auugguuagg c                                                 71

<210> SEQ ID NO 245
<211> LENGTH: 70
<212> TYPE: RNA
<213> ORGANISM: Homo sapiens

<400> SEQUENCE: 245
gccguggcca ucuuacuggg cagcauugga uggagucagg ucucuaauac ugccgguaa    60 ugaugacggc                                                   70

<210> SEQ ID NO 246
<211> LENGTH: 95
<212> TYPE: RNA
<213> ORGANISM: Homo sapiens

<400> SEQUENCE: 246
ccagcucggg cagccguggc caucuuacug ggcagcauug gauggaguca ggucucuaau    60
acugccuggu aaugaugacg gcggagcccu gcacg                       95

<210> SEQ ID NO 247
<211> LENGTH: 68
<212> TYPE: RNA
<213> ORGANISM: Homo sapiens

<400> SEQUENCE: 247
cccucgucuu acccagcagu guugggugc gguuggagu cucuaauacu gccgg guaau   60 gauggagg                                                     68

<210> SEQ ID NO 248
<211> LENGTH: 72
<212> TYPE: RNA
<213> ORGANISM: Homo sapiens
```

<400> SEQUENCE: 248
guuccuuuuu ccuaugcaua uacuucuuug aggaucuggc cuaaagaggu auagggcaug    60
ggaagaugga gc    72

<210> SEQ ID NO 249
<211> LENGTH: 110
<212> TYPE: RNA
<213> ORGANISM: Homo sapiens

<400> SEQUENCE: 249
guguugggga cucgcgcgcu ggguccagug guucuuaaca guucaacagu ucguagcgc    60 aauugugaaa uguuuaggac cacuagaccc ggcgggcgcg gcgacagcga    110

<210> SEQ ID NO 250
<211> LENGTH: 110
<212> TYPE: RNA
<213> ORGANISM: Homo sapiens

<400> SEQUENCE: 250
ggcuacaguc uuucuucaug ugacucgugg acuucccuuu gucauccuau gccugagaau    60
auaugaagga ggcugggaag gcaaagggac guucaauugu caucacuggc    110

<210> SEQ ID NO 251
<211> LENGTH: 110
<212> TYPE: RNA
<213> ORGANISM: Homo sapiens

<400> SEQUENCE: 251
aaagauccuc agacaaucca ugugcuucuc uugccuuuca uuccaccgga gucugucuca    60
uacccaacca gauuucagug gagugaaguu caggaggcau ggagcugaca    110

<210> SEQ ID NO 252
<211> LENGTH: 86
<212> TYPE: RNA
<213> ORGANISM: Homo sapiens

<400> SEQUENCE: 252
ugcuucccga ggccacaugc uucuuuauau ccccauaugg auuacuuugc uauggaaugu    60
aaggaagugu gugguuucgg caagug    86

<210> SEQ ID NO 253
<211> LENGTH: 69
<212> TYPE: RNA
<213> ORGANISM: Homo sapiens

<400> SEQUENCE: 253
aggccacaug cuucuuuaua uccccauaug gauuacuuug cuauggaaug uaaggaagug    60
ugugguuuu    69

<210> SEQ ID NO 254
<211> LENGTH: 71
<212> TYPE: RNA
<213> ORGANISM: Homo sapiens

<400> SEQUENCE: 254
ugacgggcga gcuuuuggcc cggguuauac cugaugcuca cguauaagac gagcaaaaag    60
cuuguugguc a    71

<210> SEQ ID NO 255

```
<211> LENGTH: 110
<212> TYPE: RNA
<213> ORGANISM: Homo sapiens

<400> SEQUENCE: 255
acccggcagu gccuccaggc gcagggcagc cccugcccac cgcacacugc gcugcccag      60 acccacugug cgugugacag cggcugaucu gugccugggc agcgcgaccc               110

<210> SEQ ID NO 256
<211> LENGTH: 110
<212> TYPE: RNA
<213> ORGANISM: Homo sapiens

<400> SEQUENCE: 256
ucaccuggcc augugacuug ugggcuuccc uuugucaucc uucgccuagg gcucugagca     60
gggcagggac agcaaagggg ugcucaguug ucacuuccca cagcacggag              110

<210> SEQ ID NO 257
<211> LENGTH: 110
<212> TYPE: RNA
<213> ORGANISM: Homo sapiens

<400> SEQUENCE: 257
cggggcaccc cgcccggaca gcgcgccggc accuuggcuc uagacugcuu acugcccggg    60
ccgcccucag uaacagucuc cagucacggc caccgacgcc uggccccgcc              110

<210> SEQ ID NO 258
<211> LENGTH: 110
<212> TYPE: RNA
<213> ORGANISM: Homo sapiens

<400> SEQUENCE: 258
ccugugcaga gauuauuuuu uaaaagguca caaucaacau ucauugcugu cgguggguug    60
aacugugugg acaagcucac ugaacaauga augcaacugu ggccccgcuu              110

<210> SEQ ID NO 259
<211> LENGTH: 108
<212> TYPE: RNA
<213> ORGANISM: Homo sapiens

<400> SEQUENCE: 259
gaguuuugag guugcuucag ugaacauuca acgcugucgg ugaguuugga auuaaaauca    60
aaaccaucga ccguugauug uacccuaugg cuaaccauca ucuacucc                108

<210> SEQ ID NO 260
<211> LENGTH: 110
<212> TYPE: RNA
<213> ORGANISM: Homo sapiens

<400> SEQUENCE: 260
ggccuggcug gacagaguug ucaugugucu gccugucuac acuugcugug cagaacaucc    60
gcucaccugu acagcaggca cagacaggca gucacaugac aacccagccu              110

<210> SEQ ID NO 261
<211> LENGTH: 110
<212> TYPE: RNA
<213> ORGANISM: Homo sapiens

<400> SEQUENCE: 261
aucauucaga aauggauauac aggaaaauga ccuaugaauu gacagacaau auagcugagu   60
```

| | |
|---|---|
| uugucuguca uuucuuuagg ccaauauucu guaugacugu gcuacuucaa | 110 |

<210> SEQ ID NO 262
<211> LENGTH: 110
<212> TYPE: RNA
<213> ORGANISM: Homo sapiens

<400> SEQUENCE: 262

| | |
|---|---|
| gauggcugug aguuggcuua aucucagcug gcaacuguga gauguucaua caaucccuca | 60 |
| cagugguccuc ugggauuaug cuaaacagag caauuuccua gcccucacga | 110 |

<210> SEQ ID NO 263
<211> LENGTH: 110
<212> TYPE: RNA
<213> ORGANISM: Homo sapiens

<400> SEQUENCE: 263

| | |
|---|---|
| aguauaauua uuacauaguu uuugaugucg cagauacugc aucaggaacu gauuggauaa | 60 |
| gaaucaguca ccaucaguuc cuaaugcauu gccuucagca ucuaaacaag | 110 |

<210> SEQ ID NO 264
<211> LENGTH: 110
<212> TYPE: RNA
<213> ORGANISM: Homo sapiens

<400> SEQUENCE: 264

| | |
|---|---|
| gugauaaugu agcgagauuu ucuguugugc uugaucuaac caugugguug cgagguauga | 60 |
| guaaaacaug guuccgucaa gcaccaugga acgucacgca gcuuucuaca | 110 |

<210> SEQ ID NO 265
<211> LENGTH: 110
<212> TYPE: RNA
<213> ORGANISM: Homo sapiens

<400> SEQUENCE: 265

| | |
|---|---|
| gaccagucgc ugcggggcuu uccuuugugc uugaucuaac cauguggugg aacgauggaa | 60 |
| acggaacaug guucugucaa gcaccgcgga aagcaccgug cucuccugca | 110 |

<210> SEQ ID NO 266
<211> LENGTH: 110
<212> TYPE: RNA
<213> ORGANISM: Homo sapiens

<400> SEQUENCE: 266

| | |
|---|---|
| ccgccccggg ccgcggcucc ugauugucca aacgcaauuc ucgagucuau ggcuccggcc | 60 |
| gagaguugag ucuggacguc ccgagccgcc gcccccaaac cucgagcggg | 110 |

<210> SEQ ID NO 267
<211> LENGTH: 110
<212> TYPE: RNA
<213> ORGANISM: Homo sapiens

<400> SEQUENCE: 267

| | |
|---|---|
| ccgccccggg ccgcggcucc ugauugucca aacgcaauuc ucgagucuau ggcuccggcc | 60 |
| gagaguugag ucuggacguc ccgagccgcc gcccccaaac cucgagcggg | 110 |

<210> SEQ ID NO 268
<211> LENGTH: 97
<212> TYPE: RNA
<213> ORGANISM: Homo sapiens

<400> SEQUENCE: 268

| acucaggggc uucgccacug auuguccaaa cgcaauucuu guacgagucu gcggccaacc | 60 |
| gagaauugug gcuggacauc uguggcugag cuccggg | 97 |

<210> SEQ ID NO 269
<211> LENGTH: 110
<212> TYPE: RNA
<213> ORGANISM: Homo sapiens

<400> SEQUENCE: 269

| gacagugugg cauguagggg ucccacaccg uaucugacac uuugggcgag ggcaccaugc | 60 |
| ugaaggguguu caugaugcgg ucugggaacu ccucacggau cuuacugaug | 110 |

<210> SEQ ID NO 270
<211> LENGTH: 110
<212> TYPE: RNA
<213> ORGANISM: Homo sapiens

<400> SEQUENCE: 270

| ugaacaucca ggucuggggc augaaccugg cauacaaugu agauuucugu guucguuagg | 60 |
| caacagcuac auugucugcu ggguuucagg cuaccuggaa acauguucuc | 110 |

<210> SEQ ID NO 271
<211> LENGTH: 110
<212> TYPE: RNA
<213> ORGANISM: Homo sapiens

<400> SEQUENCE: 271

| gcugcuggaa gguguaggua cccucaaugg cucaguagcc agguguagauc cugucuuucg | 60 |
| uaaucagcag cuacaucugg cuacggguc ucugauggca ucuucuagcu | 110 |

<210> SEQ ID NO 272
<211> LENGTH: 110
<212> TYPE: RNA
<213> ORGANISM: Homo sapiens

<400> SEQUENCE: 272

| ccuggccucc ugcagugcca cgcuccgugu auuugacaag cugaguugga cacuccaugu | 60 |
| gguagagugu caguuuguca aauacccccaa gugcggcaca ugcuuaccag | 110 |

<210> SEQ ID NO 273
<211> LENGTH: 81
<212> TYPE: RNA
<213> ORGANISM: Homo sapiens

<400> SEQUENCE: 273

| gggcuuucaa gucacuagug guuccguuua guagaugauu gugcauuguu ucaaaauggu | 60 |
| gcccuaguga cuacaaagcc c | 81 |

<210> SEQ ID NO 274
<211> LENGTH: 60
<212> TYPE: RNA
<213> ORGANISM: Homo sapiens

<400> SEQUENCE: 274

| caaucuuccu uuaucauggu auugauuuuu cagugcuucc cuuugugug agagaagaua | 60 |

<210> SEQ ID NO 275
<211> LENGTH: 80
<212> TYPE: RNA

-continued

<213> ORGANISM: Homo sapiens

<400> SEQUENCE: 275
aggacccuuc cagagggccc ccccucaauc cuguugugcc uaauucagag gguugggugg    60
aggcucuccu gaagggcucu                                                80

<210> SEQ ID NO 276
<211> LENGTH: 63
<212> TYPE: RNA
<213> ORGANISM: Homo sapiens

<400> SEQUENCE: 276
aagaaauggu uuaccguccc acauacauuu ugaauaugua ugugggaugg uaaaccgcuu    60
cuu                                                                  63

<210> SEQ ID NO 277
<211> LENGTH: 86
<212> TYPE: RNA
<213> ORGANISM: Homo sapiens

<400> SEQUENCE: 277
acugcuaacg aaugcucuga cuuuauugca cuacuguacu uuacagcuag cagugcaaua    60
guauugucaa agcaucugaa agcagg                                         86

<210> SEQ ID NO 278
<211> LENGTH: 69
<212> TYPE: RNA
<213> ORGANISM: Homo sapiens

<400> SEQUENCE: 278
ccaccacuua aacguggaug uacuugcuuu gaaacuaaag aaguaagugc uuccauguuu    60
uggugaugg                                                            69

<210> SEQ ID NO 279
<211> LENGTH: 73
<212> TYPE: RNA
<213> ORGANISM: Homo sapiens

<400> SEQUENCE: 279
gcucccuuca acuuuaacau ggaagugcuu ucugugacuu uaaaaguaag ugcuuccaug    60
uuuuaguagg agu                                                       73

<210> SEQ ID NO 280
<211> LENGTH: 68
<212> TYPE: RNA
<213> ORGANISM: Homo sapiens

<400> SEQUENCE: 280
ccuuugcuuu aacauggggg uaccugcugu gugaaacaaa aguaagugcu uccauguuuc    60
aguggagg                                                             68

<210> SEQ ID NO 281
<211> LENGTH: 68
<212> TYPE: RNA
<213> ORGANISM: Homo sapiens

<400> SEQUENCE: 281
ccucuacuuu aacauggagg cacuugcugu gacaugacaa aaauaagugc uuccauguuu    60
gagugugg                                                             68

-continued

```
<210> SEQ ID NO 282
<211> LENGTH: 82
<212> TYPE: RNA
<213> ORGANISM: Homo sapiens

<400> SEQUENCE: 282
gcuucgcucc ccuccgccuu cucuucccgg uucuucccgg agucgggaaa agcuggguug      60
agagggcgaa aaaggaugag gu                                              82

<210> SEQ ID NO 283
<211> LENGTH: 59
<212> TYPE: RNA
<213> ORGANISM: Homo sapiens

<400> SEQUENCE: 283
uuggccuccu aagccaggga uguggguuc gaguccacc cggggua aag aaaggccga       59

<210> SEQ ID NO 284
<211> LENGTH: 86
<212> TYPE: RNA
<213> ORGANISM: Homo sapiens

<400> SEQUENCE: 284
uugguacuug gagagaggug guccguggcg cguucgcuuu auuuauggcg cacauuacac      60
ggucgaccuc uuugcaguau cuaauc                                          86

<210> SEQ ID NO 285
<211> LENGTH: 83
<212> TYPE: RNA
<213> ORGANISM: Homo sapiens

<400> SEQUENCE: 285
cugacuaugc cuccccgcau ccccuagggc auuggguaa agcuggagac ccacugcccc      60
aggugcugcu ggggguugua guc                                             83

<210> SEQ ID NO 286
<211> LENGTH: 98
<212> TYPE: RNA
<213> ORGANISM: Homo sapiens

<400> SEQUENCE: 286
auacagugcu ugguuccuag uaggugucca guaagugu uu ugacauaau uuguuuauug      60 aggaccuccu aucaaucaag cacugugcua ggcucugg                             98

<210> SEQ ID NO 287
<211> LENGTH: 95
<212> TYPE: RNA
<213> ORGANISM: Homo sapiens

<400> SEQUENCE: 287
cucaucuguc uguugggcug gaggcagggc cuuugugaag gcgguggug cucagaucgc      60 cucugggccc uuccuccagc cccgaggcgg auuca                                95

<210> SEQ ID NO 288
<211> LENGTH: 75
<212> TYPE: RNA
<213> ORGANISM: Homo sapiens

<400> SEQUENCE: 288
uggagugggg gggcaggagg ggcucaggga gaaagugcau acagcccug gcccucucug      60
```

```
cccuuccguc cccug                                                       75

<210> SEQ ID NO 289
<211> LENGTH: 94
<212> TYPE: RNA
<213> ORGANISM: Homo sapiens

<400> SEQUENCE: 289
cuuuggcgau cacugccucu cugggccugu gucuuaggcu cugcaagauc aaccgagcaa      60
agcacacggc cugcagagag gcagcgcucu gccc                                  94

<210> SEQ ID NO 290
<211> LENGTH: 94
<212> TYPE: RNA
<213> ORGANISM: Homo sapiens

<400> SEQUENCE: 290
gaguuugguu uuguuggggu uuguucuagg uaugguccca gggaucccag aucaaaccag      60
gccccugggc cuauccuaga accaaccuaa gcuc                                  94

<210> SEQ ID NO 291
<211> LENGTH: 94
<212> TYPE: RNA
<213> ORGANISM: Homo sapiens

<400> SEQUENCE: 291
uguuuugagc gggggucaag agcaauaacg aaaaauguuu gucauaaacc guuuucauu       60 auugcuccug accuccucuc auuugcuaua uuca                                  94

<210> SEQ ID NO 292
<211> LENGTH: 93
<212> TYPE: RNA
<213> ORGANISM: Homo sapiens

<400> SEQUENCE: 292
guagucagua guugggggu gggaacggcu ucauacagga guugaugcac aguuauccag       60
cuccuauaug augccuuucu ucauccccuu caa                                   93

<210> SEQ ID NO 293
<211> LENGTH: 67
<212> TYPE: RNA
<213> ORGANISM: Homo sapiens

<400> SEQUENCE: 293
ucuccaacaa uauccuggug cugagugaug acucaggcga cuccagcauc agugauuuug      60
uugaaga                                                                67

<210> SEQ ID NO 294
<211> LENGTH: 94
<212> TYPE: RNA
<213> ORGANISM: Homo sapiens

<400> SEQUENCE: 294
cggggcggcc gcucucccug uccuccagga gcucacugu gccugccugu gagcgccucg       60
acgacagagc cggcgccugc cccagugucu gcgc                                  94

<210> SEQ ID NO 295
<211> LENGTH: 95
<212> TYPE: RNA
<213> ORGANISM: Homo sapiens
```

```
<400> SEQUENCE: 295
uuguaccugg ugugauuaua aagcaaugag acugauuguc auaugucguu ugugggaucc    60
gucucaguua cuuuauagcc auaccuggua ucuua                              95

<210> SEQ ID NO 296
<211> LENGTH: 99
<212> TYPE: RNA
<213> ORGANISM: Homo sapiens

<400> SEQUENCE: 296
gaaacugggc ucaaggugag gggugcuauc ugugauugag ggacaugguu aauggaauug    60
ucucacacag aaaucgcacc cgucaccuug gccuacuua                          99

<210> SEQ ID NO 297
<211> LENGTH: 98
<212> TYPE: RNA
<213> ORGANISM: Homo sapiens

<400> SEQUENCE: 297
acccaaaccc uaggucugcu gacuccuagu ccagggcucg ugauggcugg ugggcccuga    60
acgagggguc uggaggccug gguugaauua ucgacagc                           98

<210> SEQ ID NO 298
<211> LENGTH: 86
<212> TYPE: RNA
<213> ORGANISM: Homo sapiens

<400> SEQUENCE: 298
gucugucugc ccgcaugccu gccucucugu ugcucugaag gaggcagggg cugggccugc    60
agcugccugg gcagagcggc uccugc                                        86

<210> SEQ ID NO 299
<211> LENGTH: 68
<212> TYPE: RNA
<213> ORGANISM: Homo sapiens

<400> SEQUENCE: 299
ccauuacugu ugcuaauaug caacucuguu gaauauaaau uggaauugca cuuuagcaau    60
ggugaugg                                                            68

<210> SEQ ID NO 300
<211> LENGTH: 66
<212> TYPE: RNA
<213> ORGANISM: Homo sapiens

<400> SEQUENCE: 300
aaaaggugga uauuccuucu auguuuaugu uauuuauggu uaaacauaga ggaaauucca    60
cguuuu                                                              66

<210> SEQ ID NO 301
<211> LENGTH: 70
<212> TYPE: RNA
<213> ORGANISM: Homo sapiens

<400> SEQUENCE: 301
uugaagggag aucgaccgug uuauauucgc uuuauugacu ucgauaauaa cauggugau    60 cuuuucucag                                                          70

<210> SEQ ID NO 302
```

```
<211> LENGTH: 75
<212> TYPE: RNA
<213> ORGANISM: Homo sapiens

<400> SEQUENCE: 302
agacagagaa gccaggucac gucucugcag uuacacagcu cacgagugcc ugcuggggug    60
gaaccugguc ugucu                                                    75

<210> SEQ ID NO 303
<211> LENGTH: 67
<212> TYPE: RNA
<213> ORGANISM: Homo sapiens

<400> SEQUENCE: 303
guggcacuca aacugugggg gcacuuucug cucucuggug aaagugccgc caucuuuuga    60
guguuac                                                             67

<210> SEQ ID NO 304
<211> LENGTH: 67
<212> TYPE: RNA
<213> ORGANISM: Homo sapiens

<400> SEQUENCE: 304
gugggccuca aauguggagc acuauucuga uguccaagug gaaagugcug cgacauuuga    60
gcgucac                                                             67

<210> SEQ ID NO 305
<211> LENGTH: 69
<212> TYPE: RNA
<213> ORGANISM: Homo sapiens

<400> SEQUENCE: 305
gggauacuca aaauggggc gcuuccuuu uugucuguac ugggaagugc uucgauuuug     60
ggugucccc                                                           69

<210> SEQ ID NO 306
<211> LENGTH: 72
<212> TYPE: RNA
<213> ORGANISM: Homo sapiens

<400> SEQUENCE: 306
uacaucggcc auuauaauac aaccugauaa guguuauagc acuuaucaga uuguauugua    60
auugucugug ua                                                       72

<210> SEQ ID NO 307
<211> LENGTH: 102
<212> TYPE: RNA
<213> ORGANISM: Homo sapiens

<400> SEQUENCE: 307
auggagcugc ucacccugug ggccucaaau guggaggaac uauucugaug uccaagugga    60
aagugcugcg acauuugagc gucaccggug acgcccauau ca                     102

<210> SEQ ID NO 308
<211> LENGTH: 101
<212> TYPE: RNA
<213> ORGANISM: Homo sapiens

<400> SEQUENCE: 308 gcaucccuc agccguggc acucaaacug uggggcacu uucugcucuc uggugaaagu     60
```

```
gccgccaucu uuugagguguu accgcuugag aagacucaac c                    101
```

<210> SEQ ID NO 309
<211> LENGTH: 102
<212> TYPE: RNA
<213> ORGANISM: Homo sapiens

<400> SEQUENCE: 309

```
cgaggagcuc auacugggau acucaaaaug ggggcgcuuu ccuuuuuguc uguuacuggg    60
aagugcuucg auuuuggggu gucccuguuu gaguagggca uc                     102
```

<210> SEQ ID NO 310
<211> LENGTH: 22
<212> TYPE: RNA
<213> ORGANISM: Homo sapiens

<400> SEQUENCE: 310

```
ugagguagua gguuguauag uu                                           22
```

<210> SEQ ID NO 311
<211> LENGTH: 22
<212> TYPE: RNA
<213> ORGANISM: Homo sapiens

<400> SEQUENCE: 311

```
ugagguagua gguugugugg uu                                           22
```

<210> SEQ ID NO 312
<211> LENGTH: 22
<212> TYPE: RNA
<213> ORGANISM: Homo sapiens

<400> SEQUENCE: 312

```
ugagguagua gguuguaugg uu                                           22
```

<210> SEQ ID NO 313
<211> LENGTH: 21
<212> TYPE: RNA
<213> ORGANISM: Homo sapiens

<400> SEQUENCE: 313

```
agagguagua gguugcauag u                                            21
```

<210> SEQ ID NO 314
<211> LENGTH: 21
<212> TYPE: RNA
<213> ORGANISM: Homo sapiens

<400> SEQUENCE: 314

```
ugagguagga gguuguauag u                                            21
```

<210> SEQ ID NO 315
<211> LENGTH: 22
<212> TYPE: RNA
<213> ORGANISM: Homo sapiens

<400> SEQUENCE: 315

```
ugagguagua gauuguauag uu                                           22
```

<210> SEQ ID NO 316
<211> LENGTH: 21
<212> TYPE: RNA
<213> ORGANISM: Homo sapiens

```
<400> SEQUENCE: 316
ugagguagua guuuguacag u                                              21

<210> SEQ ID NO 317
<211> LENGTH: 19
<212> TYPE: RNA
<213> ORGANISM: Homo sapiens

<400> SEQUENCE: 317
ugagguagua guuugugcu                                                 19

<210> SEQ ID NO 318
<211> LENGTH: 21
<212> TYPE: RNA
<213> ORGANISM: Homo sapiens

<400> SEQUENCE: 318
uggaauguaa agaaguaugu a                                              21

<210> SEQ ID NO 319
<211> LENGTH: 21
<212> TYPE: RNA
<213> ORGANISM: Homo sapiens

<400> SEQUENCE: 319
uggaagacua gugauuuugu u                                              21

<210> SEQ ID NO 320
<211> LENGTH: 23
<212> TYPE: RNA
<213> ORGANISM: Homo sapiens

<400> SEQUENCE: 320
ucuuugguua ucuagcugua uga                                            23

<210> SEQ ID NO 321
<211> LENGTH: 21
<212> TYPE: RNA
<213> ORGANISM: Homo sapiens

<400> SEQUENCE: 321
uaaagcuaga uaaccgaaag u                                              21

<210> SEQ ID NO 322
<211> LENGTH: 23
<212> TYPE: RNA
<213> ORGANISM: Homo sapiens

<400> SEQUENCE: 322
uacccuguag auccgaauuu gug                                            23

<210> SEQ ID NO 323
<211> LENGTH: 22
<212> TYPE: RNA
<213> ORGANISM: Homo sapiens

<400> SEQUENCE: 323
uacccuguag aaccgaauuu gu                                             22

<210> SEQ ID NO 324
<211> LENGTH: 22
<212> TYPE: RNA
<213> ORGANISM: Homo sapiens
```

-continued

```
<400> SEQUENCE: 324
uagcagcaca uaauguuug ug                                              22

<210> SEQ ID NO 325
<211> LENGTH: 22
<212> TYPE: RNA
<213> ORGANISM: Homo sapiens

<400> SEQUENCE: 325
uagcagcaca ucauguuua ca                                              22

<210> SEQ ID NO 326
<211> LENGTH: 22
<212> TYPE: RNA
<213> ORGANISM: Homo sapiens

<400> SEQUENCE: 326
uagcagcacg uaaauauugg cg                                             22

<210> SEQ ID NO 327
<211> LENGTH: 24
<212> TYPE: RNA
<213> ORGANISM: Homo sapiens

<400> SEQUENCE: 327
caaagugcuu acagugcagg uagu                                           24

<210> SEQ ID NO 328
<211> LENGTH: 20
<212> TYPE: RNA
<213> ORGANISM: Homo sapiens

<400> SEQUENCE: 328
acugcaguga aggcacuugu                                                20

<210> SEQ ID NO 329
<211> LENGTH: 22
<212> TYPE: RNA
<213> ORGANISM: Homo sapiens

<400> SEQUENCE: 329
uaaggugcau cuagugcaga ua                                             22

<210> SEQ ID NO 330
<211> LENGTH: 23
<212> TYPE: RNA
<213> ORGANISM: Homo sapiens

<400> SEQUENCE: 330
ugugcaaauc uaugcaaaac uga                                            23

<210> SEQ ID NO 331
<211> LENGTH: 23
<212> TYPE: RNA
<213> ORGANISM: Homo sapiens

<400> SEQUENCE: 331
ugugcaaauc caugcaaaac uga                                            23

<210> SEQ ID NO 332
<211> LENGTH: 22
<212> TYPE: RNA
<213> ORGANISM: Homo sapiens
```

```
<400> SEQUENCE: 332
uaaagugcuu auagugcagg ua                                              22

<210> SEQ ID NO 333
<211> LENGTH: 22
<212> TYPE: RNA
<213> ORGANISM: Homo sapiens

<400> SEQUENCE: 333
uagcuuauca gacugauguu ga                                              22

<210> SEQ ID NO 334
<211> LENGTH: 22
<212> TYPE: RNA
<213> ORGANISM: Homo sapiens

<400> SEQUENCE: 334
aagcugccag uugaagaacu gu                                              22

<210> SEQ ID NO 335
<211> LENGTH: 21
<212> TYPE: RNA
<213> ORGANISM: Homo sapiens

<400> SEQUENCE: 335
aucacauugc cagggauuuc c                                               21

<210> SEQ ID NO 336
<211> LENGTH: 23
<212> TYPE: RNA
<213> ORGANISM: Homo sapiens

<400> SEQUENCE: 336
aucacauugc cagggauuac cac                                             23

<210> SEQ ID NO 337
<211> LENGTH: 22
<212> TYPE: RNA
<213> ORGANISM: Homo sapiens

<400> SEQUENCE: 337
uggcucaguu cagcaggaac ag                                              22

<210> SEQ ID NO 338
<211> LENGTH: 22
<212> TYPE: RNA
<213> ORGANISM: Homo sapiens

<400> SEQUENCE: 338
cauugcacuu gucucggucu ga                                              22

<210> SEQ ID NO 339
<211> LENGTH: 22
<212> TYPE: RNA
<213> ORGANISM: Homo sapiens

<400> SEQUENCE: 339
uucaaguaau ccaggauagg cu                                              22

<210> SEQ ID NO 340
<211> LENGTH: 21
<212> TYPE: RNA
<213> ORGANISM: Homo sapiens
```

-continued

<400> SEQUENCE: 340
uucaaguaau ucaggauagg u                                           21

<210> SEQ ID NO 341
<211> LENGTH: 22
<212> TYPE: RNA
<213> ORGANISM: Homo sapiens

<400> SEQUENCE: 341
uucacagugg cuaaguuccg cc                                          22

<210> SEQ ID NO 342
<211> LENGTH: 20
<212> TYPE: RNA
<213> ORGANISM: Homo sapiens

<400> SEQUENCE: 342
uucacagugg cuaaguucug                                             20

<210> SEQ ID NO 343
<211> LENGTH: 22
<212> TYPE: RNA
<213> ORGANISM: Homo sapiens

<400> SEQUENCE: 343
aaggagcuca cagucuauug ag                                          22

<210> SEQ ID NO 344
<211> LENGTH: 22
<212> TYPE: RNA
<213> ORGANISM: Homo sapiens

<400> SEQUENCE: 344
cuagcaccau cugaaaucgg uu                                          22

<210> SEQ ID NO 345
<211> LENGTH: 20
<212> TYPE: RNA
<213> ORGANISM: Homo sapiens

<400> SEQUENCE: 345
uagcaccauu ugaaaucagu                                             20

<210> SEQ ID NO 346
<211> LENGTH: 22
<212> TYPE: RNA
<213> ORGANISM: Homo sapiens

<400> SEQUENCE: 346
uagcaccauu ugaaaucggu ua                                          22

<210> SEQ ID NO 347
<211> LENGTH: 23
<212> TYPE: RNA
<213> ORGANISM: Homo sapiens

<400> SEQUENCE: 347
uguaaacauc cucgacugga agc                                         23

<210> SEQ ID NO 348
<211> LENGTH: 22
<212> TYPE: RNA
<213> ORGANISM: Homo sapiens

```
<400> SEQUENCE: 348
cuuucagucg gauguuugca gc                                        22

<210> SEQ ID NO 349
<211> LENGTH: 21
<212> TYPE: RNA
<213> ORGANISM: Homo sapiens

<400> SEQUENCE: 349
uguaaacauc cuacacucag c                                         21

<210> SEQ ID NO 350
<211> LENGTH: 23
<212> TYPE: RNA
<213> ORGANISM: Homo sapiens

<400> SEQUENCE: 350
uguaaacauc cuacacucuc agc                                       23

<210> SEQ ID NO 351
<211> LENGTH: 22
<212> TYPE: RNA
<213> ORGANISM: Homo sapiens

<400> SEQUENCE: 351
uguaaacauc cccgacugga ag                                        22

<210> SEQ ID NO 352
<211> LENGTH: 20
<212> TYPE: RNA
<213> ORGANISM: Homo sapiens

<400> SEQUENCE: 352
uguaaacauc cuugacugga                                           20

<210> SEQ ID NO 353
<211> LENGTH: 21
<212> TYPE: RNA
<213> ORGANISM: Homo sapiens

<400> SEQUENCE: 353
ggcaagaugc uggcauagcu g                                         21

<210> SEQ ID NO 354
<211> LENGTH: 21
<212> TYPE: RNA
<213> ORGANISM: Homo sapiens

<400> SEQUENCE: 354
uauugcacau uacuaaguug c                                         21

<210> SEQ ID NO 355
<211> LENGTH: 19
<212> TYPE: RNA
<213> ORGANISM: Homo sapiens

<400> SEQUENCE: 355
gugcauugua guugcauug                                            19

<210> SEQ ID NO 356
<211> LENGTH: 22
<212> TYPE: RNA
<213> ORGANISM: Homo sapiens
```

```
<400> SEQUENCE: 356
uggcaguguc uuagcugguu gu                                             22

<210> SEQ ID NO 357
<211> LENGTH: 22
<212> TYPE: RNA
<213> ORGANISM: Homo sapiens

<400> SEQUENCE: 357
aggcaguguc auuagcugau ug                                             22

<210> SEQ ID NO 358
<211> LENGTH: 22
<212> TYPE: RNA
<213> ORGANISM: Homo sapiens

<400> SEQUENCE: 358
aggcagugua guuagcugau ug                                             22

<210> SEQ ID NO 359
<211> LENGTH: 22
<212> TYPE: RNA
<213> ORGANISM: Homo sapiens

<400> SEQUENCE: 359
uauugcacuu gucccggccu gu                                             22

<210> SEQ ID NO 360
<211> LENGTH: 22
<212> TYPE: RNA
<213> ORGANISM: Homo sapiens

<400> SEQUENCE: 360
aaagugcugu ucgugcaggu ag                                             22

<210> SEQ ID NO 361
<211> LENGTH: 22
<212> TYPE: RNA
<213> ORGANISM: Homo sapiens

<400> SEQUENCE: 361
uucaacgggu auuuauugag ca                                             22

<210> SEQ ID NO 362
<211> LENGTH: 22
<212> TYPE: RNA
<213> ORGANISM: Homo sapiens

<400> SEQUENCE: 362
uuuggcacua gcacauuuuu gc                                             22

<210> SEQ ID NO 363
<211> LENGTH: 22
<212> TYPE: RNA
<213> ORGANISM: Homo sapiens

<400> SEQUENCE: 363
ugagguagua aguuguauug uu                                             22

<210> SEQ ID NO 364
<211> LENGTH: 22
<212> TYPE: RNA
<213> ORGANISM: Homo sapiens
```

```
<400> SEQUENCE: 364
aacccguaga uccgaucuug ug                                              22

<210> SEQ ID NO 365
<211> LENGTH: 22
<212> TYPE: RNA
<213> ORGANISM: Homo sapiens

<400> SEQUENCE: 365
cacccguaga accgaccuug cg                                              22

<210> SEQ ID NO 366
<211> LENGTH: 22
<212> TYPE: RNA
<213> ORGANISM: Homo sapiens

<400> SEQUENCE: 366
uacaguacug ugauaacuga ag                                              22

<210> SEQ ID NO 367
<211> LENGTH: 22
<212> TYPE: RNA
<213> ORGANISM: Homo sapiens

<400> SEQUENCE: 367
uacaguacug ugauaacuga ag                                              22

<210> SEQ ID NO 368
<211> LENGTH: 23
<212> TYPE: RNA
<213> ORGANISM: Homo sapiens

<400> SEQUENCE: 368
agcagcauug uacagggcua uga                                             23

<210> SEQ ID NO 369
<211> LENGTH: 20
<212> TYPE: RNA
<213> ORGANISM: Homo sapiens

<400> SEQUENCE: 369
ucaaaugcuc agacccugu                                                  20

<210> SEQ ID NO 370
<211> LENGTH: 24
<212> TYPE: RNA
<213> ORGANISM: Homo sapiens

<400> SEQUENCE: 370
aaaagugcuu acagugcagg uagc                                            24

<210> SEQ ID NO 371
<211> LENGTH: 21
<212> TYPE: RNA
<213> ORGANISM: Homo sapiens

<400> SEQUENCE: 371
uaaagugcug acagugcaga u                                               21

<210> SEQ ID NO 372
<211> LENGTH: 23
<212> TYPE: RNA
<213> ORGANISM: Homo sapiens
```

-continued

<400> SEQUENCE: 372
agcagcauug uacagggcua uca                                      23

<210> SEQ ID NO 373
<211> LENGTH: 23
<212> TYPE: RNA
<213> ORGANISM: Homo sapiens

<400> SEQUENCE: 373
uggaguguga caauguguu ugu                                       23

<210> SEQ ID NO 374
<211> LENGTH: 22
<212> TYPE: RNA
<213> ORGANISM: Homo sapiens

<400> SEQUENCE: 374
uuaaggcacg cggugaaugc ca                                       22

<210> SEQ ID NO 375
<211> LENGTH: 23
<212> TYPE: RNA
<213> ORGANISM: Homo sapiens

<400> SEQUENCE: 375
ucccugagac ccuuuaaccu gug                                      23

<210> SEQ ID NO 376
<211> LENGTH: 22
<212> TYPE: RNA
<213> ORGANISM: Homo sapiens

<400> SEQUENCE: 376
ucccugagac ccuaacuugu ga                                       22

<210> SEQ ID NO 377
<211> LENGTH: 21
<212> TYPE: RNA
<213> ORGANISM: Homo sapiens

<400> SEQUENCE: 377
cauuauuacu uuggguacgc g                                        21

<210> SEQ ID NO 378
<211> LENGTH: 21
<212> TYPE: RNA
<213> ORGANISM: Homo sapiens

<400> SEQUENCE: 378
ucguaccgug aguaauaaug c                                        21

<210> SEQ ID NO 379
<211> LENGTH: 22
<212> TYPE: RNA
<213> ORGANISM: Homo sapiens

<400> SEQUENCE: 379
ucggauccgu cugagcuugg cu                                       22

<210> SEQ ID NO 380
<211> LENGTH: 22
<212> TYPE: RNA
<213> ORGANISM: Homo sapiens

```
<400> SEQUENCE: 380
ucacagugaa ccggucucuu uu                                         22

<210> SEQ ID NO 381
<211> LENGTH: 22
<212> TYPE: RNA
<213> ORGANISM: Homo sapiens

<400> SEQUENCE: 381
ucacagugaa ccggucucuu uc                                         22

<210> SEQ ID NO 382
<211> LENGTH: 21
<212> TYPE: RNA
<213> ORGANISM: Homo sapiens

<400> SEQUENCE: 382
cuuuuugcgg ucugggcuug c                                          21

<210> SEQ ID NO 383
<211> LENGTH: 20
<212> TYPE: RNA
<213> ORGANISM: Homo sapiens

<400> SEQUENCE: 383
cagugcaaug uuaaaagggc                                            20

<210> SEQ ID NO 384
<211> LENGTH: 22
<212> TYPE: RNA
<213> ORGANISM: Homo sapiens

<400> SEQUENCE: 384
cagugcaaug augaaagggc au                                         22

<210> SEQ ID NO 385
<211> LENGTH: 22
<212> TYPE: RNA
<213> ORGANISM: Homo sapiens

<400> SEQUENCE: 385
uaacagucua cagccauggu cg                                         22

<210> SEQ ID NO 386
<211> LENGTH: 22
<212> TYPE: RNA
<213> ORGANISM: Homo sapiens

<400> SEQUENCE: 386
uugguccccu ucaaccagcu gu                                         22

<210> SEQ ID NO 387
<211> LENGTH: 21
<212> TYPE: RNA
<213> ORGANISM: Homo sapiens

<400> SEQUENCE: 387
uugguccccu ucaaccagcu a                                          21

<210> SEQ ID NO 388
<211> LENGTH: 21
<212> TYPE: RNA
<213> ORGANISM: Homo sapiens
```

```
<400> SEQUENCE: 388
ugugacuggu ugaccagagg g                                     21

<210> SEQ ID NO 389
<211> LENGTH: 23
<212> TYPE: RNA
<213> ORGANISM: Homo sapiens

<400> SEQUENCE: 389
uauggcuuuu uauuccuaug uga                                   23

<210> SEQ ID NO 390
<211> LENGTH: 22
<212> TYPE: RNA
<213> ORGANISM: Homo sapiens

<400> SEQUENCE: 390
uauggcuuuu cauuccuaug ug                                    22

<210> SEQ ID NO 391
<211> LENGTH: 23
<212> TYPE: RNA
<213> ORGANISM: Homo sapiens

<400> SEQUENCE: 391
acuccauuug uuuugaugau gga                                   23

<210> SEQ ID NO 392
<211> LENGTH: 22
<212> TYPE: RNA
<213> ORGANISM: Homo sapiens

<400> SEQUENCE: 392
uauugcuuaa gaauacgcgu ag                                    22

<210> SEQ ID NO 393
<211> LENGTH: 17
<212> TYPE: RNA
<213> ORGANISM: Homo sapiens

<400> SEQUENCE: 393
agcugguguu gugaauc                                          17

<210> SEQ ID NO 394
<211> LENGTH: 18
<212> TYPE: RNA
<213> ORGANISM: Homo sapiens

<400> SEQUENCE: 394
ucuacagugc acgugucu                                         18

<210> SEQ ID NO 395
<211> LENGTH: 21
<212> TYPE: RNA
<213> ORGANISM: Homo sapiens

<400> SEQUENCE: 395
agugguuuua cccuauggua g                                     21

<210> SEQ ID NO 396
<211> LENGTH: 21
<212> TYPE: RNA
<213> ORGANISM: Homo sapiens
```

```
<400> SEQUENCE: 396
aacacugucu gguaaagaug g                                              21

<210> SEQ ID NO 397
<211> LENGTH: 23
<212> TYPE: RNA
<213> ORGANISM: Homo sapiens

<400> SEQUENCE: 397
uguaguguuu ccuacuuuau gga                                            23

<210> SEQ ID NO 398
<211> LENGTH: 20
<212> TYPE: RNA
<213> ORGANISM: Homo sapiens

<400> SEQUENCE: 398
cauaaaguag aaagcacuac                                                20

<210> SEQ ID NO 399
<211> LENGTH: 22
<212> TYPE: RNA
<213> ORGANISM: Homo sapiens

<400> SEQUENCE: 399
ugagaugaag cacuguagcu ca                                             22

<210> SEQ ID NO 400
<211> LENGTH: 22
<212> TYPE: RNA
<213> ORGANISM: Homo sapiens

<400> SEQUENCE: 400
uacaguauag augauguacu ag                                             22

<210> SEQ ID NO 401
<211> LENGTH: 24
<212> TYPE: RNA
<213> ORGANISM: Homo sapiens

<400> SEQUENCE: 401
guccaguuuu cccaggaauc ccuu                                           24

<210> SEQ ID NO 402
<211> LENGTH: 22
<212> TYPE: RNA
<213> ORGANISM: Homo sapiens

<400> SEQUENCE: 402
ugagaacuga auuccauggg uu                                             22

<210> SEQ ID NO 403
<211> LENGTH: 20
<212> TYPE: RNA
<213> ORGANISM: Homo sapiens

<400> SEQUENCE: 403
guguguggaa augcuucugc                                                20

<210> SEQ ID NO 404
<211> LENGTH: 22
<212> TYPE: RNA
<213> ORGANISM: Homo sapiens
```

```
<400> SEQUENCE: 404
ucagugcacu acagaacuuu gu                                        22

<210> SEQ ID NO 405
<211> LENGTH: 22
<212> TYPE: RNA
<213> ORGANISM: Homo sapiens

<400> SEQUENCE: 405
ucagugcauc acagaacuuu gu                                        22

<210> SEQ ID NO 406
<211> LENGTH: 22
<212> TYPE: RNA
<213> ORGANISM: Homo sapiens

<400> SEQUENCE: 406
ucuggcuccg ugucuucacu cc                                        22

<210> SEQ ID NO 407
<211> LENGTH: 22
<212> TYPE: RNA
<213> ORGANISM: Homo sapiens

<400> SEQUENCE: 407
ucucccaacc cuuguaccag ug                                        22

<210> SEQ ID NO 408
<211> LENGTH: 22
<212> TYPE: RNA
<213> ORGANISM: Homo sapiens

<400> SEQUENCE: 408
acuagacuga agcuccuuga gg                                        22

<210> SEQ ID NO 409
<211> LENGTH: 21
<212> TYPE: RNA
<213> ORGANISM: Homo sapiens

<400> SEQUENCE: 409
ucagugcaug acagaacuug g                                         21

<210> SEQ ID NO 410
<211> LENGTH: 20
<212> TYPE: RNA
<213> ORGANISM: Homo sapiens

<400> SEQUENCE: 410
uugcauaguc acaaaaguga                                           20

<210> SEQ ID NO 411
<211> LENGTH: 22
<212> TYPE: RNA
<213> ORGANISM: Homo sapiens

<400> SEQUENCE: 411
uagguuaucc guguugccuu cg                                        22

<210> SEQ ID NO 412
<211> LENGTH: 22
<212> TYPE: RNA
<213> ORGANISM: Homo sapiens
```

```
<400> SEQUENCE: 412
aaucauacac gguugaccua uu                                              22

<210> SEQ ID NO 413
<211> LENGTH: 22
<212> TYPE: RNA
<213> ORGANISM: Homo sapiens

<400> SEQUENCE: 413
uuaaugcuaa ucgugauagg gg                                              22

<210> SEQ ID NO 414
<211> LENGTH: 23
<212> TYPE: RNA
<213> ORGANISM: Homo sapiens

<400> SEQUENCE: 414
aacauucaac gcugucggug agu                                             23

<210> SEQ ID NO 415
<211> LENGTH: 24
<212> TYPE: RNA
<213> ORGANISM: Homo sapiens

<400> SEQUENCE: 415
aacauucauu gcugucggug gguu                                            24

<210> SEQ ID NO 416
<211> LENGTH: 22
<212> TYPE: RNA
<213> ORGANISM: Homo sapiens

<400> SEQUENCE: 416
aacauucaac cugucgguga gu                                              22

<210> SEQ ID NO 417
<211> LENGTH: 22
<212> TYPE: RNA
<213> ORGANISM: Homo sapiens

<400> SEQUENCE: 417
uuuggcaaug guagaacuca ca                                              22

<210> SEQ ID NO 418
<211> LENGTH: 21
<212> TYPE: RNA
<213> ORGANISM: Homo sapiens

<400> SEQUENCE: 418
ugguucuaga cuugccaacu a                                               21

<210> SEQ ID NO 419
<211> LENGTH: 23
<212> TYPE: RNA
<213> ORGANISM: Homo sapiens

<400> SEQUENCE: 419
uauggcacug guagaauuca cug                                             23

<210> SEQ ID NO 420
<211> LENGTH: 22
<212> TYPE: RNA
<213> ORGANISM: Homo sapiens
```

```
<400> SEQUENCE: 420
uggacggaga acugauaagg gu                                        22

<210> SEQ ID NO 421
<211> LENGTH: 18
<212> TYPE: RNA
<213> ORGANISM: Homo sapiens

<400> SEQUENCE: 421
uggagagaaa ggcaguuc                                             18

<210> SEQ ID NO 422
<211> LENGTH: 23
<212> TYPE: RNA
<213> ORGANISM: Homo sapiens

<400> SEQUENCE: 422
caaagaauuc uccuuuggg cuu                                        23

<210> SEQ ID NO 423
<211> LENGTH: 21
<212> TYPE: RNA
<213> ORGANISM: Homo sapiens

<400> SEQUENCE: 423
ucgugucuug uguugcagcc g                                         21

<210> SEQ ID NO 424
<211> LENGTH: 22
<212> TYPE: RNA
<213> ORGANISM: Homo sapiens

<400> SEQUENCE: 424
caucccuugc augguggagg gu                                        22

<210> SEQ ID NO 425
<211> LENGTH: 23
<212> TYPE: RNA
<213> ORGANISM: Homo sapiens

<400> SEQUENCE: 425
gugccuacug agcugauauc agu                                       23

<210> SEQ ID NO 426
<211> LENGTH: 22
<212> TYPE: RNA
<213> ORGANISM: Homo sapiens

<400> SEQUENCE: 426
ugauauguuu gauauauuag gu                                        22

<210> SEQ ID NO 427
<211> LENGTH: 22
<212> TYPE: RNA
<213> ORGANISM: Homo sapiens

<400> SEQUENCE: 427
caacggaauc ccaaaagcag cu                                        22

<210> SEQ ID NO 428
<211> LENGTH: 21
<212> TYPE: RNA
<213> ORGANISM: Homo sapiens
```

```
<400> SEQUENCE: 428
cugaccuaug aauugacagc c                                              21

<210> SEQ ID NO 429
<211> LENGTH: 21
<212> TYPE: RNA
<213> ORGANISM: Homo sapiens

<400> SEQUENCE: 429
aacuggccua caaaguccca g                                              21

<210> SEQ ID NO 430
<211> LENGTH: 22
<212> TYPE: RNA
<213> ORGANISM: Homo sapiens

<400> SEQUENCE: 430
uguaacagca acuccaugug ga                                             22

<210> SEQ ID NO 431
<211> LENGTH: 21
<212> TYPE: RNA
<213> ORGANISM: Homo sapiens

<400> SEQUENCE: 431
uagcagcaca gaaauauugg c                                              21

<210> SEQ ID NO 432
<211> LENGTH: 21
<212> TYPE: RNA
<213> ORGANISM: Homo sapiens

<400> SEQUENCE: 432
uagguaguuu cauguuguug g                                              21

<210> SEQ ID NO 433
<211> LENGTH: 21
<212> TYPE: RNA
<213> ORGANISM: Homo sapiens

<400> SEQUENCE: 433
uagguaguuu ccuguuguug g                                              21

<210> SEQ ID NO 434
<211> LENGTH: 22
<212> TYPE: RNA
<213> ORGANISM: Homo sapiens

<400> SEQUENCE: 434
uucaccaccu ucuccaccca gc                                             22

<210> SEQ ID NO 435
<211> LENGTH: 19
<212> TYPE: RNA
<213> ORGANISM: Homo sapiens

<400> SEQUENCE: 435
gguccagagg ggagauagg                                                 19

<210> SEQ ID NO 436
<211> LENGTH: 23
<212> TYPE: RNA
<213> ORGANISM: Homo sapiens
```

```
<400> SEQUENCE: 436
cccaguguuc agacuaccug uuc                                        23

<210> SEQ ID NO 437
<211> LENGTH: 22
<212> TYPE: RNA
<213> ORGANISM: Homo sapiens

<400> SEQUENCE: 437
uacaguaguc ugcacauugg uu                                         22

<210> SEQ ID NO 438
<211> LENGTH: 23
<212> TYPE: RNA
<213> ORGANISM: Homo sapiens

<400> SEQUENCE: 438
cccaguguuu agacuaucug uuc                                        23

<210> SEQ ID NO 439
<211> LENGTH: 22
<212> TYPE: RNA
<213> ORGANISM: Homo sapiens

<400> SEQUENCE: 439
uaacacuguc ugguaacgau gu                                         22

<210> SEQ ID NO 440
<211> LENGTH: 24
<212> TYPE: RNA
<213> ORGANISM: Homo sapiens

<400> SEQUENCE: 440
cucuaauacu gccugguaau gaug                                       24

<210> SEQ ID NO 441
<211> LENGTH: 22
<212> TYPE: RNA
<213> ORGANISM: Homo sapiens

<400> SEQUENCE: 441
aauacugccg gguaaugaug ga                                         22

<210> SEQ ID NO 442
<211> LENGTH: 22
<212> TYPE: RNA
<213> ORGANISM: Homo sapiens

<400> SEQUENCE: 442
agagguauag ggcaugggaa ga                                         22

<210> SEQ ID NO 443
<211> LENGTH: 22
<212> TYPE: RNA
<213> ORGANISM: Homo sapiens

<400> SEQUENCE: 443
gugaaauguu uaggaccacu ag                                         22

<210> SEQ ID NO 444
<211> LENGTH: 22
<212> TYPE: RNA
<213> ORGANISM: Homo sapiens
```

-continued

```
<400> SEQUENCE: 444
uucccuuugu cauccuaugc cu                                              22

<210> SEQ ID NO 445
<211> LENGTH: 22
<212> TYPE: RNA
<213> ORGANISM: Homo sapiens

<400> SEQUENCE: 445
uccuucauuc caccggaguc ug                                              22

<210> SEQ ID NO 446
<211> LENGTH: 22
<212> TYPE: RNA
<213> ORGANISM: Homo sapiens

<400> SEQUENCE: 446
uggaauguaa ggaagugugu gg                                              22

<210> SEQ ID NO 447
<211> LENGTH: 22
<212> TYPE: RNA
<213> ORGANISM: Homo sapiens

<400> SEQUENCE: 447
auaagacgag caaaaagcuu gu                                              22

<210> SEQ ID NO 448
<211> LENGTH: 21
<212> TYPE: RNA
<213> ORGANISM: Homo sapiens

<400> SEQUENCE: 448
cugugcgugu gacagcggcu g                                               21

<210> SEQ ID NO 449
<211> LENGTH: 22
<212> TYPE: RNA
<213> ORGANISM: Homo sapiens

<400> SEQUENCE: 449
uucccuuugu cauccuucgc cu                                              22

<210> SEQ ID NO 450
<211> LENGTH: 21
<212> TYPE: RNA
<213> ORGANISM: Homo sapiens

<400> SEQUENCE: 450
uaacagucuc cagucacggc c                                               21

<210> SEQ ID NO 451
<211> LENGTH: 22
<212> TYPE: RNA
<213> ORGANISM: Homo sapiens

<400> SEQUENCE: 451
accaucgacc guugauugua cc                                              22

<210> SEQ ID NO 452
<211> LENGTH: 21
<212> TYPE: RNA
<213> ORGANISM: Homo sapiens
```

-continued

```
<400> SEQUENCE: 452
acagcaggca cagacaggca g                                            21

<210> SEQ ID NO 453
<211> LENGTH: 21
<212> TYPE: RNA
<213> ORGANISM: Homo sapiens

<400> SEQUENCE: 453
augaccuaug aauugacaga c                                            21

<210> SEQ ID NO 454
<211> LENGTH: 21
<212> TYPE: RNA
<213> ORGANISM: Homo sapiens

<400> SEQUENCE: 454
uaaucucagc uggcaacugu g                                            21

<210> SEQ ID NO 455
<211> LENGTH: 24
<212> TYPE: RNA
<213> ORGANISM: Homo sapiens

<400> SEQUENCE: 455
uacugcauca ggaacugauu ggau                                         24

<210> SEQ ID NO 456
<211> LENGTH: 21
<212> TYPE: RNA
<213> ORGANISM: Homo sapiens

<400> SEQUENCE: 456
uugugcuuga ucuaaccaug u                                            21

<210> SEQ ID NO 457
<211> LENGTH: 21
<212> TYPE: RNA
<213> ORGANISM: Homo sapiens

<400> SEQUENCE: 457
ugauugucca aacgcaauuc u                                            21

<210> SEQ ID NO 458
<211> LENGTH: 21
<212> TYPE: RNA
<213> ORGANISM: Homo sapiens

<400> SEQUENCE: 458
ccacaccgua ucugacacuu u                                            21

<210> SEQ ID NO 459
<211> LENGTH: 23
<212> TYPE: RNA
<213> ORGANISM: Homo sapiens

<400> SEQUENCE: 459
agcuacauug ucugcugggu uuc                                          23

<210> SEQ ID NO 460
<211> LENGTH: 24
<212> TYPE: RNA
<213> ORGANISM: Homo sapiens
```

```
<400> SEQUENCE: 460
agcuacaucu ggcuacuggg ucuc                                      24

<210> SEQ ID NO 461
<211> LENGTH: 21
<212> TYPE: RNA
<213> ORGANISM: Homo sapiens

<400> SEQUENCE: 461
ugucaguuug ucaaauaccc c                                         21

<210> SEQ ID NO 462
<211> LENGTH: 23
<212> TYPE: RNA
<213> ORGANISM: Homo sapiens

<400> SEQUENCE: 462
caagucacua gugguuccgu uua                                       23

<210> SEQ ID NO 463
<211> LENGTH: 21
<212> TYPE: RNA
<213> ORGANISM: Homo sapiens

<400> SEQUENCE: 463 agggccccccc cucaauccug u                                        21

<210> SEQ ID NO 464
<211> LENGTH: 22
<212> TYPE: RNA
<213> ORGANISM: Homo sapiens

<400> SEQUENCE: 464
ugguuuaccg ucccacauac au                                        22

<210> SEQ ID NO 465
<211> LENGTH: 23
<212> TYPE: RNA
<213> ORGANISM: Homo sapiens

<400> SEQUENCE: 465
cagugcaaua guauugucaa agc                                       23

<210> SEQ ID NO 466
<211> LENGTH: 23
<212> TYPE: RNA
<213> ORGANISM: Homo sapiens

<400> SEQUENCE: 466
uaagugcuuc cauguuuugg uga                                       23

<210> SEQ ID NO 467
<211> LENGTH: 23
<212> TYPE: RNA
<213> ORGANISM: Homo sapiens

<400> SEQUENCE: 467
acuuuaacau ggaagugcuu ucu                                       23

<210> SEQ ID NO 468
<211> LENGTH: 23
<212> TYPE: RNA
<213> ORGANISM: Homo sapiens
```

```
<400> SEQUENCE: 468
uaagugcuuc cauguuuag uag                                           23

<210> SEQ ID NO 469
<211> LENGTH: 22
<212> TYPE: RNA
<213> ORGANISM: Homo sapiens

<400> SEQUENCE: 469
uuuaacaugg ggguaccugc ug                                           22

<210> SEQ ID NO 470
<211> LENGTH: 23
<212> TYPE: RNA
<213> ORGANISM: Homo sapiens

<400> SEQUENCE: 470
uaagugcuuc cauguuucag ugg                                          23

<210> SEQ ID NO 471
<211> LENGTH: 23
<212> TYPE: RNA
<213> ORGANISM: Homo sapiens

<400> SEQUENCE: 471
uaagugcuuc cauguugag ugu                                           23

<210> SEQ ID NO 472
<211> LENGTH: 23
<212> TYPE: RNA
<213> ORGANISM: Homo sapiens

<400> SEQUENCE: 472
aaaagcuggg uugagagggc gaa                                          23

<210> SEQ ID NO 473
<211> LENGTH: 21
<212> TYPE: RNA
<213> ORGANISM: Homo sapiens

<400> SEQUENCE: 473
uaagccaggg auguggguu c                                             21

<210> SEQ ID NO 474
<211> LENGTH: 22
<212> TYPE: RNA
<213> ORGANISM: Homo sapiens

<400> SEQUENCE: 474
gcacauuaca cggucgaccu cu                                           22

<210> SEQ ID NO 475
<211> LENGTH: 23
<212> TYPE: RNA
<213> ORGANISM: Homo sapiens

<400> SEQUENCE: 475
cgcauccccu agggcauugg ugu                                          23

<210> SEQ ID NO 476
<211> LENGTH: 22
<212> TYPE: RNA
<213> ORGANISM: Homo sapiens
```

-continued

```
<400> SEQUENCE: 476
ccacugcccc aggugcugcu gg                                              22

<210> SEQ ID NO 477
<211> LENGTH: 21
<212> TYPE: RNA
<213> ORGANISM: Homo sapiens

<400> SEQUENCE: 477
ccuaguaggu guccaguaag u                                               21

<210> SEQ ID NO 478
<211> LENGTH: 20
<212> TYPE: RNA
<213> ORGANISM: Homo sapiens

<400> SEQUENCE: 478
ccucugggcc cuuccuccag                                                 20

<210> SEQ ID NO 479
<211> LENGTH: 22
<212> TYPE: RNA
<213> ORGANISM: Homo sapiens

<400> SEQUENCE: 479
cuggcccucu cugcccuucc gu                                              22

<210> SEQ ID NO 480
<211> LENGTH: 23
<212> TYPE: RNA
<213> ORGANISM: Homo sapiens

<400> SEQUENCE: 480
gcaaagcaca cggccugcag aga                                             23

<210> SEQ ID NO 481
<211> LENGTH: 21
<212> TYPE: RNA
<213> ORGANISM: Homo sapiens

<400> SEQUENCE: 481
gccccugggc cuauccuaga a                                               21

<210> SEQ ID NO 482
<211> LENGTH: 23
<212> TYPE: RNA
<213> ORGANISM: Homo sapiens

<400> SEQUENCE: 482
ucaagagcaa uaacgaaaaa ugu                                             23

<210> SEQ ID NO 483
<211> LENGTH: 23
<212> TYPE: RNA
<213> ORGANISM: Homo sapiens

<400> SEQUENCE: 483
uccagcuccu auaugaugcc uuu                                             23

<210> SEQ ID NO 484
<211> LENGTH: 23
<212> TYPE: RNA
<213> ORGANISM: Homo sapiens
```

```
<400> SEQUENCE: 484
uccagcauca gugauuuugu uga                                        23

<210> SEQ ID NO 485
<211> LENGTH: 21
<212> TYPE: RNA
<213> ORGANISM: Homo sapiens

<400> SEQUENCE: 485
ucccuguccu ccaggagcuc a                                          21

<210> SEQ ID NO 486
<211> LENGTH: 23
<212> TYPE: RNA
<213> ORGANISM: Homo sapiens

<400> SEQUENCE: 486
uccgucucag uuacuuuaua gcc                                        23

<210> SEQ ID NO 487
<211> LENGTH: 24
<212> TYPE: RNA
<213> ORGANISM: Homo sapiens

<400> SEQUENCE: 487
ucucacacag aaaucgcacc cguc                                       24

<210> SEQ ID NO 488
<211> LENGTH: 21
<212> TYPE: RNA
<213> ORGANISM: Homo sapiens

<400> SEQUENCE: 488
ugcugacucc uaguccaggg c                                          21

<210> SEQ ID NO 489
<211> LENGTH: 23
<212> TYPE: RNA
<213> ORGANISM: Homo sapiens

<400> SEQUENCE: 489
ugucugcccg caugccugcc ucu                                        23

<210> SEQ ID NO 490
<211> LENGTH: 22
<212> TYPE: RNA
<213> ORGANISM: Homo sapiens

<400> SEQUENCE: 490
aauugcacuu uagcaauggu ga                                         22

<210> SEQ ID NO 491
<211> LENGTH: 22
<212> TYPE: RNA
<213> ORGANISM: Homo sapiens

<400> SEQUENCE: 491
acauagagga aauuccacgu uu                                         22

<210> SEQ ID NO 492
<211> LENGTH: 21
<212> TYPE: RNA
<213> ORGANISM: Homo sapiens
```

```
<400> SEQUENCE: 492
aauaauacau gguugaucuu u                                              21

<210> SEQ ID NO 493
<211> LENGTH: 21
<212> TYPE: RNA
<213> ORGANISM: Homo sapiens

<400> SEQUENCE: 493
gccugcuggg guggaaccug g                                              21

<210> SEQ ID NO 494
<211> LENGTH: 21
<212> TYPE: RNA
<213> ORGANISM: Homo sapiens

<400> SEQUENCE: 494
gugccgccau cuuuugagug u                                              21

<210> SEQ ID NO 495
<211> LENGTH: 23
<212> TYPE: RNA
<213> ORGANISM: Homo sapiens

<400> SEQUENCE: 495
aaagugcugc gacauuugag cgu                                            23

<210> SEQ ID NO 496
<211> LENGTH: 22
<212> TYPE: RNA
<213> ORGANISM: Homo sapiens

<400> SEQUENCE: 496
acucaaaaug ggggcgcuuu cc                                             22

<210> SEQ ID NO 497
<211> LENGTH: 23
<212> TYPE: RNA
<213> ORGANISM: Homo sapiens

<400> SEQUENCE: 497
gaagugcuuc gauuuugggg ugu                                            23

<210> SEQ ID NO 498
<211> LENGTH: 22
<212> TYPE: RNA
<213> ORGANISM: Homo sapiens

<400> SEQUENCE: 498
uuauaauaca accugauaag ug                                             22
```

MICRORNA-BASED METHODS AND COMPOSITIONS FOR THE DIAGNOSIS, PROGNOSIS AND TREATMENT OF LUNG CANCER

GOVERNMENT SUPPORT

This invention was supported, in whole or in part, by grant CA76259 and intramural funds from CCR/NCI/NIH and by Federal funds from NCI/NIH under Contract No. NO1-CO-12400. The Government has certain rights in this invention.

BACKGROUND OF THE INVENTION

Lung cancer causes more deaths worldwide than any other form of cancer (Goodman, G. E., Thorax 57:994-999 (2002)). In the United States, lung cancer is the primary cause of cancer death among both men and women. In 2002, the death rate from lung cancer was an estimated 134,900 deaths. Lung cancer is also the leading cause of cancer death in all European countries, and numbers of lung cancer-related deaths are rapidly increasing in developing countries as well.

The five-year survival rate among all lung cancer patients, regardless of the stage of disease at diagnosis, is only about 13%. This contrasts with a five-year survival rate of 46% among cases detected while the disease is still localized. However, only 16% of lung cancers are discovered before the disease has spread. Early detection is difficult as clinical symptoms are often not observed until the disease has reached an advanced stage. Currently, diagnosis is aided by the use of chest x-rays, analysis of the type of cells contained in sputum and fiberoptic examination of the bronchial passages. Treatment regimens are determined by the type and stage of the cancer, and include surgery, radiation therapy and/or chemotherapy. In spite of considerable research into therapies for this and other cancers, lung cancer remains difficult to diagnose and treat effectively. Accordingly, there is a great need for improved methods of detecting and treating such cancers. Carbone, J. Clin. Oncol. 23:3219-3226 (2005); Granville and Dennis, Cell Mol. Biol. 32:169-176 (2005)). For example, defects in both the p53 and RB/p16 pathways are common in lung cancer. Several other genes, such as K-ras, PTEN, FHIT and MYO18B, are genetically altered in lung cancers, though less frequently (Minna et al., Cancer Cell 1:49-52 (2002); Sekido et al., Annu. Rev. Med. 54:73-87 (2003); Yokota and Kohno, Cancer Sci. 95:197-204 (2004)). Although focusing on known genes and proteins has yielded useful information, previously unknown markers of lung cancer may also lend insight into the biology of lung cancer.

MicroRNAs (miRNAs) are a class of small, non-coding RNAs that control gene expression by hybridizing to and triggering either translational repression or, less frequently, degradation of a messenger RNA (mRNA) target. The discovery and study of miRNAs has revealed miRNA-mediated gene regulatory mechanisms that play important roles in organismal development and various cellular processes, such as cell differentiation, cell growth and cell death (Cheng, A. M., et al., Nucleic Acids Res. 33:1290-1297 (2005)). Recent studies suggest that aberrant expression of particular miRNAs may be involved in human diseases, such as neurological disorders (Ishizuka, A., et al., Genes Dev. 16:2497-2508 (2002)) and cancer. In particular, misexpression of miR-16-1 and/or miR-15a has been found in human chronic lymphocytic leukemias (Calin, G. A., et al., Proc. Natl. Acad. Sci. U.S.A. 99:15524-15529 (2002)).

The development and use of microarrays containing all known human microRNAs has permitted a simultaneous analysis of the expression of every miRNA in a sample (Liu, C. G., et al., Proc Natl. Acad. Sci. U.S.A. 101:9740-9744 (2004)). These microRNA microarrays have not only been used to confirm that miR-16-1 is deregulated in human CLL cells, but also to generate miRNA expression signatures that are associated with well-defined clinicopathological features of human CLL (Calin, G. A., et al., Proc. Natl. Acad. Sci. U.S.A. 101:1175-11760 (2004)).

Identification of microRNAs that are differentially-expressed in lung cancer cells would aid in diagnosing, prognosticating and treating lung cancer. Furthermore, the identification of putative targets of these miRNAs would help to unravel their pathogenic role. The present invention provides novel methods and compositions for the diagnosis, prognosis and treatment of lung cancer.

SUMMARY OF THE INVENTION

The present invention is based, in part, on the identification of specific miRNAs associated with altered expression levels in lung cancer cells.

Accordingly, the invention encompasses methods of diagnosing whether a subject has, or is at risk for developing, lung cancer. According to the methods of the invention, the level of at least one miR gene product in a test sample from the subject is compared to the level of a corresponding miR gene product in a control sample. An alteration (e.g., an increase, a decrease) in the level of the miR gene product in the test sample, relative to the level of a corresponding miR gene product in a control sample, is indicative of the subject either having, or being at risk for developing, lung cancer. In certain embodiments, the at least one miR gene product is selected from the group consisting of miR-21, miR-191, miR-126*, miR-210, miR-155, miR-143, miR-205, miR-192-prec, miR-224, miR-126, miR-24-2, miR-30a-5p, miR-212, miR-140, miR-9, miR-214, miR-17-3p, miR-124a-1, miR-218-2, miR-95, miR-145, miR-198, miR-216-prec, miR-219-1, miR-106a, miR-197, miR-192, miR-125a-prec, miR-26a-1-prec, miR-146, miR-203, miR-199b-prec, let-7a-2-prec, miR-27b, miR-32, miR-29b-2, miR-220, miR-33, miR-181c-prec, miR-150, miR-101-1, miR-124a-3, miR-125a and let-7f-1. In a particular embodiment, the at least one miR gene product is selected from the group consisting of miR-21, miR-191, miR-155, miR-210, miR-126* and miR-224. In another embodiment, the at least one miR gene product is selected from the group consisting of miR-21, miR-205 and miR-216. In yet another embodiment, the lung cancer is a lung adenocarcinoma and the at least one miR gene product is selected from the group consisting of miR-21, miR-191, miR-155, miR-210, miR-126*, miR-126, miR-24-2, miR-219-1, miR-95, miR-192-prec, miR-220, miR-216-prec, miR-204-prec, miR-188, miR-198, miR-145 and miR-224.

The level of the at least one miR gene product can be measured using a variety of techniques that are well known to those of skill in the art (e.g., quantitative or semi-quantitative RT-PCR, Northern blot analysis, solution hybridization detection). In a particular embodiment, the level of at least one miR gene product is measured by reverse transcribing RNA from a test sample obtained from the subject to provide a set of target oligodeoxynucleotides, hybridizing the target oligodeoxynucleotides to one or more miRNA-specific probe oligonucleotides (e.g., a microarray that comprises miRNA-specific probe oligonucleotides) to provide a hybridization profile for the test sample, and comparing the test sample hybridization profile to a hybridization profile generated from a control sample. An alteration in the signal of at least one miRNA in the test sample relative to the control sample is indicative of the subject either having, or being at risk for developing, lung cancer. In a particular embodiment, the microarray comprises miRNA-specific probe oligonucleotides for a substantial portion of all known human miRNAs. In a further embodiment, the microarray comprises miRNA-specific probe oligonucleotides for one or more miRNAs selected from the group consisting of miR-21, miR-191, miR-126*, miR-210, miR-155, miR-143, miR-205, miR-192-prec, miR-224, miR-126, miR-24-2, miR-30a-5p, miR-212, miR-140, miR-9, miR-214, miR-17-3p, miR-124a-1, miR-218-2, miR-95, miR-145, miR-198, miR-216-prec, miR-219-1, miR-106a, miR-197, miR-192, miR-125a-prec, miR-26a-1-prec, miR-146, miR-203, miR-199b-prec, let-7a-2-prec, miR-27b, miR-32, miR-29b-2, miR-220, miR-33, miR-181c-prec, miR-150, miR-101-1, miR-124a-3, miR-125a and let-7f-1.

The invention also provides methods of determining the prognosis of a subject with lung cancer, comprising measuring the level of at least one miR gene product, which is associated with an adverse prognosis in lung cancer, in a test sample from the subject. According to these methods, an alteration in the level of a miR gene product that is associated with an adverse prognosis, in the test sample, as compared to the level of a corresponding miR gene product in a control sample, is indicative of an adverse prognosis. In certain embodiments, the at least one miR gene product is selected from the group consisting of miR-155, miR-17-3p, miR-106a, miR-93, let-7a-2, miR-145, let-7b, miR-20 and miR-21. In a particular embodiment, the lung cancer is a lung adenocarcinoma and the at least one miR gene product is selected from the group consisting of miR-155 and let-7a-2.

The level of the at least one miR gene product can be measured as described herein (e.g., quantitative or semi-quantitative RT-PCR, Northern blot analysis, solution hybridization detection, microarray analysis). An alteration in the signal of at least one miRNA in the test sample, relative to the control sample is indicative of the subject either having, or being at risk for developing, a lung cancer with an adverse prognosis. In a particular embodiment, an alteration in the signal of miR-125a, miR-125b-1, miR-224 and/or miR-21 is indicative of the subject either having, or being at risk for developing, a lung cancer with an adverse prognosis. In another embodiment, an alteration in the signal of miR-155 and/or let-7a-2 in a sample from a subject with lung adenocarcinoma is indicative of an adverse prognosis. In a certain embodiment, the microarray comprises miRNA-specific probe oligonucleotides for one or more miRNAs selected from the group consisting of miR-21, miR-191, miR-126*, miR-210, miR-155, miR-143, miR-205, miR-192-prec, miR-224, miR-126, miR-24-2, miR-30a-5p, miR-212, miR-140, miR-9, miR-214, miR-17-3p, miR-124a-1, miR-218-2, miR-95, miR-145, miR-198, miR-216-prec, miR-219-1, miR-106a, miR-197, miR-192, miR-125a-prec, miR-26a-1-prec, miR-146, miR-203, miR-199b-prec, let-7a-2-prec, miR-27b, miR-32, miR-29b-2, miR-220, miR-33, miR-181c-prec, miR-150, miR-101-1, miR-124a-3, miR-125a and let-7f-1.

The invention also encompasses methods of treating lung cancer in a subject, wherein at least one miR gene product is deregulated (e.g., down-regulated, up-regulated) in the cancer cells of the subject. When at least one isolated miR gene product is down-regulated in the lung cancer cells, the method comprises administering an effective amount of an isolated miR gene product, or an isolated variant or biologically-active fragment thereof, such that proliferation of cancer cells in the subject is inhibited. When at least one isolated miR gene product is up-regulated in the cancer cells, the method comprises administering to the subject an effective amount of at least one compound for inhibiting expression of the at least one miR gene product, such that proliferation of lung cancer cells is inhibited.

In a related embodiment, the methods of treating lung cancer in a subject additionally comprise the step of first determining the amount of at least one miR gene product in lung cancer cells from the subject, and comparing that level of the miR gene product to the level of a corresponding miR gene product in control cells. If expression of the miR gene product is deregulated (e.g., down-regulated, up-regulated) in lung cancer cells, the methods further comprise altering the amount of the at least one miR gene product expressed in the lung cancer cells. In one embodiment, the amount of the miR gene product expressed in the cancer cells is less than the amount of the miR gene product expressed in control cells, and an effective amount of the miR gene product, or an isolated variant or biologically-active fragment thereof, is administered to the subject. In another embodiment, the amount of the miR gene product expressed in the cancer cells is greater than the amount of the miR gene product expressed in control cells, and an effective amount of at least one compound for inhibiting expression of the at least one miR gene is administered to the subject.

The invention further provides pharmaceutical compositions for treating lung cancer. In one embodiment, the pharmaceutical compositions comprise at least one isolated miR gene product, or an isolated variant or biologically-active fragment thereof, and a pharmaceutically-acceptable carrier. In a particular embodiment, the at least one miR gene product corresponds to a miR gene product that has a decreased level of expression in lung cancer cells relative to suitable control cells. In certain embodiments the isolated miR gene product is selected from the group consisting of miR-126*, miR-143, miR-192, miR-224, miR-126, miR-30a-5p, miR-140, miR-9, miR-124a-1, miR-218-2, miR-95, miR-145, miR-198, miR-216, miR-219-1, miR-125a, miR-26a-1, miR-199b, let-7a-2, miR-27b, miR-32, miR-29b-2, miR-220, miR-33, miR-181c, miR-101-1, miR-124a-3, let-7f-1 and a combination thereof.

In another embodiment, the pharmaceutical compositions of the invention comprise at least one miR expression-inhibition compound. In a particular embodiment, the at least one miR expression-inhibition compound is specific for a miR gene product whose expression is greater in lung cancer cells than control cells. In certain embodiments, the miR expression-inhibition compound is specific for one or more miR gene products selected from the group consisting of miR-21, miR-191, miR-210, miR-155, miR-205, miR-24-2, miR-212, miR-214, miR-17-3p, miR-106a, miR-197, miR-192, miR-146, miR-203, miR-150 and a combination thereof.

The invention also encompasses methods of identifying an anti-lung cancer agent, comprising providing a test agent to a cell and measuring the level of at least one miR gene product in the cell. In one embodiment, the method comprises providing a test agent to a cell and measuring the level of at least one miR gene product associated with decreased expression levels in lung cancer cells. An increase in the level of the miR gene product in the cell, relative to a suitable control cell, is indicative of the test agent being an anti-lung cancer agent. In a particular embodiment, the at least one miR gene product associated with decreased expression levels in lung cancer cells is selected from the group consisting of miR-126*, miR-143, miR-192, miR-224, miR-126, miR-30a-5p, miR-140, miR-9, miR-124a-1, miR-218-2, miR-95, miR-145, miR-198, miR-216, miR-219-1, miR-125a, miR-26a-1, miR-199b, let-7a-2, miR-27b, miR-32, miR-29b-2, miR-220, miR-33, miR-181c, miR-101-1, miR-124a-3, let-7f-1 and a combination thereof.

In other embodiments, the method comprises providing a test agent to a cell and measuring the level of at least one miR gene product associated with increased expression levels in lung cancer cells. A decrease in the level of the miR gene product associated with increased expression levels in lung cancer in the cell, relative to a suitable control cell, is indicative of the test agent being an anti-lung cancer agent. In a particular embodiment, the at least one miR gene product associated with increased expression levels in lung cancer cells is selected from the group consisting of miR-21, miR-191, miR-210, miR-155, miR-205, miR-24-2, miR-212, miR-214, miR-17-3p, miR-106a, miR-197, miR-192, miR-146, miR-203, miR-150 and a combination thereof.

BRIEF DESCRIPTION OF THE DRAWINGS

The patent or application file contains at least one drawing executed in color. Copies of this patent or patent application publication with color drawings will be provided by the Office upon request and payment of the necessary fee.

DETAILED DESCRIPTION OF THE INVENTION

Figure 1:
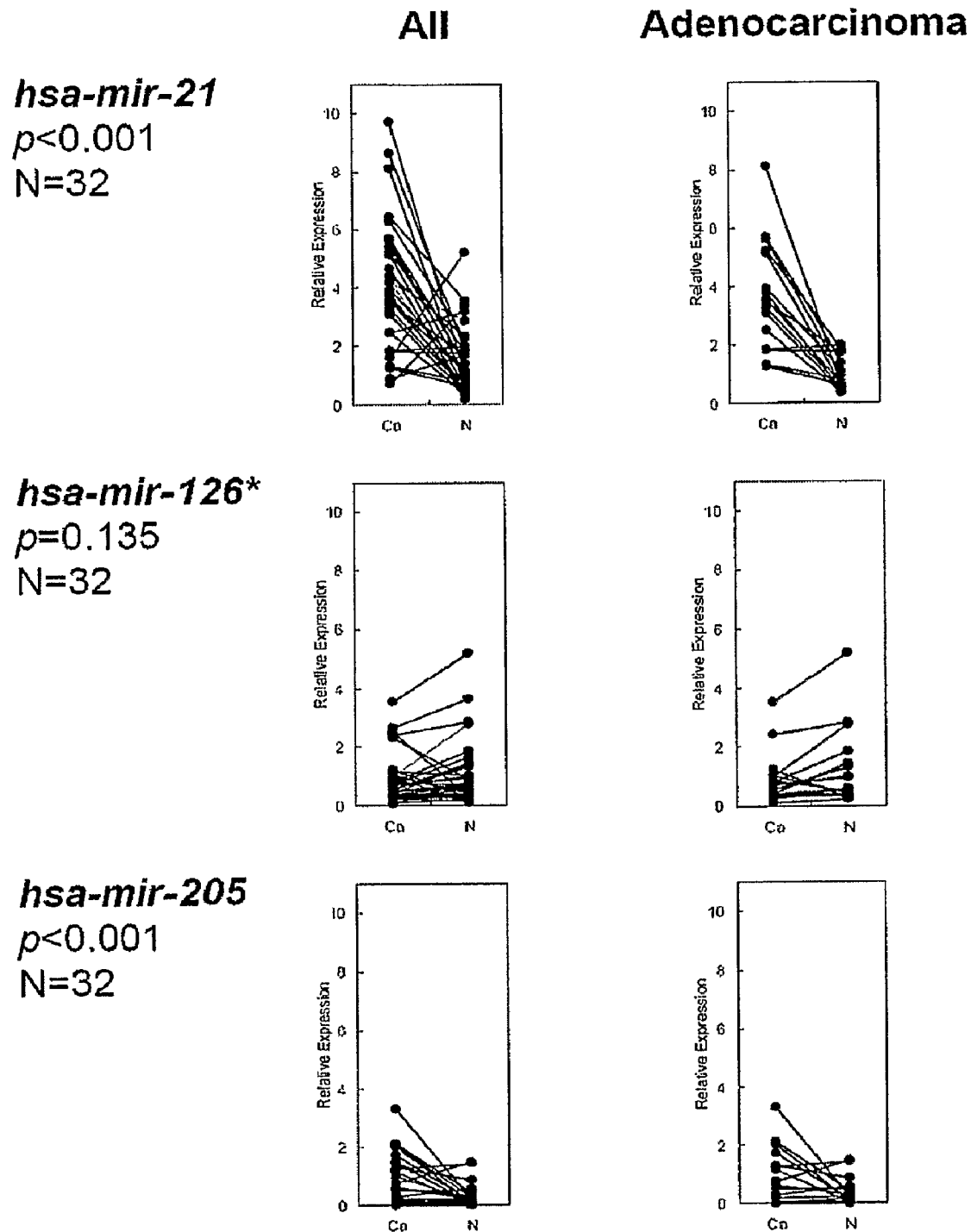
FIG. 1 shows graphs depicting the relative expression level of human miR-21 precursor (hsa-mir-21; top panels), human miR-126* precursor (hsa-mir-126*; middle panels) and human miR-205 precursor (hsa-mir-205; bottom panels) in lung cancer (Ca) and noncancerous (N) tissues, as determined by real-time RT-PCR analysis. Cancer samples were either adenocarcinoma or squamous cell carcinoma (SCC). A paired t test was performed to ascertain statistical significance between the expression levels in lung cancer tissues and noncancerous lung tissues.

The present invention is based, in part, on the identification of particular microRNAs having altered expression in lung cancer cells relative to normal control cells, and on association of these microRNAs with particular diagnostic, prognostic and therapeutic features.

As used herein interchangeably, a "miR gene product," "microRNA," "miR," or "miRNA" refers to the unprocessed or processed RNA transcript from a miR gene. As the miR gene products are not translated into protein, the term "miR gene products" does not include proteins. The unprocessed miR gene transcript is also called a "miR precursor," and typically comprises an RNA transcript of about 70-100 nucleotides in length. The miR precursor can be processed by digestion with an RNAse (for example, Dicer, Argonaut, RNAse III (e.g., *E. coli* RNAse III)) into an active 19-25 nucleotide RNA molecule. This active 19-25 nucleotide RNA molecule is also called the "processed" miR gene transcript or "mature" miRNA.

The active 19-25 nucleotide RNA molecule can be obtained from the miR precursor through natural processing routes (e.g., using intact cells or cell lysates) or by synthetic processing routes (e.g., using isolated processing enzymes, such as isolated Dicer, Argonaut, or RNAse III). It is understood that the active 19-25 nucleotide RNA molecule can also be produced directly by biological or chemical synthesis, without having to be processed from the miR precursor. When a microRNA is referred to herein by name, the name corresponds to both the precursor and mature forms, unless otherwise indicated.

The present invention encompasses methods of diagnosing whether a subject has, or is at risk for developing, lung cancer, comprising measuring the level of at least one miR gene product in a test sample from the subject and comparing the level of the miR gene product in the test sample to the level of a corresponding miR gene product in a control sample. As used herein, a "subject" can be any mammal that has, or is suspected of having, lung cancer. In a preferred embodiment, the subject is a human who has, or is suspected of having, lung cancer.

The lung cancer can be any form of lung cancer, for example, lung cancers of differing histology (e.g., adenocarcinoma, squamous cell carcinoma). Furthermore, the lung cancer may be associated with a particular prognosis (e.g., low survival rate, fast progression).

Tables 1a and 1b depict the nucleotide sequences of particular precursor and mature human microRNAs.

TABLE 1a

Human microRNA Precursor Sequences

| Precursor Name | Sequence (5' To 3')* | SEQ ID NO. |
| --- | --- | --- |
| let-7a-1 | CACUGUGGGA UGAGGUAGUAGGUUGUAUAGUU UUAGGGUCACACCCACCACUGG-GAGAUAACUA UACAAUCUACUGUCUUUCCUAACGUG | 1 |
| let-7a-2 | AGGU UGAGGUAGUAGGUUGUAUAGUUUAGAAU UACAUCAAGGGAGAUAACUGUACAGC-CUCCUA GCUUUCCU | 2 |
| let-7a-3 | GGG UGAGGUAGUAGGUUGUAUAGUUUGGGGCU CUGCCCUGCUAUGGGAUAACUAUACAAU-CUAC UGUCUUUCCU | 3 |
| let-7a-4 | GUGACUGCAUGCUCCCAGGU UGAGGUAGUAGG UUGUAUAGUUUAGAAUUACACAAGGGAGAUAA CUGUACAGCCUCCUAGCUUUCCUUGGGU-CUUG CACUAAACAAC | 4 |
| let-7b | GGCGGGG UGAGGUAGUAGGUUGUGUGGUUUCA GGGCAGUGAUGUUGCCCCUCGGAA-GAUAACUA UACAACCUACUGCCUUCCCUG | 5 |
| let-7c | GCAUCCGGGU UGAGGUAGUAGGUUGUAUGGUU UAGAGUUACACCCUGGGAGUUAACUGUA-CAAC CUUCUAGCUUUCCUUGGAGC | 6 |
| let-7d | CCUAGGA AGAGGUAGUAGGUUGCAUAGUUUUA GGGCAGGGAUUUUGCCCACAAGGAG-GUAACUA UACGACCUGCUGCCUUUCUUAGG | 7 |
| let-7d-v1 | CUAGGA AGAGGUAGUAGUUUGCAUAGUUUUAG GGCAAAGAUUUUGCCCACAAGUAG-UUAGCUAU ACGACCUGCAGCCUUUUGUAG | 8 |
| let-7d-v2 | CUGGCU GAGGUAGUAGUUUGUGCUGUUGGUCG GGUUGUGACAUUGCCCGCUGUG-GAGAUAACUG CGCAAGCUACUGCCUUGCUAG | 9 |
| let-7e | CCCGGGC UGAGGUAGGAGGUUGUAUAGUUGAG GAGGACACCCAAGGAGAUCACUAUACG-GCCUC CUAGCUUUCCCCAGG | 10 |
| let-7f-1 | UCAGAG UGAGGUAGUAGAUUGUAUAGUUGUGG GGUAGUGAUUUUACCCUGUUCAG-GAGAUAACU AUACAAUCUAUUGCCUUCCCUGA | 11 |

TABLE 1a-continued

Human microRNA Precursor Sequences

| Precursor Name | Sequence (5' To 3')* | SEQ ID NO. |
|---|---|---|
| let-7f-2-1 | CUGUGGGA UGAGGUAGUAGAUUGUAUAGUUGU GGGGUAGUGAUUUUACCCUGUUCAG-GAGAUAA CUAUACAAUCUAUUGCCUUCCCUGA | 12 |
| let-7f-2-2 | CUGUGGGA UGAGGUAGUAGAUUGUAUAGUUUU AGGGUCAUACCCCAUCUUGGAGAUAAC-UAUAC AGUCUACUGUCUUUCCCACGG | 13 |
| let-7g | UUGCCUGAUUCCAGGC UGAGGUAGUAGUUUGU ACAGUUUGAGGGUCUAUGAUACCACCCGGUAC AGGAGAUAACUGUACAGGCCACUGCCU-UGCCA GGAACAGCGCGC | 14 |
| let-7i | CUGGC UGAGGUAGUAGUUUGUGCUGUUGGUCG GGUUGUGACAUUGCCCGCUGUG-GAGAUAACUG CGCAAGCUACUGCCUUGCUAG | 15 |
| miR-1b-1-1 | ACCUACUCAGAGUACAUACUUCUUUAU-GUACC CAUAUGAACAUACAAUGCUA UGGAAUGUAAAG AAGUAUGUAUUUUUGGUAGGC | 16 |
| miR-1b-1-2 | CAGCUAACAACUUAGUAAUACCACUCA-GAGU ACAUACUUCUUUAUGUACCCAUAUGAA-CAUAC AAUGCUA UGGAAUGUAAAGAAGUAUGUAUUUU UGGUAGGCAAUA | 17 |
| miR-1b-2 | GCCUGCUUUGGGAAACAUACUUCU-UUAUAUGCC CAUAUGGACCUGCUAAGCUA UGGAAUGUAAAG AAGUAUGUAUCUCAGGCCGGG | 18 |
| miR-1b | UGGGAAACAUACUUCUUUAUAUGC-CCAUAUGG ACCUGCUAAGCUA UGGAAUGUAAAGAAGUAUG UAUCUCA | 19 |
| miR-1d | ACCUACUCAGAGUACAUACUUCUUUAU-GUACC CAUAUGAACAUACAAUGCUA UGGAAUGUAAAG AAGUAUGUAUUUUUGGUAGGC | 20 |
| miR-7-1a | UGGAUGUUGGCCUAGUUCUGUG UGGAAGACUA GUGAUUUUGUUGUUUUUAGAUAACUAAAUCGA CAACAAAUCACAGUCUGCCAUAUGGCA-CAGGC CAUGCCUCUACA | 21 |
| miR-7-1b | UUGGAUGUUGGCCUAGUUCUGUG UGGAAGACU AGUGAUUUUGUUGUUUUUAGAUAACUAAAUCG ACAACAAAUCACAGUCUGCCAUAUGGCA-CAGG CCAUGCCUCUACAG | 22 |
| miR-7-2 | CUGGAUACAGAGUGGACCGGCUGGCCCAUCU GGAAGACUAGUGAUUUUGUUGUUGUCUUACUG CGCUCAACAACAAAUCCCAGUCUAC-CUAAUGG UGCCAGCCAUCGCA | 23 |
| miR-7-3 | AGAUUAGAGUGGCUGUGGUCUAGUGCUGUG UG GAAGACUAGUGAUUUUGUUGUUCUGAUGUACU ACGACAACAAGUCACAGCCGGCCU-CAUAGCGC AGACUCCCUUCGAC | 24 |
| miR-9-1 | CGGGGUUGGUUGUUA UCUUUGGUUAUCUAGCU GUAUGAGUGUGGAGUCUUCA UAAAGCUAG AUAACCGAAAGUAAAAAUAACCCCA | 25 |
| miR-9-2 | GGAAGCGAGUUGUUA UCUUUGGUUAUCUAGCU GUAUGAGUGUAUUGGUCUUCA UAAAGCUAGAU AACCGAAAGUAAAAACUCCUUCA | 26 |
| miR-9-3 | GGAGGCCCGUUUCUC UCUUUGGUUAUCUAGCU GUAUGAGUGCCACAGAGCCGUCA UAAAGCUAG AUAACCGAAAGUAGAAAUGAUUCUCA | 27 |
| miR-10a | GAUCUGUCUGUCUUCUGUAUA UACCCUGUAGA UCCGAAUUUGUGUAAGGAAUUUUGUGGUCACA AAUUCGUAUCUAGGGGAAUAUGUAG-UUGACAU AAACACUCCGCUCU | 28 |
| miR-10b | CCAGAGGUUGUAACGUUGUCUAUAUA UACCCU GUAGAACCGAAUUUGUGUGGUAUCCGUAUAGU CACAGAUUCGAUUCUAGGGGAAUAUAUG-GUCG AUGCAAAAACUUCA | 29 |
| miR-15a-2 | GCGCGAAUGUGUGU-UUAAAAAAAAUAAAACCU UGGAGUAAAG UAGCAGCACAUAAUGGUUUGUG GAUUUUGAAAAGGUGCAGGCCAUAUU-GUGCUG CCUCAAAAAUAC | 30 |
| miR-15a | CCUUGGAGUAAAG UAGCAGCACAUAAUGGUUU GUGGAUUUUGAAAAGGUGCAGGCCAUAUUGUG CUGCCUCAAAAAUACAAGG | 31 |
| miR-15b-1 | CUG UAGCAGCACAUCAUGGUUUACAUGCUACA GUCAAGAUGCGAAUCAUUAUUUGCUGCU-CUAG | 32 |
| miR-15b-2 | UUGAGGCCUUAAAGUACUG UAGCAGCAUCA UGGUUUACAUGCUACAGUCAAGAUGCGAAUCA UUAUUUGCUGCUCUAGAAAUUUAAG-GAAAUUC AU | 33 |
| miR-16-1 | GUCAGCAGUGCCU UAGCAGCACGUAAAUAUUG GCGUUAAGAUUCUAAAAUUAUCUCCAGUAUUA ACUGUGCUGCUGAAGUAAGGUUGAC | 34 |
| miR-16-2 | GUUCCACUC UAGCAGCACGUAAAUAUUGGCGU AGUGAAAUAUAUAUUAAACACCAAUA-UUACUG UGCUGCUUUAGUGUGAC | 35 |

TABLE 1a-continued

Human microRNA Precursor Sequences

| Precursor Name | Sequence (5' To 3')* | SEQ ID NO. |
|---|---|---|
| miR-16-13 | GCAGUGCCU UAGCAGCACGUAAAUAUUGGCGU UAAGAUUCUAAAAUUAUCUCCAGUA- UUAACUG UGCUGCUGAAGUAAGGU | 36 |
| miR-17 | GUCAGAAUAAUGU CAAAGUGCUUACAGUGCAG GUAGUGAUAUGUGCAUCU ACUGCAGUGAAGGC ACUUGUAGCAUUAUGGUGAC | 37 |
| miR-18 | UGUUC UAAGGUGCAUCUAGUGCAGAUAGUGAA GUAGAUUAGCAUCUACUGC- CCUAAGUGCUCCU UCUGGCA | 38 |
| miR-18-13 | UUUUUGUUC UAAGGUGCAUCUAGUGCAGAUAG UGAAGUAGAUUAGCAUCUACUGC- CCUAAGUGC UCCUUCUGGCAUAAGAA | 39 |
| miR-19a | GCAGUCCUCUGUUAGUUUUGCAUAGUUG- CACU ACAAGAAGAAUGUAGU UGUGCAAAUCUAUGCA AAACUGAUGGUGGCCUGC | 40 |
| miR-19a-13 | CAGUCCUCUGUUAGUUUUGCAUAGUUG- CACUA CAAGAAGAAUGUAGU UGUGCAAAUCUAUGCAA AACUGAUGGUGGCCUG | 41 |
| miR-19b-1 | CACUGUUCUAUGGUUAGUUUUGCAGGU- UUGCA UCCAGCUGUGUGAUAUUCUGC UGUGCAAAUCC AUGCAAAACUGACUGUGGUAGUG | 42 |
| miR-19b-2 | ACAUUGCUACUACAAUUAGUUUUGCAG- GUUU GCAUUUCAGCGUAUAUAUGUAUAUGUGGC UGU GCAAAUCCAUGCAAAACUGAUUGUGAUAAUGU | 43 |
| miR-19b-13 | UUCUAUGGUUAGUUUUGCAGGUUUG- CAUCCAG CUGUGUGAUAUUC UGCUGUGCAAAUCCAUGCA AAACUGACUGUGGUAG | 44 |
| miR-19b-X | UUACAAUUAGUUUUGCAGGUUUGCAUU- CAGC GUAUAUAUGUAUAUG UGGCUGUGCAAAUCCAU GCAAAACUGAUUGUGAU | 45 |
| miR-20 (miR-20a) | GUAGCAC UAAAGUGCUUAUAGUGCAGGUAGUG UUUAGUUAUCUACUGCAUUAUGAGCACU- UAAA GUACUGC | 46 |
| miR-21 | UGUCGGG UAGCUUAUCAGACUGAUGUUGACUG UUGAAUCUCAUGGCAACACCAGUC- GAUGGGCU GUCUGACA | 47 |
| miR-21-17 | ACCUUGUCGGG UAGCUUAUCAGACUGAUGUUG ACUGUUGAAUCUCAUGGCAACACCAGUCGAUG GGCUGUCUGACAUUUUG | 48 |
| miR-22 | GGCUGAGCCGCAGUAGUUCUUCAGUG- GCAAGC UUUAUGUCCUGACCCAGCUA AAGCUGCCAGUU GAAGAACUGUUGCCCUCUGCC | 49 |
| miR-23a | GGCCGGCUGGGGUUCCUGGGGAUGGGA- UUUGC UUCCUGUCACAA AUCACAUUGCCAGGGAUUUC CAACCGACC | 50 |
| miR-23b | CUCAGGUGCUCUGGCUGCUUGGGUUC- CUGGCA UGCUGAUUUGUGACUUAAGAUUAAA AUCACAU UGCCAGGGAUUACCACGCAACCACGACCUUGG C | 51 |
| miR-23-19 | CCACGCCGGCUGGGGUUCCUGGG- GAUGGGAU UUGCUUCCUGUCACAA AUCACAUUGCCAGGGA UUUCCAACCGACCCUGA | 52 |
| miR-24-1 | CUCCGGUGCCUACUGAGCUGAUAUCAG- UUCUC AUUUUACACAC UGGCUCAGUUCAGCAGGAACA GGAG | 53 |
| miR-24-2 | CUCUGCCUCCCGUGC- CUACUGAGCUGAAACAC AGUUGGUUUGUGUACAC UGGCUCAGUUCAGCA GGAACAGGG | 54 |
| miR-24-19 | CCCUGGGCUCUGCCUCCCGUGC- CUACUGAGCU GAAACACAGUUGGUUUGUGUACAC UGGCUCAG UUCAGCAGGAACAGGGG | 55 |
| miR-24-9 | CCCUCCGGUGCCUACUGAGCUGAUAU- CAGUUC UCAUUUUACACAC UGGCUCAGUUCAGCAGGAA CAGCAUC | 56 |
| miR-25 | GGCCAGUGUUGAGAGGCGGAGACU- UGGGCAAU UGCUGGACGCUGCCCUGGG CAUUGCACUUGUC UCGGUCUGACAGUGCCGGCC | 57 |
| miR-26a | AGGCCGUGGCUCG UUCAAGUAAUCCAGGAUA GGCUGUGCAGGUCCCAAUGGGCCUAUCUUGGUU ACUUGCACGGGACGCGGGCCU | 58 |
| miR-26a-1 | GUGGGCUCG UUCAAGUAAUCCAGGAUAGGCUG UGCAGGUCCCAAUGGGCCUAUUCUUGG- UUACU UGCACGGGACGC | 59 |
| miR-26a-2 | GGCUGUGGCUGGA UUCAAGUAAUCCAGGAUAG GCUGUUUCCAUCUGUGAGGCCUAUUCUUGAUU ACUUGUUUCUGGAGGCAGCU | 60 |
| miR-26b | CCGGGACCCAG UUCAAGUAAUUCAGGAUAGGU UGUGUGCUGUCCAGCCUGUUCUCCA- UUACUUG GCUCGGGGACCGG | 61 |

TABLE 1a-continued

Human microRNA Precursor Sequences

| Precursor Name | Sequence (5' To 3')* | SEQ ID NO. |
|---|---|---|
| miR-27a | CUGAGGAGCAGGGCUUAGCUGCU-UGUGAGCAG GGUCCACACCAAGUCGUG UUCACAGUGGCUAA GUUCCGCCCCCAG | 62 |
| miR-27b-1 | AGGUGCAGAGCUUAGCUGAUUGGUGAA-CAGUG AUUGGUUUCCGCUUUG UUCACAGUGGCUAAGU UCUGCACCU | 63 |
| miR-27b-2 | ACCUGUCUAACAAGGUGCAGAGCU-UAGCUGAU UGGUGAACAGUGAUUGGUUUCCGCUUUG UUCA CAGUGGCUAAGUUCUGCACCUGAAGAGAAGGU G | 64 |
| miR-27-19 | CCUGAGGAGCAGGGCUUAGCUGCU-UGUGAGCA GGGUCCACACCAAGUCGUG UUCACAGUGGCUA AGUUCCGCCCCCAGG | 65 |
| miR-28 | GGUCCUUGCCCUC AAGGAGCUCACAGUCUAUU GAGUUACCUUUCUGACUUUCCCACUAGAUUGU GAGCUCCUGGAGGGCAGGCACU | 66 |
| miR-29a-2 | CCUUCUGUGACCCCUUAGAG-GAUGACUGAUUU CUUUGGUGUUCAGAGUCAAUAUAAUUUU CUA GCACCAUCUGAAAUCGGUUAUAAUGAUUGGGG AAGAGCACCAUG | 67 |
| miR-29a | AUGACUGAUUUCUUUUGGUGUUCAGAGU-CAAU AUAAUUUU CUAGCACCAUCUGAAAUCGGUUAU | 68 |
| miR-29b-1 | CUUCAGGAAGCUGGUUUCAUAUGGUGGU-UUAG AUUUAAAUAGUGAUUGUC UAGCACCAUUUGAA AUCAGUGUUCUUGGGGG | 69 |
| miR-29b-2 | CUUCUGGAAGCUGGUUUCACAUGGUG-GCUUAG AUUUUUCCAUCUUUGUAUC UAGCACCAUUUGA AAUCAGUGUUUUAGGAG | 70 |
| miR-29c | ACCACUGGCCCAUCUCUUACACAG-GCUGACCG AUUUCUCCUGGUGUUCAGAGUCUGUUUUUGU C UAGCACCAUUUGAAAUCGGUUAUGAUGUAGGG GGAAAAGCAGCAGC | 71 |
| miR-30a | GCGAC UGUAAACAUCCUCGACUGGAAGCUGUG AAGCCACAGAUGGG CUUUCAGUCGGAUGUUUG CAGCUGC | 72 |
| miR-30b-1 | A UGUAAACAUCCUACACUCAGCUGUAAUACAU GGAUUGGCUGGGAGGUGGAUGUUUACGU | 73 |
| miR-30b-2 | ACCAAGUUUCAGUUCA UGUAAACAUCCUACAC UCAGCUGUAAUACAUGGAUUGGCUGGGAGGUG GAUGUUUACUUCAGCUGACUUGGA | 74 |
| miR-30c | AGAUAC UGUAAACAUCCUACACUCUCAGCUGU GGAAAGUAAGAAAGCUGGGAGAAGGCU-GUUUA CUCUUUCU | 75 |
| miR-30d | GUUGU UGUAAACAUCCCCGACUGGAAGCUGUA AGACACAGCUAAGCUUUCAGUCAGAUGU-UUGC UGCUAC | 76 |
| miR-30e | C UGUAAACAUCCUUGACUGGAAGCUGUAAGGU GUUCAGAGGAGCUUUCAGUCGGAUGU-UUACAG | 77 |
| miR-31 | GGAGAGGA GGCAAGAUGCUGGCAUAGCUGUUG AACUGGGAACCUGCUAUGCCAACAUA-UUGCCA UCUUUCC | 78 |
| miR-32 | GGAGA UAUUGCACAUUACUAAGUUGCAUGUUG UCACGGCCUCAAUGCAAUUUAGUGUGU-GUGAU AUUUUC | 79 |
| miR-33b | GGGGGCCGAGAGAGGCGGGCGGCCCCGCG GUG CAUUGCUGUUGCAUUGCACGUGUGUGAGGCGG GUGCAGUGCCUCGGCAGUGCAGCCCG-GAGCCG GCCCCUGGCACCAC | 80 |
| miR-33b-2 | ACCAAGUUUCAGUUCA UGUAAACAUCCUACAC UCAGCUGUAAUACAUGGAUUGGCUGGGAGGUG GAUGUUUACUUCAGCUGACUUGGA | 81 |
| miR-33 | CUGUG GUGCAUUGUAGUUGCAUUGCAUGUUCU GGUGGUACCCAUGCAAUGUUUCCA-CAGUGCAU CACAG | 82 |
| miR-34-a | GGCCAGCUGUGAGUGUUUCUU UGGCAGUGUCU UAGCUGGUUGUUGUGAGCAAUAGUAAGGAAGC AAUCAGCAAGUAUACUGCCCUA-GAAGUGCUGC ACGUUGUGGGGCCC | 83 |
| miR-34-b | GUGCUCGGUUUGU AGGCAGUGUCAUUAGCUGA UUGUACUGUGGUGGUUACAAUCACUAACUCCA CUGCCAUCAAAACAAGGCAC | 84 |
| miR-34-c | AGUCUAGUUACU AGGCAGUGUAGUUAGCUGAU UGCUAAUAGUAACCAAUCACUAACCACACGGCC AGGUAAAAAGAUU | 85 |
| miR-91-13 | UCAGAAUAAUGU CAAAGUGCUUACAGUGCAGG UAGUGAUAUGUGCAUCUACUGCAGUGAAGGCA CUUGUAGCAUUAUGGUGA | 86 |
| miR-92-1 | CUUUCUACACAGGUUGGGAUCGGUUG-CAAUGC UGUGUUUCUGUAUGG UAUUGCACUUGUCCCGG CCUGUUGAGUUUGG | 87 |

TABLE 1a-continued

Human microRNA Precursor Sequences

| Precursor Name | Sequence (5' To 3')* | SEQ ID NO. |
|---|---|---|
| miR-92-2 | UCAUCCCUGGGUGGGGAUUUGUUGCA-UUACUU GUGUUCUAUAUAAAG UAUUGCACUUGUCCCGG CCUGUGGAAGA | 88 |
| miR-93-1 (miR-93-2) | CUGGGGGCUCC AAAGUGCUGUUCGUGCAGGUA GUGUGAUUACCCAACCUACUGCUGAGCUAGCA CUUCCCGAGCCCCCGG | 89 |
| miR-95-4 | AACACAGUGGGCACUCAAUAAAUGUCUG-UUGA AUUGAAAUGCGUUACA UUCAACGGGUAUUUAU UGAGCACCCACUCUGUG | 90 |
| miR-96-7 | UGGCCGAU UUUGGCACUAGCACAUUUUUGCUU GUGUCUCUCCGCUCUGAGCAAUCAUGUG-CAGU GCCAAUAUGGGAAA | 91 |
| miR-97-6 (miR-30*) | GUGAGCGAC UGUAAACAUCCUCGACUGGAAGC UGUGAAGCCACAGAUGGGCUUUCAGUCG-GAUG UUUGCAGCUGCCUACU | 92 |
| miR-98 | GUGAGGUAGUAAGUUGUAUUGUUGUGGGUA GGGAUAUUAGGCCCCAAUUAGAA-GAUAACUAU ACAACUUACUACUUUCC | 93 |
| miR-99b | GGCACC CACCCGUAGAACCGACCUUGCGGGGC CUUCGCCGCACACAAGCUCGUGUCU-GUGGGUC CGUGUC | 94 |
| miR-99a | CCCAUUGGCAUA AACCCGUAGAUCCGAUCUUG UGGUGAAGUGGACCGCACAAGCUCGCUUCUAU GGGUCUGUGUCAGUGUG | 95 |
| miR-100-1/2 | AAGAGAGAAGAUAUUGAGGCCUGUUGCCACA A ACCCGUAGAUCCGAACUUGUGGUAUUAGUCCG CACAAGCUUGUAUCUAUAGGUAUGUGU-CUGUU AGGCAAUCUCAC | 96 |
| miR-100-11 | CCUGUUGCCACA AACCCGUAGAUCCGAACUUG UGGUAUUAGUCCGCACAAGCUUGUAUCUAUAG GUAUGUGUCUGUUAGG | 97 |
| miR-101-1/2 | AGGCUGCCCUGGCUCAGUUAUCA-CAGUGCUGA UGCUGUCUAUUCUAAAGG UACAGUACUGUGAU AACUGAAGGAUGGCAGCCAUCUUACCUUCCAU CAGAGGAGCCUCAC | 98 |
| miR-101 | UCAGUUAUCACAGUGCUGAUGCUGUGCA-UUCU AAAGGUACAGUACUGUGAUAACUGA | 99 |
| miR-101-1 | UGCCCUGGCUCAGUUAUCA-CAGUGCUGAUGCU GUCUAUUCUAAAGG UACAGUACUGUGAUAACU GAAGGAUGGCA | 100 |
| miR-101-2 | ACUGUCCUUUUCGGUUAUCAUGGUAC-CGAUG CUGUAUAUCUGAAAGG UACAGUACUGUGAUAA CUGAAGAAUGGUGGU | 101 |
| miR-101-9 | UGUCCUUUUCGGUUAUCAUGGUAC-CGAUGCU GUAUAUCUGAAAGG UACAGUACUGUGAUAACU GAAGAAUGGUG | 102 |
| miR-102-1 | CUUCUGGAAGCUGGUUUCACAUGGUG-GCUUAG AUUUUUCCAUCUUUGUAUC UAGCACCAUUUGA AAUCAGUGUUUUAGGAG | 103 |
| miR-102-7.1 (miR-102-7.2) | CUUCAGGAAGCUGGUUUCAUAUGGUGGU-UUAG AUUUAAAUAGUGAUUGUC UAGCACCAUUUGAA AUCAGUGUUCUUGGGGG | 104 |
| miR-103-2 | UUGUGCUUUCAGCUUCUUUA-CAGUGCUGCCUU GUAGCAUUCAGGUCAA GCAACAUUGUACAGGG CUAUGAAAGAACCA | 105 |
| miR-103-1 | UACUGCCCUCGGCUUCUUUA-CAGUGCUGCCUU GUUGCAUAUGGAUCAA GCAGCAUUGUACAGGG CUAUGAAGGCAUUG | 106 |
| miR-104-17 | AAAUGUCAGACAGCCCAUCGACUGGUG-UUGCC AUGAGAUUCAACAG UCAACAUCAGUCUGAUAA GCUACCCGACAAGG | 107 |
| miR-105-1 | UGUGCAUCUGG UCAAAUGCUCAGACUCCUGU GGUGGCUGCUCAUGCACCACGGAUGU-UUGAGC AUGUGCUACGGUGUCUA | 108 |
| miR-105-2 | UGUGCAUCUGG UCAAAUGCUCAGACUCCUGU GGUGGCUGCUUAUGCACCACGGAUGU-UUGAGC AUGUGCUAUGGUGUCUA | 109 |
| miR-106-a | CCUUGGCCAUGU AAAAGUGCUUACAGUGCAGG UAGCUUUUUGAGAUCUACUGCAAUGUAAGCAC UUCUUACAUUACCAUGG | 110 |
| miR-106-b | CCUGCCGGGGC UAAAGUGCUGACAGUGCAGAU AGUGGUCCUCUCCGUGCUACCGCACU-GUGGGU ACUUGCUGCUCCAGCAGG | 111 |
| miR-107 | CUCUCUGCUUUCAGCUUCUUUACAGUG-UUGCC UUGUGGCAUGGAGUUCAAGC AGCAUUGUACAG GGCUAUCAAAGCACAGA | 112 |
| miR-108-1-small | ACACUGCAAGAACAAUAAGGAUUU-UUAGGGGC AUUAUGACUGAGUCAGAAAACA-CAGCUGCCCC UGAAAGUCCCUCAUUUUUCUUGCGU | 113 |

TABLE 1a-continued

Human microRNA Precursor Sequences

| Precursor Name | Sequence (5' To 3')* | SEQ ID NO. |
|---|---|---|
| miR-108-2-small | ACUGCAAGAGCAAUAAGGAUUU-UUAGGGGCAU UAUGAUAGUGGAAUGGAAACACAUCUGC-CCCC AAAAGUCCCUCAUUUU | 114 |
| miR-122a-1 | CCUUAGCAGAGCUG UGGAGUGUGACAAUGGUG UUUGUGUCUAAACUAUCAAACGCCAUUAUCAC ACUAAAUAGCUACUGCUAGGC | 115 |
| miR-122a-2 | AGCUG UGGAGUGUGACAAUGGUGUUUGUGUCC AAACUAUCAAACGCCAUUAUCACAC-UAAAUAG CU | 116 |
| miR-123 | A CAUUAUUACUUUUGGUACGCGCUGUGACACU UCAAACUCGUACCGUGAGUAAUAAUGCGC | 117 |
| miR-124a-1 | AGGCCUCUCUCUCCGUGUUCACAGCG-GACCUU GAUUUAAAUGUCCAUACAA UUAAGGCACGCGG UGAAUGCCAAGAAUGGGGCUG | 118 |
| miR-124a-2 | AUCAAGAUUAGAGGCUCUGCUCUCCGUG-UUCA CAGCGGACCUUGAUUUAAUGCAUACAA UUAA GGCACGCGGUGAAUGCCAAGAGCGGAGCCUAC GGCUGCACUUGAAG | 119 |
| miR-124a-3 | UGAGGGCCCCUCUGCGUGUUCACAGCG-GACCU UGAUUUAAUGUCUAUACAA UUAAGGCACGCGG UGAAUGCCAAGAGAGGCGCCUCC | 120 |
| miR-124a | CUCUGCGUGUUCACAGCGGACCUUGA-UUUAAU GUCUAUACAA UUAAGGCACGCGGUGAAUGCCA AGAG | 121 |
| miR-124b | CUCUCCGUGUUCACAGCGGACCUUGA-UUUAAU GUCAUACAA UUAAGGCACGCGGUGAAUGCCAA GAG | 122 |
| miR-125a-1 | UGCCAGUCUCUAGG UCCCUGAGACCCUUUAAC CUGUGAGGACAUCCAGGGUCACAGGUGAGGUU CUUGGGAGCCUGGCGUCUGGCC | 123 |
| miR-125a-2 | GG UCCCUGAGACCCUUUAACCUGUGAGGACAU CCAGGGUCACAGGUGAGGUUCUUGG-GAGCCUG G | 124 |
| miR-125b-1 | UGCGCUCCUCUCAG UCCCUGAGACCCUAACUU GUGAUGUUUACCGUUUAAAUCCACGGGUUAGG CUCUGGGGAGCUGCGAGUCGUGCU | 125 |
| miR-125b-2 | ACCAGACUUUUCCUAG UCCCUGAGACCCUAAC UUGUGAGGUAUUUUAGUAACAUCACAAGUCAG GCUCUUGGGACCUAGGCGGAGGGGA | 126 |

TABLE 1a-continued

Human microRNA Precursor Sequences

| Precursor Name | Sequence (5' To 3')* | SEQ ID NO. |
|---|---|---|
| miR-126-1 | CGCUGGCGACGGGA CAUUAUUACUUUUGGUAC GCGCUGUGACAGUUCAAAC UCGUACCGUGAGU AAUAAUGCGCCGUCCACGGCA | 127 |
| miR-126-2 | A CAUUAUUACUUUUGGUACGCGCUGUGACACU UCAAACUCGUACCGUGAGUAAUAAUGCGC | 128 |
| miR-127-1 | UGUGAUCACUGUCUCCAGC-CUGCUGAAGCUCA GAGGGCUCUGAUUCAGAAAGAUCA UCGGAUCC GUCUGAGCUUGGCUGGUCGGAAGUCUCAUCAU C | 129 |
| miR-127-2 | CCAGCCUGCUGAAGCUCAGAGGGCU-CUGAUUC AGAAAGAUCA UCGGAUCCGUCUGAGCUUGGCU GGUCGG | 130 |
| miR-128a | UGAGCUGUUGGAUUCGGGGCCGUAG-CACUGUC UGAGAGGUUUACAUUUC UCACAGUGAACCGGU CUCUUUUUCAGCUGCUUC | 131 |
| miR-128b | GCCCGGCAGCCACUGUGCAGUGG-GAAGGGGGG CCGAUACACUGUACGAGAGUGAGUAG-CAGGUC UCAGUGAACCGGUCUCUUUCCCUACUGUGU CACACUCCUAAUGG | 132 |
| miR-128 | GUUGGAUUCGGGGCCGUAGCACUGU-CUGAGAG GUUUACAUUUC UCACAGUGAACCGGUCUCUUU UUCAGC | 133 |
| miR-129-1 | UGGAU CUUUUUGCGGUCUGGGCUUGCUGUUCC UCUCAACAGUAGUCAGGAAGCCCUUAC-CCCAA AAAGUAUCUA | 134 |
| miR-129-2 | UGCCCUUCGCGAAU CUUUUUGCGGUCGGGCU UGCUGUACAUAACUCAAUAGCCGGAAGCCCUU ACCCCAAAAAGCAUUUGCGGAGGGCG | 135 |
| miR-130a | UGCUGCUGGCCAGAGCUCUUUUCACAUU-GUGC UACUGUCUGCACCUGUCACUAG CAGUGCAAUG UUAAAAGGGCAUUGGCCGUGUAGUG | 136 |
| miR-131-1 | GCCAGGAGGCGGGGUUGGUUGUUAUCU-UUGGU UAUCUAGCUGUAUGAGUGGUGUGGAGU-CUUCA UAAAGCUAGAUAACCGAAAGUAAAAAUACCC CAUACACUGCGCAG | 137 |
| miR-131-3 | CACGGCGCGGCAGCGGCACUGGCUAAGG-GAGG CCCGUUUCUCUCUUUGGUUAUCUAGCU-GUAUG AGUGCCACAGAGCCGUCA UAAAGCUAGAUAAC CGAAAGUAGAAAUG | 138 |

TABLE 1a-continued

Human microRNA Precursor Sequences

| Precursor Name | Sequence (5' To 3')* | SEQ ID NO. |
|---|---|---|
| miR-131 | GUUGUUAUCUUUGGUUAUCUAGCU-GUAUGAGU GUAUUGGUCUUCA UAAAGCUAGAUAACCGAAA GUAAAAAC | 139 |
| miR-132-1 | CCGCCCCCGCGUCUCCAGGGCAACCGUG-GCUU UCGAUUGUUACUGUGGGAACUGGAGG UAACAG UCUACAGCCAUGGUCGCCCCGCAGCACGCCCA CGCGC | 140 |
| miR-132-2 | GGGCAACCGUGGCUUUCGAUUGUUACU-GUGGG AACUGGAGG UAACAGUCUACAGCCAUGGUCGC CC | 141 |
| miR-133a-1 | ACAAUGCUUUGCUAGAGCUGGUAAAAUG-GAAC CAAAUCGCCUCUUCAAUGGA UUUGGUCCCCUU CAACCAGCUGUAGCUAUGCAUUGA | 142 |
| miR-133a-2 | GGGAGCCAAAUGCUUUGCUAGAGCUG-GUAAAA UGGAACCAAAUCGACUGUCCAAUGGAU UUGGU CCCCUUCAACCAGCUGUAGCUGUGCAUUGAUG GCGCCG | 143 |
| miR-133 | GCUAGAGCUGGUAAAAUGGAAC-CAAAUCGCCU CUUCAAUGGAU UUGGUCCCCUUCAACCAGCUG UAGC | 144 |
| miR-133b | CCUCAGAAGAAAGAUGCCCCCUGCUCUG-GCUG GUCAAACGGAACCAAGUCCGUCUUC-CUGAGAG GU UUGGUCCCCUUCAACCAGCUACAGCAGGGC UGGCAAUGCCCAGUCCUUGGAGA | 145 |
| miR-133b-small | GCCCCCUGCUCUGGCUGGUCAAACG-GAACCAA GUCCGUCUUCCUGAGAGGUUUGGUC-CCCUUCA ACCAGCUACAGCAGGG | 146 |
| miR-134-1 | CAGGGUG UGUGACUGGUUGACCAGAGGGGCAU GCACUGUGUUCACCCUGUGGGCCAC-CUAGUCA CCAACCCUC | 147 |
| miR-134-2 | AGGGUG UGUGACUGGUUGACCAGAGGGGCAUG CACUGUGUUCACCCUGUGGGCCAC-CUAGUCAC CAACCCU | 148 |
| miR-135a-1 | AGGCCUCGCUGUUCUC UAUGGCUUUUUAUUCC UAUGUGAUUCUACUGCUCACUCAUAUAGGGAU GGGAGCCGUGGCGCACGGCGGGGACA | 149 |
| miR-135a-2 (miR-135-2) | AGAUAAAUUGACUCUAGUGCUU UAUGGCUUUU UAUUCCUAUGUGAUAGUAAUAAAGUCUCAUGU AGGGAUGGAAGCCAUGAAAUACAUU-GUGAAAA AUCA | 150 |
| miR-135 | C UAUGGCUUUUAUUCCUAUGUGAUUCUACUG CUCACUCAUAUAGGGAUUGGAGCCGUGG | 151 |
| miR-135b | CACUCUGCUGUGGCC UAUGGCUUUUCAUUCCU AUGUGAUUGCUGUCCCAAACUCAUGUAGGGCU AAAAGCCAUGGGCUACAGUGAGGGGC-GAGCUC C | 152 |
| miR-136-1 | UGAGCCCUCGGAGG ACUCCAUUUGUUUUGAUG AUGGAUUCUUAUGCUCCAUCAUCGUCUCAAAU GAGUCUUCAGAGGGUUCU | 153 |
| miR-136-2 | GAGG ACUCCAUUUGUUUUGAUGAUGGAUUCUU AUGCUCCAUCAUCGUCUCAAAUGAGUCUUC | 154 |
| miR-137 | CUUCGGUGACGGGUAUUCUUGGGUG-GAUAAUA CGGAUUACGUUGU UAUUGCUUAAGAAUACGCG UAGUCGAGG | 155 |
| miR-138-1 | CCCUGGCAUGGUGUGGUGGGGC AGCUGGUGUU GUGAAUCAGGCCGUUGCCAAUCAGAGAACGGC UACUUCACAACACCAGGGCCACACCA-CACUAC AGG | 156 |
| miR-138-2 | CGUUGCUGC AGCUGGUGUUGUGAAUCAGGCCG ACGAGCAGCGCAUCCUCUUACCCGGC-UAUUUC ACGACACCAGGGUUGCAUCA | 157 |
| miR-138 | C AGCUGGUGUUGUGAAUCAGGCCGACGAGCAG CGCAUCCUCUUACCCGGCUAUUUCACGA-CACC AGGGUUG | 158 |
| miR-139 | GUGUAU UCUACAGUGCACGUGUCUCCAGUGUG GCUCGGAGGCUGGAGAGGCGGCCCUG-UUGGAG UAAC | 159 |
| miR-140 | UGUGUCUCUCUCUGUGUCCUGCC AGUGGUUUU ACCCUAUGGUAGGUUACGUCAUGCUGUUC UAC CACAGGGUAGAACCACGGACAGGAUACCGGGG CACC | 160 |
| miR-140as | UCCUGCC AGUGGUUUUACCCUAUGGUAGGUUA CGUCAUGCUGUUC UACCACAGGGUAGAACCAC GGACAGGA | 161 |
| miR-140s | CCUGCC AGUGGUUUUACCCUAUGGUAGGUUAC GUCAUGCUGUUC UACCACAGGGUAGAACCACG GACAGG | 162 |
| miR-141-1 | CGGCCGGCCCUGGGUCCAUCUUCCAGUA-CAGU GUUGGAUGGUCUAAUUGUGAAGCUCCU AACAC UGUCUGGUAAAGAUGGCUCCCGGGUGGGUUC | 163 |

TABLE 1a-continued

Human microRNA Precursor Sequences

| Precursor Name | Sequence (5' To 3')* | SEQ ID NO. |
|---|---|---|
| miR-141-2 | GGGUCCAUCUUCCAGUACAGUGUUG-GAUGGUC UAAUUGUGAAGCUCCU AACACUGUCUGGUAAA GAUGGCCC | 164 |
| miR-142 | ACC CAUAAAGUAGAAAGCACUACUAACAGCAC UGGAGGG UGUAGUGUUUCCUACUUUAUGGAUG | 165 |
| miR-143-1 | GCGCAGCGCCCUGUCUCCCAGCCUGAG-GUGCA GUGCUGCAUCUCUGGUCAGUUGGGAGUC UGAG AUGAAGCACUGUAGCUCAGGAAGAGAGAAGUU GUUCUGCAGC | 166 |
| miR-143-2 | CCUGAGGUGCAGUGCUGCAUCUCUGGU-CAGUU GGGAGUCUGAGAUGAAGCACUGUAGCUCAGG | 167 |
| miR-144-1 | UGGGGCCCUGGCUGGGAUAUCAU-CAUAUACUG UAAGUUUGCGAUGAGACAC UACAGUAUAGAUG AUGUACUAGUCCGGGCACCCCC | 168 |
| miR-144-2 | GGCUGGGAUAUCAUCAUAUACUGUAAGU-UUGC GAUGAGACAC UACAGUAUAGAUGAUGUACUAG UC | 169 |
| miR-145-1 | CACCUUGUCCUCACG GUCCAGUUUUCCCAGGA AUCCCUUAGAUGCUAAGAUGGGGAUUCCUGGA AAUACUGUUCUUGAGGUCAUGGUU | 170 |
| miR-145-2 | CUCACG GUCCAGUUUUCCCAGGAAUCCCUUAG AUGCUAAGAUGGGGAUUCCUG-GAAAUACUGUU CUUGAG | 171 |
| miR-146-1 | CCGAUGUGUAUCCUCAGCUU UGAGAACUGAAU UCCAUGGGUUGUGUCAGUGUCAGACCUCUGAA AUUCAGUUCUUCAGCUGGGAUAUCUCU-GUCAU CGU | 172 |
| miR-146-2 | AGCUU UGAGAACUGAAUUCCAUGGGUUGUGUC AGUGUCAGACCUGUGAAAUUCAGUUCU-UCAGC U | 173 |
| miR-147 | AAUCUAAAGACAACAUUUCUGCACACA-CACCA GACUAUGGAAGCCA GUGUGUGGAAAUGCUUCU GCUAGAUU | 174 |
| miR-148a (miR-148) | GAGGCAAAGUUCUGAGACACUCCGACU-CUGAG UAUGAUAGAAG UCAGUGCACUACAGAACUUUG UCUC | 175 |
| miR-148b | CAAGCACGAUUAGCAUUUGAGGUGAAG-UUCUG UUAUACACUCAGGCUGUGGCUCUCUGAAAG UC AGUGCAUACAGAACUUUGUCUCGAAAGCUUU CUA | 176 |
| miR-148b-small | AAGCACGAUUAGCAUUUGAGGUGAAGUU-CUGU UAUACACUCAGGCUGUGGCUCU-CUGAAAGUCA GUGCAU | 177 |
| miR-149-1 | GCCGGCGCCCGAGC UCUGGCUCCGUGUCUUCA CUCCCGUGCUUGUCCGAGGAGGGAGGGAGGGA CGGGGGCUGUGCUGGGGCAGCUGGA | 178 |
| miR-149-2 | GC UCUGGCUCCGUGUCUUCACUCCCGUGCUUG UCCGAGGAGGGAGGGAGGGAC | 179 |
| miR-150-1 | CUCCCCAUGGCCCUG UCUCCCAACCCUUGUAC CAGUGCUGGGCUCAGACCCUGGUACAGGCCUG GGGGACAGGGACCUGGGGAC | 180 |
| miR-150-2 | CCCUG UCUCCCAACCCUUGUACCAGUGCUGGG CUCAGACCCUGGUACAGGCCUGGGGGA-CAGGG | 181 |
| miR-151 | UUUCCUGCCCUCGAGGAGCUCACAGUC-UAGUA UGUCUCAUCCCCUA CUAGACUGAAGCUCCUUG AGGACAGG | 182 |
| miR-151-2 | CCUGUCCUCAAGGAGCUUCAGUC-UAGUAGGGG AUGAGACAUACUAGACUGUGAGCUCCUC-GAGG GCAGG | 183 |
| miR-152-1 | UGUCCCCCCGGCCCAGGUUCUGUGAUA-CACU CCGACUCGGGCUCUGGAGCAG UCAGUGCAUGA CAGAACUUGGGCCCGGAAGGACC | 184 |
| miR-152-2 | GGCCCAGGUUCUGUGAUACACUC-CGACUCGGG CUCUGGAGCAG UCAGUGCAUGACAGAACUUGG GCCCCGG | 185 |
| miR-153-1-1 | CUCACAGCUGCCAGUGUCAUUUUU-GUGAUCUG CAGCUAGUAUUCUCACUCCAG UUGCAUAGUCA CAAAAGUGAUCAUUGGCAGGUGUGGC | 186 |
| miR-153-1-2 | UCUCUCUCUCCCUCACAGCUGCCAGUGUCA UU GUCACAAAAGUGAUCAUUGGCAGGUGUGGCUG CUGCAUG | 187 |
| miR-153-2-1 | AGCGGUGGCCAGUGUCAUUUUUGUGAUG-UUGC AGCUAGUAAUAUGAGCCCAG UUGCAUAGUCAC AAAAGUGAUCAUUGGAAACUGUG | 188 |
| miR-153-2-2 | CAGUGUCAUUUUUGUGAUGUUGCAGC-UAGUAA UAUGAGCCCAG UUGCAUAGUCACAAAAGUGAU CAUUG | 189 |
| miR-154-1 | GUGGUACUUGAAGA UAGGUUAUCCGUGUUGCC UUCGCUUUAUUUGUGACG AAUCAUACACGGUU GACCUAUUUUUCAGUACCAA | 190 |

TABLE 1a-continued

Human microRNA Precursor Sequences

| Precursor Name | Sequence (5' To 3')* | SEQ ID NO. |
|---|---|---|
| miR-154-2 | GAAGA<u>UAGGUUAUCCGUGUUGCCUUCG</u>CUUUA UUUGUGACG <u>AAUCAUACACGGUUGACCUAUUU</u> UU | 191 |
| miR-155 | CUG <u>UUAAUGCUAAUCGUGAUAGGGGU</u>UUUUGC CUCCAACUGACUCCUACAUAUUAGCA-UUAACA G | 192 |
| miR-156 = miR-157 = overlap miR-141 | CCUAACACUGUCUGGUAAAGAUGGCUC-CCGGG UGGGUUCUCUCGGCAGUAACCUUCAGG-GAGCC CUGAAGACCAUGGAGGAC | 193 |
| miR-158-small = miR-192 | GCCGAGACCGAGUGCACAGGGCU<u>CUGACCUAU</u> <u>GAAUUGACAGCCAGUGCUCUCGUCUCCCCUCU</u> GGCUGCCAAUUCCAUAGGUCACAGGUAU-GUUC GCCUCAAUGCCAGC | 194 |
| miR-159-1-small | UCCCGCCCCCUGUAACAGCAACUCCAU-GUGGA AGUGCCCACUGGUUCCAGUGGGGCUGCU-GUUA UCUGGGGCGAGGGCGA | 195 |
| miR-161-small | AAAGCUGGGUUGAGAGGGCGAAAAAG-GAUGAG GUGACUGGUCUGGGCUACGC-UAUGCUGCGGCG CUCGGG | 196 |
| miR-163-1b-small | CAUUGGCCUCCUAAGCCAGGGAUU-GUGGGUUC GAGUCCCACCCGGGUAAAGAAAGGC-CGAAUU | 197 |
| miR-163-3-small | CCUAAGCCAGGGAUUGUGGGUUCGAGUC-CCAC CUGGGGUAGAGGUGAAAGUUCCUU-UUACGGAA UUUUUU | 198 |
| miR-162 | CAAUGUCAGCAGUGCCU <u>UAGCAGCACGUAAAU</u> AUUGGCGUUAAGAUUCUAAAAUUAUCUCCAGU AUUAACUGUCUGCUGAAGUAAGG-UUGACCAU ACUCUACAGUUG | 199 |
| miR-175-small = miR-224 | GGGCUUUCAAGUCACUAGUGGUUCCGU-UUAGU AGAUGAUUGUGCAUUGUUUCAAAAUG-GUGCCC UAGUGACUACAAAGCCC | 200 |
| miR-177-small | ACGCAAGUGUCCUAAGGUGAGCUCAGG-GAGCA CAGAAACCUCCAGUGGAACA-GAAGGGCAAAAG CUCAUU | 201 |
| miR-180-small | CAUGUGUCACUUUCAGGUGGAGUUUCAA-GAGU CCCUUCCUGGUUCACCGUCUCCUUUGCU-CUUC CACAAC | 202 |
| miR-181a | AGAAGGGCUAUCAGGCCAGCCUUCAGAG-GACU CCAAGG <u>AACAUUCAACGCUGUCGGUGAGUUUG</u> GGAUUUGAAAAAACCACUGACCG-UUGACUGUA CCUUGGGGUCCUUA | 203 |
| miR-181b-1 | CCUGUGCAGAGAUUAUUUUUUAAAAGGU-CACA AUC <u>AACAUUCAUUGCUGUCGGUGGGUUGAACU</u> GUGUGGACAAGCUCACUGAA-CAAUGAAUGCAA CUGUGGCCCCGCUU | 204 |
| miR-181b-2 | CUGAUGGCUGCACUC <u>AACAUUCAUUGCUGUCG</u> <u>GUGGGUUUGAGUCUGAAUCAACUCACUGAUCA</u> AUGAAUGCAAACUGCGGACCAAACA | 205 |
| miR-181c | CGGAAAAUUUGCCAAGGGUUUGGGGG <u>AACAUU</u> <u>CAACCUGUCGGUGAGUUUGGGCAGCUCAGGCA</u> AACCAUCGACCGUUGAGUGGACCCUGAG-GCCU GGAAUUGCCAUCCU | 206 |
| miR-182-as | GAGCUGCUUGCCUCCCCCCGUUU <u>UUGGCAAUG</u> <u>GUAGAACUCACACUGGUGAGGUAACAGGAUCC</u> GG UGGUUCUAGACUUGCCAACUAUGGGGCGAG GACUCAGGCGGCAC | 207 |
| miR-182 | UUU <u>UUGGCAAUGGUAGAACUCACACUGGUGAG</u> GUAACAGGAUCCGG UGGUUCUAGACUUGCCAA CUAUGG | 208 |
| miR-183 | CCGCAGAGUGUGACUCCUGUUCUGUG <u>UAUGGC</u> <u>ACUGGUAGAAUUCACUGUGAACAGUCUCAGUC</u> AGUGAAUUACCGAAGGGCCAUAAACA-GAGCAG AGACAGAUCCACGA | 209 |
| miR-184-1 | CCAGUCACGUCCCCUUAUCACUUUUCCA-GCCC AGCUUUGUGACUGUAAGUGU <u>UGGACGGAGAAC</u> <u>UGAUAAGGGUAGGUGAUUGA</u> | 210 |
| miR-184-2 | CCUUAUCACUUUUCCAGCCCAGCUUU-GUGACU GUAAGUGU <u>UGGACGGAGAACUGAUAAGGGUAG</u> G | 211 |
| miR-185-1 | AGGGGGCGAGGGAU <u>UGGAGAGAAAGGCAGUUC</u> CUGAUGGUCCCCUCCCAGGGGCUGGCU-UUCC UCUGGUCCUUCCCUCCCA | 212 |
| miR-185-2 | AGGGAU <u>UGGAGAGAAAGGCAGUUCCUGAUGGU</u> CCCCUCCCAGGGGCUGGCUUUCCUCUG-GUCC UU | 213 |
| miR-186-1 | UGCUUGUAACUUUC <u>CAAAGAAUUCUCCUUUUG</u> GGCUUUCUGGUUUUAUUUUAAGCCCAAAGGUG AAUUUUUUGGGAAGUUUGAGCU | 214 |

TABLE 1a-continued

Human microRNA Precursor Sequences

| Precursor Name | Sequence (5' To 3')* | SEQ ID NO. |
|---|---|---|
| miR-186-2 | ACUUUC CAAAGAAUUCUCCUUUUGGGCUUUCU GGUUUUAUUUUAAGCCCAAAGGUGAAU- UUUUU GGGAAGU | 215 |
| miR-187 | GGUCGGGCUCACCAUGACACAGU- GUGAGACUC GGGCUACAACACAGGAC- CCCGGGGCGCUGCUCU GACCCC UCGUGUCUUGUGUUGCAGCCGGAGGG ACGCAGGUCCGCA | 216 |
| miR-188-1 | UGCUCCCUCUCUCA CAUCCCUUGCAUGGUGGA GGGUGAGCUUUCUGAAAACCCCUCCCACAUGC AGGGUUUGCAGGAUGGCGAGCC | 217 |
| miR-188-2 | UCUCA CAUCCCUUGCAUGGUGGAGGGUGAGCU UUCUGAAAACCCCUCCCACAUGCAGGGU- UUGC AGGA | 218 |
| miR-189-1 | CUGUCGAUUGGACCCGCCCUCCG GUGCCUACU GAGCUGAUAUCAGUUCUCAUUUUACACACUGG CUCAGUUCAGCAGGAACAGGAGUCGAGC- CCUU GAGCAA | 219 |
| miR-189-2 | CUCCG GUGCCUACUGAGCUGAUAUCAGUUCUC AUUUUACACACUGGCUCAGUUCAGCAG- GAACA GGAG | 220 |
| miR-190-1 | UGCAGGCCUCUGUG UGAUAUGUUUGAUAUAUU AGGUUGUUAUUUAAUCCAACUAUAUAUCAAAC AUAUUCCUACAGUGUCUUGCC | 221 |
| miR-190-2 | CUGUG UGAUAUGUUUGAUAUAUUAGGUUGUUA UUUAAUCCAACUAUAUAUCAAACAUA- UUCCUA CAG | 222 |
| miR-191-1 | CGGCUGGACAGCGGG CAACGGAAUCCCAAAAG CAGCUGUUGUCUCCAGAGCAUUCCAGCUGCGC UUGGAUUUCGUCCCCUGCUCUCCUGCCU | 223 |
| miR-191-2 | AGCGGG CAACGGAAUCCCAAAAGCAGCUGUUG UCUCCAGAGCAUUCCAGCUGCGCUUGGA- UUUC GUCCCCUGCU | 224 |
| miR-192-2/3 | CCGAGACCGAGUGCACAGGGCU CUGACCAUG AAUUGACAGCCAGUGCUCUCGUCUCCCCUCUG GCUGCCAAUUCCAUAGGUCACAGGUAUG- UUCG CCUCAAUGCCAG | 225 |
| miR-192 | GCCGAGACCGAGUGCACAGGGCU CUGACCAU GAAUUGACAGCCAGUGCUCUCGUCUCCCCUCU GGCUGCCAAUUCCAUAGGUCACAGGUAU- GUUC GCCUCAAUGCCAGC | 226 |
| miR-193-1 | CGAGGAUGGGAGCUGAGGGCUGGGUCU- UUGCG GGCGAGAUGAGGGUGUCGGAUC AACUGGCCUA CAAAGUCCCAGUUCUCGGCCCCCG | 227 |
| miR-193-2 | GCUGGGUCUUUGCGGGCGAGAUGAGGGU- GUCG GAUC AACUGGCCUACAAAGUCCCAGU | 228 |
| miR-194-1 | AUGGUGUUAUCAAG UGUAACAGCAACUCCAUG UGGACUGUGUACCAAUUUCCAGUGGAGAUGCU GUUACUUUUGAUGGUUACCAA | 229 |
| miR-194-2 | G UGUAACAGCAACUCCAUGUGGACUGUGUACC AAUUUCCAGUGGAGAUGCUGUUACUUUUGAU | 230 |
| miR-195-1 | AGCUUCCCUGGCUC UAGCAGCACAGAAAUAUU GGCACAGGGAAGCGAGUCUGCCAAUAUUGGCU GUGCUGCUCCAGGCAGGGUGGUG | 231 |
| miR-195-2 | UAGCAGCACAGAAAUAUUGGCACAGGGAAGCG AGUCUGCCAAUAUUGGCUGUGCUGCU | 232 |
| miR-196-1 | CUAGAGCUUGAAUUGGAACUGCUGAGUGAAU U AGGUAGUUUCAUGUUGUUGGGCCUGGGUUUCU GAACACAACAACAUUAAACCACCCGAUU- CACG GCAGUUACUGCUCC | 233 |
| miR-196a-1 | GUGAAU UAGGUAGUUUCAUGUUGUUGGGCCUG GGUUUCUGAACACAACAACAUUAAAC- CACCCG AUUCAC | 234 |
| miR-196a-2 (miR-196-2) | UGCUCGCUCAGCUGAUCUGUGGCU UAGGUAGU UUCAUGUUGUGGGAUUGAGUUUUUGAACUCGG CAACAAGAAACUGCCUGAGUUACAU- CAGUCGG UUUUCGUCGAGGGC | 235 |
| miR-196 | GUGAAU UAGGUAGUUUCAUGUUGUUGGGCUG GGUUUCUGAACACAACAACAUUAAAC- CACCCG AUUCAC | 236 |
| miR-196b | ACUGGUCGGUGAUU UAGGUAGUUUCCUGUUGU UGGGAUCCACCUUUCUCUCGACAGCACGACAC UGCCUUCAUUACUUCAGUUG | 237 |
| miR-197 | GGCUGUGCCGGGUAGAGAGGGCAGUGG- GAGGU AAGAGCUCUUCACCC UUCACCACCUUCUCCAC CCAGCAUGGCC | 238 |
| miR-197-2 | GUGCAUGUGUAUGUAUGUGUGCAUGUG- CAUGU GUAUGUGUAUGAGUGCAUGCGUGUGGC | 239 |
| miR-198 | UCAUU GGUCCAGAGGGGAGAUAGGUUCCUGUG AUUUUUCCUUCUUCUCUAUAGAAUAAAUGA | 240 |
| miR-199a-1 | GCCAA CCCAGUGUUCAGACUACCUGUUCAGGA GGCUCUCAAUGUG UACAGUAGUCUGCACAUUG GUUAGGC | 241 |

TABLE 1a-continued

Human microRNA Precursor Sequences

| Precursor Name | Sequence (5' To 3')* | SEQ ID NO. |
|---|---|---|
| miR-199a-2 | AGGAAGCUUCUGGAGAUCCUGCUCCGUCGCCC<br>CAGUGUUCAGACUACCUGUUCAGGACAAUGCC<br>GUUG<br>UACAGUAGUCUGCACAUUGGUUAGACUG<br>GGCAAGGGAGAGCA | 242 |
| miR-199b | CCAGAGGACACCUCCACUCCGUCUA<br>CCCAGUG<br>UUUAGACUAUCUGUUCAGGACUCCCAAAUUG<br>U<br>ACAGUAGUCUGCACAUUGGUUAGGCUGGGCUG<br>GGUUAGACCCUCGG | 243 |
| miR-199s | GCCAACCCAGUGUUCAGACUACCUGUU-<br>CAGGA<br>GGCUCUCAAUGUG<br>UACAGUAGUCUGCACAUUG<br>GUUAGGC | 244 |
| miR-200a | GCCGUGGCCAUCUUACUGGGCAGCAUUG-<br>GAUG<br>GAGUCAGGU<br>CUCUAAUACUGCCUGGUAAUGAU<br>GACGGC | 245 |
| miR-200b | CCAGCUCGGGCAGCCGUGGCCAUCU-<br>UACUGGG<br>CAGCAUUGGAUGGAGUCAGGU<br>CUCUAAUACUG<br>CCUGGUAAUGAUGACGGCGGAGCCCUGCACG | 246 |
| miR-200c | CCCUCGUCUUACCCAGCAGUGU-<br>UUGGGUGCGG<br>UUGGGAGUCUCU<br>AAUACUGCCGGGUAAUGAUG<br>GAGG | 247 |
| miR-202 | GUUCCUUUUUCCUAUGCAUAUACUUCU-<br>UUGAG<br>GAUCUGGCCUAA<br>AGAGGUAUAGGGCAUGGGAA<br>GAUGGAGC | 248 |
| miR-203 | GUGUUUGGGACUCGCGCGCUGGGUCCA-<br>GUGGU<br>UCUUAACAGUUCAACAGUUCUGUAGCG-<br>CAAUU<br>GUGAAAUGUUUAGGACCACUAGACCCGGCGGG<br>CGCGGCGACAGCGA | 249 |
| miR-204 | GGCUACAGUCUUUCUUCAU-<br>GUGACUCGUGGAC<br>UUCCCUUUGUCAUCCUAUGCCUGAAUAUAU<br>GAAGGAGGCUGGGAAGGCAAAGGGACG-<br>UUCAA<br>UUGUCAUCACUGGC | 250 |
| miR-205 | AAAGAUCCUCAGACAAUCCAUGUGCU-<br>UCUCUU<br>G<br>UCCUUCAUUCCACCGGAGUCUGUCUCAUACC<br>CAACCAGAUUUCAGUGGAGUGAAGUU-<br>CAGGAG<br>GCAUGGAGCUGACA | 251 |
| miR-206-1 | UGCUUCCCGAGGCCACAUGCUUCU-<br>UUAUAUCC<br>CCAUAUGGAUUACUUUGCUA<br>UGGAAUGUAAGG<br>AAGUGUGGGUUUCGGCAAGUG | 252 |
| miR-206-2 | AGGCCACAUGCUUCUUUAUAUC-<br>CCCAUAUGGA<br>UUACUUUGCUA<br>UGGAAUGUAAGGAAGUGUGUG<br>GUUUU | 253 |
| miR-208 | UGACGGGCGAGCUUUUGGCCCGGG-<br>UUUAUACCU<br>GAUGCUCACGU<br>AUAAGACGAGCAAAAAGCUUG<br>UUGGUCA | 254 |
| miR-210 | ACCCGGCAGUGCCUCCAGGCG-<br>CAGGGCAGCCC<br>CUGCCCACCGCACACUGCGCUGCCCCA-<br>GACCC<br>A<br>CUGUGCGUGUGACAGCGGCUGAUCUGUGCCU<br>GGGCAGCGCGACCC | 255 |
| miR-211 | UCACCUGGCCAUGUGACUUGUGGGC<br>UUCCCUU<br>UGUCAUCCUUCGCCUAGGGCUCUGAGCAGGGC<br>AGGGACAGCAAAGGGGUGCUCAGUUGU-<br>CACUU<br>CCCACAGCACGGAG | 256 |
| miR-212 | CGGGGCACCCCGCCCGGACAGCGCGCCG-<br>GCAC<br>CUUGGCUCUAGACUGCUUACUGC-<br>CCGGGCCGC<br>CCUCAG<br>UAACAGUCUCCAGUCACGGCCACCGA<br>CGCCUGGCCCCGCC | 257 |
| miR-213-2 | CCUGUGCAGAGAUUAUUUUUUAAAAGGU-<br>CACA<br>AUC<br>AACAUUCAUUGCUGUCGGUGGGUUGAACU<br>GUGUGGACAAGCUCACUGAA-<br>CAAUGAAUGCAA<br>CUGUGGCCCCGCUU | 258 |
| miR-213 | GAGUUUUGAGGUUGCUUCAGUGAACAUU-<br>CAAC<br>GCUGUCGGUGAGUUUGGAAUUAAAAUCAAA<br>AC<br>CAUCGACCGUUGAUUGUACCCUAUGGCUAACC<br>AUCAUCUACUCC | 259 |
| miR-214 | GGCCUGGCUGGACAGAGUUGUCAUGUGU-<br>CUGC<br>CUGUCUACACUUGCUGUGCAGAACAUC-<br>CGCUC<br>ACCUGU<br>ACAGCAGGCACAGACAGGCAGUCACA<br>UGACAACCCAGCCU | 260 |
| miR-215 | AUCAUUCAGAAAUGGUAUACAGGAAA<br>AUGACC<br>UAUGAAUUGACAGACAAUAUAGCUGAGUUUGU<br>CUGUCAUUUCUUUAGGCCAAUAUUCU-<br>GUAUGA<br>CUGUGCUACUUCAA | 261 |
| miR-216 | GAUGGCUGUGAGUUGGCU<br>UAAUCUCAGCUGGC<br>AACUGUGAGAUGUUCAUACAAUCCCUCACAGU<br>GGUCUCUGGGAUUAUGCUAAACAGAG-<br>CAAUUU<br>CCUAGCCCUCACGA | 262 |
| miR-217 | AGUAUAAUUAUUCACAUAG-<br>UUUUGAUGUCGCA<br>GA<br>UACUGCAUCAGGAACUGAUUGGAUAAGAAU<br>CAGUCACCAUCAGUUCCUAAUGCAUUGC-<br>CUUC<br>AGCAUCUAAACAAG | 263 |

TABLE 1a-continued

Human microRNA Precursor Sequences

| Precursor Name | Sequence (5' To 3')* | SEQ ID NO. |
|---|---|---|
| miR-218-1 | GUGAUAAUGUAGCGAGAUUUUCUG UUGUGCUU GAUCUAACCAUGUGGUUGCGAGGUAUGAGUAA AACAUGGUUCCGUCAAGCACCAUG-GAACGUCA CGCAGCUUUCUACA | 264 |
| miR-218-2 | GACCAGUCGCUGCGGGGCUUUCCU UUGUGCUU GAUCUAACCAUGUGGUUGGAACGAUGGAAACGG AACAUGGUUCUGUCAAGCACCGCG-GAAAGCAC CGUGCUCUCCUGCA | 265 |
| miR-219 | CCGCCCCGGGCCGCGGCUCC UGAUUGUCCAAA CGCAAUUCUCGAGUCUAUGGCUCCGGCCGAGA GUUGAGUCUGGACGUCCCGAGCCGCCGC-CCCC AAACCUCGAGCGGG | 266 |
| miR-219-1 | CCGCCCCGGGCCGCGGCUCC UGAUUGUCCAAA CGCAAUUCUCGAGUCUAUGGCUCCGGCCGAGA GUUGAGUCUGGACGUCCCGAGCCGCCGC-CCCC AAACCUCGAGCGGG | 267 |
| miR-219-2 | ACUCAGGGGCUUCGCCAC UGAUUGUCCAAACG CAAUUCUUGUACGAGUCUGCGGCCAACCGAGA AUUGUGGCUGGACAUCUGUG-GCUGAGCUCCGG G | 268 |
| miR-220 | GACAGUGUGGCAUUGUAGGGCU CCACACCGUA UCUGACACUUUGGGCGAGGGCACCAUGCUGAA GGUGUUCAUGAUGCGGUCUGGGAACUC-CUCAC GGAUCUUACUGAUG | 269 |
| miR-221 | UGAACAUCCAGGUCUGGGGCAUGAAC-CUGGCA UACAAUGUAGAUUUCUGUGUUCGUUAG-GCAAC AGCUACAUUGUCUGCUGGGUUUCAGGCUACCU GGAAACAUGUUCU | 270 |
| miR-222 | GCUGCUGGAAGGUGUAGGUACCCU-CAAUGGCU CAGUAGCCAGUGUAGAUCCUGUCU-UUCGUAAU CAGC AGCUACAUCUGGCUACUGGGUCUCUGAU GGCAUCUUCUAGCU | 271 |
| miR-223 | CCUGGCCUCCUGCAGUGCCACGCUCCGU-GUAU UUGACAAGCUGAGUUGGACACUCCAU-GUGGUA GAG UGUCAGUUUGUCAAAUACCCCAAGUGCGG CACAUGCUUACCAG | 272 |
| miR-224 | GGGCUUU CAAGUCACUAGUGGUUCCGUUUAGU AGAUGAUUGUGCAUUGUUUCAAAAUG-GUGCCC UAGUGACUACAAAGCCC | 273 |
| miR-294-1 (chr16) | CAAUCUUCCUUUAUCAUGGUAUUGAUUU-UUCA GUGCUUCCCUUUUGUGUGAGAGAAGAUA | 274 |

| Precursor Name | Sequence (5' To 3')* | SEQ ID NO. |
|---|---|---|
| miR-296 | AGGACCCUUCCAGAGGGCCCCCCU-CAAUCCU GUUGUGCCUAAUUCAGAGGGUUGGGUG-GAGGC UCUCCUGAAGGGCUCU | 275 |
| miR-299 | AAGAAAUGGUUUACCGUCCCACAUACAU-UUUG AAUAUGUAUGUGGGGAUGGUAAACCGCUUCUU | 276 |
| miR-301 | ACUGCUAACGAAUGCUCUGACUUUAUUG-CACU ACUGUACUUUACAGCUAGCAGUG-CAAUAGUAU UGUCAAAGCAUCUGAAAGCAGG | 277 |
| miR-302a | CCACCACUUAAACGUGGAUGUACUUGCU-UUGA AACUAAAGAAG UAAGUGCUUCCAUGUUUUGGU GAUGG | 278 |
| miR-302b | GCUCCCUUCA ACUUUAACAUGGAAGUGCUUUC UGUGACUUUAAAAG UAAGUGCUUCCAUGUUUU AGUAGGAGU | 279 |
| miR-302c | CCUUUGC UUUAACAUGGGGGUACCUGCUGUGU GAAACAAAAG UAAGUGCUUCCAUGUUUCAGUG GAGG | 280 |
| miR-302d | CCUCUACUUUAACAUGGAGGCACUUGCU-GUGA CAUGACAAAAA UAAGUGCUUCCAUGUUUGAGU GUGG | 281 |
| miR-320 | GCUUCGCUCCCCUCCGCCUUCUCUUC-CCGGUU CUUCCCGGAGUCGGG AAAAGCUGGGUUGAGAG GGCGAAAAAGGAUGAGGU | 282 |
| miR-321 | UUGGCCUCC UAAGCCAGGGAUUGUGGGUUCGA GUCCCACCCGGGGUAAAGAAAGGCCGA | 283 |
| miR-323 | UUGGUACUUGGAGAGAGGUGGUCCGUG-GCGCG UUCGCUUUAUUUAUGGCGCACAUUA-CACGGUC GACCUCUUUGCAGUAUCUAAUC | 284 |
| miR-324 | CUGACUAUGCCUCCC CGCAUCCCUAGGGCAU UGGUGUAAAGCUGGAGAC CCACUGCCCCAGGU GCUGCUGGGGGUUGUAGUC | 285 |
| miR-325 | AUACAGUGCUUGGUUCCUAGUAGGUGUC-CAGU AAGUGUUUGUGACAUAAUUUGUUUA-UUGAGGA CCUCCUAUCAAUCAAGCACUGUGCUAG-GCUCU GG | 286 |
| miR-326 | CUCAUCUGUCUGUUGGGCUGGAG-GCAGGGCCU UUGUGAAGGCGGGUGGUGCUCAGAUCGC-CUCU GGGCCCUUCCUCCAGCCCCGAGGCGGAUUCA | 287 |

TABLE 1a-continued

Human microRNA Precursor Sequences

| Precursor Name | Sequence (5' To 3')* | SEQ ID NO. |
|---|---|---|
| miR-328 | UGGAGUGGGGGGCAGGAGGGGCUCAGG-GAGA AAGUGCAUACAGCCC <u>CUGGCCCUCUCUGCCCU</u> <u>UCCGUCCCUG</u> | 288 |
| miR-330 | CUUUGGCGAUCACUGCCUCUCUGGGCCU-GUGU CUUAGGCUCUGCAAGAUCAACCGA <u>GCAAAGCA</u> <u>CACGGCCUGCAGAGAGGCAGCGCUCUGCCC</u> | 289 |
| miR-331 | GAGUUUGGUUUUGUUUGGGUUUGUUC-UAGGUA UGGUCCCAGGGAUCCCAGAUCAAACCAG <u>GCCC</u> <u>CUGGGCCUAUCCUAGAA</u>CCAACCUAAGCUC | 290 |
| miR-335 | UGUUUUGAGCGGGGG <u>UCAAGAGCAAUAACGAA</u> <u>AAAUGUUUGUCAUAAACCGUUUUUCAUUAUUG</u> CUCCUGACCUCCUCUCAUUUGCUAUAUUCA | 291 |
| miR-337 | GUAGUCAGUAGUUGGGGGUGGGAACG-GCUUC AUAGAGGAGUUGAUGCACAGUUA <u>UCCAGCUCC</u> <u>UAUAUGAUGCCUUUCUUCAUCCCCUUCAA</u> | 292 |
| miR-338 | UCUCCAACAAUAUCCUG-GUGCUGAGUGAUGAC UCAGGCGAC <u>UCCAGCAUCAGUGAUUUUGUUGA</u> <u>AGA</u> | 293 |
| miR-339 | CGGGGCGGCCGCUC <u>UCCCUGUCCUCCAGGAGC</u> <u>UCACGUGUGCCUGCCUGUGAGCGCCUCGACGA</u> CAGAGCCGGCGCCUGCCCCAGUGUCUGCGC | 294 |
| miR-340 | UUGUACCUGGUGUGAUUAUAAAG-CAAUGAGAC UGAUUGUCAUAUGUCGUUUGUGGGA <u>UCCGUCU</u> <u>CAGUUACUUUAUAGCC</u>AUACCUGGUAUCUUA | 295 |
| miR-342 | GAAACUGGGCUCAAGGUGAGGGGUGC-UAUCUG UGAUUGAGGGACAUGGUUAAUGGAAUUG <u>UCUC</u> <u>ACACAGAAAUCGCACCCGUC</u>ACCUUGGCCUAC UUA | 296 |
| miR-345 | ACCCAAACCCUAGGUC <u>UGCUGACUCCUAGUCC</u> <u>AGGGCU</u>CGUGAUGGCUGGUGGGCCCUGAACGA GGGGUCUGGAGGCCUGGGUUUGAAUAUC-GACA GC | 297 |
| miR-346 | GUC <u>UGUCUGCCCGCAUGCCUGCCUCUCUGUUG</u> CUCUGAGGAGGCAGGGGCUGGGCCUG-CAGCU GCCUGGGCAGAGCGGCUCCUGC | 298 |
| miR-367 | CCAUUACUGUUGCUAAUAUGCAACUCUG-UUGA AUAUAAAUUGGAAUUGCACUUUAG-CAAUGGUG AUGG | 299 |
| miR-368 | AAAAGGUGGAUAUUCCUUCUAUGUUUAU-GUUA UUUAUGGUUAA <u>ACAUAGAGGAAAUUCCACGUU</u> <u>UU</u> | 300 |
| miR-369 | UUGAAGGGAGAUCGACCGUGUUAUA-UUCGCUU UAUUGACUUCG <u>AAUAAUACAUGGUUGAUCUUU</u> <u>UCUCAG</u> | 301 |
| miR-370 | AGACAGAGAAGCCAGGUCACGUCUCUG-CAGUU ACACAGCUCACGAGU <u>GCCUGCUGGGGUGGAAC</u> <u>CUGGUCUGUCU</u> | 302 |
| miR-371 | GUGGCACUCAAACUGUGGGGGCACUUU-CUGCU CUCUGGUGAAA <u>GUGCCGCCAUCUUUUGAGUGU</u> UAC | 303 |
| miR-372 | GUGGGCCUCAAAUGUGGAGCACUAUU-CUGAUG UCCAAGUGG <u>AAAGUGCUGCGACAUUUGAGCGU</u> CAC | 304 |
| miR-373 | GGGAUACUCAAAAUGGGGGCGCUUUC-CUUUUU GUCUGUACUGGGAAGUGCUUCGAUU-UUGGGGU GUCCC | 305 |
| miR-374 | UACAUCGGCCA <u>UUAUAAUACAACCUGAUAAGU</u> <u>G</u>UUAUAGCACUUAUCAGAUUGUAUUGUAAUUG UCUGUGUA | 306 |
| miR-hes1 | AUGGAGCUGCUCACCCUGUGGGCCU-CAAAUGU GGAGGAACUAUUCUGAUGUCCAAGUG-GAAAGU GCUGCGACAUUUGAGCUGACCG-GUGACGCCC AUAUCA | 307 |
| miR-hes2 | GCAUCCCCUCAGCCUGUGGCACU-CAAACUGUG GGGGCACUUUCUGCUCUCUG-GUGAAAGUGCCG CCAUCUUUUGAGUGUUACCGCUUGAGAA-GACU CAACC | 308 |
| miR-hes3 | CGAGGAGCUCAUACUGGGAUACU-CAAAAUGGG GGCGCUUUCCUUUUUGUCUGUUACUGG-GAAGU GCUUCGAUUUUGGGGUGUCCCUGU-UUGAGUAG GGCAUC | 309 |

*An underlined sequence within a precursor sequence corresponds to a mature processed miR transcript (see Table 1b). Some precursor sequences have two underlined sequences denoting two different mature miRs that are derived from the same precursor. All sequences are human.

TABLE 1b

Human Mature microRNA Sequences.

| Mature miRNA Name | Mature miRNA Sequence (5' to 3') | SEQ ID NO. | Corresponding precursor microRNA(s); see Table 1a |
|---|---|---|---|
| let-7a | ugagguaguagguuguauaguu | 310 | let-7a-1; let-7a-2; let-7a-3; let-7a-4 |
| let-7b | ugagguaguagguugugugguu | 311 | let-7b |
| let-7c | ugagguaguagguuguaugguu | 312 | let-7c |
| let-7d | agagguaguagguugcauagu | 313 | let-7d; let-7d-v1 |
| let-7e | ugagguaggagguuguauagu | 314 | let-7e |
| let-7f | ugagguaguagauuguauaguu | 315 | let-7f-1; let-7f-2-1; let-7f-2-2 |
| let-7g | ugagguaguaguuuguacagu | 316 | let-7g |
| let-7i | ugagguaguaguuugugcu | 317 | let-7i |
| miR-1 | uggaauguaaagaaguaugua | 318 | miR-1b; miR-1b-1; miR-1b-2 |
| miR-7 | uggaagacuagugauuuuguu | 319 | miR-7-1; miR-7-1a; miR-7-2; miR-7-3 |
| miR-9 | ucuuugguuaucuagcuguauga | 320 | miR-9-1; miR-9-2; miR-9-3 |
| miR-9* | uaaagcuagauaaccgaaagu | 321 | miR-9-1; miR-9-2; miR-9-3 |
| miR-10a | uacccuguagauccgaauuugug | 322 | miR-10a |
| miR-10b | uacccuguagaaccgaauuugu | 323 | miR-10b |
| miR-15a | uagcagcacauaaugguuugug | 324 | miR-15a; miR-15a-2 |
| miR-15b | uagcagcacaucaugguuuaca | 325 | miR-15b |
| miR-16 | uagcagcacguaaauauuggcg | 326 | miR-16-1; miR-16-2; miR-16-13 |
| miR-17-5p | caaagugcuuacagugcagguagu | 327 | miR-17 |
| miR-17-3p | acugcagugaaggcacuugu | 328 | miR-17 |
| miR-18 | uaaggugcaucuagugcagaua | 329 | miR-18; miR-18-13 |
| miR-19a | ugugcaaaucuaugcaaaacuga | 330 | miR-19a; miR-19a-13 |
| miR-19b | ugugcaaauccaugcaaaacuga | 331 | miR-19b-1; miR-19b-2 |
| miR-20 | uaaagugcuuauagugcaggua | 332 | miR-20 (miR-20a) |
| miR-21 | uagcuuaucagacugauguuga | 333 | miR-21; miR-21-17 |
| miR-22 | aagcugccaguugaagaacugu | 334 | miR-22 |
| miR-23a | aucacauugccagggauuucc | 335 | miR-23a |
| miR-23b | aucacauugccagggauuaccac | 336 | miR-23b |
| miR-24 | uggcucaguucagcaggaacag | 337 | miR-24-1; miR-24-2; miR-24-19; miR-24-9 |
| miR-25 | cauugcacuugucucggucuga | 338 | miR-25 |
| miR-26a | uucaaguaauccaggauaggcu | 339 | miR-26a; miR-26a-1; miR-26a-2 |
| miR-26b | uucaaguaauucaggauaggu | 340 | miR-26b |
| miR-27a | uucacaguggcuaaguuccgcc | 341 | miR-27a |

TABLE 1b-continued

Human Mature microRNA Sequences.

| Mature miRNA Name | Mature miRNA Sequence (5' to 3') | SEQ ID NO. | Corresponding precursor microRNA(s); see Table 1a |
|---|---|---|---|
| miR-27b | uucacaguggcuaaguucug | 342 | miR-27b-1; miR-27b-2 |
| miR-28 | aaggagcucacagucuauugag | 343 | miR-28 |
| miR-29a | cuagcaccaucugaaaucgguu | 344 | miR-29a-2; miR-29a |
| miR-29b | uagcaccauuugaaaucagu | 345 | miR-29b-1; miR-29b-2 |
| miR-29c | uagcaccauuugaaaucgguua | 346 | miR-29c |
| miR-30a-5p | uguaaacauccucgacuggaagc | 347 | miR-30a |
| miR-30a-3p | cuuucagucggauguuugcagc | 348 | miR-30a |
| miR-30b | uguaaacauccuacacucagc | 349 | miR-30b-1; miR-30b-2 |
| miR-30c | uguaaacauccuacacucucagc | 350 | miR-30c |
| miR-30d | uguaaacaucccgacuggaag | 351 | miR-30d |
| miR-30e | uguaaacauccuugacugga | 352 | miR-30e |
| miR-31 | ggcaagaugcuggcauagcug | 353 | miR-31 |
| miR-32 | uauugcacauuacuaaguugc | 354 | miR-32 |
| miR-33 | gugcauuguaguugcauug | 355 | miR-33; miR-33b |
| miR-34a | uggcagugucuuagcugguugu | 356 | miR-34a |
| miR-34b | aggcagugucauuagcugauug | 357 | miR-34b |
| miR-34c | aggcaguguaguagcugauug | 358 | miR-34c |
| miR-92 | uauugcacuugucccggccugu | 359 | miR-92-2; miR-92-1 |
| miR-93 | aaagugcuguucgugcagguag | 360 | miR-93-1; miR-93-2 |
| miR-95 | uucaacggguauuuauugagca | 361 | miR-95 |
| miR-96 | uuuggcacuagcacauuuuugc | 362 | miR-96 |
| miR-98 | ugagguaguaaguuguauuguu | 363 | miR-98 |
| miR-99a | aacccguagauccgaucuugug | 364 | miR-99a |
| miR-99b | cacccguagaaccgaccuugcg | 365 | miR-99b |
| miR-100 | uacaguacugugauaacugaag | 366 | miR-100 |
| miR-101 | uacaguacugugauaacugaag | 367 | miR-101-1; miR-101-2 |
| miR-103 | agcagcauuguacagggcuauga | 368 | miR-103-1 |
| miR-105 | ucaaaugcucagacuccugu | 369 | miR-105 |
| miR-106-a | aaaagugcuuacagugcagguagc | 370 | miR-106-a |
| miR-106-b | uaaagugcugacagugcagau | 371 | miR-106-b |
| miR-107 | agcagcauuguacagggcuauca | 372 | mir-107 |
| miR-122a | uggagugugacaauggguguuugu | 373 | miR-122a-1; miR-122a-2 |
| miR-124a | uuaaggcacgcggugaaugcca | 374 | miR-124a-1; miR-124a-2; miR-124a-3 |
| miR-125a | ucccugagacccuuuaaccugug | 375 | miR-125a-1; miR-125a-2 |
| miR-125b | ucccugagacccuaacuuguga | 376 | miR-125b-1; miR-125b-2 |
| miR-126* | cauuauuacuuuugguacgcg | 377 | miR-126-1; miR-126-2 |

TABLE 1b-continued

Human Mature microRNA Sequences.

| Mature miRNA Name | Mature miRNA Sequence (5' to 3') | SEQ ID NO. | Corresponding precursor microRNA(s); see Table 1a |
|---|---|---|---|
| miR-126 | ucguaccgugaguaauaaugc | 378 | miR-126-1; miR-126-2 |
| miR-127 | ucggauccgucugagcuuggcu | 379 | miR-127-1; miR-127-2 |
| miR-128a | ucacagugaaccggucucuuuu | 380 | miR-128; miR-128a |
| miR-128b | ucacagugaaccggucucuuuc | 381 | miR-128b |
| miR-129 | cuuuuugcggucugggcuugc | 382 | miR-129-1; miR-129-2 |
| miR-130a | cagugcaauguuaaaagggc | 383 | miR-130a |
| miR-130b | cagugcaaugaugaaagggcau | 384 | miR-130b |
| miR-132 | uaacagucuacagccauggucg | 385 | miR-132-1 |
| miR-133a | uuggucccuucaaccagcugu | 386 | miR-133a-1; miR-133a-2 |
| miR-133b | uuggucccuucaaccagcua | 387 | miR-133b |
| miR-134 | ugugacugguugaccagaggg | 388 | miR-134-1; miR-134-2 |
| miR-135a | uauggcuuuuuauuccuauguga | 389 | miR-135a; miR-135a-2 (miR-135-2) |
| miR-135b | uauggcuuuucauuccuaugug | 390 | miR-135b |
| miR-136 | acuccauuuguuugaugaugga | 391 | miR-136-1; miR-136-2 |
| miR-137 | uauugcuuaagaauacgcguag | 392 | miR-137 |
| miR-138 | agcugguguugugaauc | 393 | miR-138-1; miR-138-2 |
| miR-139 | ucuacagugcacgugucu | 394 | miR-139 |
| miR-140 | agugguuuuacccuaugguag | 395 | miR-140; miR-140as; miR-140s |
| miR-141 | aacacugucugguaaagaugg | 396 | miR-141-1; miR-141-2 |
| miR-142-3p | uguaguguuuccuacuuuaugga | 397 | miR-142 |
| miR-142-5p | cauaaaguagaaagcacuac | 398 | miR-142 |
| miR-143 | ugagaugaagcacuguagcuca | 399 | miR-143-1 |
| miR-144 | uacaguauagaugauguacuag | 400 | miR-144-1; miR-144-2 |
| miR-145 | guccaguuuucccaggaaucccuu | 401 | miR-145-1; miR-145-2 |
| miR-146 | ugagaacugaauuccauggguu | 402 | miR-146-1; miR-146-2 |
| miR-147 | guguguggaaaugcuucugc | 403 | miR-147 |
| miR-148a | ucagugcacuacagaacuuugu | 404 | miR-148a (miR-148) |
| miR-148b | ucagugcaucacagaacuuugu | 405 | miR-148b |
| miR-149 | ucuggcuccgugucuucacucc | 406 | miR-149 |
| miR-150 | ucucccaacccuuguaccagug | 407 | miR-150-1; miR-150-2 |
| miR-151 | acuagacugaagcuccuugagg | 408 | miR-151 |
| miR-152 | ucagugcaugacagaacuugg | 409 | miR-152-1; miR-152-2 |
| miR-153 | uugcauagucacaaaaguga | 410 | miR-153-1-1; miR-153-1-2; miR-153-2-1; miR-153-2-2 |
| miR-154 | uagguuauccguguugccucg | 411 | miR-154-1; miR-154-2 |
| miR-154* | aaucauacacgguugaccuauu | 412 | miR-154-1; miR-154-2 |

TABLE 1b-continued

Human Mature microRNA Sequences.

| Mature miRNA Name | Mature miRNA Sequence (5' to 3') | SEQ ID NO. | Corresponding precursor microRNA(s); see Table 1a |
|---|---|---|---|
| miR-155 | uuaaugcuaaucugugauagggg | 413 | miR-155 |
| miR-181a | aacauucaacgcugucggugagu | 414 | miR-181a |
| miR-181b | aacauucauugcugucgguggguu | 415 | miR-181b-1; miR-181b-2 |
| miR-181c | aacauucaaccugucggugagu | 416 | miR-181c |
| miR-182 | uuuggcaaugguagaacucaca | 417 | miR-182; miR-182as |
| miR-182* | ugguucuagacuugccaacua | 418 | miR-182; miR-182as |
| miR-183 | uauggcacugguagaauucacug | 419 | miR-183 |
| miR-184 | uggacggagaacugauaagggu | 420 | miR-184-1; miR-184-2 |
| miR-185 | uggagagaaaggcaguuc | 421 | miR-185-1; miR-185-2 |
| miR-186 | caaagaauucuccuuuugggcuu | 422 | miR-186-1; miR-186-2 |
| miR-187 | ucgugucuuguguugcagccg | 423 | miR-187 |
| miR-188 | caucccuugcaugguggagggu | 424 | miR-188 |
| miR-189 | gugccuacugagcugauaucagu | 425 | miR-189-1; miR-189-2 |
| miR-190 | ugauauguuugauauauuaggu | 426 | miR-190-1; miR-190-2 |
| miR-191 | caacggaaucccaaaagcagcu | 427 | miR-191-1; miR-191-2 |
| miR-192 | cugaccuaugaauugacagcc | 428 | miR-192 |
| miR-193 | aacuggccuacaaagucccag | 429 | miR-193-1; miR-193-2 |
| miR-194 | uguaacagcaacuccaugugga | 430 | miR-194-1; miR-194-2 |
| miR-195 | uagcagcacagaaauauuggc | 431 | miR-195-1; miR-195-2 |
| miR-196a | uagguaguuucauguuguugg | 432 | miR-196a; miR-196a-2 (miR196-2) |
| miR-196b | uagguaguuuccuguuguugg | 433 | miR-196b |
| miR-197 | uucaccaccuucuccacccagc | 434 | miR-197 |
| miR-198 | gguccagaggggagauagg | 435 | miR-198 |
| miR-199a | cccaguguucagacuaccuguuc | 436 | miR-199a-1; miR-199a-2 |
| miR-199a* | uacaguagucugcacauugguu | 437 | miR-199a-1; miR-199a-2; miR-199s; miR-199b |
| miR-199b | cccaguguuuagacuaucuguuc | 438 | miR-199b |
| miR-200a | uaacacugucuggaacgaugu | 439 | miR-200a |
| miR-200b | cucuaauacugccugguaaugaug | 440 | miR-200b |
| miR-200c | aauacugccggguaaugaugga | 441 | miR-200c |
| miR-202 | agagguauagggcaugggaaga | 442 | miR-202 |
| miR-203 | gugaaauguuuaggaccacuag | 443 | miR-203 |
| miR-204 | uucccuuugucauccuaugccu | 444 | miR-204 |
| miR-205 | uccuucauuccaccggagucug | 445 | miR-205 |
| miR-206 | uggaauguaaggaagugugugg | 446 | miR-206-1; miR-206-2 |
| miR-208 | auaagacgagcaaaaagcuugu | 447 | miR-208 |
| miR-210 | cugugcgugugacagcggcug | 448 | miR-210 |

TABLE 1b-continued

Human Mature microRNA Sequences.

| Mature miRNA Name | Mature miRNA Sequence (5' to 3') | SEQ ID NO. | Corresponding precursor microRNA(s); see Table 1a |
|---|---|---|---|
| miR-211 | uccccuuugucauccuucgccu | 449 | miR-211 |
| miR-212 | uaacagucuccagucacggcc | 450 | miR-212 |
| miR-213 | accaucgaccguugauuguacc | 451 | miR-213 |
| miR-214 | acagcaggcacagacaggcag | 452 | miR-214 |
| miR-215 | augaccuaugaauugacagac | 453 | miR-215 |
| miR-216 | uaaucucagcuggcaacugug | 454 | miR-216 |
| miR-217 | uacugcaucaggaacugauuggau | 455 | miR-217 |
| miR-218 | uugugcuugaucuaaccaugu | 456 | miR-218-1; miR-218-2 |
| miR-219 | ugauuguccaaacgcaauucu | 457 | miR-219; miR-219-1; miR-219-2 |
| miR-220 | ccacaccguaucugacacuuu | 458 | miR-220 |
| miR-221 | agcuacauugucugcuggguuuc | 459 | miR-221 |
| miR-222 | agcuacaucuggcuacugggucuc | 460 | miR-222 |
| miR-223 | ugucaguuugucaaauacccc | 461 | miR-223 |
| miR-224 | caagucacuaguguuccguuua | 462 | miR-224 |
| miR-296 | agggccccccucaauccugu | 463 | miR-296 |
| miR-299 | igguuuaccgucccacauacau | 464 | miR-299 |
| miR-301 | cagugcaauaguauugucaaagc | 465 | miR-301 |
| miR-302a | uaagugcuuccauguuuuggga | 466 | miR-302a |
| miR-302b* | acuuuaacauggaagugcuuucu | 467 | miR-302b |
| miR-302b | uaagugcuuccauguuuuaguag | 468 | miR-302b |
| miR-302c* | uuuaacauggggguaccugcug | 469 | miR-302c |
| miR-302c | uaagugcuuccauguuucagugg | 470 | miR-302c |
| miR-302d | uaagugcuuccauguuugagugu | 471 | miR-302d |
| miR-320 | aaaagcuggguugagagggcgaa | 472 | miR-320 |
| miR-321 | uaagccagggauuguggguuc | 473 | miR-321 |
| miR-323 | gcacauuacacggucgaccucu | 474 | miR-323 |
| miR-324-5p | cgcaucccuagggcauuggugu | 475 | miR-324 |
| miR-324-3p | ccacugccccaggugcugcugg | 476 | miR-324 |
| miR-325 | ccuaguagguguccaguaagu | 477 | miR-325 |
| miR-326 | ccucugggcccuuccuccag | 478 | miR-326 |
| miR-328 | cuggcccucucugcccuuccgu | 479 | miR-328 |
| miR-330 | gcaaagcacacggccugcagaga | 480 | miR-330 |
| miR-331 | gccccugggccuauccuagaa | 481 | miR-331 |
| miR-335 | ucaagagcaauaacgaaaaaugu | 482 | miR-335 |
| miR-337 | uccagcuccauauugaugccuuu | 483 | miR-337 |
| miR-338 | uccagcaucagugauuuuguuga | 484 | miR-338 |

TABLE 1b-continued

Human Mature microRNA Sequences.

| Mature miRNA Name | Mature miRNA Sequence (5' to 3') | SEQ ID NO. | Corresponding precursor microRNA(s); see Table 1a |
|---|---|---|---|
| miR-339 | ucccuguccuccaggagcuca | 485 | miR-339 |
| miR-340 | uccgucucaguuacuuuauagcc | 486 | miR-340 |
| miR-342 | ucucacacagaaaucgcacccguc | 487 | miR-342 |
| miR-345 | ugcugacuccuaguccagggc | 488 | miR-345 |
| miR-346 | ugucugcccgcaugccugccucu | 489 | miR-346 |
| miR-367 | aauugcacuuuagcaaugguga | 490 | miR-367 |
| miR-368 | acauagaggaaauuccacguuu | 491 | miR-368 |
| miR-369 | aauaauacaugguugaucuuu | 492 | miR-369 |
| miR-370 | gccugcugggguggaaccugg | 493 | miR-370 |
| miR-371 | gugccgccaucuuuugagugu | 494 | miR-371 |
| miR-372 | aaagugcugcgacauuugagcgu | 495 | miR-372 |
| miR-373* | acucaaaauggggcgcuuucc | 496 | miR-373 |
| miR-373 | gaagugcuucgauuuuggggugu | 497 | miR-373 |
| miR-374 | uuauaauacaaccugauaagug | 498 | miR-374 |

The level of at least one miR gene product can be measured in cells of a biological sample obtained from the subject. For example, a tissue sample can be removed from a subject suspected of having lung cancer by conventional biopsy techniques. In another embodiment, a blood sample can be removed from the subject, and white blood cells can be isolated for DNA extraction by standard techniques. The blood or tissue sample is preferably obtained from the subject prior to initiation of radiotherapy, chemotherapy or other therapeutic treatment. A corresponding control tissue or blood sample, or a control reference sample, can be obtained from unaffected tissues of the subject, from a normal human individual or population of normal individuals, or from cultured cells corresponding to the majority of cells in the subject's sample. The control tissue or blood sample is then processed along with the sample from the subject, so that the levels of miR gene product produced from a given miR gene in cells from the subject's sample can be compared to the corresponding miR gene product levels from cells of the control sample. Alternatively, a reference sample can be obtained and processed separately (e.g., at a different time) from the test sample and the level of a miR gene product produced from a given miR gene in cells from the test sample can be compared to the corresponding miR gene product level from the reference sample.

In one embodiment, the level of the at least one miR gene product in the test sample is greater than the level of the corresponding miR gene product in the control sample (i.e., expression of the miR gene product is "up-regulated"). As used herein, expression of a miR gene product is "up-regulated" when the amount of miR gene product in a cell or tissue sample from a subject is greater than the amount of the same gene product in a control cell or tissue sample. In another embodiment, the level of the at least one miR gene product in the test sample is less than the level of the corresponding miR gene product in the control sample (i.e., expression of the miR gene product is "down-regulated"). As used herein, expression of a miR gene is "down-regulated" when the amount of miR gene product produced from that gene in a cell or tissue sample from a subject is less than the amount produced from the same gene in a control cell or tissue sample. The relative miR gene expression in the control and normal samples can be determined with respect to one or more RNA expression standards. The standards can comprise, for example, a zero miR gene expression level, the miR gene expression level in a standard cell line, the miR gene expression level in unaffected tissues of the subject, or the average level of miR gene expression previously obtained for a population of normal human controls.

An alteration (i.e., an increase or decrease) in the level of a miR gene product in the sample obtained from the subject, relative to the level of a corresponding miR gene product in a control sample, is indicative of the presence of lung cancer in the subject. In one embodiment, the level of at least one miR gene product in the test sample is greater than the level of the corresponding miR gene product in the control sample. In another embodiment, the level of at least one miR gene product in the test sample is less than the level of the corresponding miR gene product in the control sample. In a certain embodiment, the at least one miR gene product is selected from the group consisting of miR-21, miR-191, miR-126*, miR-210, miR-155, miR-143, miR-205, miR-192-prec, miR-224, miR-126, miR-24-2, miR-30a-5p, miR-212, miR-140, miR-9, miR-214, miR-17-3p, miR-124a-1, miR-218-2, miR-95, miR-145, miR-198, miR-216-prec, miR-219-1, miR-106a, miR-197, miR-192, miR-125a-prec, miR-26a-1-prec, miR-146, miR-203, miR-199b-prec, let-7a-2-prec, miR-27b, miR-32, miR-29b-2, miR-220, miR-33, miR-181c-prec, miR-150, miR-101-1, miR-124a-3, miR-125a and let-7f-1. In a particular embodiment, the at least one miR gene product is selected from the group consisting of miR-21, miR-205 and miR-216. In another embodiment, the lung cancer is a lung adenocarcinoma and the at least one miR gene product is selected from the group consisting of miR-21, miR-191, miR-155, miR-210, miR-126* and miR-224.

In a particular embodiment, the miR gene product is not one or more of let7a-2, let-7c, let-7g, let-7i, miR-7-2, miR-7-3, miR-9, miR-9-1, miR-10a, miR-15a, miR-15b, miR-16-1, miR-16-2, miR-17-5p, miR-20a, miR-21, miR-24-1, miR-24-2, miR-25, miR-29b-2, miR-30, miR-30a-5p, miR-30c, miR-30d, miR-31, miR-32, miR-34, miR-34a, miR-34a prec, miR-34a-1, miR-34a-2, miR-92-2, miR-96, miR-99a, miR-99b prec, miR-100, miR-103, miR-106a, miR-107, miR-123, miR-124a-1, miR-125b-1, miR-125b-2, miR-126*, miR-127, miR-128b, miR-129, miR-129-1/2 prec, miR-132, miR-135-1, miR-136, miR-137, miR-141, miR-142-as, miR-143, miR-146, miR-148, miR-149, miR-153, miR-155, miR 159-1, miR-181, miR-181b-1, miR-182, miR-186, miR-191, miR-192, miR-195, miR-196-1, miR-196-1 prec, miR-196-2, miR-199a-1, miR-199a-2, miR-199b, miR-200b, miR-202, miR-203, miR-204, miR-205, miR-210, miR-211, miR-212, miR-214, miR-215, miR-217, miR-221 and/or miR-223.

The level of a miR gene product in a sample can be measured using any technique that is suitable for detecting RNA expression levels in a biological sample. Suitable techniques (e.g., Northern blot analysis, RT-PCR, in situ hybridization) for determining RNA expression levels in a biological sample (e.g., cells, tissues) are well known to those of skill in the art. In a particular embodiment, the level of at least one miR gene product is detected using Northern blot analysis. For example, total cellular RNA can be purified from cells by homogenization in the presence of nucleic acid extraction buffer, followed by centrifugation. Nucleic acids are precipitated, and DNA is removed by treatment with DNase and precipitation. The RNA molecules are then separated by gel electrophoresis on agarose gels according to standard techniques, and transferred to nitrocellulose filters. The RNA is then immobilized on the filters by heating. Detection and quantification of specific RNA is accomplished using appropriately labeled DNA or RNA probes complementary to the RNA in question. See, for example, Molecular Cloning: A Laboratory Manual, J. Sambrook et al., eds., 2nd edition, Cold Spring Harbor Laboratory Press, 1989, Chapter 7, the entire disclosure of which is incorporated by reference.

Suitable probes (e.g., DNA probes, RNA probes) for Northern blot hybridization of a given miR gene product can be produced from the nucleic acid sequences provided in Table 1a and Table 1b and include, but are not limited to, probes having at least about 70%, 75%, 80%, 85%, 90%, 95%, 98% or 99% complementarity to a miR gene product of interest, as well as probes that have complete complementarity to a miR gene product of interest. Methods for preparation of labeled DNA and RNA probes, and the conditions for hybridization thereof to target nucleotide sequences, are described in Molecular Cloning: A Laboratory Manual, J. Sambrook et al., eds., 2nd edition, Cold Spring Harbor Laboratory Press, 1989, Chapters 10 and 11, the disclosures of which are incorporated herein by reference.

For example, the nucleic acid probe can be labeled with, e.g., a radionuclide, such as $^3$H, $^{32}$P, $^{33}$P, $^{14}$C, or $^{35}$S; a heavy metal; a ligand capable of functioning as a specific binding pair member for a labeled ligand (e.g., biotin, avidin or an antibody); a fluorescent molecule; a chemiluminescent molecule; an enzyme or the like.

Probes can be labeled to high specific activity by either the nick translation method of Rigby et al. (1977), *J. Mol. Biol.* 113:237-251 or by the random priming method of Fienberg et al. (1983), *Anal. Biochem.* 132:6-13, the entire disclosures of which are incorporated herein by reference. The latter is the method of choice for synthesizing $^{32}$P-labeled probes of high specific activity from single-stranded DNA or from RNA templates. For example, by replacing preexisting nucleotides with highly radioactive nucleotides according to the nick translation method, it is possible to prepare $^{32}$P-labeled nucleic acid probes with a specific activity well in excess of $10^8$ cpm/microgram. Autoradiographic detection of hybridization can then be performed by exposing hybridized filters to photographic film. Densitometric scanning of the photographic films exposed by the hybridized filters provides an accurate measurement of miR gene transcript levels. Using another approach, miR gene transcript levels can be quantified by computerized imaging systems, such as the Molecular Dynamics 400-B 2D Phosphorimager available from Amersham Biosciences, Piscataway, N.J.

Where radionuclide labeling of DNA or RNA probes is not practical, the random-primer method can be used to incorporate an analogue, for example, the dTTP analogue 5-(N—(N-biotinyl-epsilon-aminocaproyl)-3-aminoallyl)deoxyuridine triphosphate, into the probe molecule. The biotinylated probe oligonucleotide can be detected by reaction with biotin-binding proteins, such as avidin, streptavidin and antibodies (e.g., anti-biotin antibodies) coupled to fluorescent dyes or enzymes that produce color reactions.

In addition to Northern and other RNA hybridization techniques, determining the levels of RNA transcripts can be accomplished using the technique of in situ hybridization. This technique requires fewer cells than the Northern blotting technique and involves depositing whole cells onto a microscope cover slip and probing the nucleic acid content of the cell with a solution containing radioactive or otherwise labeled nucleic acid (e.g., cDNA or RNA) probes. This technique is particularly well-suited for analyzing tissue biopsy samples from subjects. The practice of the in situ hybridization technique is described in more detail in U.S. Pat. No. 5,427,916, the entire disclosure of which is incorporated herein by reference. Suitable probes for in situ hybridization of a given miR gene product can be produced from the nucleic acid sequences provided in Table 1a and Table 1b, and include, but are not limited to, probes having at least about 70%, 75%, 80%, 85%, 90%, 95%, 98% or 99% complementarity to a miR gene product of interest, as well as probes that have complete complementarity to a miR gene product of interest, as described above.

The relative number of miR gene transcripts in cells can also be determined by reverse transcription of miR gene transcripts, followed by amplification of the reverse-transcribed transcripts by polymerase chain reaction (RT-PCR). The levels of miR gene transcripts can be quantified in comparison with an internal standard, for example, the level of mRNA from a "housekeeping" gene present in the same sample. A suitable "housekeeping" gene for use as an internal standard includes, e.g., myosin or glyceraldehyde-3-phosphate dehydrogenase (G3PDH). Methods for performing quantitative and semi-quantitative RT-PCR, and variations thereof, are well known to those of skill in the art.

In some instances, it may be desirable to simultaneously determine the expression level of a plurality of different miR gene products in a sample. In other instances, it may be desirable to determine the expression level of the transcripts of all known miR genes correlated with a cancer Assessing cancer-specific expression levels for hundreds of miR genes or gene products is time consuming and requires a large amount of total RNA (e.g., at least 20 μg for each Northern blot) and autoradiographic techniques that require radioactive isotopes.

To overcome these limitations, an oligolibrary, in microchip format (i.e., a microarray), may be constructed containing a set of oligonucleotide (e.g., oligodeoxynucleotide) probes that are specific for a set of miR genes. Using such a microarray, the expression level of multiple microRNAs in a biological sample can be determined by reverse transcribing the RNAs to generate a set of target oligodeoxynucleotides, and hybridizing them to probe the oligonucleotides on the microarray to generate a hybridization, or expression, profile. The hybridization profile of the test sample can then be compared to that of a control sample to determine which microRNAs have an altered expression level in lung cancer cells. As used herein, "probe oligonucleotide" or "probe oligodeoxynucleotide" refers to an oligonucleotide that is capable of hybridizing to a target oligonucleotide. "Target oligonucleotide" or "target oligodeoxynucleotide" refers to a molecule to be detected (e.g., via hybridization). By "miR-specific probe oligonucleotide" or "probe oligonucleotide specific for a miR" is meant a probe oligonucleotide that has a sequence selected to hybridize to a specific miR gene product, or to a reverse transcript of the specific miR gene product.

An "expression profile" or "hybridization profile" of a particular sample is essentially a fingerprint of the state of the sample; while two states may have any particular gene similarly expressed, the evaluation of a number of genes simultaneously allows the generation of a gene expression profile that is unique to the state of the cell. That is, normal tissue may be distinguished from lung cancer tissue, and within lung cancer tissue, different prognosis states (for example, good or poor long term survival prospects) may be determined. By comparing expression profiles of lung cancer tissue in different states, information regarding which genes are important (including both up- and down-regulation of genes) in each of these states is obtained. The identification of sequences that are differentially expressed in lung cancer tissue or normal lung tissue, as well as differential expression resulting in different prognostic outcomes, allows the use of this information in a number of ways. For example, a particular treatment regime may be evaluated (e.g., to determine whether a chemotherapeutic drug acts to improve the long-term prognosis in a particular patient). Similarly, diagnosis may be done or confirmed by comparing patient samples with known expression profiles. Furthermore, these gene expression profiles (or individual genes) allow screening of drug candidates that suppress the lung cancer expression profile or convert a poor prognosis profile to a better prognosis profile.

Accordingly, the invention provides methods of diagnosing whether a subject has, or is at risk for developing, lung cancer, comprising reverse transcribing RNA from a test sample obtained from the subject to provide a set of target oligodeoxynucleotides, hybridizing the target oligodeoxynucleotides to a microarray comprising miRNA-specific probe oligonucleotides to provide a hybridization profile for the test sample, and comparing the test sample hybridization profile to a hybridization profile generated from a control sample, wherein an alteration in the signal of at least one miRNA is indicative of the subject either having, or being at risk for developing, lung cancer. In one embodiment, the microarray comprises miRNA-specific probe oligonucleotides for a substantial portion of all known human miRNAs. In a particular embodiment, the microarray comprises miRNA-specific probe oligonucleotides for one or more miRNAs selected from the group consisting of miR-21, miR-191, miR-126*, miR-210, miR-155, miR-143, miR-205, miR-192-prec, miR-224, miR-126, miR-24-2, miR-30a-5p, miR-212, miR-140, miR-9, miR-214, miR-17-3p, miR-124a-1, miR-218-2, miR-95, miR-145, miR-198, miR-216-prec, miR-219-1, miR-106a, miR-197, miR-192, miR-125a-prec, miR-26a-1-prec, miR-146, miR-203, miR-199b-prec, let-7a-2-prec, miR-27b, miR-32, miR-29b-2, miR-220, miR-33, miR-181c-prec, miR-150, miR-101-1, miR-124a-3, miR-125a, let-7f-1 and a combination thereof.

The microarray can be prepared from gene-specific oligonucleotide probes generated from known miRNA sequences. The array may contain two different oligonucleotide probes for each miRNA, one containing the active, mature sequence and the other being specific for the precursor of the miRNA. The array may also contain controls, such as one or more mouse sequences differing from human orthologs by only a few bases, which can serve as controls for hybridization stringency conditions. tRNAs and other RNAs (e.g., rRNAs, mRNAs) from both species may also be printed on the microchip, providing an internal, relatively stable, positive control for specific hybridization. One or more appropriate controls for non-specific hybridization may also be included on the microchip. For this purpose, sequences are selected based upon the absence of any homology with any known miRNAs.

The microarray may be fabricated using techniques known in the art. For example, probe oligonucleotides of an appropriate length, e.g., 40 nucleotides, are 5'-amine modified at position C6 and printed using commercially available microarray systems, e.g., the GeneMachine OmniGrid™ 100 Microarrayer and Amersham CodeLink™ activated slides. Labeled cDNA oligomer corresponding to the target RNAs is prepared by reverse transcribing the target RNA with labeled primer. Following first strand synthesis, the RNA/DNA hybrids are denatured to degrade the RNA templates. The labeled target cDNAs thus prepared are then hybridized to the microarray chip under hybridizing conditions, e.g., 6×SSPE/30% formamide at 25° C. for 18 hours, followed by washing in 0.75×TNT at 37° C. for 40 minutes. At positions on the array where the immobilized probe DNA recognizes a complementary target cDNA in the sample, hybridization occurs. The labeled target cDNA marks the exact position on the array where binding occurs, allowing automatic detection and quantification. The output consists of a list of hybridization events, indicating the relative abundance of specific cDNA sequences, and therefore the relative abundance of the corresponding complementary miRs, in the patient sample. According to one embodiment, the labeled cDNA oligomer is a biotin-labeled cDNA, prepared from a biotin-labeled primer. The microarray is then processed by direct detection of the biotin-containing transcripts using, e.g., Streptavidin-Alexa647 conjugate, and scanned utilizing conventional scanning methods. Image intensities of each spot on the array are proportional to the abundance of the corresponding miR in the patient sample.

The use of the array has several advantages for miRNA expression detection. First, the global expression of several hundred genes can be identified in the same sample at one time point. Second, through careful design of the oligonucleotide probes, expression of both mature and precursor molecules can be identified. Third, in comparison with Northern blot analysis, the chip requires a small amount of RNA, and provides reproducible results using 2.5 µg of total RNA. The relatively limited number of miRNAs (a few hundred per species) allows the construction of a common microarray for several species, with distinct oligonucleotide probes for each. Such a tool would allow for analysis of trans-species expression for each known miR under various conditions.

In addition to use for quantitative expression level assays of specific miRs, a microchip containing miRNA-specific probe oligonucleotides corresponding to a substantial portion of the miRNome, preferably the entire miRNome, may be employed to carry out miR gene expression profiling, for analysis of miR expression patterns. Distinct miR signatures can be associated with established disease markers, or directly with a disease state.

According to the expression profiling methods described herein, total RNA from a sample from a subject suspected of having a cancer (e.g., lung cancer) is quantitatively reverse transcribed to provide a set of labeled target oligodeoxynucleotides complementary to the RNA in the sample. The target oligodeoxynucleotides are then hybridized to a microarray comprising miRNA-specific probe oligonucleotides to provide a hybridization profile for the sample. The result is a hybridization profile for the sample representing the expression pattern of miRNA in the sample. The hybridization profile comprises the signal from the binding of the target oligodeoxynucleotides from the sample to the miRNA-specific probe oligonucleotides in the microarray. The profile may be recorded as the presence or absence of binding (signal vs. zero signal). More preferably, the profile recorded includes the intensity of the signal from each hybridization. The profile is compared to the hybridization profile generated from a normal, e.g., noncancerous, control sample. An alteration in the signal is indicative of the presence of, or propensity to develop, cancer in the subject.

Other techniques for measuring miR gene expression are also within the skill in the art, and include various techniques for measuring rates of RNA transcription and degradation.

The invention also provides methods of determining the prognosis of a subject with lung cancer, comprising measuring the level of at least one miR gene product, which is associated with a particular prognosis in lung cancer (e.g., a good or positive prognosis, a poor or adverse prognosis), in a test sample from the subject. According to these methods, an alteration in the level of a miR gene product that is associated with a particular prognosis, in the test sample, as compared to the level of a corresponding miR gene product in a control sample, is indicative of the subject having a lung cancer with a particular prognosis. In one embodiment, the miR gene product is associated with an adverse (i.e., poor) prognosis. Examples of an adverse prognosis include, but are not limited to, low survival rate and rapid disease progression. In certain embodiments, the at least one miR gene product associated with a particular prognosis is selected from the group consisting of miR-155, miR-17-3p, miR-106a, miR-93, let-7a-2, miR-145, let-7b, miR-20 and miR-21. In a particular embodiment, the lung cancer is a lung adenocarcinoma and the at least one miR gene product associated with a particular prognosis is selected from the group consisting of miR-155 and let-7a-2. In certain embodiments, the level of the at least one miR gene product is measured by reverse transcribing RNA from a test sample obtained from the subject to provide a set of target oligodeoxynucleotides, hybridizing the target oligodeoxynucleotides to a microarray that comprises miRNA-specific probe oligonucleotides to provide a hybridization profile for the test sample, and comparing the test sample hybridization profile to a hybridization profile generated from a control sample.

Without wishing to be bound by any one theory, it is believed that alterations in the level of one or more miR gene products in cells can result in the deregulation of one or more intended targets for these miRs, which can lead to the formation of lung cancer. Therefore, altering the level of the miR gene product (e.g., by decreasing the level of a miR that is up-regulated in lung cancer cells, by increasing the level of a miR that is down-regulated in lung cancer cells) may successfully treat the lung cancer.

Accordingly, the present invention encompasses methods of treating lung cancer in a subject, wherein at least one miR gene product is deregulated (e.g., down-regulated, up-regulated) in the cells (e.g., lung cancer cells) of the subject. In one embodiment, the level of at least one miR gene product in a test sample (e.g., a lung cancer sample) is greater than the level of the corresponding miR gene product in a control sample. In another embodiment, the level of at least one miR gene product in a test sample (e.g., a lung cancer sample) is less than the level of the corresponding miR gene product in a control sample. When the at least one isolated miR gene product is down-regulated in the lung cancer cells, the method comprises administering an effective amount of the at least one isolated miR gene product, or an isolated variant or biologically-active fragment thereof, such that proliferation of cancer cells in the subject is inhibited. For example, when a miR gene product is down-regulated in a cancer cell in a subject, administering an effective amount of an isolated miR gene product to the subject can inhibit proliferation of the cancer cell. The isolated miR gene product that is administered to the subject can be identical to an endogenous wild-type miR gene product (e.g., a miR gene product shown in Table 1a or Table 1b) that is down-regulated in the cancer cell or it can be a variant or biologically-active fragment thereof. As defined herein, a "variant" of a miR gene product refers to a miRNA that has less than 100% identity to a corresponding wild-type miR gene product and possesses one or more biological activities of the corresponding wild-type miR gene product. Examples of such biological activities include, but are not limited to, inhibition of expression of a target RNA molecule (e.g., inhibiting translation of a target RNA molecule, modulating the stability of a target RNA molecule, inhibiting processing of a target RNA molecule) and inhibition of a cellular process associated with lung cancer (e.g., cell differentiation, cell growth, cell death). These variants include species variants and variants that are the consequence of one or more mutations (e.g., a substitution, a deletion, an insertion) in a miR gene. In certain embodiments, the variant is at least about 70%, 75%, 800%, 85%, 90%, 95%, 98%, or 99% identical to a corresponding wild-type miR gene product.

As defined herein, a "biologically-active fragment" of a miR gene product refers to an RNA fragment of a miR gene product that possesses one or more biological activities of a corresponding wild-type miR gene product. As described above, examples of such biological activities include, but are not limited to, inhibition of expression of a target RNA molecule and inhibition of a cellular process associated with lung cancer. In certain embodiments, the biologically-active fragment is at least about 5, 7, 10, 12, 15, or 17 nucleotides in length. In a particular embodiment, an isolated miR gene product can be administered to a subject in combination with one or more additional anti-cancer treatments. Suitable anti-cancer treatments include, but are not limited to, chemotherapy, radiation therapy and combinations thereof (e.g., chemoradiation).

When the at least one isolated miR gene product is up-regulated in the cancer cells, the method comprises administering to the subject an effective amount of a compound that inhibits expression of the at least one miR gene product, such that proliferation of lung cancer cells is inhibited. Such compounds are referred to herein as miR gene expression-inhibition compounds. Examples of suitable miR gene expression-inhibition compounds include, but are not limited to, those described herein (e.g., double-stranded RNA, antisense nucleic acids and enzymatic RNA molecules). In a particular embodiment, a miR gene expression-inhibiting compound can be administered to a subject in combination with one or more additional anti-cancer treatments. Suitable anti-cancer treatments include, but are not limited to, chemotherapy, radiation therapy and combinations thereof (e.g., chemoradiation).

In a certain embodiment, the isolated miR gene product that is deregulated in lung cancer is selected from the group consisting of miR-21, miR-191, miR-126*, miR-210, miR-155, miR-143, miR-205, miR-192-prec, miR-224, miR-126, miR-24-2, miR-30a-5p, miR-212, miR-140, miR-9, miR-214, miR-17-3p, miR-124a-1, miR-218-2, miR-95, miR-145, miR-198, miR-216-prec, miR-219-1, miR-106a, miR-197, miR-192, miR-125a-prec, miR-26a-1-prec, miR-146, miR-203, miR-199b-prec, let-7a-2-prec, miR-27b, miR-32, miR-29b-2, miR-220, miR-33, miR-181c-prec, miR-150, miR-101-1, miR-124a-3, miR-125a and let-7f-1. In a particular embodiment, the at least one miR gene product is selected from the group consisting of miR-21, miR-205 and miR-216. In another embodiment, the lung cancer is a lung adenocarcinoma and the at least one miR gene product is selected from the group consisting of miR-21, miR-191, miR-155, miR-210, miR-126* and miR-224.

In a particular embodiment, the miR gene product is not one or more of let7a-2, let-7c, let-7g, let-7i, miR-7-2, miR-7-3, miR-9, miR-9-1, miR-10a, miR-15a, miR-15b, miR-16-1, miR-16-2, miR-17-5p, miR-20a, miR-21, miR-24-1, miR-24-2, miR-25, miR-29b-2, miR-30, miR-30a-5p, miR-30c, miR-30d, miR-31, miR-32, miR-34, miR-34a, miR-34a prec, miR-34a-1, miR-34a-2, miR-92-2, miR-96, miR-99a, miR-99b prec, miR-100, miR-103, miR-106a, miR-107, miR-123, miR-124a-1, miR-125b-1, miR-125b-2, miR-126*, miR-127, miR-128b, miR-129, miR-129-1/2 prec, miR-132, miR-135-1, miR-136, miR-137, miR-141, miR-142-as, miR-143, miR-146, miR-148, miR-149, miR-153, miR-155, miR 159-1, miR-181, miR-181b-1, miR-182, miR-186, miR-191, miR-192, miR-195, miR-196-1, miR-196-1 prec, miR-196-2, miR-199a-1, miR-199a-2, miR-199b, miR-200b, miR-202, miR-203, miR-204, miR-205, miR-210, miR-211, miR-212, miR-214, miR-215, miR-217, miR-221 and/or miR-223.

The terms "treat", "treating" and "treatment", as used herein, refer to ameliorating symptoms associated with a disease or condition, for example, lung cancer, including preventing or delaying the onset of the disease symptoms, and/or lessening the severity or frequency of symptoms of the disease or condition. The terms "subject" and "individual" are defined herein to include animals, such as mammals, including, but not limited to, primates, cows, sheep, goats, horses, dogs, cats, rabbits, guinea pigs, rats, mice or other bovine, ovine, equine, canine, feline, rodent, or murine species. In a preferred embodiment, the animal is a human.

As used herein, an "effective amount" of an isolated miR gene product is an amount sufficient to inhibit proliferation of a cancer cell in a subject suffering from lung cancer. One skilled in the art can readily determine an effective amount of a miR gene product to be administered to a given subject, by taking into account factors, such as the size and weight of the subject; the extent of disease penetration; the age, health and sex of the subject; the route of administration; and whether the administration is regional or systemic.

For example, an effective amount of an isolated miR gene product can be based on the approximate weight of a tumor mass to be treated. The approximate weight of a tumor mass can be determined by calculating the approximate volume of the mass, wherein one cubic centimeter of volume is roughly equivalent to one gram. An effective amount of the isolated miR gene product based on the weight of a tumor mass can be in the range of about 10-500 micrograms/gram of tumor mass. In certain embodiments, the tumor mass can be at least about 10 micrograms/gram of tumor mass, at least about 60 micrograms/gram of tumor mass or at least about 100 micrograms/gram of tumor mass.

An effective amount of an isolated miR gene product can also be based on the approximate or estimated body weight of a subject to be treated. Preferably, such effective amounts are administered parenterally or enterally, as described herein; For example, an effective amount of the isolated miR gene product that is administered to a subject can range from about 5-3000 micrograms/kg of body weight, from about 700-1000 micrograms/kg of body weight, or greater than about 1000 micrograms/kg of body weight.

One skilled in the art can also readily determine an appropriate dosage regimen for the administration of an isolated miR gene product to a given subject. For example, a miR gene product can be administered to the subject once (e.g., as a single injection or deposition). Alternatively, a miR gene product can be administered once or twice daily to a subject for a period of from about three to about twenty-eight days, more particularly from about seven to about ten days. In a particular dosage regimen, a miR gene product is administered once a day for seven days. Where a dosage regimen comprises multiple administrations, it is understood that the effective amount of the miR gene product administered to the subject can comprise the total amount of gene product administered over the entire dosage regimen.

As used herein, an "isolated" miR gene product is one that is synthesized, or altered or removed from the natural state through human intervention. For example, a synthetic miR gene product, or a miR gene product partially or completely separated from the coexisting materials of its natural state, is considered to be "isolated." An isolated miR gene product can exist in a substantially-purified form, or can exist in a cell into which the miR gene product has been delivered. Thus, a miR gene product that is deliberately delivered to, or expressed in, a cell is considered an "isolated" miR gene product. A miR gene product produced inside a cell from a miR precursor molecule is also considered to be an "isolated" molecule. According to the invention, the isolated miR gene products described herein can be used for the manufacture of a medicament for treating lung cancer in a subject (e.g., a human).

Isolated miR gene products can be obtained using a number of standard techniques. For example, the miR gene products can be chemically synthesized or recombinantly produced using methods known in the art. In one embodiment, miR gene products are chemically synthesized using appropriately protected ribonucleoside phosphoramidites and a conventional DNA/RNA synthesizer. Commercial suppliers of synthetic RNA molecules or synthesis reagents include, e.g., Proligo (Hamburg, Germany), Dharmacon Research (Lafayette, Colo., U.S.A.), Pierce Chemical (part of Perbio Science, Rockford, Ill., U.S.A.), Glen Research (Sterling, Va., U.S.A.), ChemGenes (Ashland, Mass., U.S.A.) and Cruachem (Glasgow, UK).

Alternatively, the miR gene products can be expressed from recombinant circular or linear DNA plasmids using any suitable promoter. Suitable promoters for expressing RNA from a plasmid include, e.g., the U6 or H1 RNA pol III promoter sequences, or the cytomegalovirus promoters. Selection of other suitable promoters is within the skill in the art. The recombinant plasmids of the invention can also comprise inducible or regulatable promoters for expression of the miR gene products in cancer cells.

The miR gene products that are expressed from recombinant plasmids can be isolated from cultured cell expression systems by standard techniques. The miR gene products that are expressed from recombinant plasmids can also be delivered to, and expressed directly in, the cancer cells. The use of recombinant plasmids to deliver the miR gene products to cancer cells is discussed in more detail below.

The miR gene products can be expressed from a separate recombinant plasmid, or they can be expressed from the same recombinant plasmid. In one embodiment, the miR gene products are expressed as RNA precursor molecules from a single plasmid, and the precursor molecules are processed into the functional miR gene product by a suitable processing system, including, but not limited to, processing systems extant within a cancer cell. Other suitable processing systems include, e.g., the in vitro *Drosophila* cell lysate system (e.g., as described in U.S. Published Patent Application No. 2002/0086356 to Tuschl et al., the entire disclosure of which is incorporated herein by reference) and the *E. coli* RNAse III system (e.g., as described in U.S. Published Patent Application No. 2004/0014113 to Yang et al., the entire disclosure of which is incorporated herein by reference).

Selection of plasmids suitable for expressing the miR gene products, methods for inserting nucleic acid sequences into the plasmid to express the gene products, and methods of delivering the recombinant plasmid to the cells of interest are within the skill in the art. See, for example, Zeng et al. (2002), *Molecular Cell* 9:1327-1333; Tuschl (2002), *Nat. Biotechnol*, 20:446-448; Brummelkamp et al. (2002), *Science* 296:550-553; Miyagishi et al. (2002), *Nat. Biotechnol.* 20:497-500; Paddison et al. (2002), *Genes Dev.* 16:948-958; Lee et al. (2002), *Nat. Biotechnol.* 20:500-505; and Paul et al. (2002), *Nat. Biotechnol.* 20:505-508, the entire disclosures of which are incorporated herein by reference.

In one embodiment, a plasmid expressing the miR gene products comprises a sequence encoding a miR precursor RNA under the control of the CMV intermediate-early promoter. As used herein, "under the control" of a promoter means that the nucleic acid sequences encoding the miR gene product are located 3' of the promoter, so that the promoter can initiate transcription of the miR gene product coding sequences.

The miR gene products can also be expressed from recombinant viral vectors. It is contemplated that the miR gene products can be expressed from two separate recombinant viral vectors, or from the same viral vector. The RNA expressed from the recombinant viral vectors can either be isolated from cultured cell expression systems by standard techniques, or can be expressed directly in cancer cells. The use of recombinant viral vectors to deliver the miR gene products to cancer cells is discussed in more detail below.

The recombinant viral vectors of the invention comprise sequences encoding the miR gene products and any suitable promoter for expressing the RNA sequences. Suitable promoters include, but are not limited to, the U6 or H1 RNA pol III promoter sequences, or the cytomegalovirus promoters. Selection of other suitable promoters is within the skill in the art. The recombinant viral vectors of the invention can also comprise inducible or regulatable promoters for expression of the miR gene products in a cancer cell.

Any viral vector capable of accepting the coding sequences for the miR gene products can be used; for example, vectors derived from adenovirus (AV); adeno-associated virus (AAV); retroviruses (e.g., lentiviruses (LV), Rhabdoviruses, murine leukemia virus); herpes virus, and the like. The tropism of the viral vectors can be modified by pseudotyping the vectors with envelope proteins or other surface antigens from other viruses, or by substituting different viral capsid proteins, as appropriate.

For example, lentiviral vectors of the invention can be pseudotyped with surface proteins from vesicular stomatitis virus (VSV), rabies, Ebola, Mokola, and the like. AAV vectors of the invention can be made to target different cells by engineering the vectors to express different capsid protein serotypes. For example, an AAV vector expressing a serotype 2 capsid on a serotype 2 genome is called AAV 2/2. This serotype 2 capsid gene in the AAV 2/2 vector can be replaced by a serotype 5 capsid gene to produce an AAV 2/5 vector. Techniques for constructing AAV vectors that express different capsid protein serotypes are within the skill in the art; see, e.g., Rabinowitz, J. E., et al. (2002), *J. Virol.* 76:791-801, the entire disclosure of which is incorporated herein by reference.

Selection of recombinant viral vectors suitable for use in the invention, methods for inserting nucleic acid sequences for expressing RNA into the vector, methods of delivering the viral vector to the cells of interest, and recovery of the expressed RNA products are within the skill in the art. See, for example, Dornburg (1995), *Gene Therap.* 2:301-310; Eglitis (1988), *Biotechniques* 6:608-614; Miller (1990), *Hum. Gene Therap.* 1:5-14; and Anderson (1998), *Nature* 392:25-30, the entire disclosures of which are incorporated herein by reference.

Particularly suitable viral vectors are those derived from AV and AAV. A suitable AV vector for expressing the miR gene products, a method for constructing the recombinant AV vector, and a method for delivering the vector into target cells, are described in Xia et al. (2002), *Nat. Biotech.* 20:1006-1010, the entire disclosure of which is incorporated herein by reference. Suitable AAV vectors for expressing the miR gene products, methods for constructing the recombinant AAV vector, and methods for delivering the vectors into target cells are described in Samulski et al. (1987), *J. Virol.* 61:3096-3101; Fisher et al. (1996), *J. Virol.,* 70:520-532; Samulski et al. (1989), *J. Virol.* 63:3822-3826; U.S. Pat. No. 5,252,479; U.S. Pat. No. 5,139,941; International Patent Application No. WO 94/13788; and International Patent Application No. WO 93/24641, the entire disclosures of which are incorporated herein by reference. In one embodiment, the miR gene products are expressed from a single recombinant AAV vector comprising the CMV intermediate early promoter.

In a certain embodiment, a recombinant AAV viral vector of the invention comprises a nucleic acid sequence encoding a miR precursor RNA in operable connection with a polyT termination sequence under the control of a human U6 RNA promoter. As used herein, "in operable connection with a polyT termination sequence" means that the nucleic acid sequences encoding the sense or antisense strands are immediately adjacent to the polyT termination signal in the 5' direction. During transcription of the miR sequences from the vector, the polyT termination signals act to terminate transcription.

In other embodiments of the treatment methods of the invention, an effective amount of at least one compound that inhibits miR expression can be administered to the subject. As used herein, "inhibiting miR expression" means that the production of the precursor and/or active, mature form of miR gene product after treatment is less than the amount produced prior to treatment. One skilled in the art can readily determine whether miR expression has been inhibited in a cancer cell, using, for example, the techniques for determining miR transcript level discussed herein. Inhibition can occur at the level of gene expression (i.e., by inhibiting transcription of a miR gene encoding the miR gene product) or at the level of processing (e.g., by inhibiting processing of a miR precursor into a mature, active miR).

As used herein, an "effective amount" of a compound that inhibits miR expression is an amount sufficient to inhibit proliferation of a cancer cell in a subject suffering from a cancer (e.g., lung cancer). One skilled in the art can readily determine an effective amount of a miR expression-inhibiting compound to be administered to a given subject, by taking into account factors, such as the size and weight of the subject; the extent of disease penetration; the age, health and sex of the subject; the route of administration; and whether the administration is regional or systemic.

For example, an effective amount of the expression-inhibiting compound can be based on the approximate weight of a tumor mass to be treated, as described herein. An effective amount of a compound that inhibits miR expression can also be based on the approximate or estimated body weight of a subject to be treated, as described herein.

One skilled in the art can also readily determine an appropriate dosage regimen for administering a compound that inhibits miR expression to a given subject, as described herein. Suitable compounds for inhibiting miR gene expression include double-stranded RNA (such as short- or small-interfering RNA or "siRNA"), antisense nucleic acids, and enzymatic RNA molecules, such as ribozymes. Each of these compounds can be targeted to a given miR gene product and interfere with the expression (e.g., by inhibiting translation, by inducing cleavage and/or degradation) of the target miR gene product.

For example, expression of a given miR gene can be inhibited by inducing RNA interference of the miR gene with an isolated double-stranded RNA ("dsRNA") molecule which has at least 90%, for example at least 95%, at least 98%, at least 99%, or 100%, sequence homology with at least a portion of the miR gene product. In a particular embodiment, the dsRNA molecule is a "short or small interfering RNA" or "siRNA."

siRNA useful in the present methods comprise short double-stranded RNA from about 17 nucleotides to about 29 nucleotides in length, preferably from about 19 to about 25 nucleotides in length. The siRNA comprise a sense RNA strand and a complementary antisense RNA strand annealed together by standard Watson-Crick base-pairing interactions (hereinafter "base-paired"). The sense strand comprises a nucleic acid sequence that is substantially identical to a nucleic acid sequence contained within the target miR gene product.

As used herein, a nucleic acid sequence in an siRNA that is "substantially identical" to a target sequence contained within the target mRNA is a nucleic acid sequence that is identical to the target sequence, or that differs from the target sequence by one or two nucleotides. The sense and antisense strands of the siRNA can comprise two complementary, single-stranded RNA molecules, or can comprise a single molecule in which two complementary portions are base-paired and are covalently linked by a single-stranded "hairpin" area.

The siRNA can also be altered RNA that differs from naturally-occurring RNA by the addition, deletion, substitution and/or alteration of one or more nucleotides. Such alterations can include addition of non-nucleotide material, such as to the end(s) of the siRNA or to one or more internal nucleotides of the siRNA, or modifications that make the siRNA resistant to nuclease digestion, or the substitution of one or more nucleotides in the siRNA with deoxyribonucleotides.

One or both strands of the siRNA can also comprise a 3' overhang. As used herein, a "3' overhang" refers to at least one unpaired nucleotide extending from the 3'-end of a duplexed RNA strand. Thus, in certain embodiments, the siRNA comprises at least one 3' overhang of from 1 to about 6 nucleotides (which includes ribonucleotides or deoxyribonucleotides) in length, from 1 to about 5 nucleotides in length, from 1 to about 4 nucleotides in length, or from about 2 to about 4 nucleotides in length. In a particular embodiment, the 3' overhang is present on both strands of the siRNA; and is 2 nucleotides in length. For example, each strand of the siRNA can comprise 3' overhangs of dithymidylic acid ("TT") or diuridylic acid ("uu").

The siRNA can be produced chemically or biologically, or can be expressed from a recombinant plasmid or viral vector, as described above for the isolated miR gene products. Exemplary methods for producing and testing dsRNA or siRNA molecules are described in U.S. Published Patent Application No. 2002/0173478 to Gewirtz and in U.S. Published Patent Application No. 2004/0018176 to Reich et al., the entire disclosures of both of which are incorporated herein by reference.

Expression of a given miR gene can also be inhibited by an antisense nucleic acid. As used herein, an "antisense nucleic acid" refers to a nucleic acid molecule that binds to target RNA by means of RNA-RNA, RNA-DNA or RNA-peptide nucleic acid interactions, which alters the activity of the target RNA. Antisense nucleic acids suitable for use in the present methods are single-stranded nucleic acids (e.g., RNA, DNA, RNA-DNA chimeras, peptide nucleic acids (PNA)) that generally comprise a nucleic acid sequence complementary to a contiguous nucleic acid sequence in a miR gene product. The antisense nucleic acid can comprise a nucleic acid sequence that is 50-100% complementary, 75-100% complementary, or 95-100% complementary to a contiguous nucleic acid sequence in a miR gene product. Nucleic acid sequences of particular human miR gene products are provided in Table 1a and Table 1b. Without wishing to be bound by any theory, it is believed that the antisense nucleic acids activate RNase H or another cellular nuclease that digests the miR gene product/antisense nucleic acid duplex.

Antisense nucleic acids can also contain modifications to the nucleic acid backbone or to the sugar and base moieties (or their equivalent) to enhance target specificity, nuclease resistance, delivery or other properties related to efficacy of the molecule. Such modifications include cholesterol moieties, duplex intercalators, such as acridine, or one or more nuclease-resistant groups.

Antisense nucleic acids can be produced chemically or biologically, or can be expressed from a recombinant plasmid or viral vector, as described above for the isolated miR gene products. Exemplary methods for producing and testing are within the skill in the art; see, e.g., Stein and Cheng (1993), *Science* 261:1004 and U.S. Pat. No. 5,849,902 to Woolf et al., the entire disclosures of which are incorporated herein by reference.

Expression of a given miR gene can also be inhibited by an enzymatic nucleic acid. As used herein, an "enzymatic nucleic acid" refers to a nucleic acid comprising a substrate binding region that has complementarity to a contiguous nucleic acid sequence of a miR gene product, and which is able to specifically cleave the miR gene product. The enzymatic nucleic acid substrate binding region can be, for example, 50-100% complementary, 75-100% complementary, or 95-100% complementary to a contiguous nucleic acid sequence in a miR gene product. The enzymatic nucleic acids can also comprise modifications at the base, sugar, and/or phosphate groups. An exemplary enzymatic nucleic acid for use in the present methods is a ribozyme.

The enzymatic nucleic acids can be produced chemically or biologically, or can be expressed from a recombinant plasmid or viral vector, as described above for the isolated miR gene products. Exemplary methods for producing and testing dsRNA or siRNA molecules are described in Werner and Uhlenbeck (1995), *Nucl. Acids Res.* 23:2092-96; Hammann et al. (1999), *Antisense and Nucleic Acid Drug Dev.* 9:25-31; and U.S. Pat. No. 4,987,071 to Cech et al, the entire disclosures of which are incorporated herein by reference.

Administration of at least one miR gene product, or at least one compound for inhibiting miR expression, will inhibit the proliferation of cancer cells in a subject who has a cancer (e.g., lung cancer). As used herein, to "inhibit the proliferation of a cancer cell" means to kill the cell, or permanently or temporarily arrest or slow the growth of the cell. Inhibition of cancer cell proliferation can be inferred if the number of such cells in the subject remains constant or decreases after administration of the miR gene products or miR gene expression-inhibiting compounds. An inhibition of cancer cell proliferation can also be inferred if the absolute number of such cells increases, but the rate of tumor growth decreases.

The number of cancer cells in the body of a subject can be determined by direct measurement, or by estimation from the size of primary or metastatic tumor masses. For example, the number of cancer cells in a subject can be measured by immunohistological methods, flow cytometry, or other techniques designed to detect characteristic surface markers of cancer cells.

The size of a tumor mass can be ascertained by direct visual observation, or by diagnostic imaging methods, such as X-ray, magnetic resonance imaging, ultrasound, and scintigraphy. Diagnostic imaging methods used to ascertain size of the tumor mass can be employed with or without contrast agents, as is known in the art. The size of a tumor mass can also be ascertained by physical means, such as palpation of the tissue mass or measurement of the tissue mass with a measuring instrument, such as a caliper.

The miR gene products or miR gene expression-inhibiting compounds can be administered to a subject by any means suitable for delivering these compounds to cancer cells of the subject. For example, the miR gene products or miR expression-inhibiting compounds can be administered by methods suitable to transfect cells of the subject with these compounds, or with nucleic acids comprising sequences encoding these compounds. In one embodiment, the cells are transfected with a plasmid or viral vector comprising sequences encoding at least one miR gene product or miR gene expression-inhibiting compound.

Transfection methods for eukaryotic cells are well known in the art, and include, e.g., direct injection of the nucleic acid into the nucleus or pronucleus of a cell; electroporation; liposome transfer or transfer mediated by lipophilic materials; receptor-mediated nucleic acid delivery, bioballistic or particle acceleration; calcium phosphate precipitation, and transfection mediated by viral vectors.

For example, cells can be transfected with a liposomal transfer compound, e.g., DOTAP (N-[1-(2,3-dioleoyloxy) propyl]-N,N,N-trimethyl-ammonium methylsulfate, Boehringer-Mannheim) or an equivalent, such as LIPOFECTIN. The amount of nucleic acid used is not critical to the practice of the invention; acceptable results may be achieved with 0.1-100 micrograms of nucleic acid/$10^5$ cells. For example, a ratio of about 0.5 micrograms of plasmid vector in 3 micrograms of DOTAP per $10^5$ cells can be used.

A miR gene product or miR gene expression-inhibiting compound can also be administered to a subject by any suitable enteral or parenteral administration route. Suitable enteral administration routes for the present methods include, e.g., oral, rectal, or intranasal delivery. Suitable parenteral administration routes include, e.g., intravascular administration (e.g., intravenous bolus injection, intravenous infusion, intra-arterial bolus injection, intra-arterial infusion and catheter instillation into the vasculature); peri- and intra-tissue injection (e.g., peri-tumoral and intra-tumoral injection, intra-retinal injection, or subretinal injection); subcutaneous injection or deposition, including subcutaneous infusion (such as by osmotic pumps); direct application to the tissue of interest, for example by a catheter or other placement device (e.g., a retinal pellet or a suppository or an implant comprising a porous, non-porous, or gelatinous material); and inhalation. Particularly suitable administration routes are injection, infusion and direct injection into the tumor.

In the present methods, a miR gene product or miR gene product expression-inhibiting compound can be administered to the subject either as naked RNA, in combination with a delivery reagent, or as a nucleic acid (e.g., a recombinant plasmid or viral vector) comprising sequences that express the miR gene product or miR gene expression-inhibiting compound. Suitable delivery reagents include, e.g., the Mirus Transit TKO lipophilic reagent; LIPOFECTIN; lipofectamine; cellfectin; polycations (e.g., polylysine) and liposomes.

Recombinant plasmids and viral vectors comprising sequences that express the miR gene products or miR gene expression-inhibiting compounds, and techniques for delivering such plasmids and vectors to cancer cells, are discussed herein and/or are well known in the art.

In a particular embodiment, liposomes are used to deliver a miR gene product or miR gene expression-inhibiting compound (or nucleic acids comprising sequences encoding them) to a subject. Liposomes can also increase the blood half-life of the gene products or nucleic acids. Suitable liposomes for use in the invention can be formed from standard vesicle-forming lipids, which generally include neutral or negatively charged phospholipids and a sterol, such as cholesterol. The selection of lipids is generally guided by consideration of factors, such as the desired liposome size and half-life of the liposomes in the blood stream. A variety of methods are known for preparing liposomes, for example, as described in Szoka et al. (1980), *Ann. Rev. Biophys. Bioeng.* 9:467; and U.S. Pat. Nos. 4,235,871, 4,501,728, 4,837,028, and 5,019,369, the entire disclosures of which are incorporated herein by reference.

The liposomes for use in the present methods can comprise a ligand molecule that targets the liposome to cancer cells. Ligands that bind to receptors prevalent in cancer cells, such as monoclonal antibodies that bind to tumor cell antigens, are preferred.

The liposomes for use in the present methods can also be modified so as to avoid clearance by the mononuclear macrophage system ("MMS") and reticuloendothelial system ("RES"). Such modified liposomes have opsonization-inhibition moieties on the surface or incorporated into the liposome structure. In a particularly preferred embodiment, a liposome of the invention can comprise both an opsonization-inhibition moiety and a ligand.

Opsonization-inhibiting moieties for use in preparing the liposomes of the invention are typically large hydrophilic polymers that are bound to the liposome membrane. As used herein, an opsonization-inhibiting moiety is "bound" to a liposome membrane when it is chemically or physically attached to the membrane, e.g., by the intercalation of a lipid-soluble anchor into the membrane itself, or by binding directly to active groups of membrane lipids. These opsonization-inhibiting hydrophilic polymers form a protective surface layer that significantly decreases the uptake of the liposomes by the MMS and RES; e.g., as described in U.S. Pat. No. 4,920,016, the entire disclosure of which is incorporated herein by reference.

Opsonization-inhibiting moieties suitable for modifying liposomes are preferably water-soluble polymers with a number-average molecular weight from about 500 to about 40,000 daltons, and more preferably from about 2,000 to about 20,000 daltons. Such polymers include polyethylene glycol (PEG) or polypropylene glycol (PPG) or derivatives thereof; e.g., methoxy PEG or PPG, and PEG or PPG stearate; synthetic polymers, such as polyacrylamide or poly N-vinyl pyrrolidone; linear, branched, or dendrimeric polyamidoamines; polyacrylic acids; polyalcohols, e.g., polyvinylalcohol and polyxylitol to which carboxylic or amino groups are chemically linked, as well as gangliosides, such as ganglioside GM1. Copolymers of PEG, methoxy PEG, or methoxy PPG, or derivatives thereof, are also suitable. In addition, the opsonization-inhibiting polymer can be a block copolymer of PEG and either a polyamino acid, polysaccharide, polyamidoamine, polyethyleneamine, or polynucleotide. The opsonization-inhibiting polymers can also be natural polysaccharides containing amino acids or carboxylic acids, e.g., galacturonic acid, glucuronic acid, mannuronic acid, hyaluronic acid, pectic acid, neuraminic acid, alginic acid, carrageenan; aminated polysaccharides or oligosaccharides (linear or branched); or carboxylated polysaccharides or oligosaccharides, e.g., reacted with derivatives of carbonic acids with resultant linking of carboxylic groups. Preferably, the opsonization-inhibiting moiety is a PEG, PPG, or a derivative thereof. Liposomes modified with PEG or PEG-derivatives are sometimes called "PEGylated liposomes."

The opsonization-inhibiting moiety can be bound to the liposome membrane by any one of numerous well-known techniques. For example, an N-hydroxysuccinimide ester of PEG can be bound to a phosphatidyl-ethanolamine lipid-soluble anchor, and then bound to a membrane. Similarly, a dextran polymer can be derivatized with a stearylamine lipid-soluble anchor via reductive amination using $Na(CN)BH_3$ and a solvent mixture, such as tetrahydrofuran and water in a 30:12 ratio at 60° C.

Liposomes modified with opsonization-inhibition moieties remain in the circulation much longer than unmodified liposomes. For this reason, such liposomes are sometimes called "stealth" liposomes. Stealth liposomes are known to accumulate in tissues fed by porous or "leaky" microvasculature. Thus, tissue characterized by such microvasculature defects, for example, solid tumors (e.g., lung cancers), will efficiently accumulate these liposomes; see Gabizon, et al (1988), Proc. Natl. Acad. Sci., U.S.A., 18:6949-53. In addition, the reduced uptake by the RES lowers the toxicity of stealth liposomes by preventing significant accumulation of the liposomes in the liver and spleen. Thus, liposomes that are modified with opsonization-inhibition moieties are particularly suited to deliver the miR gene products or miR gene expression-inhibition compounds (or nucleic acids comprising sequences encoding them) to tumor cells.

The miR gene products or miR gene expression-inhibition compounds can be formulated as pharmaceutical compositions, sometimes called "medicaments," prior to administering them to a subject, according to techniques known in the art. Accordingly, the invention encompasses pharmaceutical compositions for treating lung cancer. In one embodiment, the pharmaceutical composition comprises at least one isolated miR gene product, or an isolated variant or biologically-active fragment thereof, and a pharmaceutically-acceptable carrier. In a particular embodiment, the at least one miR gene product corresponds to a miR gene product that has a decreased level of expression in lung cancer cells relative to suitable control cells. In certain embodiments the isolated miR gene product is selected from the group consisting of miR-126*, miR-192, miR-224, miR-126, miR-30a-5p, miR-140, miR-9, miR-124a-1, miR-218-2, miR-95, miR-145, miR-198, miR-216, miR-219-1, miR-125a, miR-26a-1, miR-199b, let-7a-2, miR-27b, miR-32, miR-29b-2, miR-220, miR-33, miR-181c, miR-101-1, miR-124a-3, miR-125b-1, let-7f-1 and a combination thereof. In one embodiment, the isolated miR gene product is not miR-15a or miR-16-1. In an additional embodiment, the miR gene product is not miR-210 or miR-212. In another embodiment, the miR gene product is not miR-21, miR-143, miR-205 or miR-9. In yet another embodiment, the miR gene product is not miR-21, miR-191, miR-126*, miR-210, miR-155, miR-143, miR-205, miR-126, miR-30a-5p, miR-140, miR-214, miR-218-2, miR-145, miR-106a, miR-192, miR-203, miR-150, miR-220, miR-212 or miR-9.

In other embodiments, the pharmaceutical compositions of the invention comprise at least one miR expression-inhibition compound. In a particular embodiment, the at least one miR gene expression-inhibition compound is specific for a miR gene whose expression is greater in lung cancer cells than control cells. In certain embodiments, the miR gene expression-inhibition compound is specific for one or more miR gene products selected from the group consisting of miR-21, miR-191, miR-210, miR-155, miR-205, miR-24-2, miR-212, miR-214, miR-17-3p, miR-106a, miR-197, miR-192, miR-146, miR-203, miR-150 and a combination thereof. In one embodiment, the isolated miR gene product is not specific for miR-15a or miR-16-1. In an additional embodiment, the miR gene product is not specific for miR-210 or miR-212. In another embodiment, the miR gene product is not specific for miR-21, miR-143, miR-205 or miR-9. In yet another embodiment, the miR gene product is not specific for miR-21, miR-191, miR-126*, miR-210, miR-155, miR-143, miR-205, miR-126, miR-30a-5p, miR-140, miR-214, miR-218-2, miR-145, miR-106a, miR-192, miR-203, miR-150, miR-220, miR-212 or miR-9. Pharmaceutical compositions of the present invention are characterized as being at least sterile and pyrogen-free. As used herein, "pharmaceutical compositions" include formulations for human and veterinary use. Methods for preparing pharmaceutical compositions of the invention are within the skill in the art, for example, as described in Remington's Pharmaceutical Science, 17th ed., Mack Publishing Company, Easton, Pa. (1985), the entire disclosure of which is incorporated herein by reference.

The present pharmaceutical compositions comprise at least one miR gene product or miR gene expression-inhibition compound (or at least one nucleic acid comprising a sequence encoding the miR gene product or miR gene expression-inhibition compound) (e.g., 0.1 to 90% by weight), or a physiologically-acceptable salt thereof, mixed with a pharmaceutically-acceptable carrier. In certain embodiments, the pharmaceutical composition of the invention additionally comprises one or more anti-cancer agents (e.g., chemotherapeutic agents). The pharmaceutical formulations of the invention can also comprise at least one miR gene product or miR gene expression-inhibition compound (or at least one nucleic acid comprising a sequence encoding the miR gene product or miR gene expression-inhibition compound), which are encapsulated by liposomes and a pharmaceutically-acceptable carrier. In one embodiment, the pharmaceutical composition comprises a miR gene or gene product that is not miR-15, miR-16, miR-143 and/or miR-145.

Especially suitable pharmaceutically-acceptable carriers are water, buffered water, normal saline, 0.4% saline, 0.3% glycine, hyaluronic acid and the like.

In a particular embodiment, the pharmaceutical compositions of the invention comprise at least one miR gene product or miR gene expression-inhibition compound (or at least one nucleic acid comprising a sequence encoding the miR gene product or miR gene expression-inhibition compound) that is resistant to degradation by nucleases. One skilled in the art can readily synthesize nucleic acids that are nuclease resistant, for example by incorporating one or more ribonucleotides that is modified at the 2'-position into the miR gene product. Suitable 2'-modified ribonucleotides include those modified at the 2'-position with fluoro, amino, alkyl, alkoxy and O-allyl.

Pharmaceutical compositions of the invention can also comprise conventional pharmaceutical excipients and/or additives. Suitable pharmaceutical excipients include stabilizers, antioxidants, osmolality adjusting agents, buffers, and pH adjusting agents. Suitable additives include, e.g., physiologically biocompatible buffers (e.g., tromethamine hydrochloride), additions of chelants (such as, for example, DTPA or DTPA-bisamide) or calcium chelate complexes (such as, for example, calcium DTPA, CaNaDTPA-bisamide), or, optionally, additions of calcium or sodium salts (for example, calcium chloride, calcium ascorbate, calcium gluconate or calcium lactate). Pharmaceutical compositions of the invention can be packaged for use in liquid form, or can be lyophilized.

For solid pharmaceutical compositions of the invention, conventional nontoxic solid pharmaceutically-acceptable carriers can be used; for example, pharmaceutical grades of mannitol, lactose, starch, magnesium stearate, sodium saccharin, talcum, cellulose, glucose, sucrose, magnesium carbonate, and the like.

For example, a solid pharmaceutical composition for oral administration can comprise any of the carriers and excipients listed above and 10-95%, preferably 25%-75%, of the at least one miR gene product or miR gene expression-inhibition compound (or at least one nucleic acid comprising sequences encoding them). A pharmaceutical composition for aerosol (inhalational) administration can comprise 0.01-20% by weight, preferably 1%-10% by weight, of the at least one miR gene product or miR gene expression-inhibition compound (or at least one nucleic acid comprising a sequence encoding the miR gene product or miR gene expression-inhibition compound) encapsulated in a liposome as described above, and a propellant. A carrier can also be included as desired; e.g., lecithin for intranasal delivery.

The pharmaceutical compositions of the invention can further comprise one or more anti-cancer agents. In a particular embodiment, the compositions comprise at least one miR gene product or miR gene expression-inhibition compound (or at least one nucleic acid comprising a sequence encoding the miR gene product or miR gene expression-inhibition compound) and at least one chemotherapeutic agent. Chemotherapeutic agents that are suitable for the methods of the invention include, but are not limited to, DNA-alkylating agents, anti-tumor antibiotic agents, anti-metabolic agents, tubulin stabilizing agents, tubulin destabilizing agents, hormone antagonist agents, topoisomerase inhibitors, protein kinase inhibitors, HMG-CoA inhibitors, CDK inhibitors, cyclin inhibitors, caspase inhibitors, metalloproteinase inhibitors, antisense nucleic acids, triple-helix DNAs, nucleic acids aptamers, and molecularly-modified viral, bacterial and exotoxic agents. Examples of suitable agents for the compositions of the present invention include, but are not limited to, cytidine arabinoside, methotrexate, vincristine, etoposide (VP-16), doxorubicin (adriamycin), cisplatin (CDDP), dexamethasone, arglabin, cyclophosphamide, sarcolysin, methylnitrosourea, fluorouracil, 5-fluorouracil (5FU), vinblastine, camptothecin, actinomycin-D, mitomycin C, hydrogen peroxide, oxaliplatin, irinotecan, topotecan, leucovorin, carmustine, streptozocin, CPT-11, taxol, tamoxifen, dacarbazine, rituximab, daunorubicin, 1-β-D-arabinofuranosylcytosine, imatinib, fludarabine, docetaxel and FOLFOX4.

The invention also encompasses methods of identifying an anti-lung cancer agent, comprising providing a test agent to a cell and measuring the level of at least one miR gene product in the cell. In one embodiment, the method comprises providing a test agent to a cell and measuring the level of at least one miR gene product associated with decreased expression levels in lung cancer cells. An increase in the level of the miR gene product in the cell, relative to a suitable control (e.g., the level of the miR gene product in a control cell), is indicative of the test agent being an anti-lung cancer agent. In a particular embodiment, the at least one miR gene product associated with decreased expression levels in lung cancer cells is selected from the group consisting of miR-126*, miR-192, miR-224, miR-126, miR-30a-5p, miR-140, miR-9, miR-124a-1, miR-218-2, miR-95, miR-145, miR-198, miR-216, miR-219-1, miR-125a, miR-26a-1, miR-199b, let-7a-2, miR-27b, miR-32, miR-29b-2, miR-220, miR-33, miR-181c, miR-101-1, miR-124a-3, miR-125b-1, let-7f-1 and a combination thereof. In one embodiment, the miR gene product is not one or more of let7a-2, let-7c, let-7g, let-7i, miR-7-2, miR-7-3, miR-9, miR-9-1, miR-10a, miR-15a, miR-15b, miR-16-1, miR-16-2, miR-17-5p, miR-20a, miR-21, miR-24-1, miR-24-2, miR-25, miR-29b-2, miR-30, miR-30a-5p, miR-30c, miR-30d, miR-31, miR-32, miR-34, miR-34a, miR-34a prec, miR-34a-1, miR-34a-2, miR-92-2, miR-96, miR-99a, miR-99b prec, miR-100, miR-103, miR-106a, miR-107, miR-123, miR-124a-1, miR-125b-1, miR-125b-2, miR-126*, miR-127, miR-128b, miR-129, miR-129-1/2 prec, miR-132, miR-135-1, miR-136, miR-137, miR-141, miR-142-as, miR-143, miR-146, miR-148, miR-149, miR-153, miR-155, miR 159-1, miR-181, miR-181b-1, miR-182, miR-186, miR-191, miR-192, miR-195, miR-196-1, miR-196-1 prec, miR-196-2, miR-199a-1, miR-199a-2, miR-199b, miR-200b, miR-202, miR-203, miR-204, miR-205, miR-210, miR-211, miR-212, miR-214, miR-215, miR-217, miR-221 and/or miR-223.

In other embodiments the method comprises providing a test agent to a cell and measuring the level of at least one miR gene product associated with increased expression levels in lung cancer cells. A decrease in the level of the miR gene product in the cell, relative to a suitable control (e.g., the level of the miR gene product in a control cell), is indicative of the test agent being an anti-lung cancer agent. In a particular embodiment, at least one miR gene product associated with increased expression levels in lung cancer cells is selected from the group consisting of miR-21, miR-191, miR-210, miR-155, miR-205, miR-24-2, miR-212, miR-214, miR-17-3p, miR-106a, miR-197, miR-192, miR-146, miR-203, miR-150 and a combination thereof. In one embodiment, the miR gene product is not one or more of let7a-2, let-7c, let-7g, let-7i, miR-7-2, miR-7-3, miR-9, miR-9-1, miR-10a, miR-15a, miR-15b, miR-16-1, miR-16-2, miR-17-5p, miR-20a, miR-21, miR-24-1, miR-24-2, miR-25, miR-29b-2, miR-30, miR-30a-5p, miR-30c, miR-30d, miR-31, miR-32, miR-34, miR-34a, miR-34a prec, miR-34a-1, miR-34a-2, miR-92-2, miR-96, miR-99a, miR-99b prec, miR-100, miR-103, miR-106a, miR-107, miR-123, miR-124a-1, miR-125b-1, miR-125b-2, miR-126*, miR-127, miR-128b, miR-129, miR-129-

1/2 prec, miR-132, miR-135-1, miR-136, miR-137, miR-141, miR-142-as, miR-143, miR-146, miR-148, miR-149, miR-153, miR-155, miR 159-1, miR-181, miR-181b-1, miR-182, miR-186, miR-191, miR-192, miR-195, miR-196-1, miR-196-1 prec, miR-196-2, miR-199a-1, miR-199a-2, miR-199b, miR-200b, miR-202, miR-203, miR-204, miR-205, miR-210, miR-211, miR-212, miR-214, miR-215, miR-217, miR-221 and/or miR-223.

Suitable agents include, but are not limited to drugs (e.g., small molecules, peptides), and biological macromolecules (e.g., proteins, nucleic acids). The agent can be produced recombinantly, synthetically, or it may be isolated (i.e., purified) from a natural source. Various methods for providing such agents to a cell (e.g., transfection) are well known in the art, and several of such methods are described hereinabove. Methods for detecting the expression of at least one miR gene product (e.g., Northern blotting, in situ hybridization, RT-PCR, expression profiling) are also well known in the art. Several of these methods are also described herein.

The invention will now be illustrated by the following non-limiting examples.

EXEMPLIFICATION

Example 1

Altered miRNA Expression in Primary Lung Cancers

Materials and Methods
Samples 104 pairs of primary lung cancer and corresponding non-cancerous lung tissues were used in this study. An additional 32 cases, which could be followed up until 5 years, were used for an independent validation dataset. These tissues were obtained between 1990 and 1999 as surgical specimens from patients in the Baltimore metropolitan area, with informed consent and in agreement with the Institutional Review Board. Lung cancer tissues were obtained from 65 lung adenocarcinoma patients and 39 lung squamous cell carcinoma patients. 65 male and 39 female patients, having a median age of 65 (range 38-84), comprised the set. 65 tumors were classified as stage I, 17 as stage II, and 22 as stage III or IV tumors. For the majority of samples, clinical and biological information was available. Total RNA from tissues was isolated by TRIzol® Reagent (Invitrogen), according to the manufacturer's instructions.
Microarray Analysis Microarray analysis was performed as previously described (Liu, C. G., et al., *Proc. Natl. Acad. Sci. U.S.A.* 101:9740-9744 (2004)). Briefly, 5 μg of total RNA was hybridized with miRNA microarray chips containing 352 probes in triplicate. Specifically, these chips contain gene-specific 40-mer oligonucleotide probes, spotted by contacting technologies and covalently attached to a polymeric matrix, which were generated from 161 human miRNAs, 84 mouse miRNAs, miRNAs from three other species and tRNA. The microarrays were hybridized in 6×SSPE (0.9 M NaCl/60 mM NaH$_2$PO$_4$.H$_2$O/8 mM EDTA, pH 7.4)/30% formamide at 25° C. for 18 hr, washed in 0.75×TNT (Tris.HCl/NaCl/Tween 20) at 37° C. for 40 min, and processed using a method of direct detection of biotin-containing transcripts by streptavidin-Alexa647 conjugate (Molecular Probes, Carlsbad, Calif.). Processed slides were scanned using a PerkinElmer ScanArray XL5K Scanner, with the laser set to 635 nm, at Power 80 and PMT 70 setting, and a scan resolution of 10 μm. An average value of the three spot replicates for each miRNA was normalized and analyzed in BRB-ArrayTools version 3.2.3. After excluding negative values with hybridization intensity below background, normalization was performed by using a per chip on median normalization method and normalization to median array as reference. Finally, 147 miRNAs with consistent log values present in more than 50% of the samples were selected. Genes that were differently expressed among groups were identified using t- or F-test and genes were considered statistically significant if their p value was less than 0.001. A global test of whether the expression profiles differed between the groups was also performed by permutating the labels of which arrays corresponded to which groups. For each permutation, the p values were re-computed and the number of genes significant at the 0.001 level was noted. The proportion of the permutations that gave at least as many significant genes as with the actual data was the significance level of the global test.
Solution Hybridization Detection Analysis and Real-Time RT-PCR Analysis The expression levels of mature miRNAs were measured by solution hybridization detection using the mirVana™ miRNA Detection Kit (Ambion Inc., TX). Briefly, 1 μg total RNA was incubated with radiolabeled probes corresponding to these miRNAs. Following digestion to remove any probe that was not bound by target miRNA, the radiolabeled products were fractionated by denaturing polyacrylamide gel electrophoresis. Probes were prepared by 5' end labeling using T4 Polynucleotide Kinase with mirVana™ Probe & Marker Kit (Ambion Inc., TX), according to the manufacturer's instructions. Quantitative real-time PCR was performed as described (Schmittgen et al., *Nucl. Acids Res.* 32:e43 (2004)) on an Applied Biosystem's Sequence Detection System, and all reactions were run in triplicate. Briefly, RNA was reverse-transcribed to cDNA with gene-specific primers and Thermoscript, and the relative amount of each miRNA to tRNA for initiator methionine was determined, using the equation: $2^{-dCT}$, where $dC_T=(C_{TmiRNA}-C_{TU6})$.
Survival Analysis Genes whose expression was significantly related to survival of the patient were identified. A statistical significance level for each gene was computed based on univariate Cox proportional hazard regression model in BRB-ArrayTools version 3.2.3. These p values were then used in a multivariate permutation test in which the survival times and censoring indicators were randomly permuted among arrays. Genes were considered statistically significant if their p value was less than 0.05.

Survival curves were estimated by the Kaplan-Meier method (SAS Institute, Cary, N.C.), and the resulting curves were compared using the log-rank test. The joint effect of co-variables was examined using the Cox proportional hazard regression model. Statistical analysis was performed using StatMate (ATMS Co. Ltd., Tokyo, Japan).
Results miRNA expression in 104 pairs of primary lung cancer and corresponding noncancerous lung tissues was analyzed to investigate the involvement of miRNAs in lung cancer. Comparisons of miRNA expression for several specific group pairs are listed in the Table 2. miRNAs, which were expressed differently in 5 phenotypical and histological classifications (Table 2), were identified.

Upon comparison of miRNA expression in lung cancer tissues and corresponding noncancerous lung tissues, 43 miRNAs were identified that displayed statistically-significant differences in expression between groups (Table 3). In class comparison analysis using our microarray analysis tool, the multivariate permutation test, was performed to control for multiple comparisons. The test provides a specific confidence level for ensuring that the number of false discoveries does not exceed a target level, or for ensuring that the proportion of the gene list representing false discoveries does not exceed a target level. Thus, the probability of getting at least 43 differentially-expressed miRNAs that are statistically significant by chance at the <0.001 level, if there are no real differences between the classes, was 0 as estimated by the multivariate permutation test. Furthermore, 91% of 104 lung cancers were correctly classified using the leave-one-out cross-validated class prediction method based on the compound covariate predictor. Based on 2000 random permutations, the p value, which is defined as the proportion of the random permutations that gave a cross-validated error rate no greater than the cross-validated error rate with the real data, was <0.0005.

Several of these miRNAs were associated with FRAs (Table 3). In particular, three miRNAs are located inside fragile sites (hsa-mir-21 at FRA17B, hsa-mir-27b at FRA9D, and hsa-mir-32 at FRA9E). Furthermore, many of these identified miRNAs are located at frequently deleted or amplified regions in several malignancies (Table 3). For example, hsa-mir-21 and hsa-mir-205 are located at the region amplified in lung cancer, whereas hsa-mir-126* and hsa-mir-126 are at 9q34.3, a region deleted in lung cancer. Reduced expression of precursor let-7a-2 and let-7f-1 was also found in adenocarcinoma and squamous cell carcinoma at a p value cutoff of 0.05. In the same way, comparison analyses between lung adenocarcinoma vs. noncancerous tissues and squamous cell carcinoma vs. noncancerous tissues revealed 17 and 16 miRNAs with statistically different expression, respectively (Table 4). Six miRNAs (hsa-mir-21, hsa-mir-191, hsa-mir-155, hsa-mir-210, hsa-mir-126*, and hsa-mir-224) were shared in both histological types of non-small cell lung carcinoma (NSCLC).

TABLE 2

Comparison analysis of clinicopathological classifications

| Classification (Number) | Total | No. of genes[a] | FDR[b] | % correctly classified[c] (p-value) |
|---|---|---|---|---|
| Phenotypical classification | | | | |
| All tumor (104) vs. All normal (104) | 208 | 43 | 0 | 91 (<0.0005) |
| Adeno[d] tumor(65) vs. Adeno normal (65) | 130 | 17 | 0.001 | 80 (<0.0005) |
| SCC[e] tumor (39) vs. SCC normal (39) | 78 | 16 | 0 | 92 (<0.0005) |
| Histological classification | | | | |
| Adeno tumor (65) vs. SCC tumor (39) | 104 | 6 | 0.001 | 81 (<0.0005) |
| Age classification | | | | |
| All; Age <67 (56) vs. Age ≧67 (48) | 104 | 0 | | |
| Adeno; Age <67 (37) vs. Age ≧67 (28) | 65 | 0 | | |
| SCC; Age <67 (19) vs. Age ≧67 (20) | 39 | 0 | | |
| Sex classification | | | | |
| All; Male (65) vs. Female (39) | 104 | 0 | | |
| Adeno; Male (39) vs. Female (26) | 65 | 0 | | |
| SCC; Male (26) vs. Female (13) | 39 | 0 | | |
| Race classification | | | | |
| All; African American (21) vs. White American (83) | 104 | 0 | | |
| Adeno; African American (13) vs. White American (52) | 65 | 0 | | |
| SCC; African American (8) vs. White American (31) | 39 | 0 | | |
| Stage classification | | | | |
| All; Stage I (65) vs. stage II (17) vs. stage III, IV (22) | 104 | 0 | | |
| Adeno; Stage I (41) vs. stage II (8) vs. stage III, IV (16) | 65 | 1 | | |
| SCC; Stage I (24) vs. stage II (9) vs. stage III, IV (6) | 39 | 0 | | |

[a] No. of genes, Number of genes significant at 0.001.
[b] FDR, False discovery rate which is probability of significant genes by chance.
[c] % correctly classified (p-value). The leave-one-out cross-validated class prediction method based on the compound covariate predictor. The p-value is the proportion of the random permutations that gave a cross-validated error rate no greater than the cross-validated error rate with the real data.
[d] Adeno, Adenocarcinoma.
[e] SCC, Squamous cell carcinoma.

TABLE 3

43 miRNAs differentially expressed in lung cancer tissues vs. noncancerous lung tissues.

| miRNA | Location | p-value | Type | FRA association[a] | Cancer-associated genomic regions[a] | Host gene[b] |
|---|---|---|---|---|---|---|
| hsa-mir-21 | 17q23.2 | p < 1e−07 | Up | FRA17B | Amp[c]-neuroblastoma; lung ca | TMEM49 |
| hsa-mir-191 | 3p21.31 | p < 1e−07 | Up | | | Novel protein |
| hsa-mir-126* | 9q34.3 | p < 1e−07 | Down | | Del[d]-NSCLC[e]; HCC[f] | EGFL-7 |
| hsa-mir-210 | 11p15.5 | 1.00E−07 | Up | | Del-ovarian: lung ca | Novel protein |
| hsa-mir-155 | 21q21.3 | 1.00E−07 | Up | | Amp-colon ca | BIC |
| hsa-mir-143 | 5q32 | 4.00E−07 | Down | | Del-prostate ca | mlncRNA[g] |
| hsa-mir-205 | 1q32.2 | 4.00E−07 | Up | | Amp-lung ca | mlncRNA |

TABLE 3-continued 43 miRNAs differentially expressed in lung cancer tissues vs. noncancerous lung tissues.

| miRNA | Location | p-value | Type | FRA association[a] | Cancer-associated genomic regions[a] | Host gene[b] |
|---|---|---|---|---|---|---|
| hsa-mir-192-prec | 11q13.1 | 5.00E−07 | Down | FRA11A | Del-thyroid ca | mlncRNA |
| hsa-mir-224 | Xq28 | 5.00E−07 | Down | FRAXF | | GABRE |
| hsa-mir-126 | 9q34.3 | 7.00E−07 | Down | | Del-NSCLC: HCC | EGFL-7 |
| hsa-mir-24-2 | 19p13.1 | 1.30E−06 | Up | | | ND[h] |
| hsa-mir-30a-5p | 6q13 | 4.80E−06 | Down | | | mlncRNA |
| hsa-mir-212 | 17p13.3 | 5.00E−06 | Up | | | ND |
| hsa-mir-140 | 16q22.1 | 5.10E−06 | Down | | | ATROPIN-1 |
| hsa-mir-9 | 15q26.1 | 6.50E−06 | Down | | | Novel protein |
| hsa-mir-214 | 1q24.3 | 8.60E−06 | Up | | | ND |
| hsa-mir-17-3p | 13q31.3 | 9.40E−06 | Up | | | Novel protein |
| hsa-mir-224a-1 | 8p23.1 | 1.23E−05 | Down | | Amp-MFHs[i] | Novel protein |
| hsa-mir-218-2 | 5q34 | 1.34E−05 | Down | | | SLIT3 |
| hsa-mir-95 | 4p16.1 | 1.48E−05 | Down | | | ABLIM2 |
| hsa-mir-145 | 5q32 | 1.90E−05 | Down | | Del-prostate ca | mlncRNA |
| hsa-mir-198 | 3q13.33 | 2.43E−05 | Down | | | FSTL1 |
| hsa-mir-216-prec | 2p16.1 | 3.05E−05 | Down | | | ND |
| hsa-mir-219-1 | 6p21.32 | 5.56E−05 | Down | | | ND |
| hsa-mir-106a | Xq26.2 | 6.20E−05 | Up | | Del-ovarian ca | ND |
| hsa-mir-197 | 1p13.3 | 7.23E−05 | Up | | | ND |
| hsa-mir-192 | 11q13.1 | 0.000119 | Up | FRA11A | Del-thyroid ca | ND |
| hsa-mir-125a-prec | 19q13.41 | 0.000143 | Down | | | mlncRNA |
| hsa-mir-26a-1-prec | 3p22.3 | 0.000148 | Down | | Del-epithelial ca | NIF1 |
| hsa-mir-146 | 5q33.3 | 0.000163 | Up | | | mlncRNA |
| hsa-mir-203 | 14q32.33 | 0.000267 | Up | | | ND |
| hsa-mir-199b-prec | 9q34.11 | 0.000304 | Down | | Del-bladder ca | GOLGA2 |
| hsa-let-7a-2-prec | 11q24.1 | 0.000398 | Down | FRA11B | Del-lung ca | mlncRNA |
| hsa-mir-27b | 9q22.32 | 0.000454 | Down | FRA9D | Del-bladder ca | Novel protein |
| hsa-mir-32 | 9q31.3 | 0.000458 | Down | FRA9E | Del-lung ca | Novel protein |
| hsa-mir-29b-2 | 1q32.2 | 0.000466 | Down | | | mlncRNA |
| hsa-mir-220 | Xq25 | 0.000630 | Down | | | ND |
| hsa-mir-33 | 22q13.2 | 0.000683 | Down | | Del-colon ca | SREBF2 |
| hsa-mir-181c-prec | 19p13.12 | 0.000736 | Down | | | NANOS3 |
| hsa-mir-150 | 19q13.33 | 0.000784 | Up | | | ND |
| hsa-mir-101-1 | 1p31.3 | 0.000844 | Down | FRA1C | Del-ovarian; breast ca | ND |
| hsa-mir-124a-3 | 20q13.33 | 0.000968 | Down | | | ND |
| hsa-mir-125a | 19q13.41 | 0.000993 | Down | | | ND |

[a]Information was obtained from previous report (Calin, G. A., et al., Proc. Natl. Acad. Sci. U.S.A. 101: 2999-3004 (2004)).
[b]Information was obtained from previous report (Rodriguez, A., et al., Genome Res. 14: 1902-1910 (2004)).
[c]Amp, Amplification;
[d]Del, Deletion;
[e]NSCLC, Non-small cell lung carcinoma;
[f]HCC, hepatocellular carcinoma;
[g]mlncRNA, mRNA-like noncoding RNA;
[h]ND, not defined;
[i]MFHs, Malignant fibrous histocytomas.

Real-time RT-PCR analysis of select precursor miRNAs was performed to validate the results from the microarray analysis. First, cDNA from 16 pairs of lung adenocarcinoma, and 16 pairs of lung squamous cell carcinoma, were prepared using gene-specific primers for hsa-mir-21, hsa-mir-126*, hsa-mir-205 and U6 (as a control). Subsequently, real-time RT-PCR analyses were performed to determine the expression levels of these miRNAs in the different samples. At least a two-fold up-regulation of hsa-mir-21 and hsa-mir-205 precursor miRNA expression was found in 66% and 56% of 32 cases, respectively, when compared with the expression levels of these miRNAs in corresponding noncancerous tissues (FIG. 1). The differences were statistically significant at $p<0.001$ by paired t-test. In contrast, 31% of 32 lung cancer cases examined exhibited a greater than 50% reduction in precursor hsa-mir-126* expression, although these results were not statistically significant (FIG. 1). These findings show that specific precursor miRNAs are frequently upregulated or reduced in lung cancers, consistent with the expression patterns of their mature miRNAs, as determined using microarray analysis.

TABLE 4 miRNAs differentially-expressed in adenocarcinoma tissues/squamous cell lung carcinoma tissues vs. noncancerous lung tissues.

| miRNA | Location | p-value | Type |
|---|---|---|---|
| Adenocarcinoma | | | |
| hsa-mir-21 | 17q23.2 | $p < 1e{-}07$ | Up |
| hsa-mir-191 | 3p21.31 | 1.20E−06 | Up |
| hsa-mir-155 | 21q21.3 | 4.10E−06 | Up |
| hsa-mir-210 | 11p15.5 | 9.90E−06 | Up |
| hsa-mir-126* | 9q34.3 | 1.92E−05 | Down |
| hsa-mir-126 | 9q34.3 | 4.13E−05 | Down |
| hsa-mir-24-2 | 19p13.1 | 0.000228 | Up |
| hsa-mir-219-1 | 6p21.32 | 0.000251 | Down |
| hsa-mir-95 | 4p16.1 | 0.000303 | Down |
| hsa-mir-192-prec | 11q13.1 | 0.000307 | Down |
| hsa-mir-220 | Xq25 | 0.000309 | Down |
| hsa-mir-216-prec | 2p16.1 | 0.00042 | Down |
| hsa-mir-204-prec | 9q21.11 | 0.000449 | Down |
| hsa-mir-188 | Xp11.23 | 0.000475 | Down |
| hsa-mir-198 | 3q13.33 | 0.000494 | Down |
| hsa-mir-145 | 5q32 | 0.000579 | Down |
| hsa-mir-224 | Xq28 | 0.000925 | Down |

TABLE 4-continued miRNAs differentially-expressed in adenocarcinoma tissues/squamous cell lung carcinoma tissues vs. noncancerous lung tissues.

| miRNA | Location | p-value | Type |
|---|---|---|---|
| Squamous cell carcinoma | | | |
| hsa-mir-205 | 1q32.2 | p < 1e−07 | Up |
| hsa-mir-224 | Xq28 | 4.14E−05 | Down |
| hsa-mir-191 | 3p21.31 | 5.18E−05 | Up |
| hsa-mir-126* | 9q34.3 | 9.74E−05 | Down |
| hsa-mir-140 | 16q22.1 | 0.000132 | Down |
| hsa-mir-210 | 11p15.5 | 0.0001383 | Up |
| hsa-mir-17-3p | 13q31.3 | 0.0001772 | Up |
| hsa-mir-29b | 1q32.2 | 0.0002046 | Down |
| hsa-mir-143 | 5q32 | 0.0003141 | Down |
| hsa-mir-203 | 14q32.33 | 0.0003293 | Up |
| hsa-mir-155 | 21q21.3 | 0.0003688 | Up |
| hsa-mir-21 | 17q23.2 | 0.0003904 | Up |
| hsa-mir-214 | 1q24.3 | 0.0004546 | Up |
| hsa-mir-212 | 17p13.3 | 0.0005426 | Up |
| hsa-mir-30a-5p | 6q13 | 0.0006165 | Down |
| hsa-mir-197 | 1p13.3 | 0.0008507 | Up |

Figure 2:
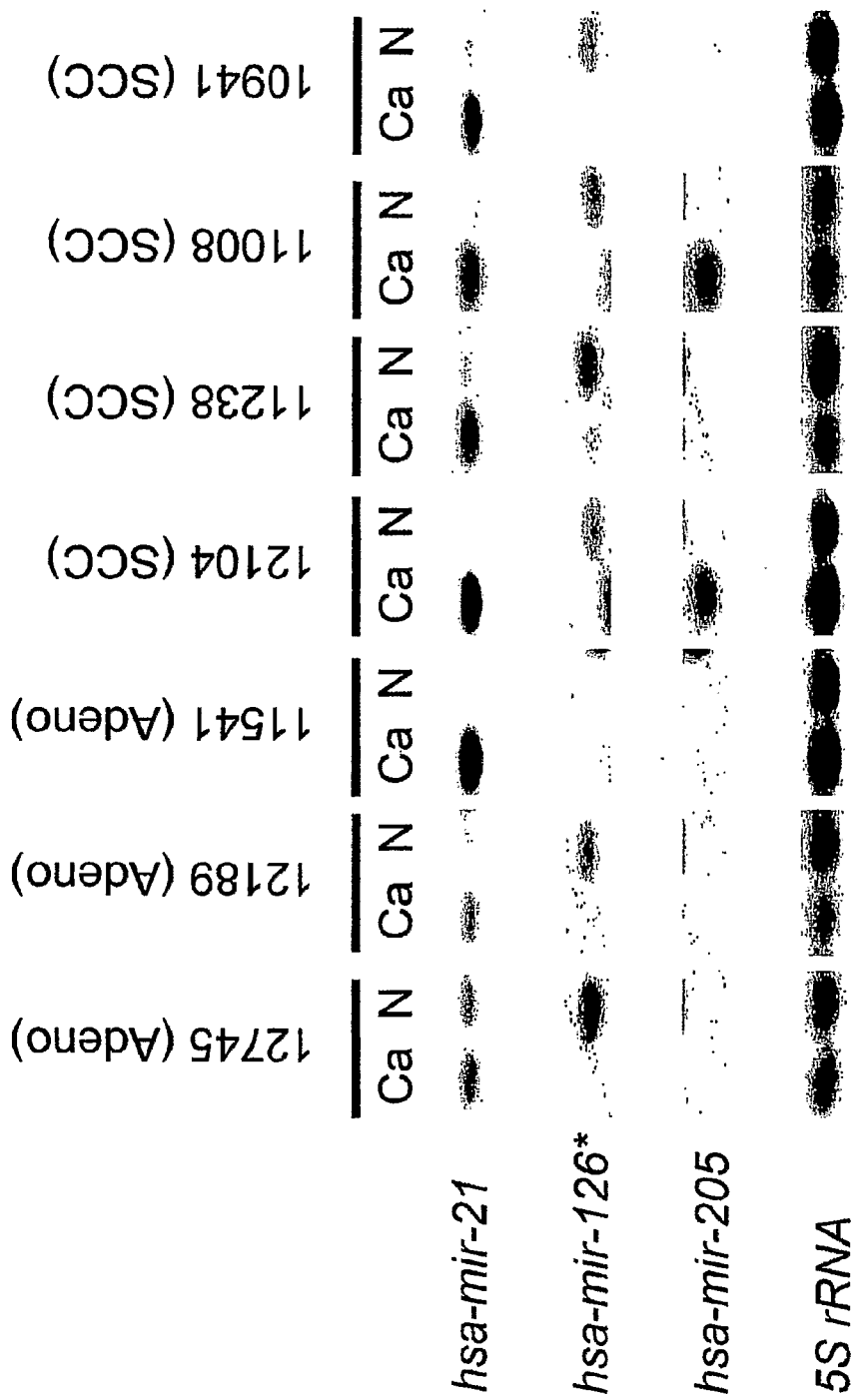
FIG. 2 depicts the expression of mature miRNAs for miR-21 (hsa-mir-21), miR-126* (hsa-mir-126*) and miR-205 (hsa-mir-205) in lung cancer samples (i.e., adenocarcinomas (Adeno) and squamous cell carcinomas (SCC)), as detected by solution hybridization. Ca represents cancerous lung tissues and N represents noncancerous lung tissues. 5S rRNA served as a loading control.

In addition, the microarray data for the three precursor miRNAs, hsa-mir-21, hsa-mir-126*, and hsa-mir-205, were confirmed for their mature miRNAs by solution hybridization detection method. Specifically, seven pairs of primary lung cancer tissues and corresponding noncancerous lung tissues, for which sufficient amounts of RNA were available, were analyzed. The mature forms of hsa-mir-21 and hsa-mir-205 were clearly up-regulated in lung cancer tissues when compared with the corresponding noncancerous lung tissues (FIG. 2), while hsa-mir-126* was down-regulated in most of the lung cancer tissues examined. Therefore, like the RT-PCR results, these analyses confirmed the microarray expression data for these three miRNAs.

Example 2

Distinct miRNA Expression Signatures in Human Lung Cancer Cell Lines

Materials and Methods
Samples

Figure 3B:
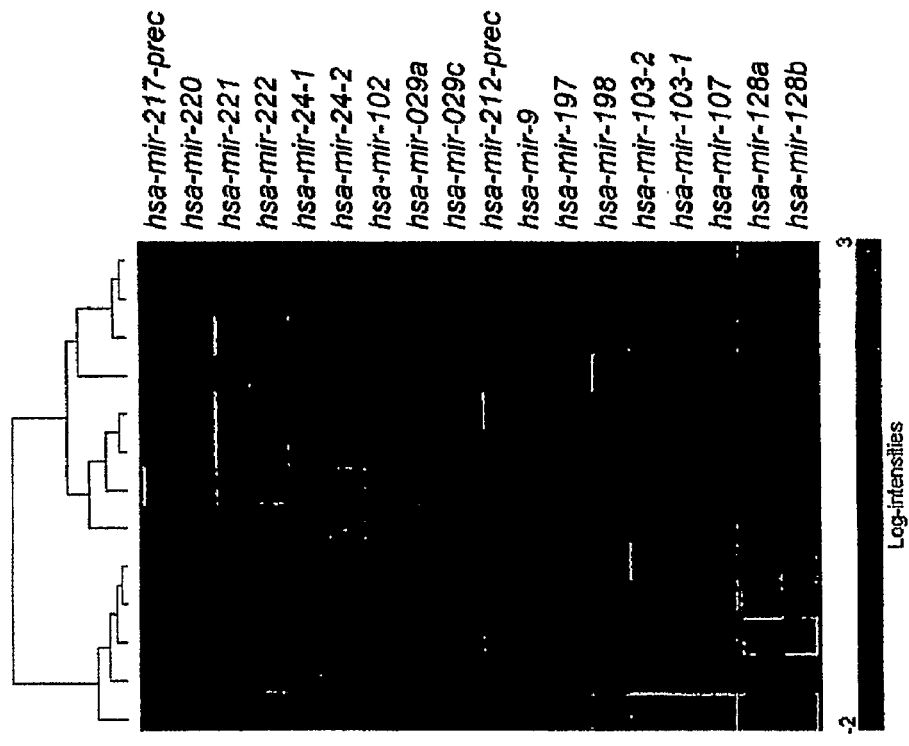
FIG. 3B depicts a miRNA expression cluster view for 13 lung cancer cell lines (top), corresponding to those listed in FIG. 3A. The expression levels of various miRNAs, listed at the right of the figure, are indicated according to color. Blue indicates expression levels below the median, black indicates expression levels that are about equal to the median, and orange indicates expression levels that are greater than the median. Gray indicates missing data points.
Figure 3A:
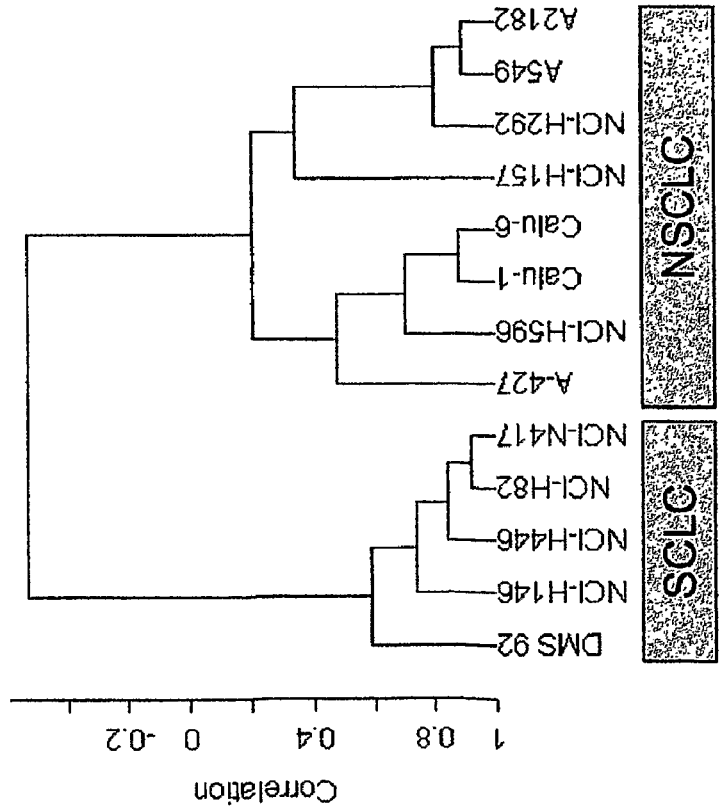
FIG. 3A is a dendrogram depicting a hierarchical clustering based on microRNA expression profiles of 13 lung cancer cell lines representing small cell lung carcinomas (SCLC) and non-small cell lung carcinomas (NSCLC).

Thirteen lung cancer cell lines, consisting of five small cell lung carcinoma (SCLCs) cell lines and eight non-small cell lung carcinoma (NSCLCs) cell lines, were used in this study. The 5 SCLC cell lines were DMS 92, NCI-H82, NCI-H146, NCI-H446, and NCI-H417 (American Tissue Culture Collection). The eight NSCLC cell lines were NCI-H157, Calu-1, Calu-6, NCI-H292, NCI-H596, A-427, A549, and A2182 (American Tissue Culture Collection, Manassas, Va.). Total RNA from tissues and cultured cells was isolated by TRIzol® Reagent (Invitrogen, Carlsbad, Calif.), according to the manufacturer's instructions.
Microarray Analysis Microarray analysis was performed as previously described (Liu, C. G., et al., Proc. Natl. Acad. Sci. U.S.A. 101:9740-9744 (2004), see also, Example 1);
Statistical Analysis Statistical analyses were performed as described hereinabove (see, e.g., Example 1).
Results miRNA expression profiles of five small cell lung carcinoma (SCLCs) cell lines, and eight non-small cell lung carcinoma (NSCLCs) cell lines, were generated by microarray analysis. Comparison of miRNA expression profiles of NSCLCs and SCLCs revealed statistically-significant differences (p<0.001 by t-test) in the expression level of 3 miRNAs (hsa-mir-24-1, hsa-mir-29a, and hsa-mir-29c). Furthermore, when hierarchical clustering analysis was applied to the 18 most differentially-expressed miRNAs for each sample type, distinct clusters were revealed, with all NSCLC cell lines falling into a cluster that was distinct from that of SCLC cell lines (FIG. 3A, FIG. 3B). These results indicate that miRNA expression profiles may differ in cells with different origins and/or types, as was found in previous studies (see, e.g., Liu, C. G., et al., Proc. Natl. Acad. Sci. U.S.A. 101:9740-9744 (2004); Bhattacharjee, A., et al., Proc. Natl. Acad. Sci. USA. 98:13790-13795 (2001); Garber, M. E., et al., Proc. Natl. Acad. Sci. U.S.A. 98:13784-13789 (2001)).

Example 3

Identification of miRNAs Associated with Clinicopathological Features of Lung Cancer Materials and Methods
Microarray Analysis Microarray analysis was performed as previously described (Liu, C. G., et al., Proc. Natl. Acad. Sci. U.S.A. 101:9740-9744 (2004), see also, Example 1).
Statistical Analysis Statistical analyses were performed as described hereinabove (see, e.g., Example 1).
Results Whether the microarray data revealed specific molecular signatures for subsets of lung cancer that differ in clinical behavior was analyzed. For this analysis, the relationship of five types of clinical and pathological information were examined (Table 2). In the histological classification, six miRNAs (hsa-mir-205, hsa-mir-99b, hsa-mir-203, hsa-mir-202, hsa-mir-102, and hsa-mir-204-prec) that were expressed differently in the two most common histological types of NSCLC, adenocarcinoma and squamous cell carcinoma, were identified. The expression levels of hsa-mir-99b and hsa-mir-102 were higher in adenocarcinoma. No differentially-expressed miRNAs were identified for groups that were differentiated by age, gender, or race.

Example 4

Correlation Between hsa-mir-155 and hsa-let-7a-2 Expression and Prognosis of Patients with Lung Adenocarcinoma Materials and Methods
Microarray Analysis Microarray analysis was performed as previously described (Liu, C. G., et al., Proc. Natl. Acad. Sci. U.S.A. 101:9740-9744 (2004), see also, Example 1).
Statistical Analysis Statistical analyses were performed as described hereinabove (see, e.g., Example 1).
Gene Ontology Analysis Predicted targets of hsa-mir-155 and hsa-let-7a were determined by the methods of Lewis et al., (Lewis, B. P., et al., Cell 120: 15-20 (2005)) and PicTar (Krek, A., et al., Nat. Genet. 37: 495-500 (2005)) and were analyzed with respect to the over-representation within particular Gene Ontology (GO) biological groupings. GO term lists were subjected to analysis using the Whole Pathway Scope (WPS) application and those terms with Fisher Exact scores of less than 0.005 were listed.

Results

The correlation of miRNA expression with patient survival was assessed. Univariate Cox proportional hazard regression model with global permutation test in BRB-ArrayTools indicated eight miRNAs (hsa-mir-155, hsa-mir-17-3p, hsa-mir-106a, hsa-mir-93, hsa-let-7a-2, hsa-mir-145, hsa-let-7b and hsa-mir-21) were related to adenocarcinoma patient survival. High expression of either hsa-mir-155, hsa-mir-17-3p, hsa-mir-106a, hsa-mir-93, or hsa-mir-21 and low expression of either hsa-let-7a-2, hsa-let-7b or hsa-mir-145 were found to have a significantly worse prognosis. In addition, the survival analysis among 41 stage I adenocarcinoma patients revealed that three miRNAs (hsa-mir-155, hsa-mir-17-3p, and hsa-mir-20) were associated with patient outcome. These results demonstrate the important relationship between miRNA expression profiles and patient survival, independent of disease stage.

Figure 4:
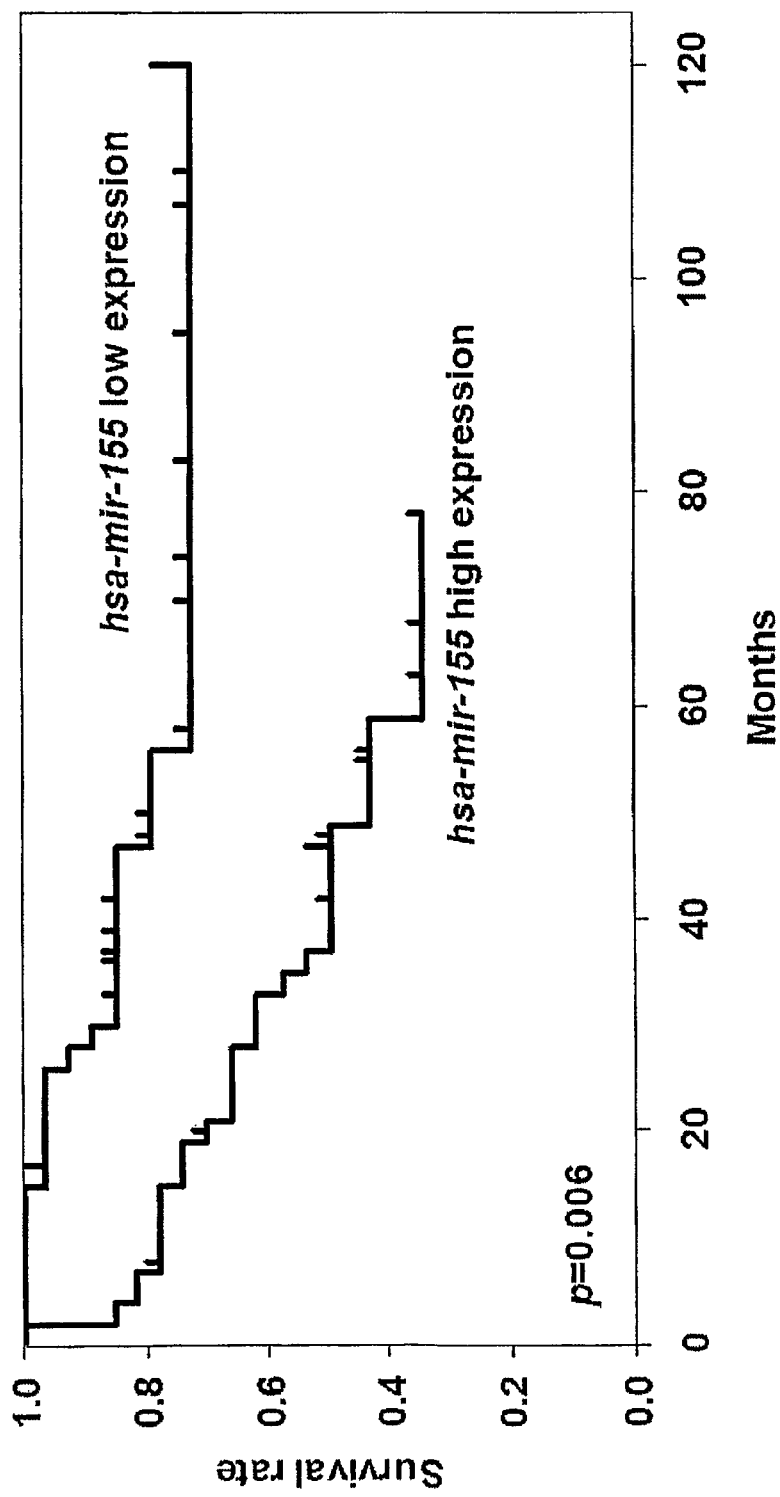
FIG. 4 is a Kaplan-Meier survival curve for adenocarcinoma patients. Adenocarcinoma cases in which hybridization intensity was different from background (see Example 4) were classified according to hsa-mir-155 expression, and the survival data were compared using the log-rank test. The mean expression ratio is defined as mean expression ratio=mean of tumor expression/mean of noncancerous tissue expression. The hsa-mir-155 high expression group (i.e., group with an expression ratio of ≧mean expression ratio (1.42); n=27) was compared with corresponding noncancerous lung tissues. The hsa-mir-155 low expression group (i.e., group with an expression ratio of <mean expression ratio (1.42); n=28) was compared with corresponding noncancerous lung tissues. The ratios represent the intensity of hybridization signal in the lung cancer sample relative to noncancerous controls.
Figure 5:
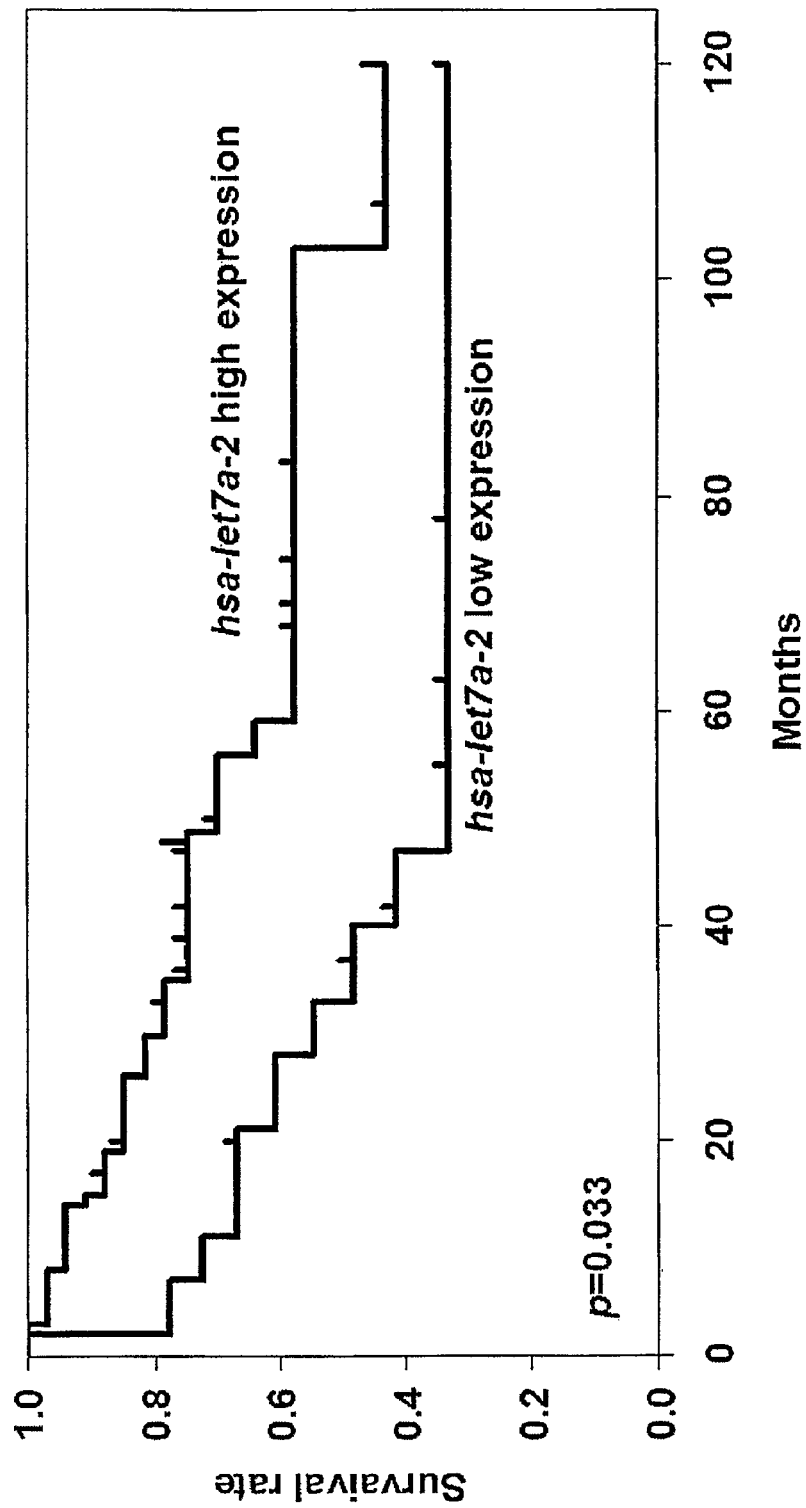
FIG. 5 is a Kaplan-Meier survival curve for adenocarcinoma patients. Adenocarcinoma cases in which hybridization intensity was different from background (see Example 4) were classified according to hsa-let-7a-2 expression, and the survival data were compared using the log-rank test. The mean expression ratio is defined as mean expression ratio=mean of tumor expression/mean of noncancerous tissue expression. The hsa-let-7a-2 high expression group (i.e., group with an expression ratio of ≧mean expression ratio (0.95); n=34) was compared with corresponding noncancerous lung tissues. The hsa-let-7a-2 low expression group (i.e., group with an expression ratio of <mean expression ratio (0.95); n=18) was compared with corresponding noncancerous lung tissues.

Because five of these miRNAs (hsa-mir-155, hsa-mir-17-3p, hsa-let-7a-2, hsa-mir-145, and hsa-mir-21) were expressed differently among lung cancer tissues vs. corresponding noncancerous lung tissues, these miRNAs were used for further survival analysis. The ratio of lung cancer expression to corresponding noncancerous lung tissue expression for each of these five miRNAs was calculated and the cases were classified according to the expression ratio. Using these groupings for each miRNA, Kaplan-Meier survival analysis was performed. Kaplan-Meier survival estimates showed that lung adenocarcinoma patients with either high hsa-mir-155 expression or reduced hsa-let-7a-2 expression had poorer survival prospects than patients with low hsa-mir-155 or high hsa-let-7a-2 expression (FIG. 4 and FIG. 5). The difference in prognosis of these two groups was highly significant for hsa-mir-155 (p=0.006; log-rank test), but less significant for hsa-let-7a-2 (p=0.033; log-rank test). Survival analysis of the clinicopathological factors showed that stage was significantly associated with survival p=0.01; log-rank test), while age, race, sex, and smoking history did not account for poor prognosis (Tables 5A and 5B). To adjust for multiple comparisons, we used the method by Storey et al., (Storey, J. D. and Tibshirani, R., *Proc. Natl. Acad. Sci. U.S.A.* 100: 9440-9445 (2003)) limiting the false discovery rates to 0.05. Using this rate, hsa-mir-155 and disease stage were still statistically significant. Subsequently, a multivariate Cox proportional hazard regression analysis was performed using all of these clinicopathological and molecular factors. High hsa-mir-155 expression was determined to be an unfavorable prognosis factor, independent of other clinicopathological factors (p=0.027; risk ratio 3.03; 95% CI, 1.13-8.14), in addition to disease stage (p=0.013; risk ratio 3.27; 95% CI, 1.31-8.37; Table 5A).

TABLE 5A

Postoperative survival of patients with lung adenocarcinoma in relation to molecular and clinicopathological characteristics and miRNA expression analyzed by microarray analysis.

| Variable | Subset | Hazard ratio (95% CI[a]) | p |
|---|---|---|---|
| Univariate analysis (n = 65) | | | |
| Age | Age ≥67/Age <67 | 1.41 (0.67-3.06) | 0.348 |
| Sex | Male/female | 1.36 (0.64-2.93) | 0.413 |
| Stage | II-IV/I | 2.51 (1.29-6.82) | 0.010 |
| Smoking history | Current/former | 1.32 (0.63-2.79) | 0.456 |
| hsa-mir-155 (n = 55) | High/low | 3.42 (1.42-8.19) | 0.006 |
| hsa-let-7a-2 (n = 52) | Low/high | 2.35 (1.08-6.86) | 0.033 |
| Multivariate analysis (n = 55)[b,c] | | | |
| Age | Age ≥67/Age <67 | 1.92 (0.71-5.17) | 0.195 |
| Sex | Male/female | 1.23 (0.47-3.22) | 0.669 |
| Stage | II-IV/I | 3.27 (1.31-8.37) | 0.013 |
| Smoking history | Current/former | 1.49 (0.51-4.34) | 0.457 |
| hsa-mir-155 | High/low | 3.03 (1.13-8.14) | 0.027 |

[a]95% CI, 95% confidence interval.
[b]Multivariate analysis, Cox proportional hazard regression model.
[c]hsa-let-7a-2 low/high was not statistically significant (p = 0.089).

TABLE 5B

Postoperative survival of patients with lung adenocarcinoma in relation to clinicopathological characteristics and precursor miRNA expression analyzed by real-time RT-PCR analysis.

| | | Original cohort (n = 32) | | Additional cohort (n = 32) | | All cases (n = 64) | |
|---|---|---|---|---|---|---|---|
| Variable | Subset | Hazard ratio (95% CI[a]) | p | Hazard ratio (95% CI) | p | Hazard ratio (95% CI) | p |
| Univariate analysis | | | | | | | |
| Age | Age ≥67/Age <67 | 1.89 (0.62-5.34) | 0.274 | 1.21 (0.46-3.21) | 0.679 | 1.28 (0.64-2.58) | 0.482 |
| Sex | Male/female | 0.53 (0.14-1.56) | 0.232 | 1.37 (0.54-3.63) | 0.479 | 0.99 (0.49-1.98) | 0.975 |
| Stage | II-IV/I | 4.22 (1.91-23.6) | 0.003 | 2.37 (1.01-7.83) | 0.048 | 3.07 (1.82-8.84) | <0.001 |
| Smoking history | Current/former | 0.92 (0.31-2.66) | 0.921 | 1.22 (0.47-3.16) | 0.674 | 1.12 (0.56-2.25) | 0.757 |
| precursor hsa-mir-155 | High/low | 2.75 (1.05-12.1) | 0.047 | 2.52 (1.10-7.45) | 0.033 | 2.74 (1.53-6.91) | 0.002 |
| precursor hsa-let-7a-2 | Low/high | 3.01 (1.09-9.86) | 0.037 | 2.22 (0.91-5.71) | 0.084 | 2.73 (1.42-5.88) | 0.003 |
| Multivariate analysis[b] | | | | | | | |
| Age | Age ≥67/Age <67 | 0.91 (0.22-3.68) | 0.899 | 0.93 (0.30-2.91) | 0.914 | 1.22 (0.58-2.53) | 0.593 |
| Sex | Male/female | 0.35 (0.11-1.17) | 0.089 | 0.92 (0.32-2.66) | 0.885 | 0.85 (0.41-1.74) | 0.659 |
| Stage | II-IV/I | 8.99 (1.95-41.2) | 0.004 | 4.91 (1.51-15.9) | 0.008 | 5.58 (2.42-12.8) | <0.001 |
| Smoking history | Current/former | 1.01 (0.30-3.38) | 0.980 | 2.27 (0.70-7.34) | 0.170 | 1.89 (0.85-4.21) | 0.117 |
| precursor hsa-mir-155 | High/low | 13.3 (2.59-69.0) | 0.002 | 3.77 (1.32-10.6) | 0.013 | 4.98 (2.29-10.8) | <0.001 |
| precursor hsa-let-7a-2 | Low/high | 3.93 (1.06-14.5) | 0.040 | 2.97 (1.07-8.23) | 0.036 | 3.55 (1.64-7.69) | 0.001 |

[a]95% CI, 95% confidence interval.
[b]Multivariate analysis, Cox proportional hazard regression model.

To investigate the biological consequences of altered hsa-mir-155 and hsa-let-7a-2 expression, a bioinformatic analysis was conducted to group the predicted targets of these miRNAs according to Gene Ontology (GO) terms (Table 6). In addition to associations with more general functional GO terms, a significant enrichment for targets associated with transcription was seen for hsa-mir-155. hsa-let-7a showed an over-representation of gene targets linked with protein kinase and intracellular signaling cascades, a finding consistent with the reported functional interaction between let-7 and RAS (Johnson, S. M., et al., *Cell* 120:635-647 (2005)).

TABLE 6

Gene ontology analysis (biological process) for the predicted transcript targets of hsa-mir-155 and hsa-let-7a.

| Biological process | Gene Ontology | p-value |
|---|---|---|
| hsa-mir-155 | | |
| regulation of biological process | GO:0050789 | 3.44343E-05 |
| regulation of nucleobase\nucleoside\ nucleotide and nucleic acid metabolism | GO:0019219 | 0.000149553 |
| regulation of physiological process | GO:0050791 | 0.000192938 |
| regulation of transcription\DNA-dependent | GO:0006355 | 0.000244233 |
| regulation of metabolism | GO:0019222 | 0.000310887 |
| regulation of transcription | GO:0045449 | 0.000367426 |
| transcription\, DNA-dependent | GO:0006351 | 0.000373583 |
| transcription | GO:0006350 | 0.000749403 |
| NLS-bearing substrate-nucleus import | GO:0006607 | 0.000871079 |
| B-cell differentiation | GO:0030183 | 0.00142995 |
| nucleobase\nucleoside\nucleotide and nucleic acid metabolism | GO:0006139 | 0.0021327 |
| protein targeting | GO:0006605 | 0.00238267 |
| hemopoiesis | GO:0030097 | 0.00243434 |
| cellular process | GO:0009987 | 0.00270393 |
| uridine metabolism | GO:0046108 | 0.0040568 |
| B-cell activation | GO:0042113 | 0.00458041 |
| hsa-let-7a | | |
| protein modification | GO:0006464 | 9.02643E-05 |
| cell growth and/or maintenance | GO:0008151 | 9.99217E-05 |
| cellular physiological process | GO:0050875 | 0.000128316 |
| protein kinase cascade | GO:0007243 | 0.000703203 |
| cellular process | GO:0009987 | 0.000870863 |
| intracellular signaling cascade | GO:0007242 | 0.001290613 |
| transport | GO:0006810 | 0.004305096 |
| chromatin modification | GO:0016568 | 0.004414505 |
| localization | GO:0051179 | 0.004492152 |
| phosphorus metabolism | GO:0006793 | 0.00481218 |
| phosphate metabolism | GO:0006796 | 0.00481218 |

Figure 6:
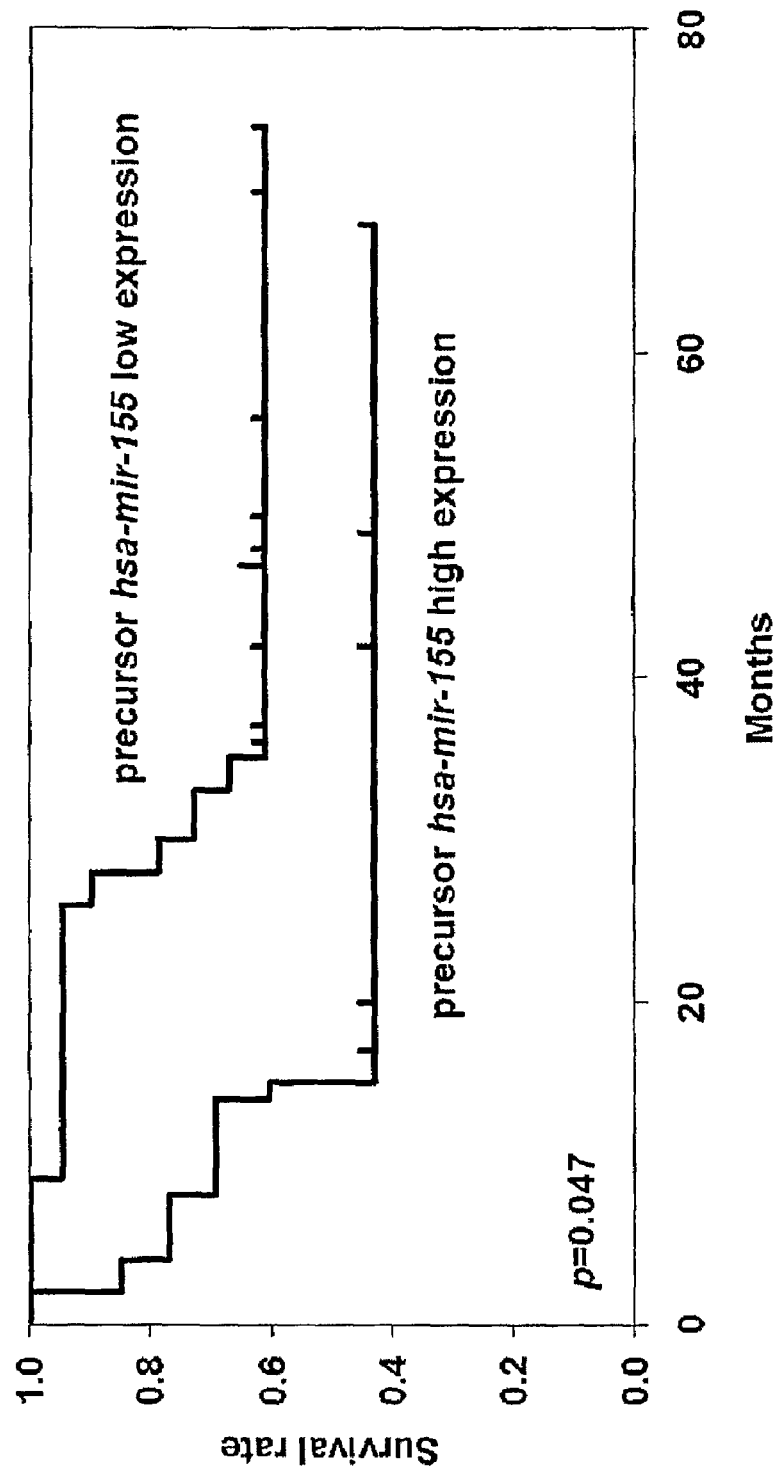
FIG. 6 is a Kaplan-Meier survival curve for adenocarcinoma patients. Thirty two adenocarcinoma cases from an original cohort were classified according to precursor hsa-miR-155 expression, and the survival data were compared using the log-rank test. The mean expression ratio is defined as mean expression ratio=mean of tumor expression/mean of noncancerous tissue expression. The precursor hsa-miR-155 high expression group (i.e., group with an expression ratio of ≧mean expression ratio (1.19); n=13) was compared with corresponding noncancerous lung tissues. The precursor hsa-miR-155 low expression group (i.e., group with an expression ratio of <mean expression ratio (1.19); n=19) was compared with corresponding noncancerous lung tissues.
Figure 7:
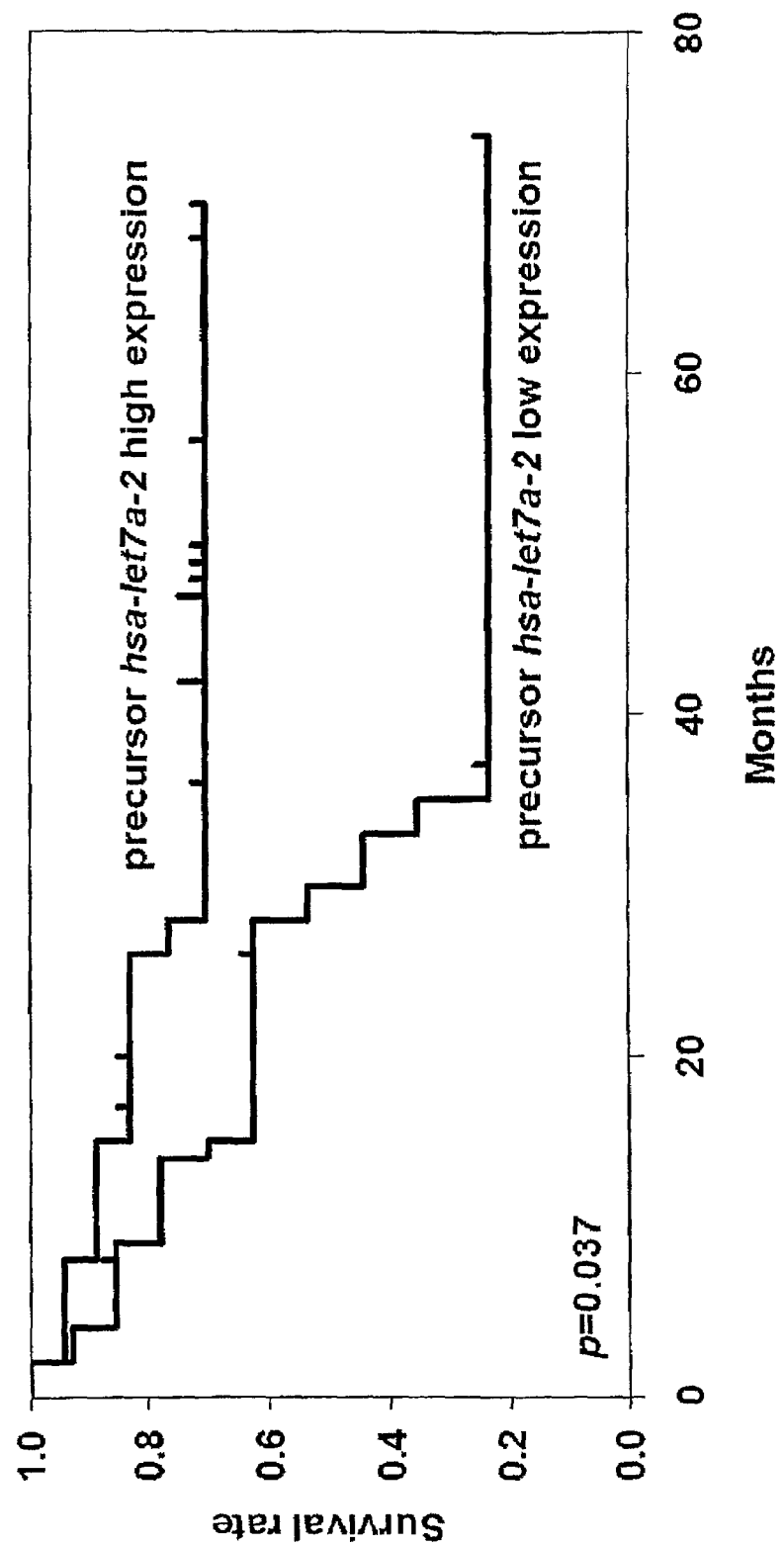
FIG. 7 is a Kaplan-Meier survival curve for adenocarcinoma patients. Thirty two adenocarcinoma cases from an original cohort were classified according to precursor hsa-let-7a-2 expression, and the survival data were compared using the log-rank test. The mean expression ratio is defined as mean expression ratio=mean of tumor expression/mean of noncancerous tissue expression. The precursor hsa-let-7a-2 high expression group (i.e., group with an expression ratio of ≧mean expression ratio (0.92); n=18) was compared with corresponding noncancerous lung tissues. The precursor hsa-let-7a-2 low expression group (i.e., group with an expression ratio of <mean expression ratio (0.92); n=14) was compared with corresponding noncancerous lung tissues.
Figure 8:
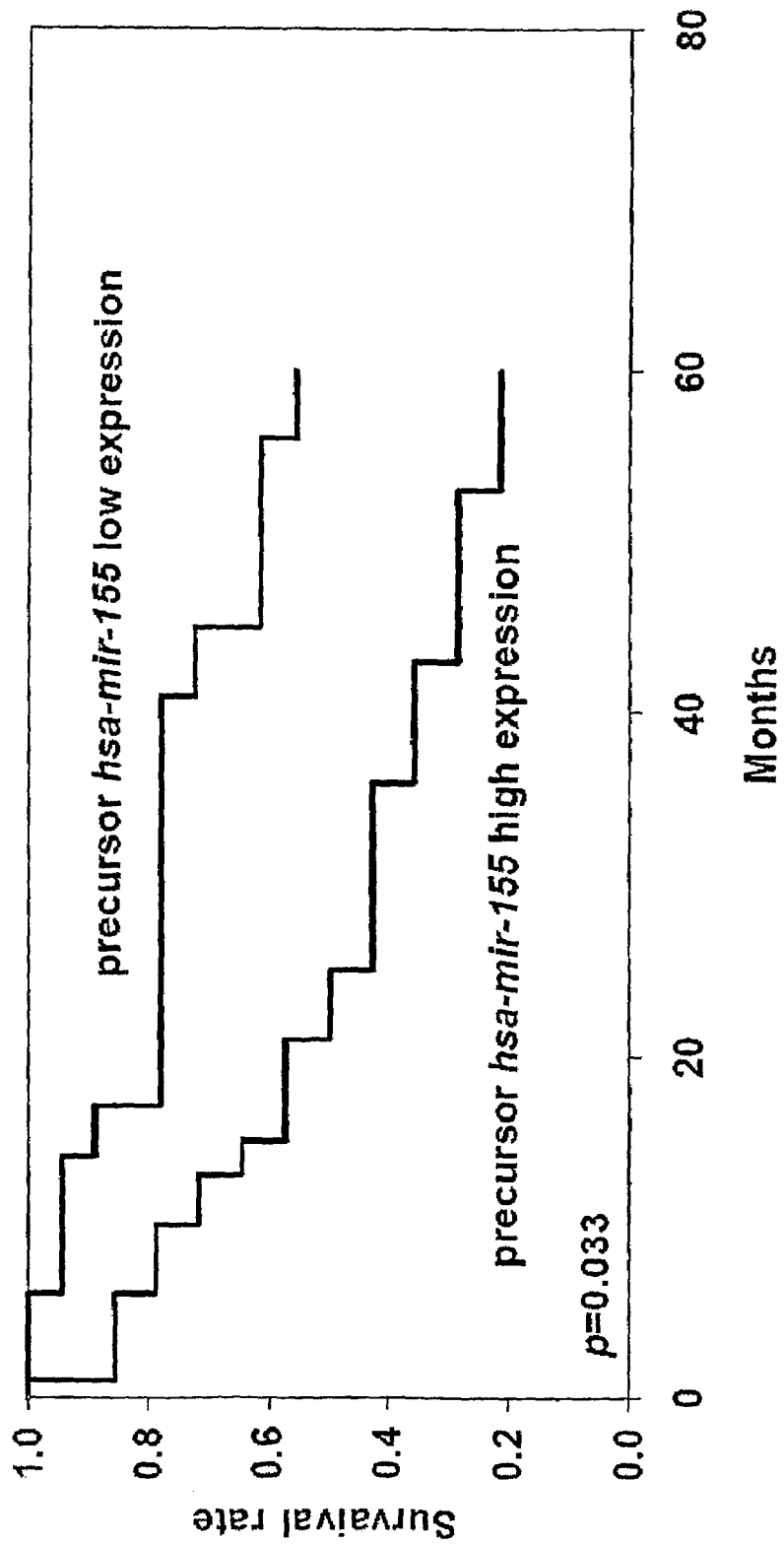
FIG. 8 is a Kaplan-Meier survival curve for adenocarcinoma patients. Thirty two adenocarcinoma cases from an independent additional cohort were classified according to precursor hsa-let-7a-2 expression, and the survival data were compared using the log-rank test. Precursor hsa-mir-155 high expression group (n=14); precursor hsa-mir-155 low expression group (n=18).
Figure 9:
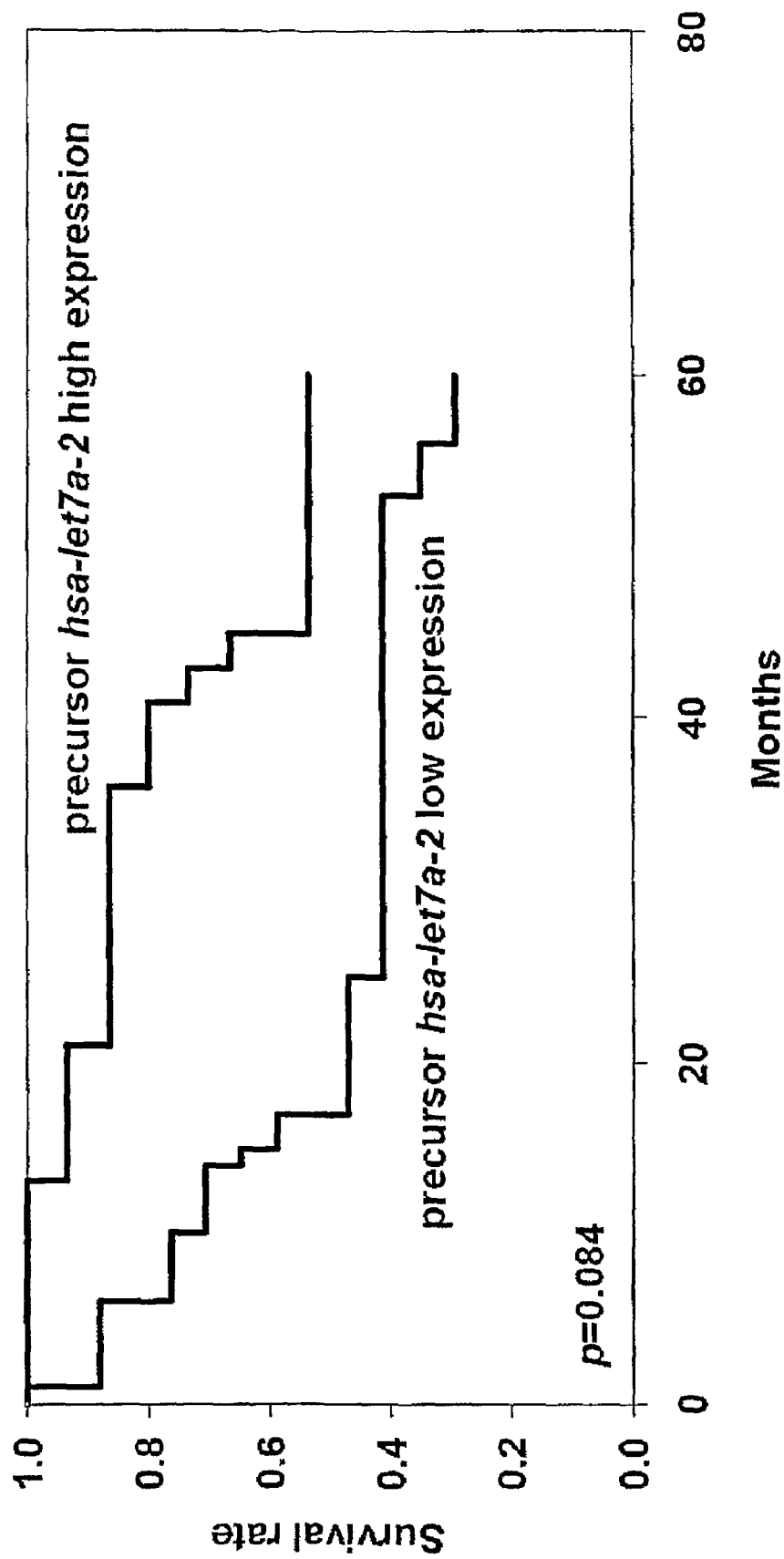
FIG. 9 is a Kaplan-Meier survival curve for adenocarcinoma patients. Thirty two adenocarcinoma cases from an independent additional cohort were classified according to precursor hsa-let-7a-2 expression, and the survival data were compared using the log-rank test. Precursor hsa-let-7a-2 high expression group (n=15); precursor hsa-let-7a-2 low expression group (n=17).
Figure 10:
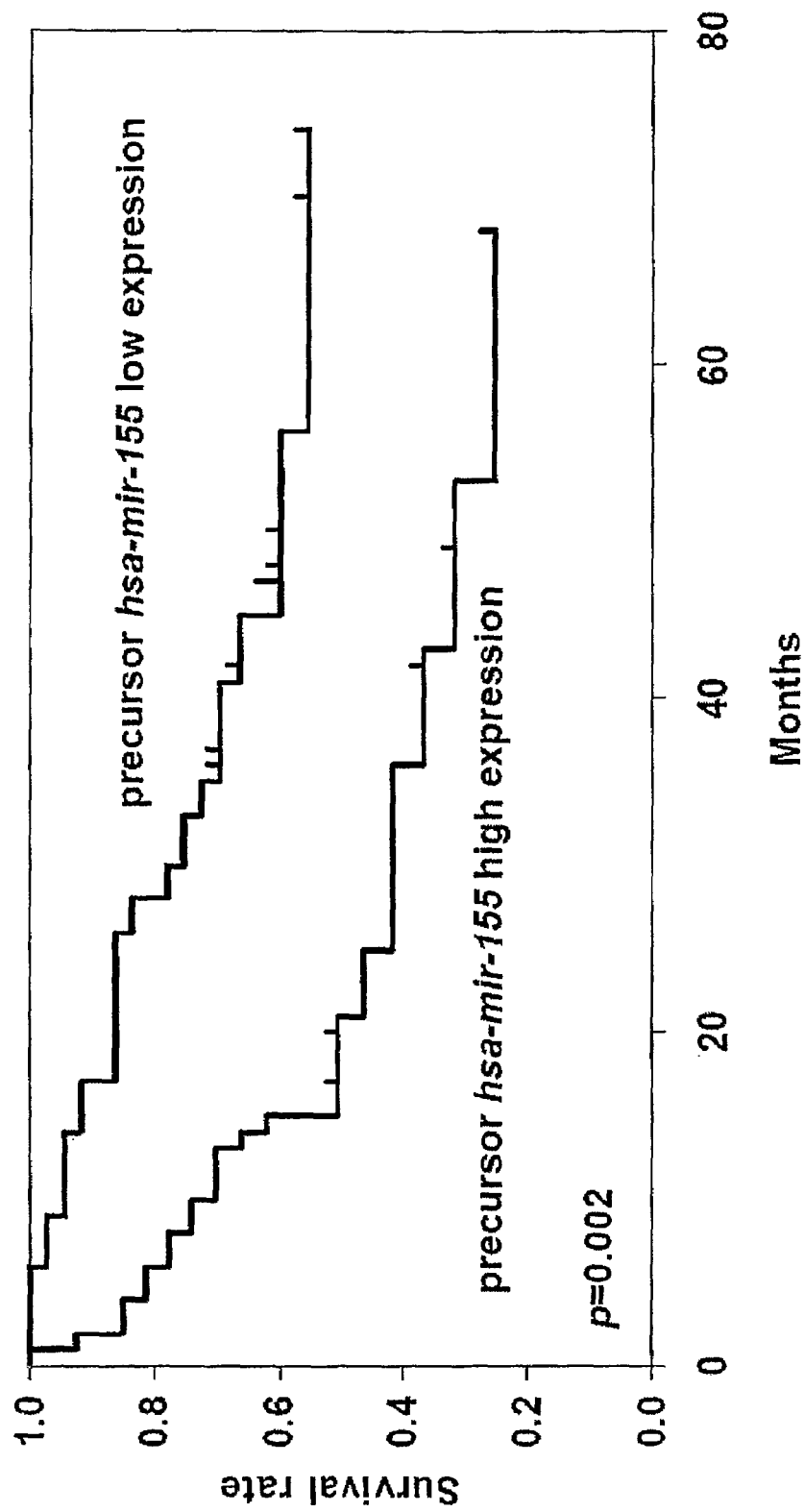
FIG. 10 is a Kaplan-Meier survival curve for adenocarcinoma patients. Sixty four adenocarcinoma cases from a combination of 2 independent cohorts were classified according to precursor hsa-mir-155 expression, as estimated by real-time RT-PCR analysis. The survival data were compared using the log-rank test. The mean expression ratio is defined as mean expression ratio=mean of tumor expression/mean of noncancerous tissue expression. The precursor hsa-miR-155 high expression group (i.e., group with an expression ratio of ≧mean expression ratio (1.19); n=27) was compared with corresponding noncancerous lung tissues. The precursor hsa-miR-155 low expression group (i.e., group with an expression ratio of <mean expression ratio (1.19); n=37) was compared with corresponding noncancerous lung tissues.
Figure 11:
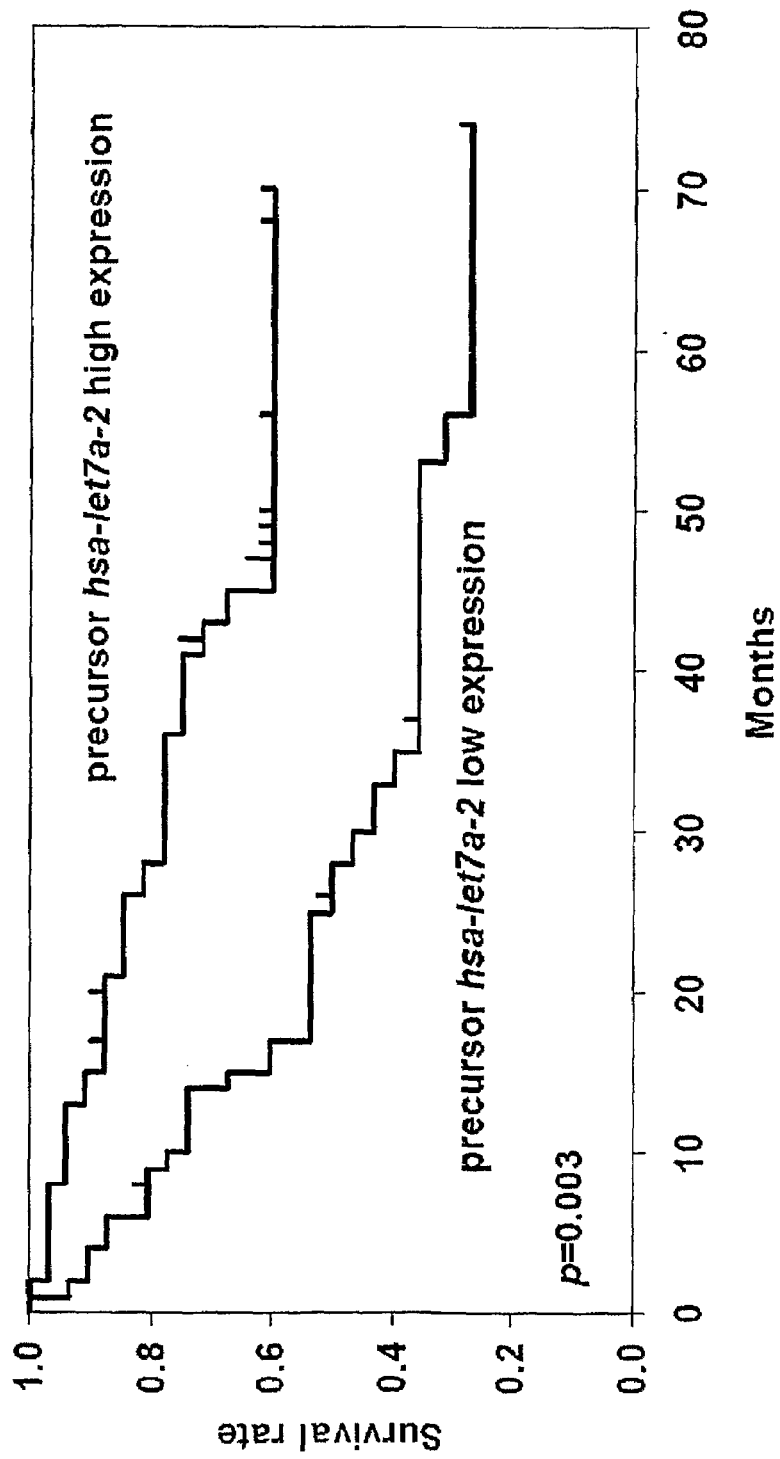
FIG. 11 is a Kaplan-Meier survival curve for adenocarcinoma patients. Sixty four adenocarcinoma cases from a combination of 2 independent cohorts were classified according to precursor hsa-let-7a-2 expression, as estimated by real-time RT-PCR analysis. The survival data were compared using the log-rank test. The mean expression ratio is defined as mean expression ratio=mean of tumor expression/mean of noncancerous tissue expression. The precursor hsa-let-7a-2 high expression group (i.e., group with an expression ratio of ≧mean expression ratio (0.92); n=33) was compared with corresponding noncancerous lung tissues. The precursor hsa-let-7a-2 low expression group (i.e., group with an expression ratio of <mean expression ratio (0.92); n=31) was compared with corresponding noncancerous lung tissues.

Real-time RT-PCR analysis was performed for hsa-mir-155 and hsa-let-7a-2 to determine whether the precursor miRNAs expression also had prognostic impact on adenocarcinoma patients. First, 32 pairs of adenocarcinoma from the original set, in which RNA was available, were subjected to real-time RT-PCR analysis. The ratio of lung cancer expression to corresponding noncancerous lung tissue expression was calculated and the cases were classified according to the expression ratio. Kaplan-Meier survival analysis (FIG. 6, FIG. 7) demonstrated a significantly worse survival for patients with either high precursor hsa-mir-155 expression (p=0.047; log-rank test) or reduced precursor hsa-let-7a-2 expression (p=0.037; log-rank test) (Table 5B). To further validate the prognosis classifiers described here, an additional independent set of 32 adenocarcinomas was analyzed using real-time RT-PCR analysis. Kaplan-Meier survival curves (FIG. 8, FIG. 9) showed a clear relationship in precursor hsa-mir-155 expression (p=0.033; log-rank test) and approaching significance in hsa-let-7a-2 expression (p=0.084; log-rank test) in this cohort as well (Table 5B). In addition, high precursor hsa-mir-155 expression was found to be an independent predictor of poor prognosis by a multivariate Cox proportional hazard regression analysis (Table 5B). To further confirm whether there was any grouping bias in the original set (32 cases) and the additional set (32 cases), univariate and multivariate survival analyses were performed for all 64 cases. Consistent with previous results, these analyses showed the significance of precursor hsa-mir-155 expression (Table 5B; FIG. 10). Of note, reduced precursor hsa-let-7a-2 expression also had similar prognostic impact on adenocarcinoma patients (Table 5B; FIG. 11), consistent with a previous report (Takamizawa, J., et al., *Cancer Res.* 64, 3753-3756 (2004)).

Example 5

Lack of Epigenetic Regulation of miRNA Expression in NSCLC Cell Lines

Materials and Methods

Microarray Analysis

Microarray analysis was performed as previously described (Liu, C. G., et al., *Proc. Natl. Acad. Sci. U.S.A.* 101:9740-9744 (2004), see also, Example 1).

Statistical Analysis

Statistical analyses were performed as described hereinabove (see, e.g., Example 1).

5-aza-dC and/or TSA Treatment

A549 and NCI-H157 lung cancer cells (available from the American Tissue Culture Collection) were incubated with medium containing 1.0 µM 5-aza-dC (Sigma, St. Louis, Mo.) for 48 hr, then were incubated for an additional 24 hr in the presence of 1.0 µM TSA (Sigma, St. Louis, Mo.). Total RNA was isolated with TRIzol® Reagent (Invitrogen), and microarray analysis was performed as described above. Each treatment was performed in triplicate.

Figure 12:
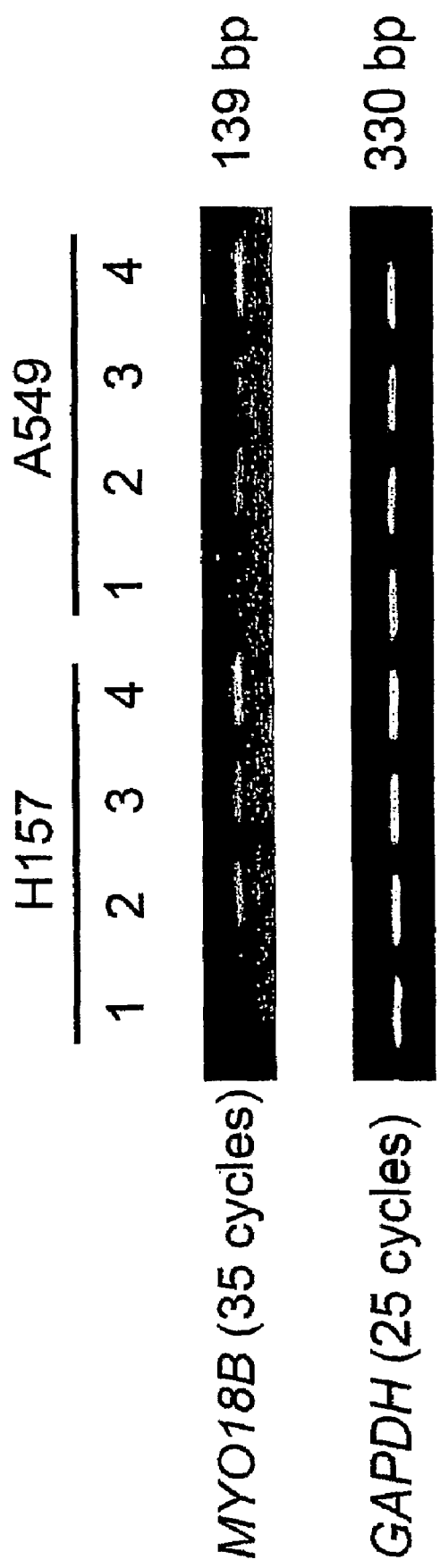
FIG. 12 depicts the expression of MYO18B mRNA after treatment with 5-aza-dC and/or TSA in two lung cancer cell lines (H157, A549), as determined by RT-PCR analysis. Lane 1, no treatment; lane 2, treatment with 1.0 μM 5-aza-dC for 72 hr; lane 3, treatment with 1.0 μM TSA for 24 hr; lane 4, treatment with 1.0 μM 5-aza-dC for 72 hours, followed by treatment with 1.0 μM TSA for 24 hr. GAPDH expression served as a loading control.

Results miRNA microarrays were used to analyze the expression of various miRNAs upon treatment with 5-aza-2'-deoxycytidine (5-aza-dC), a DNA methylation inhibitor, and/or Trichostatin A (TSA), a potent histone deacetylase inhibitor, in two lung cancer cell lines (A549 and NCI-H157). Although increased expression of a gene that is known to be transcriptionally-silenced (MYO18B) was confirmed following treatment with 5-aza-dC or TSA (FIG. 12), no miRNAs from the microarray displayed statistically-significant changes in expression after treatment with either compound, suggesting that hypermethylation and histone deacetylation were not responsible for reduced levels of miRNA expression in at least these two cell lines.

The relevant teachings of all publications cited herein that have not explicitly been incorporated by reference, are incorporated herein by reference in their entirety. While this invention has been particularly shown and described with references to preferred embodiments thereof, it will be understood by those skilled in the art that various changes in form and details may be made therein without departing from the scope of the invention encompassed by the appended claims.

What is claimed is:

1. A method of determining the prognosis of a subject with lung cancer, comprising
measuring the level of at least one miR gene product comprised of at least miR-155 in a test sample from said subject,
determining the prognosis of a subject with lung cancer,
wherein: the miR gene product is associated with an adverse prognosis in lung cancer; and an increase in the level of the at least one miR gene product in the lung test sample, relative to the level of a corresponding miR gene product in a control sample, is indicative of an adverse prognosis.

2. The method of claim 1, wherein the at least one miR gene product is selected from the group consisting of miR-155, miR-17-3p, miR-106a, miR-93, miR-20 and miR-21.

3. The method of claim 1, wherein the lung cancer is a lung adenocarcinoma.

4. The method of claim 1, wherein a prediction of prognosis is given by a likelihood score derived from using Kaplan-Meier survival curves.

5. The method of claim 4, further comprising the step of performing a Kaplan-Meier survival analysis, wherein the performance of at least one miR-gene product of the subject is assessed.

6. The method of claim 5, further comprising the step of performing a Kaplan-Meier survival analysis, wherein the performance of at least one miR-gene product of the subject is assessed.

7. The method of claim 1, further including assessing overall survival prognosis in the subject at any point during therapy.

8. The method of claim 1, wherein determining a prognosis involves estimating the likelihood of recurrence of lung cancer.

9. The method of claim 1, further comprising providing a report of the prognosis.

10. The method of claim 1, wherein the level of expression of at least one miR gene product is compared with a previous sample taken from the same subject.

11. The method of claim 1, wherein the level of expression of at least one miR gene product is compared with a standard level.

12. The method of claim 1, wherein the prognosis is used, at least in part, to determine whether the subject would benefit from treatment of the lung cancer.

13. The method of claim 1, wherein the prognosis is used, at least in part, to develop a treatment strategy for the subject.

14. The method of claim 1, wherein the prognosis is used, at least in part, to determine disease progression in the subject.

15. The method of claim 1, wherein prognosis is defined as an estimated time of survival.

16. The method of claim 1, further including determining suitability of the subject for treatment based, at least in part, on the prognosis.

17. A method of claim 1, wherein the at least one miR gene product is miR-155.

18. A method of claim 1, which further comprises
measuring the level of at least a second miR gene product in the test sample from said subject,
wherein: the miR gene product is associated with an adverse prognosis in lung cancer; and a decrease in the level of the at least one miR gene product in the lung test sample, relative to the level of a corresponding miR gene product in a control sample, is indicative of an adverse prognosis.

19. A method of claim 18, wherein the second miR gene product is selected from the group consisting of: let 7a-2; let-7b; and miR 145.

20. A method of claim 17, wherein the second miR gene product is selected from the group consisting of: let 7a-2; let-7b; and miR 145.

21. A method of claim 18, wherein the second miR gene product is selected from the group consisting of: let 7a-2.

22. A method of claim 17, wherein the second miR gene product is selected from the group consisting of: let 7a-2.

* * * * *